US009586952B2

(12) United States Patent
Smith et al.

(10) Patent No.: US 9,586,952 B2
(45) Date of Patent: Mar. 7, 2017

(54) POLYCYCLIC ESTROGEN RECEPTOR MODULATORS AND USES THEREOF

(71) Applicant: SERAGON PHARMACEUTICALS, INC., San Diego, CA (US)

(72) Inventors: Nicholas D. Smith, San Diego, CA (US); Steven P. Govek, San Diego, CA (US); Mehmet Kahraman, La Jolla, CA (US); Celine Bonnefous, San Diego, CA (US); Jackaline D. Julien, Del Mar, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/851,215

(22) PCT Filed: Mar. 13, 2014

(86) PCT No.: PCT/US2014/026632
§ 371 (c)(1),
(2) Date: Sep. 11, 2015

(87) PCT Pub. No.: WO2014/151899
PCT Pub. Date: Sep. 25, 2014

(65) Prior Publication Data
US 2016/0355508 A1    Dec. 8, 2016

Related U.S. Application Data

(60) Provisional application No. 61/784,578, filed on Mar. 14, 2013.

(51) Int. Cl.
| | | |
|---|---|---|
| A61K 31/415 | (2006.01) |
| C07D 231/12 | (2006.01) |
| C07D 277/22 | (2006.01) |
| A61K 31/426 | (2006.01) |
| C07D 417/04 | (2006.01) |
| C07D 277/30 | (2006.01) |
| C07D 295/155 | (2006.01) |
| C07D 213/55 | (2006.01) |
| C07D 275/02 | (2006.01) |
| C07D 233/60 | (2006.01) |
| C07D 263/32 | (2006.01) |
| C07D 261/08 | (2006.01) |
| C07D 417/10 | (2006.01) |
| C07D 401/10 | (2006.01) |
| C07D 257/04 | (2006.01) |
| C07D 403/12 | (2006.01) |
| C07D 211/14 | (2006.01) |
| C07D 409/10 | (2006.01) |

(52) U.S. Cl.
CPC .......... *C07D 417/04* (2013.01); *C07D 211/14* (2013.01); *C07D 213/55* (2013.01); *C07D 231/12* (2013.01); *C07D 233/60* (2013.01); *C07D 257/04* (2013.01); *C07D 261/08* (2013.01); *C07D 263/32* (2013.01); *C07D 275/02* (2013.01); *C07D 277/30* (2013.01); *C07D 295/155* (2013.01); *C07D 401/10* (2013.01); *C07D 403/12* (2013.01); *C07D 409/10* (2013.01); *C07D 417/10* (2013.01)

(58) Field of Classification Search
CPC .. A61K 31/415; A61K 31/426; C07D 231/12; C07D 277/22
USPC ...... 514/406, 365; 548/376.1, 204; 546/342; 544/171
See application file for complete search history.

(56) References Cited

U.S. PATENT DOCUMENTS

| | | |
|---|---|---|
| 8,299,112 B2 | 10/2012 | Smith et al. |
| 8,455,534 B2 | 6/2013 | Smith et al. |
| 2013/0231333 A1 | 9/2013 | Smith et al. |
| 2015/0105403 A1 | 4/2015 | Smith et al. |
| 2015/0157606 A1 | 6/2015 | Maneval |
| 2015/0258099 A1 | 9/2015 | Hager |

FOREIGN PATENT DOCUMENTS

| | | |
|---|---|---|
| WO | 01/77057 A2 | 10/2001 |
| WO | 2005/033056 A2 | 4/2005 |
| WO | 2012/037410 A2 | 3/2012 |
| WO | 2012/037411 A2 | 3/2012 |
| WO | 2013/142266 A1 | 9/2013 |

OTHER PUBLICATIONS

Rowlands et al., "Variation of the Inhibition of Calmodulin Dependent Cyclic AMP Phosphodiesterase Amongst Analogues of Tamoxifen; Correlations With Cytotoxicity" Biochemical Pharmacology 40(2):283-289 ( 1990).
Schmidt et al., "In vitro evaluation of the anti-estrogenic activity of hydroxyl substituted diphenylnaphthyl alkene ligands for the estrogen recepto" Bioorganic & Medicinal Chemistry 13:1819-1828 ( 2005).

*Primary Examiner* — Charanjit Aulakh
(74) *Attorney, Agent, or Firm* — Alex Andrus

(57) ABSTRACT

Described herein are compounds that are estrogen receptor modulators. Also described are pharmaceutical compositions and medicaments that include the compounds described herein, as well as methods of using such estrogen receptor modulators, alone and in combination with other compounds, for treating diseases or conditions that are mediated or dependent upon estrogen receptors.

37 Claims, No Drawings

POLYCYCLIC ESTROGEN RECEPTOR MODULATORS AND USES THEREOF

RELATED APPLICATIONS

This application is a national stage filing under 35 USC §371 of international application PCT/US2014/026632, filed Mar. 13, 2014, which claims the benefit of U.S. provisional patent application No. 61/784,578 entitled "POLYCYCLIC ESTROGEN RECEPTOR MODULATORS AND USES THEREOF" filed on Mar. 14, 2013. These applications are incorporated by reference in its entireties.

FIELD OF THE INVENTION

Described herein are compounds, including pharmaceutically acceptable salts, solvates, metabolites, prodrugs thereof, methods of making such compounds, pharmaceutical compositions comprising such compounds, and methods of using such compounds to treat, prevent or diagnose diseases or conditions that are estrogen sensitive, estrogen receptor dependent or estrogen receptor mediated.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as breast cancer, ovarian cancer, colon cancer, prostate cancer, endometrial cancer, uterine cancer, as well as others diseases or conditions.

SUMMARY OF THE INVENTION

In one aspect, presented herein are compounds that diminish the effects of estrogens with estrogen receptors and/or lower the concentrations of estrogen receptors, and therefore, are useful as agents for the treatment or prevention of diseases or conditions in which the actions of estrogens and/or estrogen receptors are involved in the etiology or pathology of the disease or condition or contribute to at least one symptom of the disease or condition and wherein such actions of estrogens and/or estrogen receptors are undesirable. In some embodiments, compounds disclosed herein are estrogen receptor degrader compounds.

In one aspect, the compound described herein, or a pharmaceutically acceptable salt, or N-oxide thereof, is useful for the treatment of ER-related diseases or conditions including, but not limited to, ER-α dysfunction associated with cancer (e.g. bone cancer, breast cancer, colorectal cancer, endometrial cancer, prostate cancer, ovarian and uterine cancer), leiomyoma (e.g. uterine leiomyoma), central nervous system (CNS) defects (e.g. alcoholism, migraine), cardiovascular system defects (e.g. aortic aneurysm, susceptibility to myocardial infarction, aortic valve sclerosis, cardiovascular disease, coronary artery disease, hypertension), hematological system defects (e.g. deep vein thrombosis), immune and inflammation diseases (e.g. Graves' Disease, arthritis, multiple sclerosis, cirrhosis), susceptibility to infection (e.g. hepatitis B, chronic liver disease), metabolic defects (e.g. bone density, cholestasis, hypospadias, obesity, osteoarthritis, osteopenia, osteoporosis), neurological defects (e.g. Alzheimer's disease, Parkinson's disease, migraine, vertigo), psychiatric defects (e.g. anorexia nervosa, attention deficit hyperactivity disorder (ADHD), dementia, major depressive disorder, psychosis) and reproductive defects (e.g. age of menarche, endometriosis, infertility).

In one aspect, described herein are compounds, pharmaceutically acceptable salts, solvates, metabolites and prodrugs thereof. Compounds described herein (e.g. compounds of Formula (I), (II), (III), (IV), (V), (VI), (VII), (VIII), (IX), (X), (XI), (XII), (XIII), (XIV) and compounds in Table 1), are estrogen receptor modulators. In some embodiments, the compounds of Formula (I), (II), (III), (IV), (V), (VI), (VII), (VIII), (IX), (X), (XI), (XII), (XIII), or (XIV) or compounds in Table 1 are estrogen receptor antagonists. In some embodiments, the compounds of Formula (I), (II), (III), (IV), (V), (VI), (VII), (VIII), (IX), (X), (XI), (XII), (XIII), or (XIV) or compounds in Table 1 are estrogen receptor degraders. In some embodiments, the compounds of Formula (I), (II), (III), (IV), (V), (VI), (VII), (VIII), (IX), (X), (XI), (XII), (XIII), or (XIV) or compounds in Table 1 are estrogen receptor antagonists as well as estrogen receptor degraders. In some embodiments, the compounds of Formula (I), (II), (III), (IV), (V), (VI), (VII), (VIII), (IX), (X), (XI), (XII), (XIII), or (XIV) or compounds in Table 1 display miminal or no estrogen receptor agonist activity. In some embodiments, in the context of treating cancers, the compounds of Formula (I), (II), (III), (IV), (V), (VI), (VII), (VIII), (IX), (X), (XI), (XII), (XIII), or (XIV) or compounds in Table 1 offer improved therapeutic activity characterized by complete or longer-lasting tumor regression, a lower incidence or rate of development of resistance to treatment, and/or a reduction in tumor invasiveness.

In one aspect, described herein is a compound of Formula (I), or a pharmaceutically acceptable salt, solvate, metabolite or prodrug thereof:

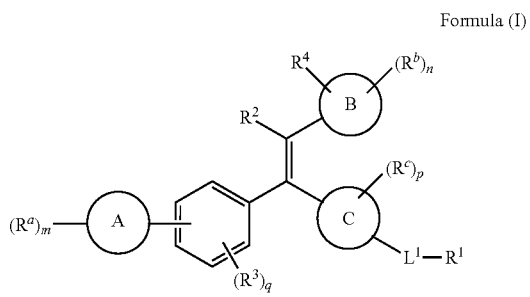

Formula (I)

wherein,
ring A is 3-7 membered monocyclic $C_2$-$C_6$heterocycloalkyl, 5-membered monocyclic heteroaryl, or 6-membered monocyclic heteroaryl;
each $R^a$ is independently selected from the group consisting of H, halogen, —$NR^7R^8$, —CN, —OH, —$OR^9$, —$SR^8$, substituted or unsubstituted $C_1$-$C_6$alkyl, substituted or unsubstituted $C_1$-$C_6$fluoroalkyl, and substituted or unsubstituted $C_1$-$C_6$heteroalkyl;
m is 0, 1, 2, 3, or 4;
ring B is phenyl, indanyl, indenyl, naphthyl, 5-membered monocyclic heteroaryl, 6-membered monocyclic heteroaryl, or 8-, 9- or 10-membered bicyclic heteroaryl;

each $R^b$ is independently selected from the group consisting of H, halogen, —$NR^7R^8$, —CN, —OH, —$OR^9$, —$SR^8$, —S(=O)$R^9$, —S(=O)$_2R^9$, —NHS(=O)$_2R^9$, —S(=O)$_2N(R^8)_2$, —C(=O)$R^9$, —OC(=O)$R^9$, —CO$_2R^8$, —OCO$_2R^9$, —C(=O)N(R^8)_2$, —OC(=O)N(R^8)_2$, —NR^7C(=O)N(R^8)_2$, —NR^7C(=O)R^9$, —NR^7C(=O)OR^9$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;

n is 0, 1, 2, 3, or 4;

ring C is phenyl, 5-membered monocyclic heteroaryl or a 6-membered monocyclic heteroaryl;

each $R^c$ is independently selected from the group consisting of H, halogen, —CN, —OH, —$OR^9$, $C_1$-$C_6$alkyl, or $C_1$-$C_6$fluoroalkyl;

p is 0, 1, 2, 3 or 4;

$L^1$ is absent, —$C_1$-$C_6$alkylene-, —X—$C_1$-$C_6$alkylene-, or —C($R^5$)=C($R^6$)—;

X is $NR^7$, O, S, S(=O) or S(=O)$_2$;

$R^5$ is H, $C_1$-$C_4$alkyl, or halogen;

$R^6$ is H, $C_1$-$C_4$alkyl, or halogen;

$R^1$ is —C(=O)—Z, a carboxylic acid bioisostere, or a substituted or unsubstituted N-containing $C_2$-$C_8$heterocycloalkyl;

Z is —OH, —$OR^9$, —$NR^7R^8$, —$NR^7S(=O)_2R^9$, —NHOH or —$NR^7OR^9$;

$R^2$ is halogen, —CN, —NO$_2$, —$SR^9$, —S(=O)$R^{10}$, —S(=O)$_2R^{10}$, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, —$C_1$-$C_4$fluoroalkylene-W, —$C_3$-$C_6$cycloalkylene-W;

W is hydroxy, halogen, —CN, —NO$_2$, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl;

each $R^3$ is independently selected from the group consisting of H, halogen, —CN, $C_1$-$C_6$alkyl, $C_1$-$C_6$fluoroalkyl, and $C_1$-$C_6$heteroalkyl;

q is 0, 1, 2, 3 or 4;

$R^4$ is H, halogen, —CN, —OH, —$OR^9$, —$SR^8$, —S(=O)$R^9$, —S(=O)$_2R^9$, —NHS(=O)$_2R^9$, —S(=O)$_2N(R^8)_2$, —C(=O)$R^9$, —OC(=O)$R^9$, —CO$_2R^8$, —C(=O)N(R^8)_2$, —OC(=O)N(R^8)_2$, $C_1$-$C_6$alkyl, $C_2$-$C_6$alkenyl, $C_2$-$C_6$alkynyl, $C_1$-$C_6$fluoroalkyl, or $C_1$-$C_6$heteroalkyl;

each $R^7$ is independently H or $C_1$-$C_6$alkyl;

each $R^8$ is independently selected from H, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, or substituted or unsubstituted benzyl;

each $R^9$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted heteroaryl and substituted or unsubstituted benzyl.

For any and all of the embodiments described herein, substituents are selected from among a subset of the listed alternatives. For example in some embodiments, $R^1$ is —C(=O)—Z, a carboxylic acid bioisostere, or a substituted or unsubstituted N-containing $C_2$-$C_8$heterocycloalkyl. In other embodiments, $R^1$ is —C(=O)—Z or a carboxylic acid bioisostere. In yet other embodiments, $R^1$ is —C(=O)—Z. In some embodiments, $R^1$ is —C(=O)—OH. In some embodiments, $R^1$ is a carboxylic acid bioisostere. In some other embodiments, $R^1$ is a substituted or unsubstituted N-containing $C_2$-$C_8$heterocycloalkyl.

In some embodiments, ring A is 3-7 membered monocyclic N-containing $C_2$-$C_6$heterocycloalkyl, N-containing 5-membered monocyclic heteroaryl, or N-containing 6-membered monocyclic heteroaryl; ring B is phenyl, indanyl, indenyl, naphthyl, 5-membered monocyclic heteroaryl, 6-membered monocyclic heteroaryl, or 8-, 9- or 10-membered bicyclic heteroaryl; ring C is phenyl or an N-containing 6-membered monocyclic heteroaryl.

In some embodiments, ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl; ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl; ring C is phenyl, pyridinyl, pyridazinyl, pyrimidinyl, pyrazinyl, or triazinyl.

In some embodiments,

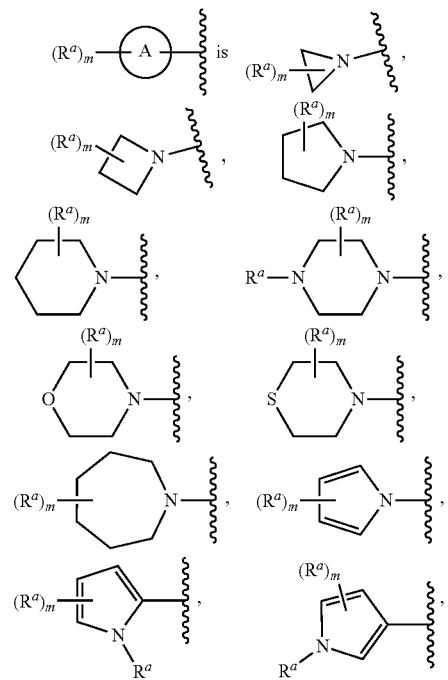

-continued

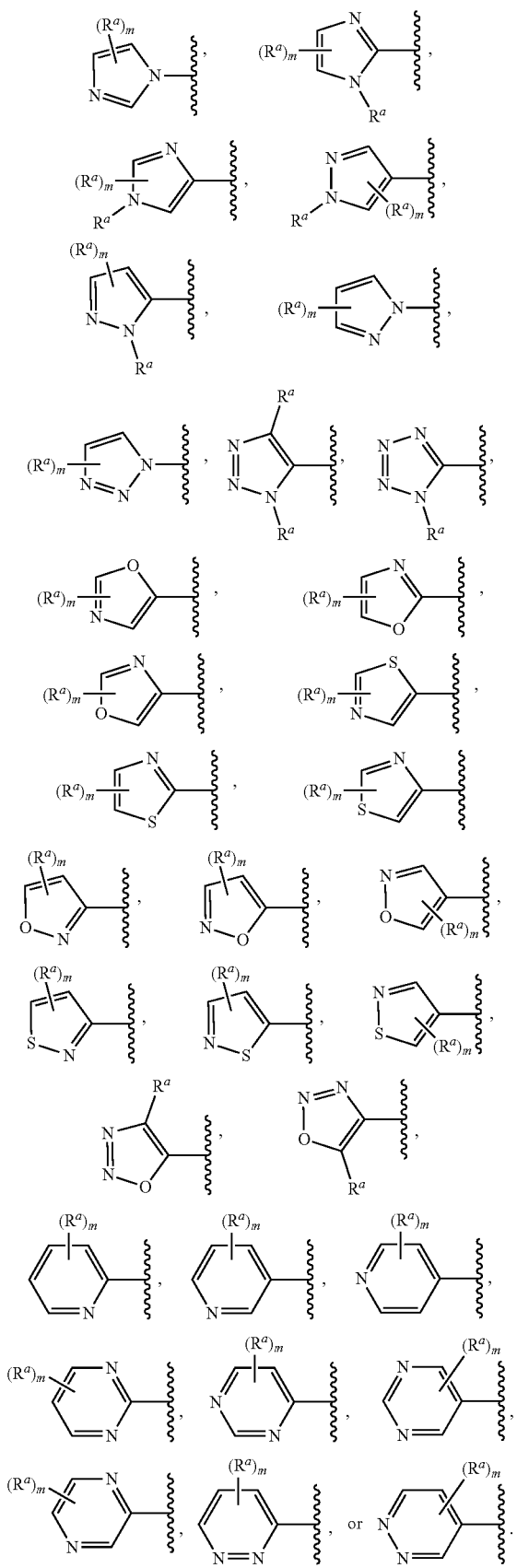

In some embodiments,

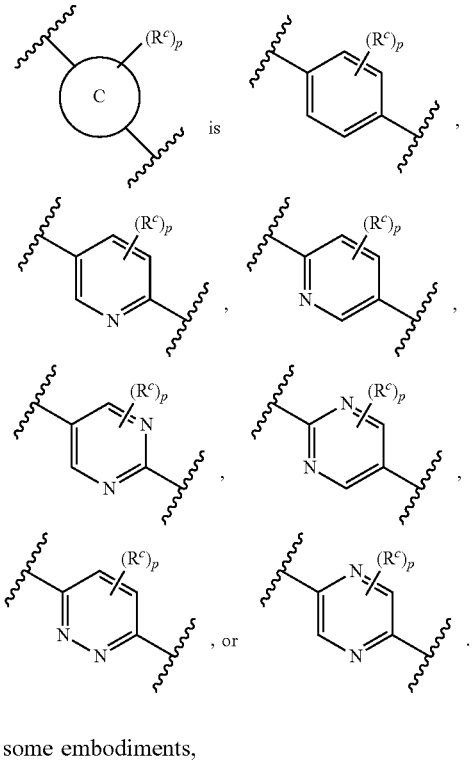

In some embodiments,

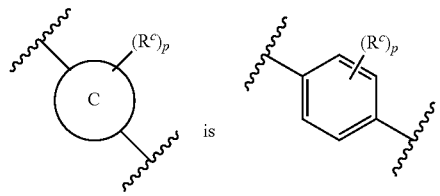

In some embodiments, ring A is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl.

In some embodiments, the compound of Formula (I) has the following structure of Formula (II):

Formula (II)

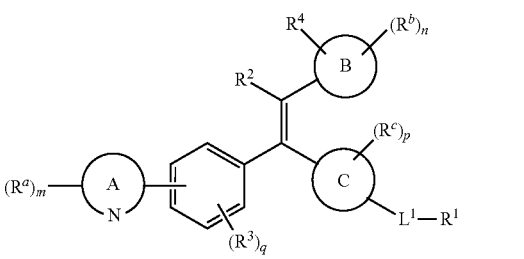

or is a pharmaceutically acceptable salt thereof.

In some embodiments, ring A is N-linked 3-7 membered monocyclic N-containing $C_2$-$C_6$heterocycloalkyl or N-linked N-containing 5-membered monocyclic heteroaryl.

In some embodiments, the compound of Formula (I) has the following structure of Formula (III):

Formula (III)

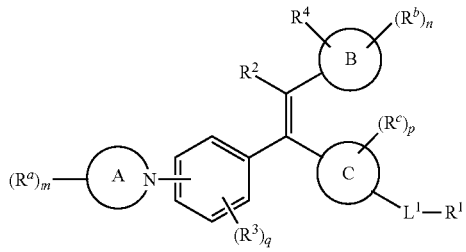

or is a pharmaceutically acceptable salt thereof.

In some embodiments, $L^1$ is —C($R^5$)═C($R^6$)—; $R^5$ is H, $C_1$-$C_4$alkyl, or halogen; $R^6$ is H, $C_1$-$C_4$alkyl, or halogen; $R^1$ is —C(═O)—Z, or a a carboxylic acid bioisostere.

In some embodiments, $L^1$ is —C($R^5$)═C($R^6$)—; $R^5$ is H, —$CH_3$, F, or Cl; $R^6$ is H, —$CH_3$, F, or Cl; $R^1$ is —C(═O)—Z,

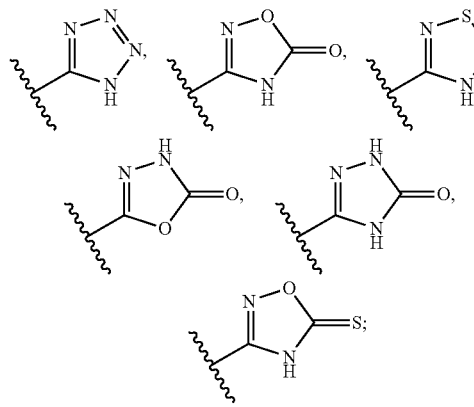

Z is —OH, —$OR^9$, or —$NR^7R^8$.

In some embodiments, $L^1$ is —X—$C_1$-$C_6$alkylene-; X is O; $R^1$ is a substituted or unsubstituted aziridinyl, azetidinyl, pyrrolidinyl, piperidininyl, azepanyl, morpholinyl, thiomorpholinyl, or piperazinyl.

In some embodiments, $L^1$ is —X—$C_1$-$C_6$alkylene-; X is O; $R^1$ is a substituted or unsubstituted pyrrolidinyl.

In some embodiments, the compound of Formula (I) has the following structure of Formula (IV):

Formula (IV)

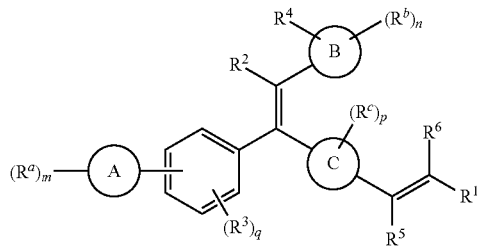

or is a pharmaceutically acceptable salt thereof.

In some embodiments, the compound of Formula (I) or Formula (IV) has the following structure of Formula (V):

Formula (V)

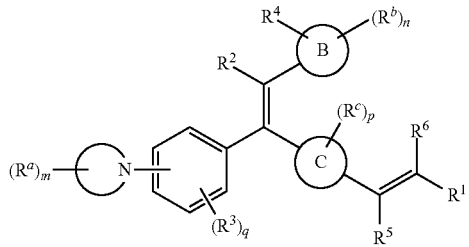

or is a pharmaceutically acceptable salt thereof.

In some embodiments, the compound of Formula (I) or Formula (IV) has the following structure of Formula (VI):

Formula (VI)

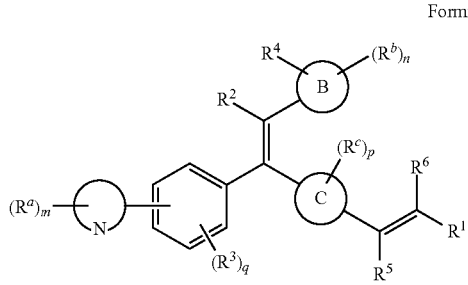

or is a pharmaceutically acceptable salt thereof.

In some embodiments, the compound has the following structure of Formula (VII):

Formula (VII)

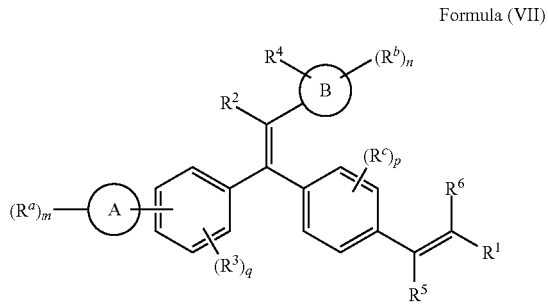

or is a pharmaceutically acceptable salt thereof.

In some embodiments, the compound of Formula (VII) has the following structure of Formula (VIII) or Formula (IX):

Formula (VIII)

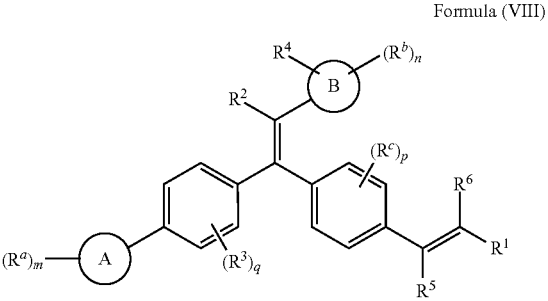

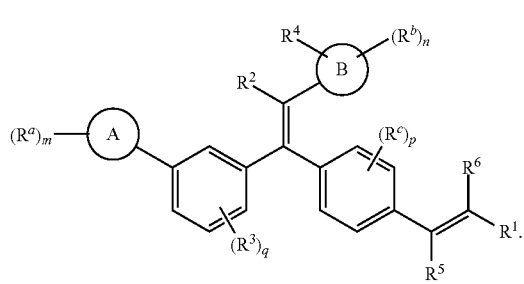

or is a pharmaceutically acceptable salt thereof.

In some embodiments, ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl.

In some embodiments, ring A is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl.

In some embodiments,

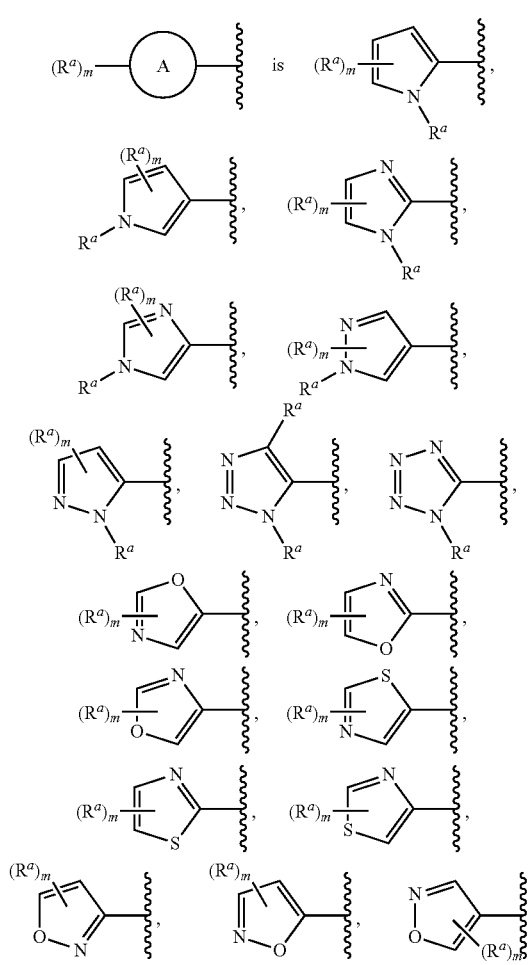

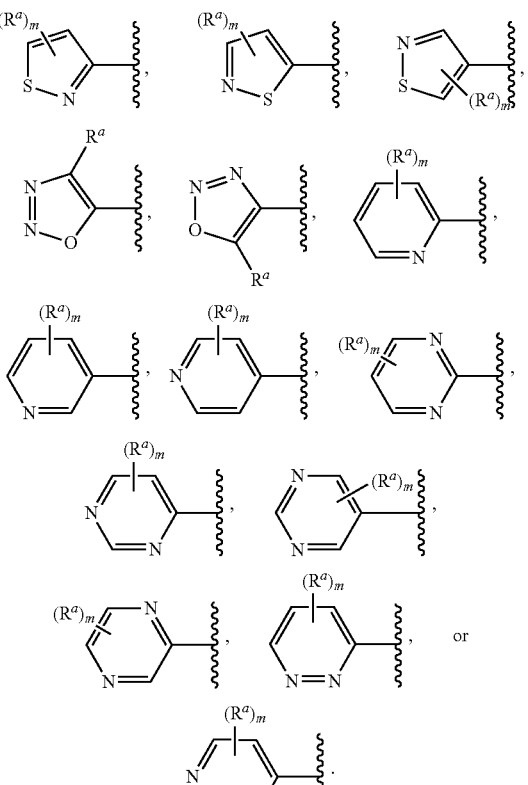

In some embodiments, ring A is N-linked 3-7 membered monocyclic N-containing $C_2$-$C_6$heterocycloalkyl, or N-linked N-containing 5-membered monocyclic heteroaryl.

In some embodiments,

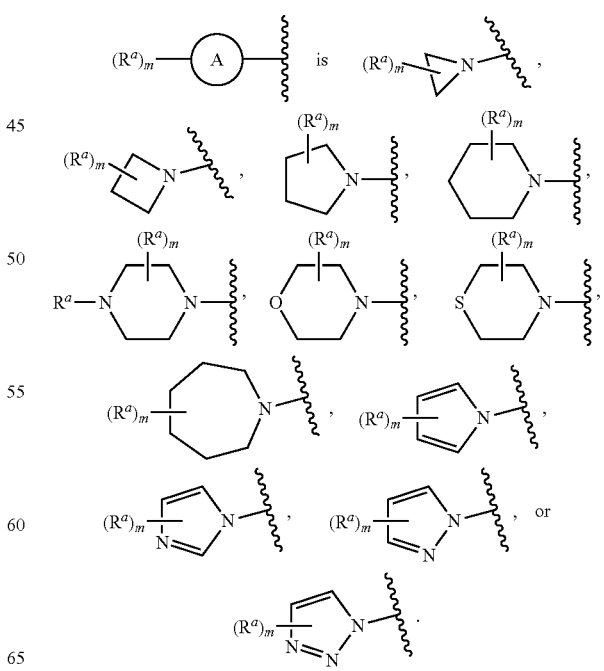

In some embodiments,
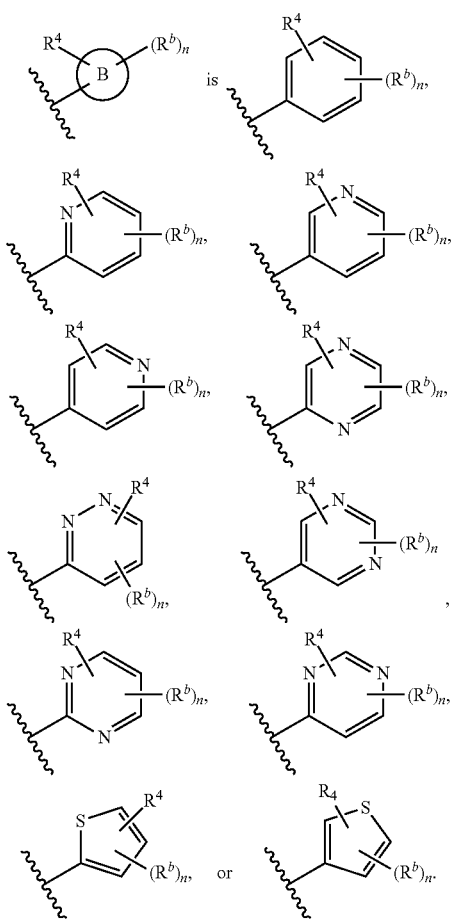
In some embodiments,
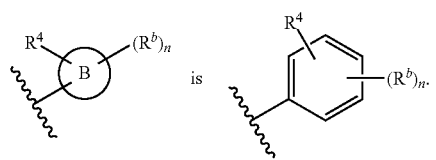
In some embodiments,
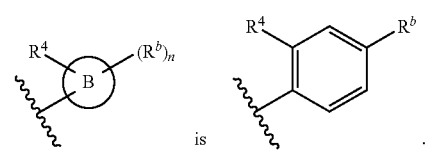
In some embodiments,
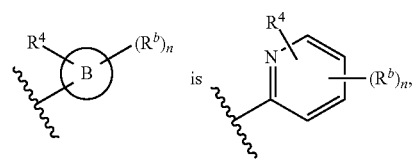
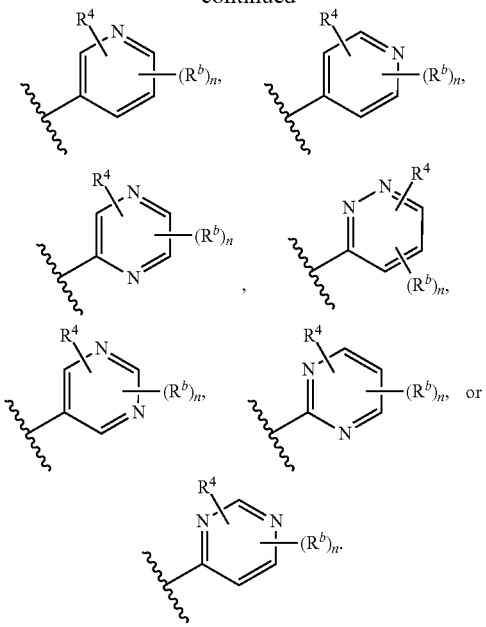
In some embodiments,
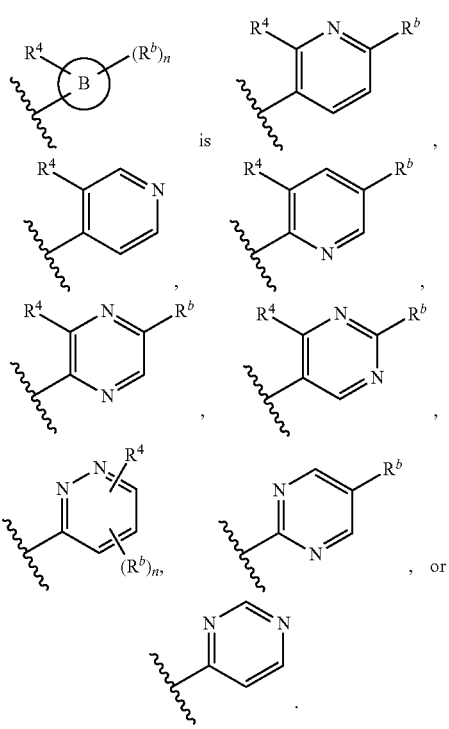
In some embodiments,
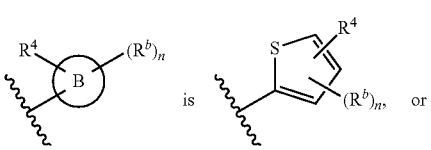

-continued

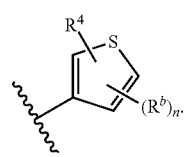

In some embodiments,

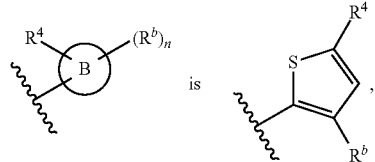

In some embodiments, $R^5$ is H; $R^6$ is H.

In some embodiments, $R^2$ is halogen, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, —$C_1$-$C_4$fluoroalkylene-W, —$C_3$-$C_6$cycloalkylene-W; W is hydroxy, halogen, —CN, —NO$_2$, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl.

In some embodiments, $R^2$ is $C_1$-$C_6$alkyl, $C_1$-$C_6$fluoroalkyl, $C_1$-$C_6$deuteroalkyl, $C_3$-$C_6$cycloalkyl, or —$C_1$-$C_4$alkylene-W; W is hydroxy, halogen, —CN, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl.

In some embodiments, $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, -CD$_3$, —CH$_2$CD$_3$, -CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl.

In some embodiments, $R^2$ is $C_1$-$C_6$alkyl or $C_3$-$C_6$cycloalkyl.

In some embodiments, $R^2$ is $C_1$-$C_6$alkyl.

In some embodiments, $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, or —CH$_2$CH(CH$_3$)$_2$, In some embodiments, $R^2$ is —CH$_2$CH$_3$.

In some embodiments, $R^2$ is $C_3$-$C_6$cycloalkyl.

In some embodiments, $R^2$ is cyclopropyl, cyclobutyl, cyclopentyl, or cyclohexyl.

In some embodiments, $R^2$ is cyclobutyl.

In some embodiments, the compound of Formula (I) has the following structure of Formula (X):

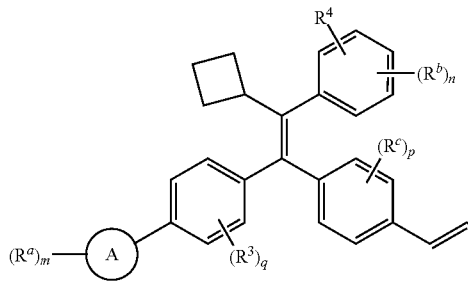

Formula (X)

or is a pharmaceutically acceptable salt thereof.

In some embodiments, the compound of Formula (X) has the following structure of Formula (XI):

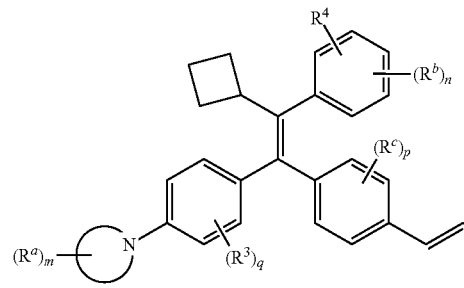

Formula (XI)

or is a pharmaceutically acceptable salt thereof.

In some embodiments, the compound of Formula (X) has the following structure of Formula (XII):

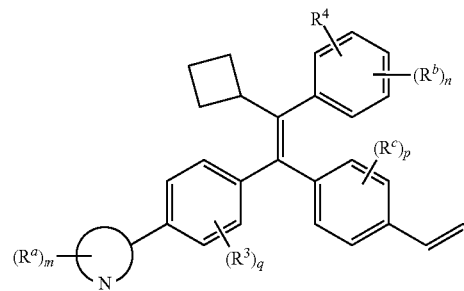

Formula (XII)

or is a pharmaceutically acceptable salt thereof.

In some embodiments, $R^b$ is H, F, Cl, —CN, —OH, —OR$^9$, —SR$^8$, —S(=O)R$^9$, —S(=O)$_2$R$^9$, $C_1$-$C_6$alkyl, $C_1$-$C_6$fluoroalkyl, or $C_1$-$C_6$heteroalkyl; $R^4$ is H, F, Cl, —CN, —OH, —OR$^9$, —SR$^8$, —S(=O)R$^9$, —S(=O)$_2$R$^9$, $C_1$-$C_6$alkyl, $C_1$-$C_6$fluoroalkyl, or $C_1$-$C_6$heteroalkyl.

In some embodiments, $R^b$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH; $R^4$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH.

In some embodiments, each $R^a$ is independently selected from the group consisting of H, halogen, —CN, —OH, —OR$^9$, $C_1$-$C_6$alkyl, $C_1$-$C_6$fluoroalkyl, and $C_1$-$C_6$heteroalkyl; m is 0 or 1.

In some embodiments, m is 0.

In some embodiments, p is 0.

In some embodiments, $R^1$ is —C(=O)—OH.

In some embodiments, compounds described herein include compounds in Table 1, or a pharmaceutically acceptable salt thereof.

Throughout the specification, groups and substituents thereof can be chosen by one skilled in the field to provide stable moieties and compounds.

Compounds disclosed herein are estrogen receptor modulators. In some embodiments, compounds disclosed herein have high specificity for the estrogen receptor and have desirable, tissue-selective pharmacological activities. Desirable, tissue-selective pharmacological activities include, but are not limited to, ER antagonist activity in breast cells and miminal or no ER agonist activity in uterine cells. In some embodiments, compounds disclosed herein are estrogen receptor degraders that display full estrogen receptor antagonist activity with negligible or minimal estrogen receptor agonist activity.

In some embodiments, compounds disclosed herein are estrogen receptor degraders. In some embodiments, compounds disclosed herein are estrogen receptor antagonists. In some embodiments, compounds disclosed herein have minimal or negligible estrogen receptor agonist activity.

In some embodiments, presented herein are compounds selected from active metabolites, tautomers, pharmaceutically acceptable solvates, pharmaceutically acceptable salts or prodrugs of a compound described herein (e.g. a compound of Formula (I), (II), (III), (IV), (V), (VI), (VII), (VIII), (IX), (X), (XI), (XII), (XIII), or (XIV), or a compound in Table 1).

Also described are pharmaceutical compositions comprising a therapeutically effective amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof. In some embodiments, the pharmaceutical composition also contains at least one pharmaceutically acceptable inactive ingredient. In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a suspension, a solution, an emulsion, an ointment, or a lotion.

In some embodiments, the pharmaceutical composition further comprises one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, poly ADP-ribose polymerase (PARP) inhibitors, and aromatase inhibitors.

In some embodiments, provided herein is a method comprising administering a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, to a human with a disease or condition that is estrogen sensitive, estrogen receptor meditated or estrogen receptor dependent. In some embodiments, the human is already being administered one or more additional therapeutically active agents. In some embodiments, the method further comprises administering one or more additional therapeutically active agents other than a compound described herein, or a pharmaceutically acceptable salt thereof.

In some embodiments, the one or more additional therapeutically active agents other than a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, are selected from: corticosteroids, anti-emetic agents, analgesics, anti-cancer agents, anti-inflammatories, kinase inhibitors, antibodies, HSP90 inhibitors, histone deacetylase (HDAC) inhibitors, and aromatase inhibitors.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used to treat hormone receptor positive metastatic breast cancer in a postmenopausal woman with disease progression following anti-estrogen therapy. In some embodiments, compounds are used to treat a hormonal dependent benign or malignant disease of the breast or reproductive tract in a mammal.

Pharmaceutical formulations described herein are administered to a mammal in a variety of ways, including but not limited to, oral, parenteral (e.g., intravenous, subcutaneous, intramuscular), buccal, topical or transdermal administration routes. The pharmaceutical formulations described herein include, but are not limited to, aqueous liquid dispersions, self-emulsifying dispersions, solid solutions, liposomal dispersions, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered orally to a mammal. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered systemically to a mammal. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered intravenously to a mammal. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered subcutaneously to a mammal.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered topically to a mammal. In such embodiments, the compound, or a pharmaceutically acceptable salt thereof, is formulated into a variety of topically administrable compositions, such as solutions, suspensions, lotions, gels, pastes, shampoos, scrubs, rubs, smears, medicated sticks, medicated bandages, balms, creams or ointments. In some embodiments, the compound, or a pharmaceutically acceptable salt thereof, is administered topically to the skin of mammal.

In another aspect is the use of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in the manufacture of a medicament for treating a disease, disorder or conditions in which the activity of estrogen receptors contributes to the pathology and/or symptoms of the disease or condition. In one aspect, the disease or condition is any of the diseases or conditions specified herein.

In any of the aforementioned aspects are further embodiments in which the effective amount of the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of reducing ER activation in a mammal comprising administering to the mammal a compound of Formula (I), (II), (III), (IV), (V), (VI), (VII), (VIII), (IX), (X), (XI), (XII), (XIII), or (XIV), or a compound in Table 1, or a pharmaceutically acceptable salt thereof. In some embodiments, the method comprises reducing ER activation in breast cells, ovarian cells, colon cells, prostate cells, endometrial cells, or uterine cells in the mammal. In some embodiments, the method of reducing ER activation in the mammal comprises reducing the binding of estrogens to estrogen receptors in the mammal. In some embodiments, the method of reducing ER activation in the mammal comprises reducing ER concentrations in the mammal.

In one aspect is the use of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in the manufacture of a medicament for the treatment of diseases or conditions that are estrogen sensitive, estrogen receptor dependent or estrogen receptor mediated. In some embodiments, the disease or condition is breast cancer, ovarian cancer, colon cancer, prostate cancer, endometrial cancer, or uterine cancer. In some embodiments, the disease or condition is described herein.

In some cases disclosed herein is the use of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in the treatment or prevention of diseases or conditions that are estrogen sensitive, estrogen receptor dependent or estrogen receptor mediated. In some embodiments, the disease or condition is described herein.

In any of the embodiments disclosed herein, the mammal is a human.

In some embodiments, compounds provided herein are used to diminish, reduce, or eliminate the activity of estrogen receptors.

Articles of manufacture, which include: packaging material; a compound of Formula (I), (II), (III), (IV), (V), (VI), (VII), (VIII), (IX), (X), (XI), (XII), (XIII), or (XIV), or a compound in Table 1, or pharmaceutically acceptable salt, active metabolite, prodrug, or pharmaceutically acceptable solvate thereof, or composition thereof, within the packaging material; and a label that indicates that the compound or pharmaceutically acceptable salt, active metabolite, prodrug, or pharmaceutically acceptable solvate thereof, or composition thereof, or composition thereof, is used for reducing, diminishing or eliminating the effects of estrogen receptors, or for the treatment, prevention or amelioration of one or more symptoms of a disease or condition that would benefit from a reduction or elimination of estrogen receptor activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineralcorticoid receptor), which regulate a wide spectrum of reproductive, metabolic and developmental activities. The activities of ER are controlled by the binding of endogenous estrogens, including 17β-estradiol and estrones.

The ER-α gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., Nature 389: 753-758, 1997). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, Biofactors 35: 528-536, 2009). One of the involved phosphorylation sites (S 118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for disease or conditions that estrogen-sensitive and/or resistant to available anti-hormonal treatments.

ER signaling is crucial for the development and maintenance of female reproductive organs including breasts, ovulation and thickening of the endometrium. ER signaling also has a role in bone mass, lipid metabolism, cancers, etc. About 70% of breast cancers express ER-α (ER-α positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (Faslodex™) a steroid-based ER antagonist is used to treat breast cancer in women which has have progressed despite therapy with tamoxifen. Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracylines, platins, taxanes. In some cases, ER positive breast cancers that harbor genetic amplification of the ERB-B/HER2 tyrosine kinase receptor are treated with the monoclonal antibody trastuzumab (Herceptin™) or the small molecule pan-ERB-B inhibitor lapatinib. Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance.

In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies. In some embodiments, compounds disclosed herein minimize levels of the estrogen receptor in the nucleus.

Given the central role of ER-α in breast cancer development and progression, compounds disclosed herein are useful in the treatment of breast cancer, either alone or in combination with other agent or agents that modulate other critical pathways in breast cancer, including but not limited to those that target IGF1R, EGFR, erB-B2 and 3 the PI3K/AKT/mTOR axis, HSP90, PARP or histone deacetylases.

Given the central role of ER-α in breast cancer development and progression, compounds disclosed herein are useful in the treatment of breast cancer, either alone or in combination with other agent used to treat breast cancer, including but not limited to aromatase inhibitors, anthracylines, platins, nitrogen mustard alkylating agents, taxanes. Illustrative agent used to treat breast cancer, include, but are not limited to, paclitaxel, anastrozole, exemestane, cyclophosphamide, epirubicin, fulvestrant, letrozole, gemcitabine, trastuzumab, pegfilgrastim, filgrastim, tamoxifen, docetaxel, toremifene, vinorelbine, capecitabine, ixabepilone, as well as others described herein.

ER-related diseases or conditions (for which the agents disclosed herein are therapeutically relevant) include ER-α dysfunction is also associated with cancer (bone cancer, breast cancer, colorectal cancer, endometrial cancer, prostate cancer, ovarian and uterine cancer), leiomyoma (uterine leiomyoma), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility).

In some embodiments, compounds disclosed herein are used to treat cancer in a mammal. In some embodiments, the cancer is breast cancer, ovarian cancer, endometrial cancer, prostate cancer, uterine cancer, cervical cancer or lung cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, compounds disclosed herein are used to treat cancer in a mammal, wherein the mammal is chemotherapy-naïve.

In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment of endometriosis in a mammal.

In some embodiments, compounds disclosed herein are used in the treatment of leiomyoma in a mammal. In some embodiments, the leiomyoma is an uterine leiomyoma, esophageal leiomyoma, cutaneous leiomyoma or small bowel leiomyoma. In some embodiments, compounds disclosed herein are used in the treatment of fibroids in a mammal (e.g. uterine fibroids).

In some embodiments, compounds disclosed herein are used in the treatment of hot flashes in a mammal.

Compounds

Compounds described herein (e.g. a compound of Formula (I), (II), (III), (IV), (V), (VI), (VII), (VIII), (IX), (X), (XI), (XII), (XIII), or (XIV), or a compound in Table 1), including pharmaceutically acceptable salts, prodrugs, active metabolites and pharmaceutically acceptable solvates thereof, are estrogen receptor modulators. In specific embodiments, the compounds described herein are estrogen receptor degraders. In specific embodiments, the compounds described herein are estrogen receptor antagonists. In specific embodiments, the compounds described herein are estrogen receptor degraders and estrogen receptor antagonists with minimal or no estrogen receptor agonist activity.

In some embodiments, compounds disclosed herein are estrogen receptor degraders and estrogen receptor antagonists that exhibit: miminal or no estrogen receptor agonism; and/or anti-proliferative activity against breast cancer, ovarian cancer, endometrial cancer, cervical cancer cell lines; and/or maximal anti-proliferative efficacy against breast cancer, ovarian cancer, endometrial cancer, cervical cell lines in-vitro; and/or maximal anti-proliferative efficacy against patient-derived breast cancer, patient-derived ovarian cancer, patient-derived endometrial cancer, patient-derived cervical cell lines in-vitro; and/or minimal agonism in the human endometrial (Ishikawa) cell line; and/or no agonism in the human endometrial (Ishikawa) cell line; and/or miminal or no agonism in the immature rat uterine assay in-vivo; and/or inverse agonism in the immature rat uterine assay in-vivo; and/or anti-tumor activity in patient-derived breast cancer, patient-derived ovarian cancer, patient-derived endometrial cancer, or patient-derived cervical cancer cell lines in xenograft assays in-vivo or other rodent models of these cancers.

In one aspect, described herein is a compound of Formula (I), or a pharmaceutically acceptable salt, solvate, metabolite or prodrug thereof:

In one aspect, described herein is a compound of Formula (I), or a pharmaceutically acceptable salt, solvate, metabolite or prodrug thereof:

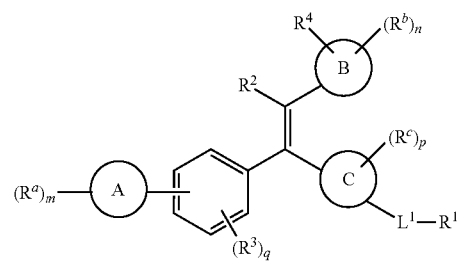

Formula (I)

wherein,
ring A is 3-7 membered monocyclic $C_2$-$C_6$heterocycloalkyl, 5-membered monocyclic heteroaryl, or 6-membered monocyclic heteroaryl;
each $R^a$ is independently selected from the group consisting of H, halogen, —$NR^7R^8$, —CN, —OH, —$OR^9$, —$SR^8$, substituted or unsubstituted $C_1$-$C_6$alkyl, substituted or unsubstituted $C_1$-$C_6$fluoroalkyl, and substituted or unsubstituted $C_1$-$C_6$heteroalkyl;
m is 0, 1, 2, 3, or 4;
ring B is phenyl, indanyl, indenyl, naphthyl, 5-membered monocyclic heteroaryl, 6-membered monocyclic heteroaryl, or 8-, 9- or 10-membered bicyclic heteroaryl;
each $R^b$ is independently selected from the group consisting of H, halogen, —$NR^7R^8$, —CN, —OH, —$OR^9$, —$SR^8$, —S(=O)$R^9$, —S(=O)$_2R^9$, —NHS(=O)$_2R^9$, —S(=O)$_2N(R^8)_2$, —C(=O)$R^9$, —OC (=O)R$^9$, —CO$_2$R$^8$, —OCO$_2$R$^9$, —C(=O)N(R$^8$)$_2$, —OC(=O)N(R$^8$)$_2$, —NR$^7$C(=O)N(R$^8$)$_2$, —NR$^7$C(=O)R$^9$, —NR$^7$C(=O)OR$^9$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

n is 0, 1, 2, 3, or 4;

ring C is phenyl, 5-membered monocyclic heteroaryl or a 6-membered monocyclic heteroaryl;

each R$^c$ is independently selected from the group consisting of H, halogen, —CN, —OH, —OR$^9$, C$_1$-C$_6$alkyl, or C$_1$-C$_6$fluoroalkyl;

p is 0, 1, 2, 3 or 4;

L$^1$ is absent, —C$_1$-C$_6$alkylene-, —X—C$_1$-C$_6$alkylene-, or —C(R$^5$)=C(R$^6$)—;

X is NR$^7$, O, S, S(=O) or S(=O)$_2$;

R$^5$ is H, C$_1$-C$_4$alkyl, or halogen;

R$^6$ is H, C$_1$-C$_4$alkyl, or halogen;

R$^1$ is —C(=O)—Z, a carboxylic acid bioisostere, or a substituted or unsubstituted N-containing C$_2$-C$_8$heterocycloalkyl;

Z is —OH, —OR$^9$, —NR$^7$R$^8$, —NR$^7$S(=O)$_2$R$^9$, —NHOH or —NR$^7$OR$^9$;

R$^2$ is halogen, —CN, —NO$_2$, —SR$^9$, —S(=O)R$^{10}$, —S(=O)$_2$R$^{10}$, C$_1$-C$_6$alkyl, C$_1$-C$_6$fluoroalkyl, C$_1$-C$_6$deuteroalkyl, C$_3$-C$_6$cycloalkyl, —C$_1$-C$_4$alkylene-W, —C$_1$-C$_4$fluoroalkylene-W, —C$_3$-C$_6$cycloalkylene-W;

W is hydroxy, halogen, —CN, —NO$_2$, C$_1$-C$_6$alkyl, C$_1$-C$_6$haloalkyl, C$_1$-C$_6$alkoxy, C$_1$-C$_6$haloalkoxy, and C$_3$-C$_6$cycloalkyl;

each R$^3$ is independently selected from the group consisting of H, halogen, —CN, C$_1$-C$_6$alkyl, C$_1$-C$_6$fluoroalkyl, and C$_1$-C$_6$heteroalkyl;

q is 0, 1, 2, 3 or 4;

R$^4$ is H, halogen, —CN, —OH, —OR$^9$, —SR$^8$, —S(=O)R$^9$, —S(=O)$_2$R$^9$, —NHS(=O)$_2$R$^9$, —S(=O)$_2$N(R$^8$)$_2$, —C(=O)R$^9$, —OC(=O)R$^9$, —CO$_2$R$^8$, —C(=O)N(R$^8$)$_2$, —OC(=O)N(R$^8$)$_2$, C$_1$-C$_6$alkyl, C$_2$-C$_6$alkenyl, C$_2$-C$_6$alkynyl, C$_1$-C$_6$fluoroalkyl, or C$_1$-C$_6$heteroalkyl;

each R$^7$ is independently H or C$_1$-C$_6$alkyl;

each R$^8$ is independently selected from H, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, or substituted or unsubstituted benzyl;

each R$^9$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted heteroaryl and substituted or unsubstituted benzyl.

For any and all of the embodiments described herein, substituents are selected from among a subset of the listed alternatives. For example in some embodiments, R$^1$ is —C(=O)—Z, a carboxylic acid bioisostere, or a substituted or unsubstituted N-containing C$_2$-C$_8$heterocycloalkyl. In other embodiments, R$^1$ is —C(=O)—Z or a carboxylic acid bioisostere. In yet other embodiments, R$^1$ is —C(=O)—Z. In some embodiments, R$^1$ is —C(=O)—OH. In some embodiments, R$^1$ is a carboxylic acid bioisostere. In some other embodiments, R$^1$ is a substituted or unsubstituted N-containing C$_2$-C$_8$heterocycloalkyl.

In some embodiments, ring A is 3-7 membered monocyclic C$_2$-C$_6$heterocycloalkyl, 5-membered monocyclic heteroaryl, or 6-membered monocyclic heteroaryl. In some embodiments, ring A is 3-7 membered monocyclic C$_2$-C$_6$heterocycloalkyl. In some embodiments, ring A is 5-membered monocyclic heteroaryl, or 6-membered monocyclic heteroaryl. In some embodiments, ring A is 5-membered monocyclic heteroaryl. In some embodiments, ring A is 6-membered monocyclic heteroaryl.

In some embodiments, ring A is 3-7 membered monocyclic N-containing C$_2$-C$_6$heterocycloalkyl, N-containing 5-membered monocyclic heteroaryl, or N-containing 6-membered monocyclic heteroaryl; ring B is phenyl, indanyl, indenyl, naphthyl, 5-membered monocyclic heteroaryl, 6-membered monocyclic heteroaryl, or 8-, 9- or 10-membered bicyclic heteroaryl; ring C is phenyl or an N-containing 6-membered monocyclic heteroaryl.

In some embodiments, ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl; ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl; ring C is phenyl, pyridinyl, pyridazinyl, pyrimidinyl, pyrazinyl, or triazinyl.

In some embodiments,

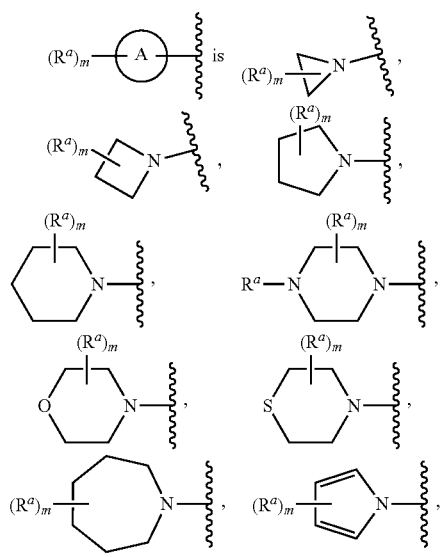

-continued

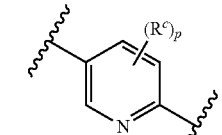

In some embodiments,

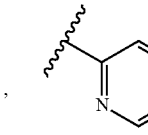

In some embodiments,

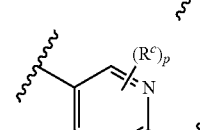

In some embodiments,

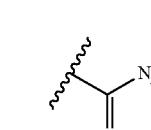

(i.e. C-linked) or

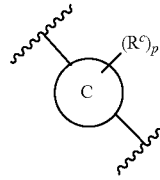

(i.e. N-linked). If ring A is C-linked, then $R^a$ (if present) can be on any open position of the ring, including on the N-atom (if the N atom allows for a $R^a$ group)

In some embodiments, ring A is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl.

In some embodiments, the compound of Formula (I) has the following structure of Formula (II):

Formula (II)

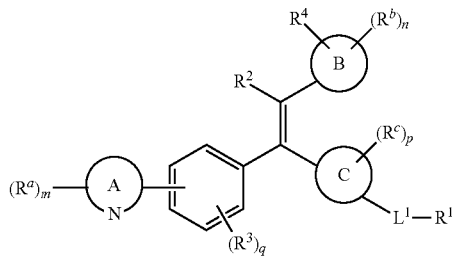

or is a pharmaceutically acceptable salt thereof.

In some embodiments, ring A is N-linked 3-7 membered monocyclic N-containing $C_2$-$C_6$heterocycloalkyl or N-linked N-containing 5-membered monocyclic heteroaryl.

In some embodiments, the compound of Formula (I) has the following structure of Formula (III):

Formula (III)

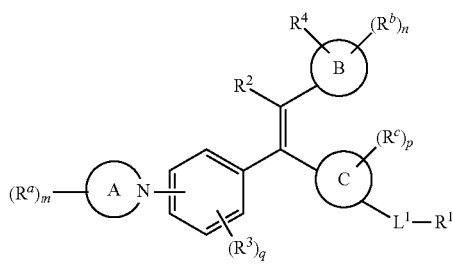

or is a pharmaceutically acceptable salt thereof.

In some embodiments, $L^1$ is —C($R^5$)═C($R^6$)—; $R^5$ is H, $C_1$-$C_4$alkyl, or halogen; $R^6$ is H, $C_1$-$C_4$alkyl, or halogen; $R^1$ is —C(═O)—Z, or a a carboxylic acid bioisostere.

In some embodiments, $L^1$ is —C($R^5$)═C($R^6$)—; $R^5$ is H, —$CH_3$, F, or Cl; $R^6$ is H, —$CH_3$, F, or Cl; $R^1$ is —C(═O)—Z,

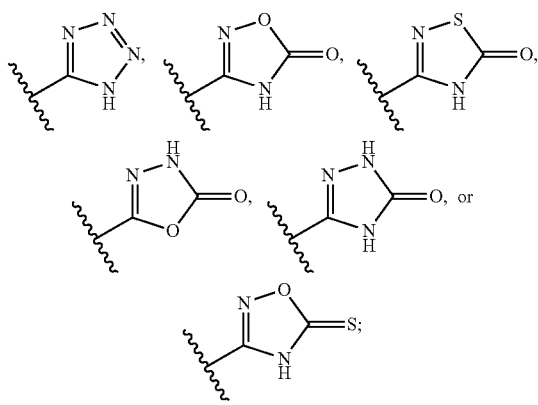

Z is —OH, —$OR^9$, or —$NR^7R^8$.

In some embodiments, $L^1$ is —X—$C_1$-$C_6$alkylene-; X is O; $R^1$ is a substituted or unsubstituted aziridinyl, azetidinyl, pyrrolidinyl, piperidininyl, azepanyl, morpholinyl, thiomorpholinyl, or piperazinyl.

In some embodiments, $L^1$ is —X—$C_1$-$C_6$alkylene-; X is O; $R^1$ is a substituted or unsubstituted pyrrolidinyl.

In some embodiments, the compound of Formula (I) has the following structure of Formula (IV):

Formula (IV)

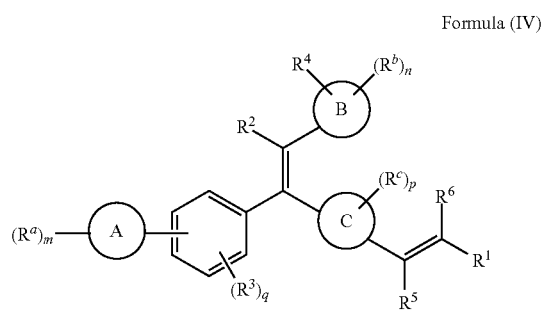

or is a pharmaceutically acceptable salt thereof.

In some embodiments,

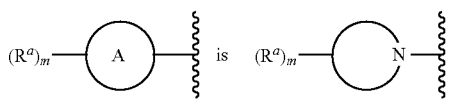

(i.e. N-linked).

In some embodiments, the compound of Formula (I) or Formula (IV) has the following structure of Formula (V):

Formula (V)

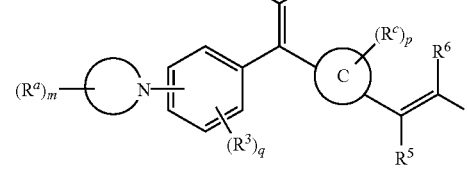

or is a pharmaceutically acceptable salt thereof.

In some embodiments,

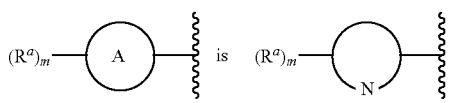

(i.e. C-linked).

In some embodiments, the compound of Formula (I) or Formula (IV) has the following structure of Formula (VI):

Formula (VI)

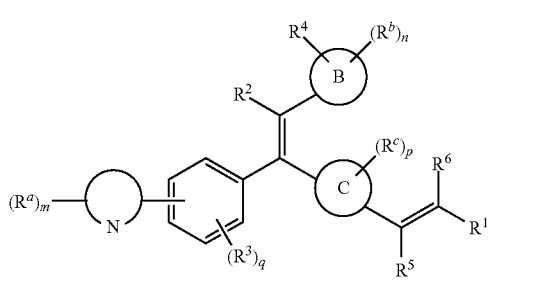

or is a pharmaceutically acceptable salt thereof.

In some embodiments, the compound has the following structure of Formula (VII):

Formula (VII)

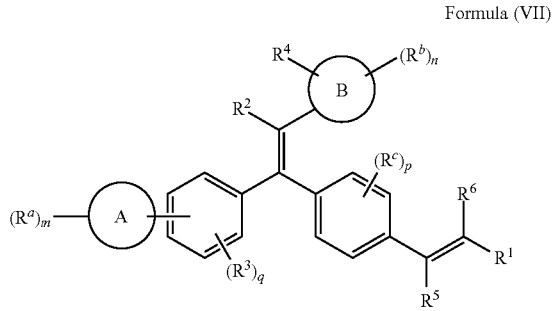

or is a pharmaceutically acceptable salt thereof.

In some embodiments, the compound of Formula (VII) has the following structure of Formula (VIII) or Formula (IX):

Formula (VIII)

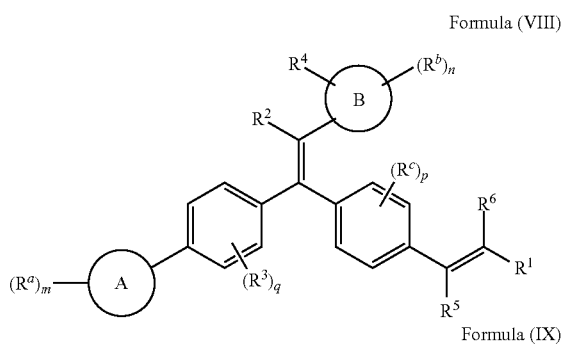

Formula (IX)

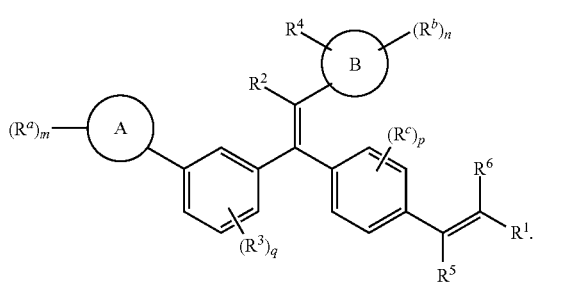

or is a pharmaceutically acceptable salt thereof.

In some embodiments, ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl.

In some embodiments, ring A is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl.

In some embodiments,

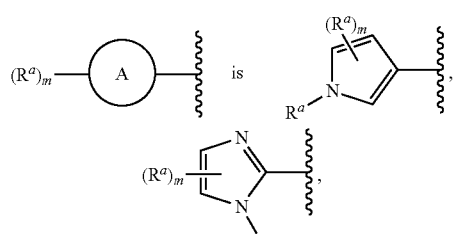

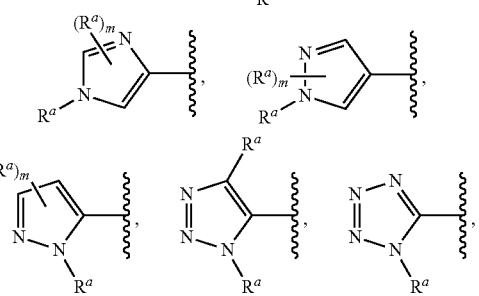

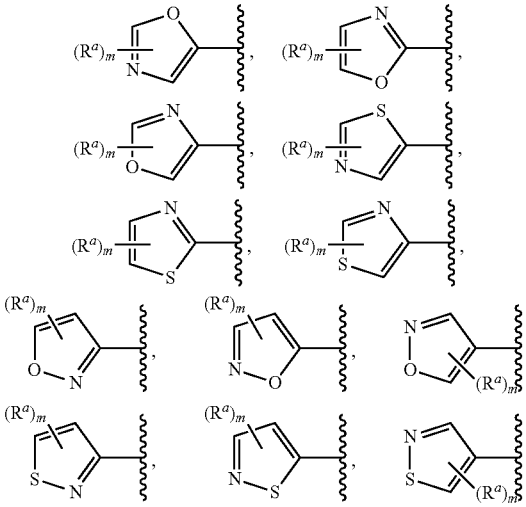

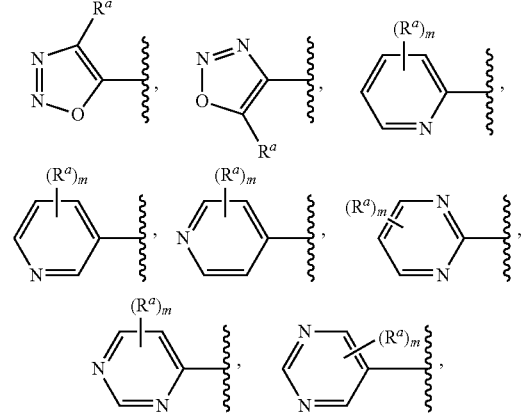

-continued
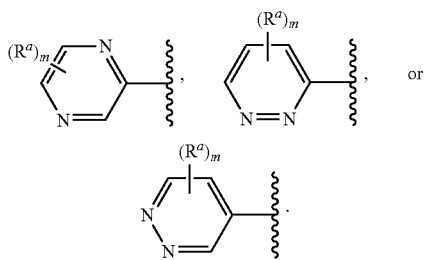
In some embodiments,
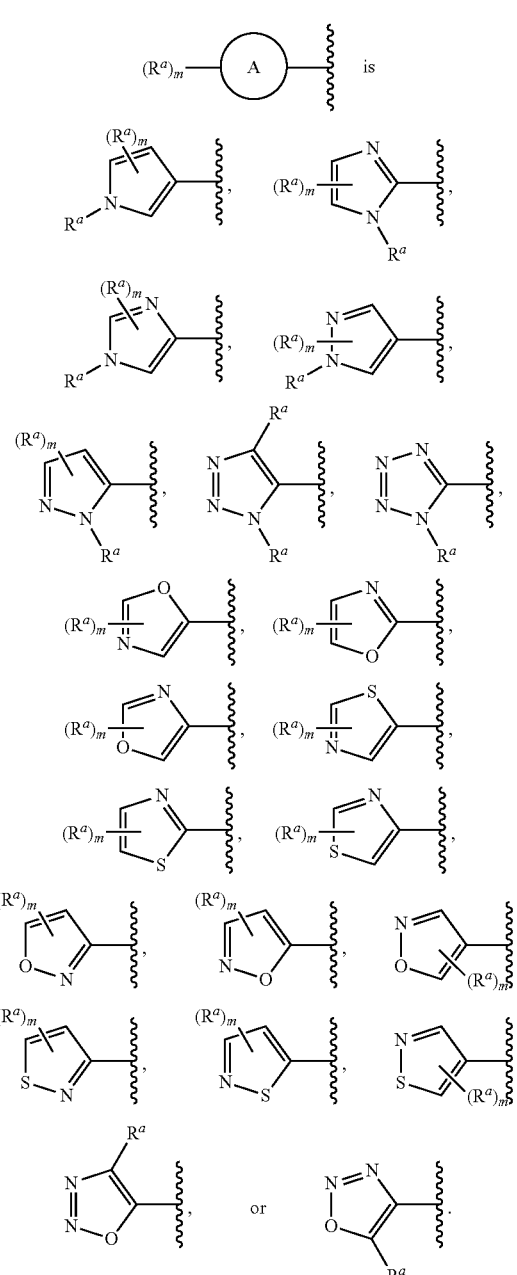
In some embodiments,
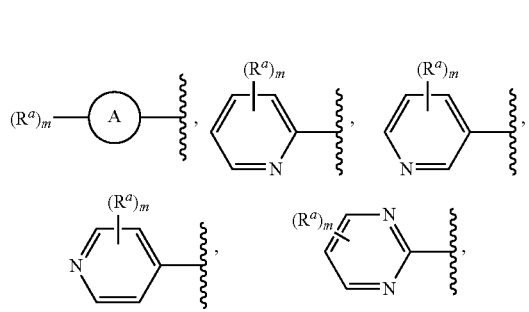
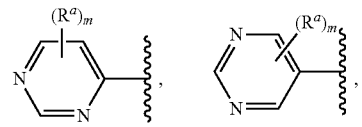
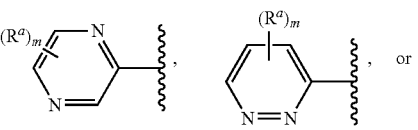
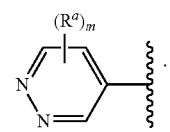
In some embodiments, ring A is N-linked 3-7 membered monocyclic N-containing $C_2$-$C_6$heterocycloalkyl, or N-linked N-containing 5-membered monocyclic heteroaryl.
In some embodiments,
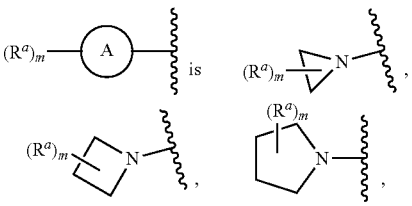
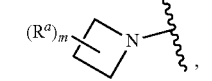
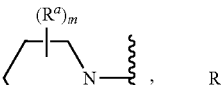
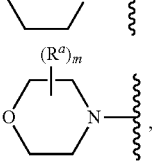
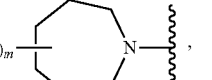
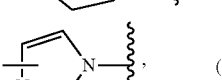
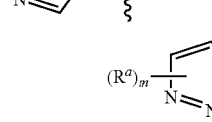
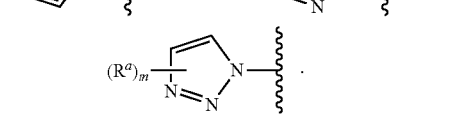

In some embodiments,
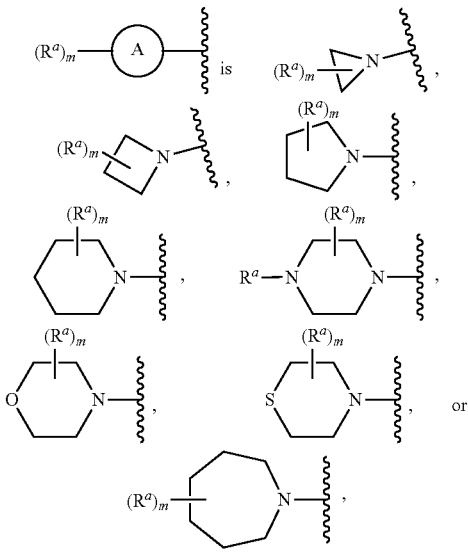
In some embodiments,
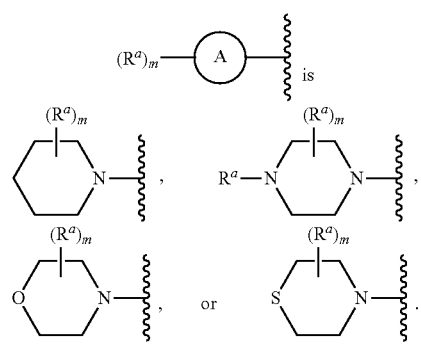
In some embodiments,
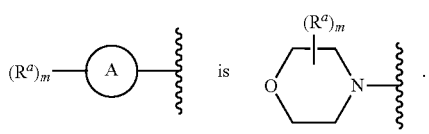
In some embodiments,
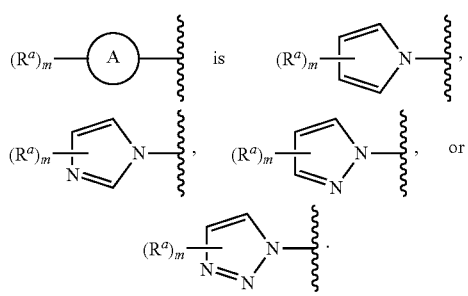
In some embodiments,
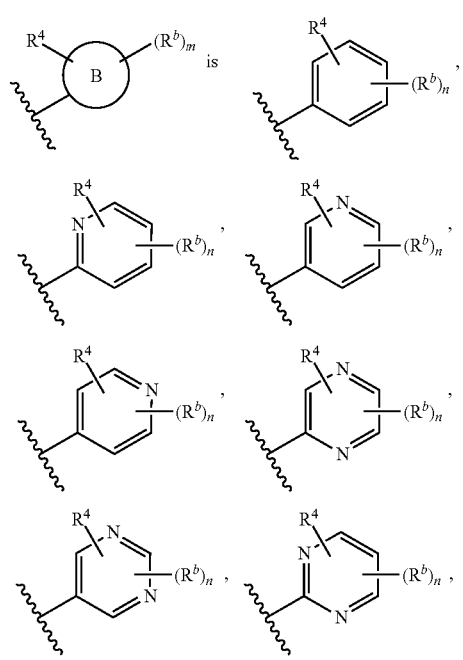
In some embodiments,
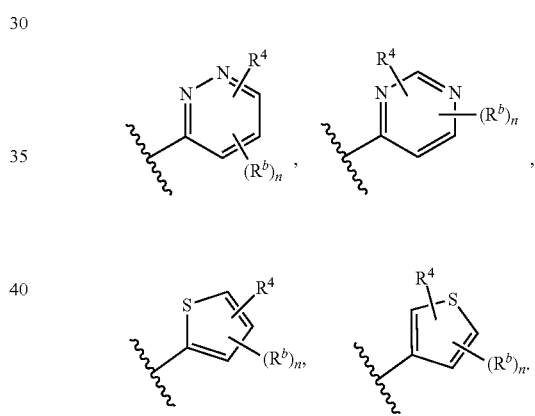
In some embodiments,
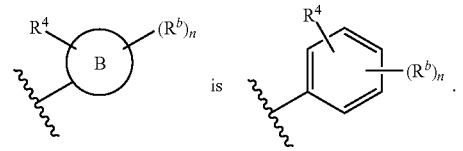
In some embodiments,
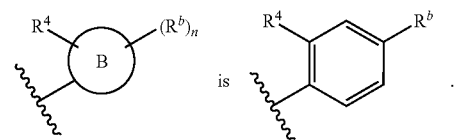

In some embodiments,

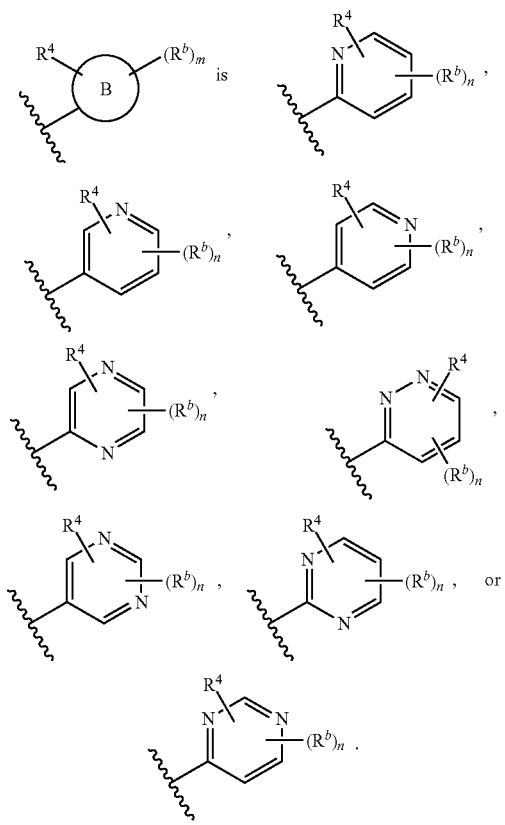

In some embodiments,

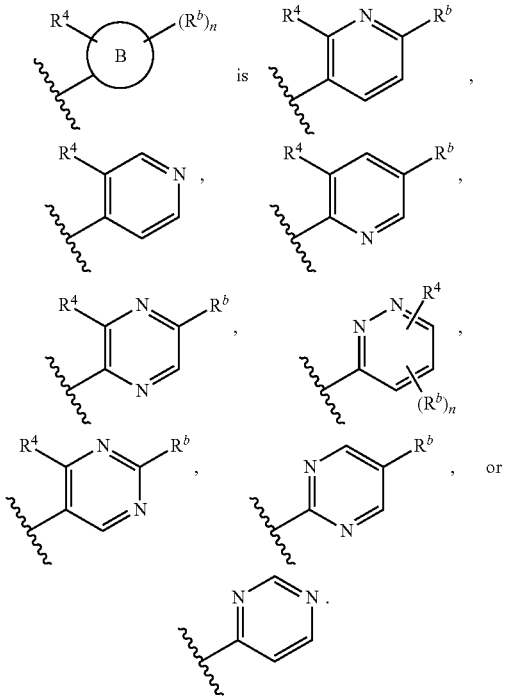

In some embodiments,

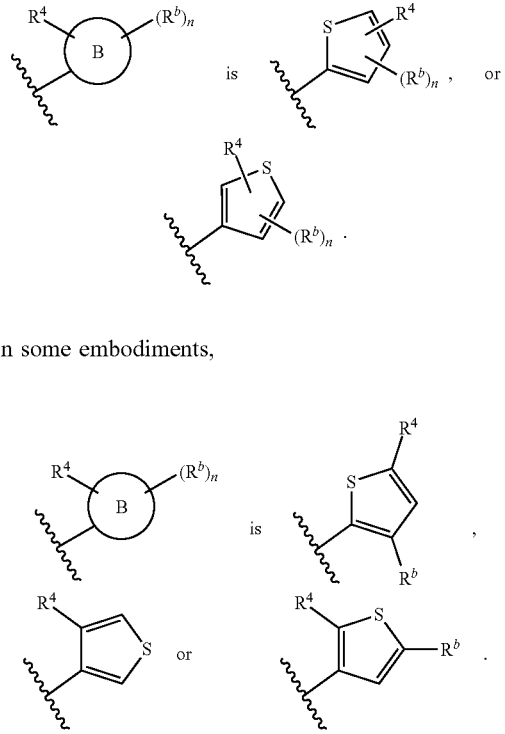

In some embodiments,

[image of B ring equals thiophene variants]

In some embodiments, $R^5$ is H; $R^6$ is H.

In some embodiments, $R^2$ is halogen, $C_1$-$C_6$alkyl, $C_1$-$C_6$fluoroalkyl, $C_1$-$C_6$deuteroalkyl, $C_3$-$C_6$cycloalkyl, —$C_1$-$C_4$alkylene-W, —$C_1$-$C_4$fluoroalkylene-W, —$C_3$-$C_6$cycloalkylene-W; W is hydroxy, halogen, —CN, —NO$_2$, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl.

In some embodiments, $R^2$ is $C_1$-$C_6$alkyl, $C_1$-$C_6$fluoroalkyl, $C_1$-$C_6$deuteroalkyl, $C_3$-$C_6$cycloalkyl, or —$C_1$-$C_4$alkylene-W; W is hydroxy, halogen, —CN, $C_1$-$C_6$alkyl, $C_1$-$C_6$haloalkyl, $C_1$-$C_6$alkoxy, $C_1$-$C_6$haloalkoxy, and $C_3$-$C_6$cycloalkyl.

In some embodiments, $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$F, —CHF$_2$, —CF$_3$, —CH$_2$CF$_3$, -CD$_3$, —CH$_2$CD$_3$, -CD$_2$CD$_3$, cyclopropyl, cyclobutyl, cyclopentyl, cyclohexyl, —CH$_2$—W, or —CH$_2$CH$_2$—W; W is hydroxy, F, Cl, —CN, —OCH$_3$, —OCH$_2$CH$_3$, —OCH$_2$CH$_2$CH$_3$, —OCH(CH$_3$)$_2$, cyclopropyl, cyclobutyl, cyclopentyl, or cyclohexyl.

In some embodiments, $R^2$ is $C_1$-$C_6$alkyl or $C_3$-$C_6$cycloalkyl.

In some embodiments, $R^2$ is $C_1$-$C_6$alkyl.

In some embodiments, $R^2$ is —CH$_3$, —CH$_2$CH$_3$, —CH$_2$CH$_2$CH$_3$, —CH(CH$_3$)$_2$, —CH$_2$CH$_2$CH$_2$CH$_3$, or —CH$_2$CH(CH$_3$)$_2$, In some embodiments, $R^2$ is —CH$_2$CH$_3$.

In some embodiments, $R^2$ is $C_3$-$C_6$cycloalkyl.

In some embodiments, $R^2$ is cyclopropyl, cyclobutyl, cyclopentyl, or cyclohexyl.

In some embodiments, $R^2$ is cyclobutyl.

In some embodiments, the compound of Formula (I) has the following structure of Formula (X):

Formula (X)

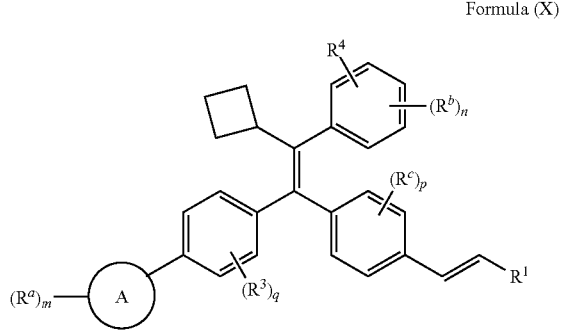

or is a pharmaceutically acceptable salt thereof.

In some embodiments, the compound of Formula (X) has the following structure of Formula (XI):

Formula (XI)

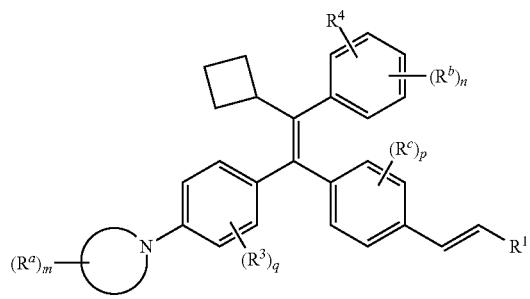

or is a pharmaceutically acceptable salt thereof.

In some embodiments,

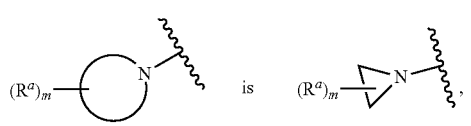

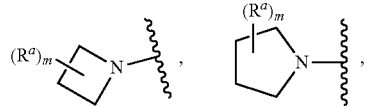

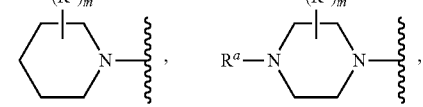

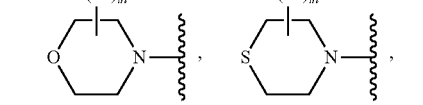

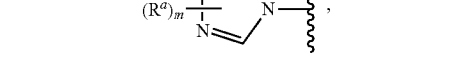

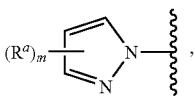 or 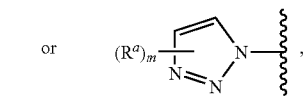

In some embodiments,

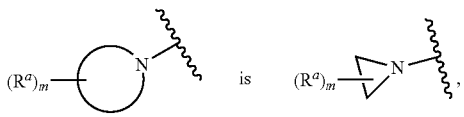

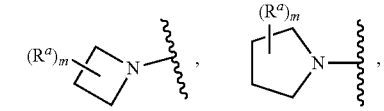

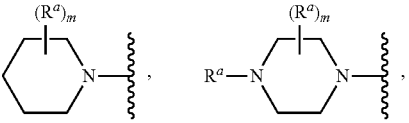

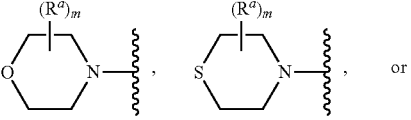, or

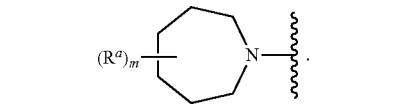

In some embodiments,

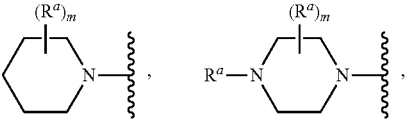

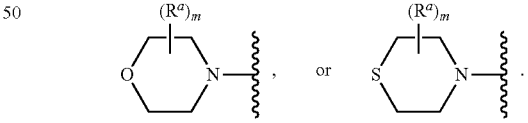

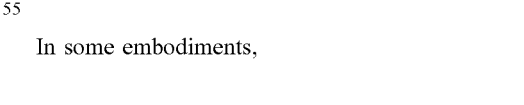, or

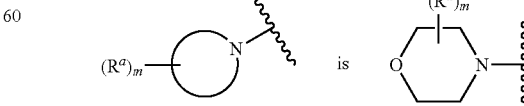

In some embodiments,

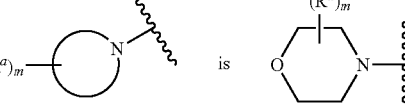 is 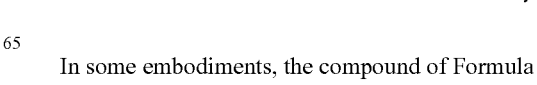

In some embodiments, the compound of Formula (X) has the following structure of Formula (XII):

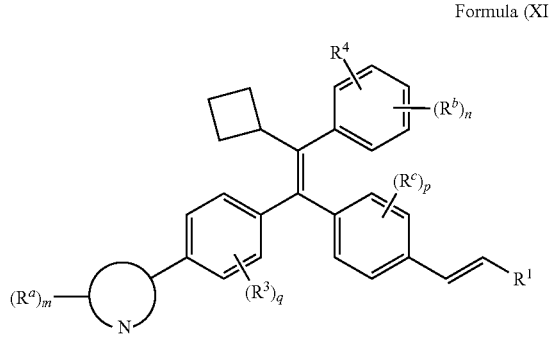
Formula (XII)
or is a pharmaceutically acceptable salt thereof.
In some embodiments,
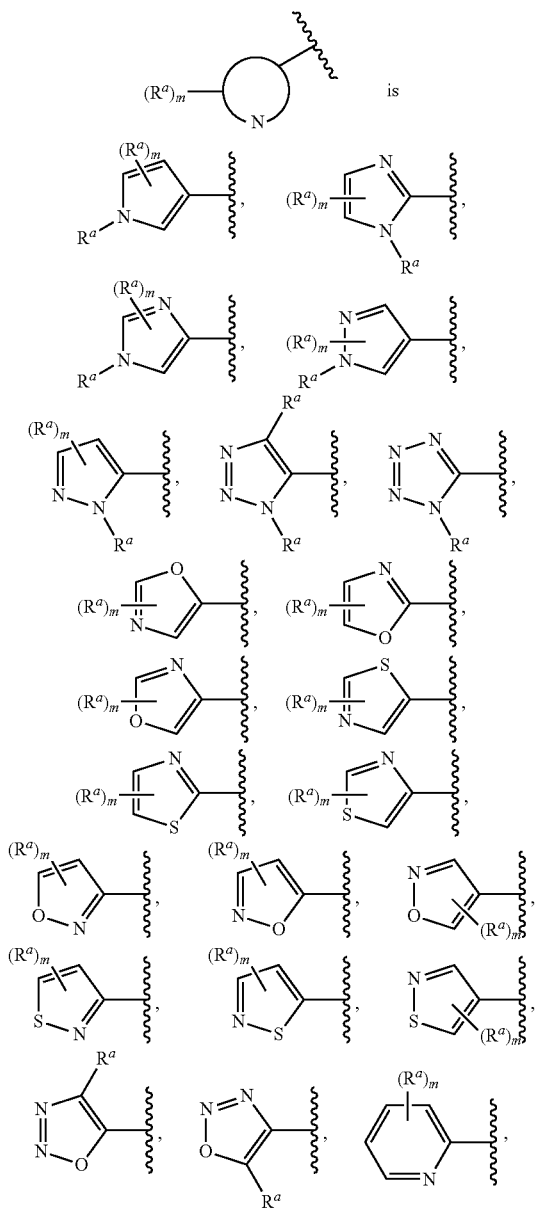
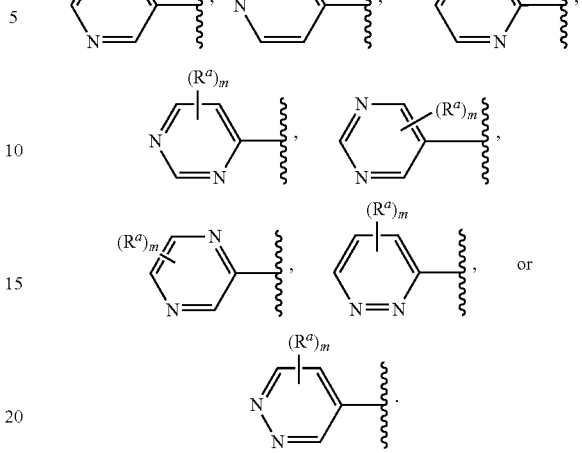
In some embodiments,
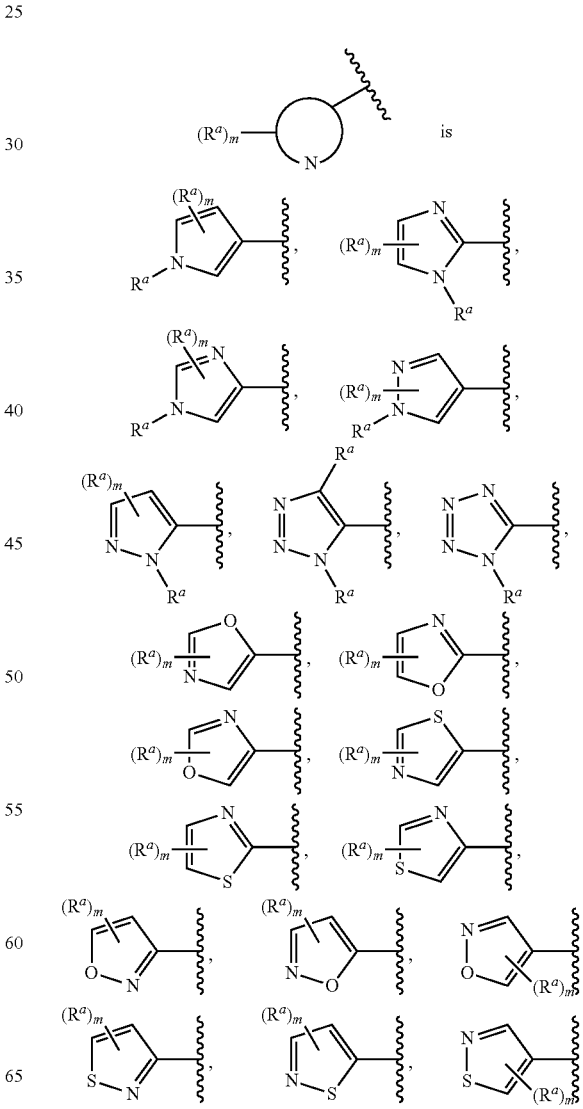

-continued

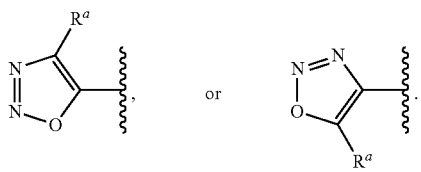

In some embodiments,

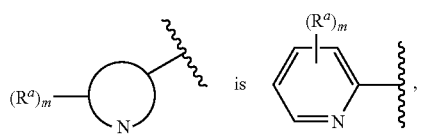 is 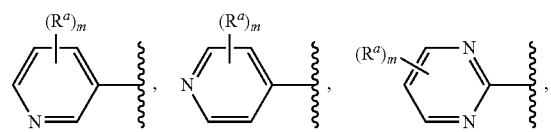,

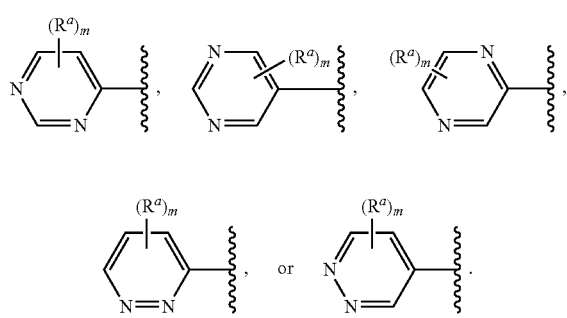

In some embodiments, $R^b$ is H, F, Cl, —CN, —OH, —OR$^9$, —SR$^8$, —S(=O)R$^9$, —S(=O)$_2$R$^9$, C$_1$-C$_6$alkyl, C$_1$-C$_6$fluoroalkyl, or C$_1$-C$_6$heteroalkyl; $R^4$ is H, F, Cl, —CN, —OH, —OR$^9$, —SR$^8$, —S(=O)R$^9$, —S(=O)$_2$R$^9$, C$_1$-C$_6$alkyl, C$_1$-C$_6$fluoroalkyl, or C$_1$-C$_6$heteroalkyl.

In some embodiments, $R^b$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH; $R^4$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH.

In some embodiments, each $R^a$ is independently selected from the group consisting of H, halogen, —CN, —OH, —OR$^9$, C$_1$-C$_6$alkyl, C$_1$-C$_6$fluoroalkyl, and C$_1$-C$_6$heteroalkyl; m is 0 or 1.

In some embodiments, m is 0.

In some embodiments, p is 0.

In some embodiments, each $R^7$ is independently H or C$_1$-C$_6$alkyl. In some embodiments, each $R^7$ is H.

In some embodiments, described herein is a compound of Formula (XIII) or a pharmaceutically acceptable salt, or solvate thereof:

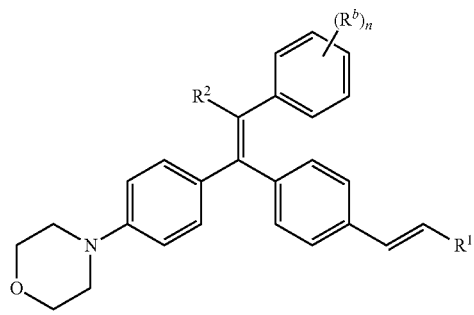

wherein, $R^1$ is —CO$_2$H or a 5-membered heterocycle selected from the group consisting of

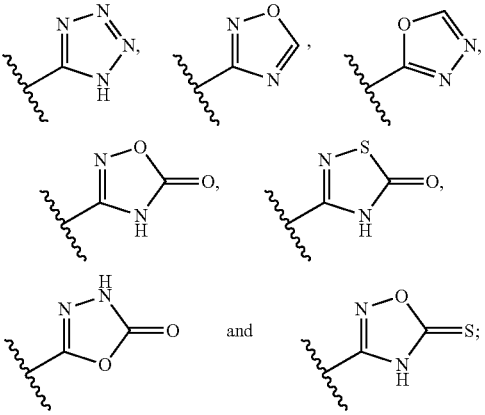

$R^2$ is C$_1$-C$_6$alkyl or C$_3$-C$_6$cycloalkyl;

each $R^b$ is independently selected from H, halogen, —CN, OH, —OR$^9$, —NR$^7$R$^8$, —SR$^8$, —S(=O)R$^9$, —S(=O)$_2$R$^9$, C$_1$-C$_6$alkyl, and C$_1$-C$_6$fluoroalkyl;

each $R^7$ is independently H or C$_1$-C$_6$alkyl;

each $R^8$ is independently selected from H, —C(=O)R$^9$, —C(=O)OR$^9$, —C(=O)NHR$^9$, C$_1$-C$_6$alkyl, C$_1$-C$_6$fluoroalkyl, C$_3$-C$_6$cycloalkyl, substituted or unsubstituted monocyclic C$_2$-C$_6$heterocycloalkyl, substituted or unsubstituted phenyl, and substituted or unsubstituted monocyclic heteroaryl;

each $R^9$ is independently selected from C$_1$-C$_6$alkyl, C$_1$-C$_6$fluoroalkyl, C$_3$-C$_6$cycloalkyl, substituted or unsubstituted monocyclic C$_2$-C$_6$heterocycloalkyl, substituted or unsubstituted phenyl, and substituted or unsubstituted monocyclic heteroaryl;

n is 0, 1, or 2.

In some embodiments, $R^1$ is —CO$_2$H.

In some embodiments, $R^2$ is —CH$_3$, —CH$_2$CH$_3$, cyclopropyl, or cyclobutyl. In some embodiments, $R^2$ is —CH$_2$CH$_3$. In some embodiments, $R^2$ is cyclobutyl.

In some embodiments, n is 1 or 2. In some embodiments, n is 1. In some embodiments, n is 2. In some embodiments, n is 0.

In some embodiments,

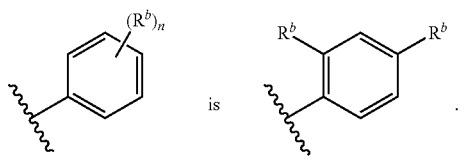

is

In some embodiments, each $R^b$ is independently selected from H, F, Cl, —CN, —OH, —OCH$_3$, —OCH$_2$CH$_3$, —S(=O)$_2$CH$_3$, —CH$_3$, —CH$_2$H$_3$, and —CF$_3$. In some embodiments, each $R^b$ is independently selected from H, F, Cl, —CN, —OH, —OCH$_3$, —OCH$_2$CH$_3$, —CH$_3$, —CH$_2$H$_3$, and —CF$_3$.

In some embodiments, the compound of Formula (XIII) has the structure of Formula (XIV), or a pharmaceutically acceptable salt, or solvate thereof:

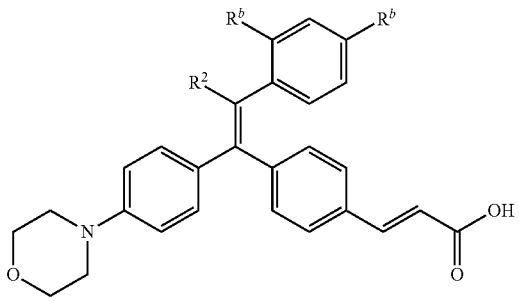

Formula (XIV)

Any combination of the groups described above for the various variables is contemplated herein. Throughout the specification, groups and substituents thereof are chosen by one skilled in the field to provide stable moieties and compounds.

In some embodiments, described herein is a compound in Table 1, or a pharmaceutically acceptable salt thereof:

TABLE 1

| Example no. | Name | Structure |
|---|---|---|
| 1 | (E)-3-(4-((E)-1-(4-(1H-Pyrazol-4-yl)phenyl)-2-cyclobutyl-2-phenylvinyl)phenyl)acrylic acid | 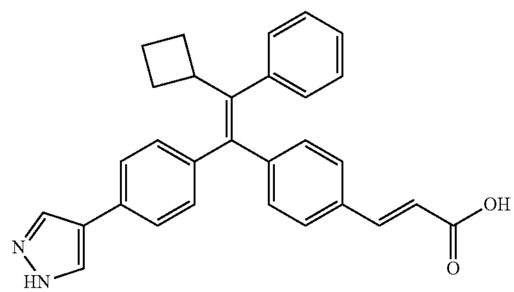 |
| 2 | (E)-3-(4-((E)-2-(2-Chloro-4-fluorophenyl)-1-(4-(thiazol-5-yl)phenyl)but-1-en-1-yl)phenyl)acrylic acid | 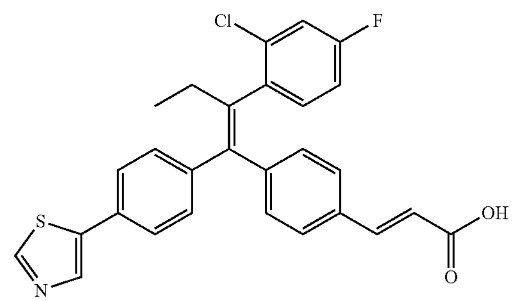 [SMILES: CC/C(=C(/c1ccc(/C=C/C(=O)O)cc1)c1ccc(-c2cncs2)cc1)c1ccc(F)cc1Cl] |
| 3 | (E)-3-(4-((E)-1-(4-(1H-Pyrazol-4-yl)phenyl)-2-(2-chloro-4-cyanophenyl)-2-cyclobutylvinyl)phenyl) acrylic acid | 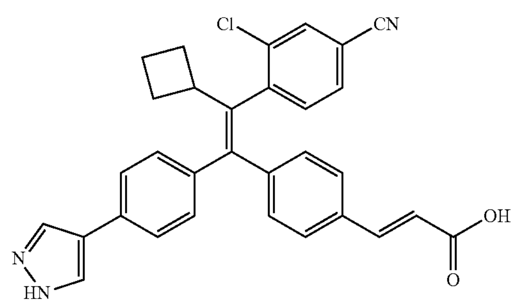 |

TABLE 1-continued

| Example no. | Name | Structure |
|---|---|---|
| 4 | (E)-3-(4-((E)-2-(2-Chloro-4-methoxyphenyl)-2-cyclobutyl-1-(4-morpholinophenyl)vinyl)phenyl)acrylic acid | 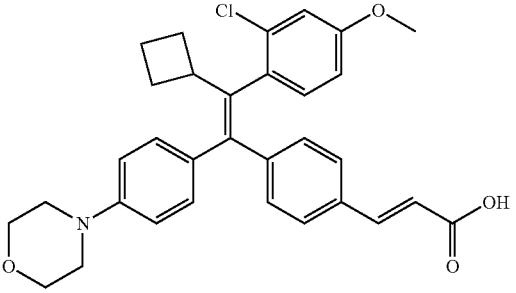 |
| 5 | (E)-3-(4-((E)-2-(2-Chloro-4-cyanophenyl)-2-cyclobutyl-1-(4-(thiazol-5-yl)phenyl)vinyl)phenyl)acrylic acid | 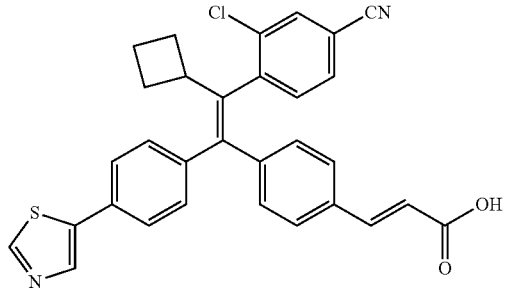 [SMILES: N#Cc1ccc(/C(=C(\c2ccc(/C=C/C(=O)O)cc2)c2ccc(-c3cncs3)cc2)C2CCC2)c(Cl)c1] |
| 6 | (E)-3-(4-((E)-1-(4-(1H-Pyrazol-5-yl)phenyl)-2-phenylbut-1-en-1-yl)phenyl)acrylic acid | 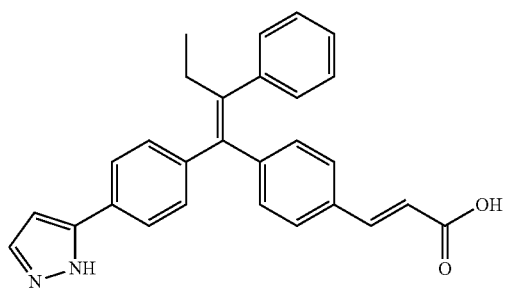 [SMILES: CC/C(=C(/c1ccc(/C=C/C(=O)O)cc1)c1ccc(-c2ccn[nH]2)cc1)c1ccccc1] |
| 7 | (E)-3-(4-((E)-1-(3-(1H-Pyrazol-5-yl)phenyl)-2-phenylbut-1-en-1-yl)phenyl)acrylic acid | 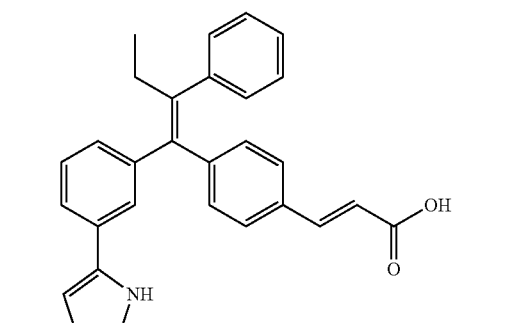 |
| 8 | (E)-3-(4-((E)-2-Phenyl-1-(4-(thiazol-2-yl)phenyl)but-1-en-1-yl)phenyl)acrylic acid | 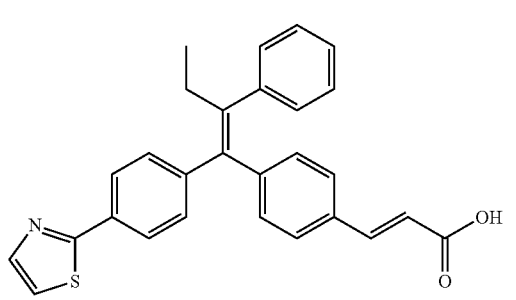 [SMILES: CC/C(=C(/c1ccc(/C=C/C(=O)O)cc1)c1ccc(-c2nccs2)cc1)c1ccccc1] |

TABLE 1-continued

| Example no. | Name | Structure |
|---|---|---|
| 9 | (E)-3-(4-((E)-2-Phenyl-1-(4-(thiazol-5-yl)phenyl)but-1-en-1-yl)phenyl)acrylic acid | 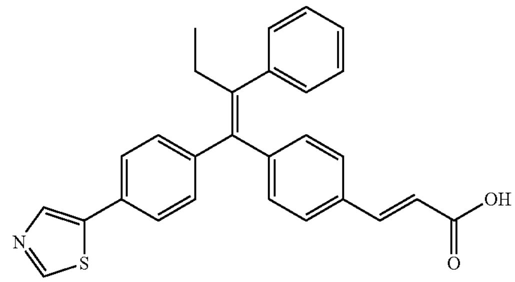 [SMILES: CC/C(=C(/c1ccc(/C=C/C(=O)O)cc1)c1ccc(-c2cncs2)cc1)c1ccccc1] |
| 10 | (E)-3-(4-((E)-2-Phenyl-1-(4-(thiazol-4-yl)phenyl)but-1-en-1-yl)phenyl)acrylic acid | 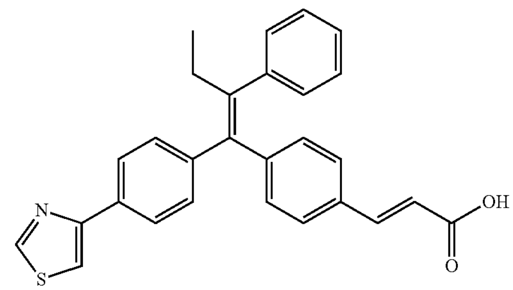 [SMILES: CC/C(=C(/c1ccc(/C=C/C(=O)O)cc1)c1ccc(-c2cscn2)cc1)c1ccccc1] |
| 11 | (E)-3-(4-((E)-2-Phenyl-1-(3-(thiazol-2-yl)phenyl)but-1-en-1-yl)phenyl)acrylic acid | 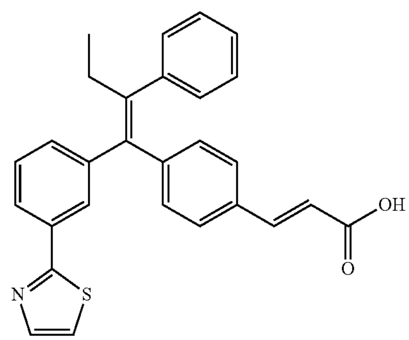 [SMILES: CC/C(=C(/c1ccc(/C=C/C(=O)O)cc1)c1cccc(-c2nccs2)c1)c1ccccc1] |
| 12 | (E)-3-(4-((E)-2-Phenyl-1-(3-(thiazol-4-yl)phenyl)but-1-en-1-yl)phenyl)acrylic acid | 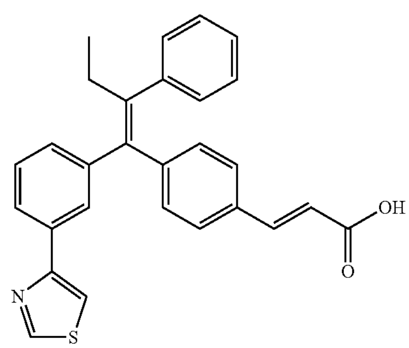 [SMILES: CC/C(=C(/c1ccc(/C=C/C(=O)O)cc1)c1cccc(-c2cscn2)c1)c1ccccc1] |
| 13 | (E)-3-(4-((E)-2-Cyclobutyl-2-phenyl-1-(4-(thiazol-5-yl)phenyl)vinyl)phenyl)acrylic acid | 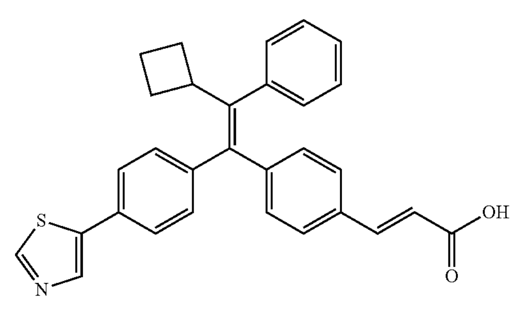 [SMILES: O=C(O)/C=C/c1ccc(/C(=C(\c2ccccc2)C2CCC2)c2ccc(-c3cncs3)cc2)cc1] |

TABLE 1-continued

| Example no. | Name | Structure |
|---|---|---|
| 14 | (E)-3-(4-((E)-2-Phenyl-1-(4-(pyridin-3-yl)phenyl)but-1-en-1-yl)phenyl)acrylic acid | 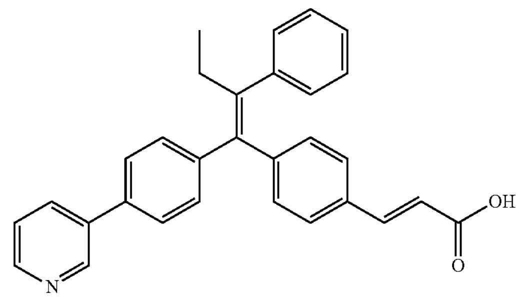 [SMILES: CC/C(=C(/c1ccc(/C=C/C(=O)O)cc1)c1ccc(-c2cccnc2)cc1)c1ccccc1] |
| 15 | (E)-3-(4-((E)-1-(4-(Isothiazol-4-yl)phenyl)-2-phenylbut-1-en-1-yl)phenyl)acrylic acid | 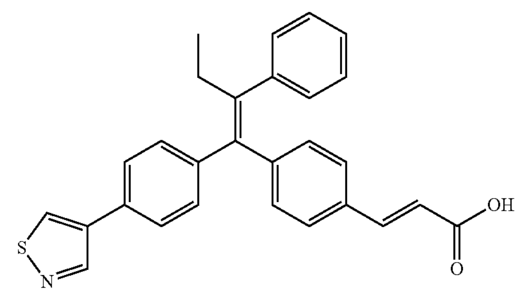 [SMILES: CC/C(=C(/c1ccc(/C=C/C(=O)O)cc1)c1ccc(-c2cnsc2)cc1)c1ccccc1] |
| 16 | (E)-3-(4-((E)-1-(4-Morpholinophenyl)-2-phenylbut-1-en-1-yl)phenyl)acrylic acid | 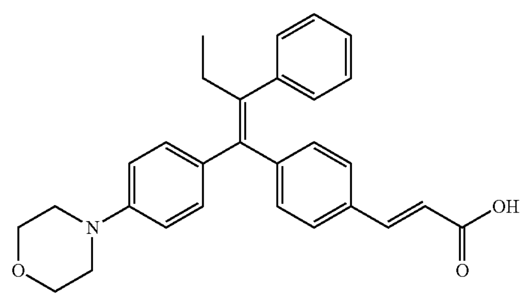 [SMILES: CC/C(=C(/c1ccc(/C=C/C(=O)O)cc1)c1ccc(N2CCOCC2)cc1)c1ccccc1] |
| 17 | (E)-3-(4-((E)-1-(4-(1H-Imidazol-1-yl)phenyl)-2-phenylbut-1-en-1-yl)phenyl)acrylic acid | 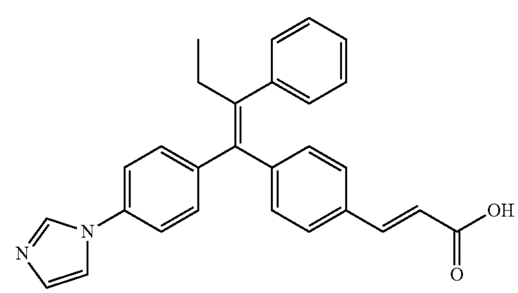 [SMILES: CC/C(=C(/c1ccc(/C=C/C(=O)O)cc1)c1ccc(-n2ccnc2)cc1)c1ccccc1] |
| 18 | (E)-3-(4-((E)-1-(4-(Oxazol-5-yl)phenyl)-2-phenylbut-1-en-1-yl)phenyl)acrylic acid | 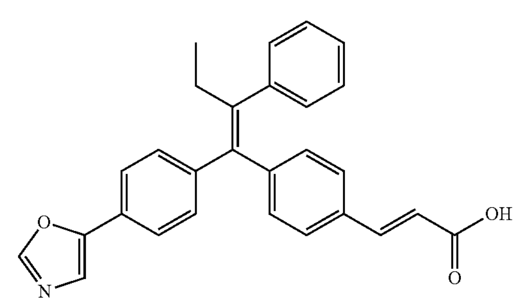 [SMILES: CC/C(=C(/c1ccc(/C=C/C(=O)O)cc1)c1ccc(-c2cnco2)cc1)c1ccccc1] |

TABLE 1-continued

| Example no. | Name | Structure |
|---|---|---|
| 19 | (E)-3-(4-((E)-1-(4-(1-Methyl-1H-pyrazol-4-yl)phenyl)-2-phenylbut-1-en-1-yl)phenyl)acrylic acid | 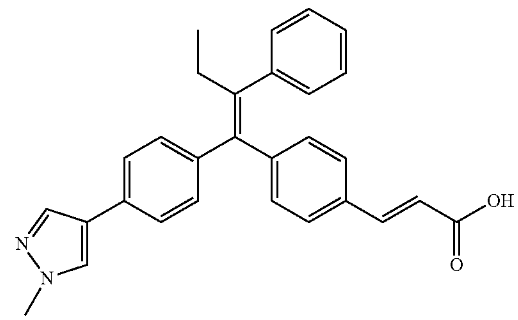 [SMILES: CC/C(=C(/c1ccc(/C=C/C(=O)O)cc1)c1ccc(-c2cnn(C)c2)cc1)c1ccccc1] |
| 20 | (E)-3-(4-((E)-1-(2-Fluoro-4-(thiazol-5-yl)phenyl)-2-phenylbut-1-en-1-yl)phenyl)acrylic acid | 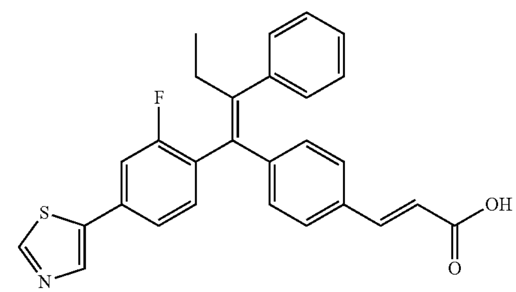 |
| 21 | (E)-3-(4-((E)-1-(3-Fluoro-4-(thiazol-5-yl)phenyl)-2-phenylbut-1-en-1-yl)phenyl)acrylic acid | 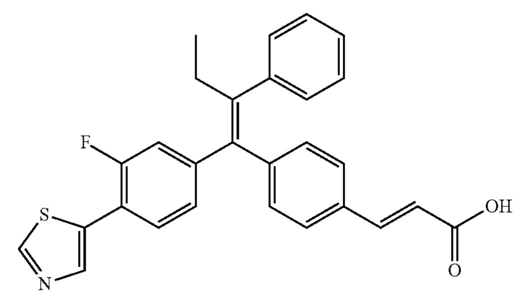 [SMILES: CC/C(=C(/c1ccc(/C=C/C(=O)O)cc1)c1ccc(-c2cncs2)c(F)c1)c1ccccc1] |
| 22 | (E)-3-(4-((E)-1-(4-(1H-Pyrazol-4-yl)phenyl)-2-phenylbut-1-en-1-yl)phenyl)acrylic acid | 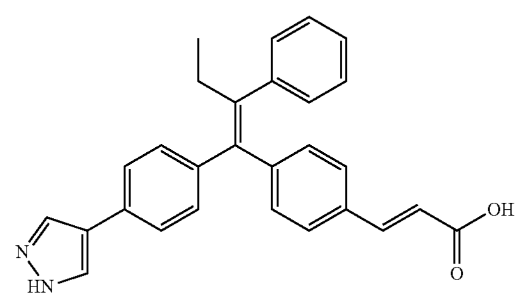 [SMILES: CC/C(=C(/c1ccc(/C=C/C(=O)O)cc1)c1ccc(-c2cn[nH]c2)cc1)c1ccccc1] |
| 23 | (E)-3-(4-((E)-1-(4-(4-Methylpiperazin-1-yl)phenyl)-2-phenylbut-1-en-1-yl)phenyl)acrylic acid | 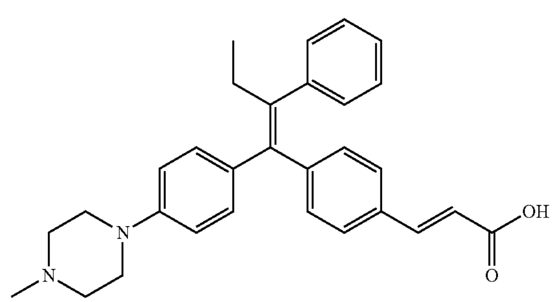 [SMILES: CC/C(=C(/c1ccc(/C=C/C(=O)O)cc1)c1ccc(N2CCN(C)CC2)cc1)c1ccccc1] |

TABLE 1-continued

| Example no. | Name | Structure |
|---|---|---|
| 24 | (E)-3-(4-((E)-2-Phenyl-1-(4-(piperidin-1-yl)phenyl)but-1-en-1-yl)phenyl)acrylic acid | 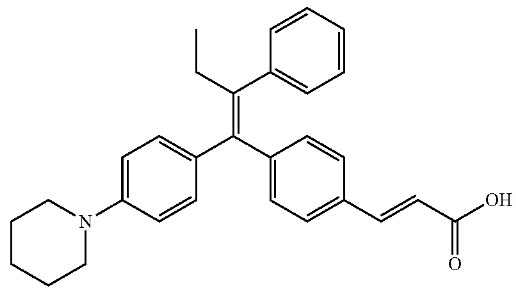 [SMILES: CC/C(=C(/c1ccc(/C=C/C(=O)O)cc1)c1ccc(N2CCCCC2)cc1)c1ccccc1] |
| 25 | (E)-3-(4-((E)-2-Cyclobutyl-2-phenyl-1-(5-(thiazol-5-yl)pyridin-2-yl)vinyl)phenyl)acrylic acid | 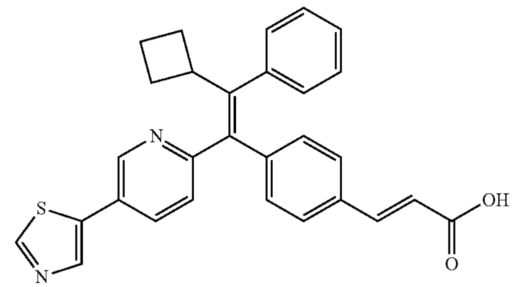 |
| 26 | (E)-3-(4-((E)-1-(3-(1H-Pyrazol-4-yl)phenyl)-2-cyclobutyl-2-phenylvinyl)phenyl)acrylic acid | 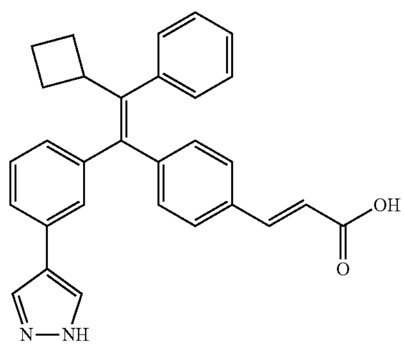 [SMILES: O=C(O)/C=C/c1ccc(/C(=C(\c2ccccc2)C2CCC2)c2cccc(-c3cn[nH]c3)c2)cc1] |
| 27 | (E)-3-(4-((E)-2-Cyclobutyl-1-(4-(isoxazol-3-yl)phenyl)-2-phenylvinyl)phenyl)acrylic acid | 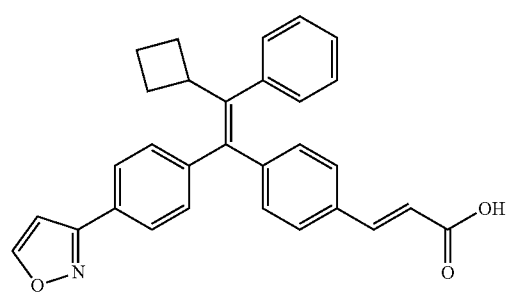 [SMILES: O=C(O)/C=C/c1ccc(/C(=C(\c2ccccc2)C2CCC2)c2ccc(-c3ccon3)cc2)cc1] |
| 28 | (E)-3-(4-((E)-2-(3-Chloropyridin-4-yl)-1-(4-(thiazol-5-yl)phenyl)but-1-en-1-yl)phenyl)acrylic acid | 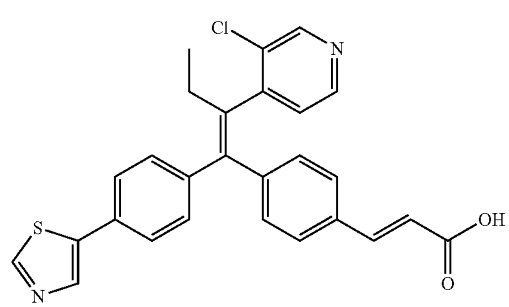 [SMILES: CC/C(=C(/c1ccc(/C=C/C(=O)O)cc1)c1ccc(-c2cncs2)cc1)c1ccncc1Cl] |

TABLE 1-continued

| Example no. | Name | Structure |
|---|---|---|
| 29 | (E)-3-(4-((E)-2-(2-Chlorophenyl)-1-(4-(thiazol-5-yl)phenyl)but-1-en-1-yl)phenyl)acrylic acid | 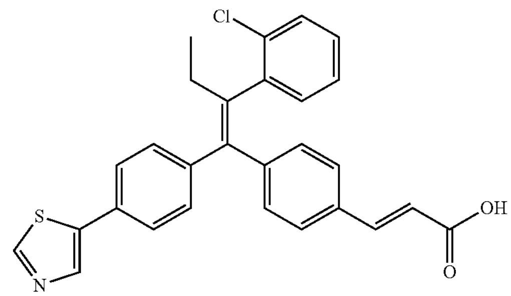 |
| 30 | (E)-3-(4-((E)-2-(3-Methoxyphenyl)-1-(4-(thiazol-5-yl)phenyl)but-1-en-1-yl)phenyl)acrylic acid | 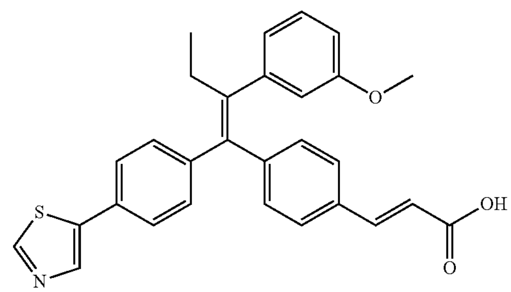 [SMILES: CC/C(=C(/c1ccc(/C=C/C(=O)O)cc1)c1ccc(-c2cncs2)cc1)c1cccc(OC)c1] |
| 31 | (E)-3-(4-((E)-2-(Benzofuran-5-yl)-1-(4-(thiazol-5-yl)phenyl)but-1-en-1-yl)phenyl)acrylic acid | 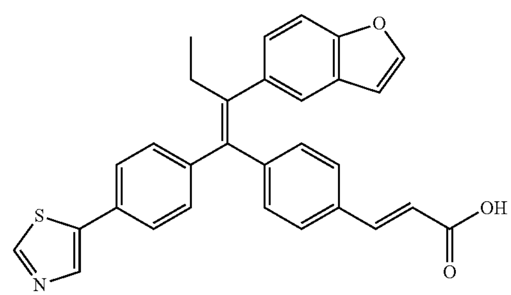 [SMILES: CC/C(=C(/c1ccc(/C=C/C(=O)O)cc1)c1ccc(-c2cncs2)cc1)c1ccc2occc2c1] |
| 32 | (E)-3-(4-((E)-2-(4-Methylthiophen-3-yl)-1-(4-(thiazol-5-yl)phenyl)but-1-en-1-yl)phenyl)acrylic acid | 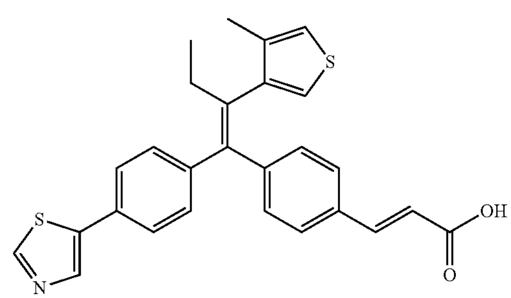 [SMILES: CC/C(=C(/c1ccc(/C=C/C(=O)O)cc1)c1ccc(-c2cncs2)cc1)c1cscc1C] |
| 33 | (E)-3-(4-((E)-2-(2-Chloro-4-fluorophenyl)-2-cyclobutyl-1-(4-(thiazol-5-yl)phenyl)vinyl)phenyl)acrylic acid | 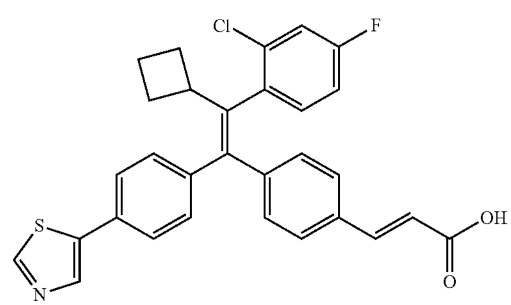 |

TABLE 1-continued

| Example no. | Name | Structure |
|---|---|---|
| 34 | (E)-3-(4-((E)-2-(3-Chloropyridin-4-yl)-2-cyclobutyl-1-(4-(thiazol-5-yl)phenyl)vinyl)phenyl)acrylic acid | 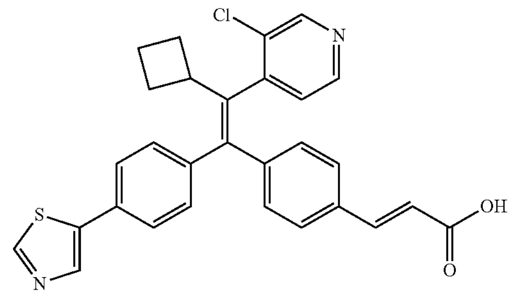 [SMILES: O=C(O)/C=C/c1ccc(/C(=C(\c2ccncc2Cl)C2CCC2)c2ccc(-c3cncs3)cc2)cc1] |
| 35 | (E)-3-(4-((E)-2-Cyclobutyl-2-(4-methylthiophen-3-yl)-1-(4-(thiazol-5-yl)phenyl)vinyl)phenyl)acrylic acid | 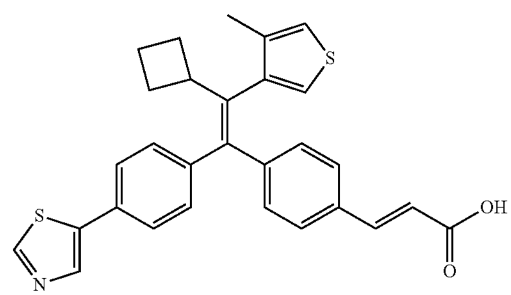 [SMILES: Cc1cscc1/C(=C(\c1ccc(/C=C/C(=O)O)cc1)c1ccc(-c2cncs2)cc1)C1CCC1] |
| 36 | (E)-3-(4-((E)-2-(2-Chloro-4-fluorophenyl)-2-cyclobutyl-1-(4-morpholinophenyl)vinyl)phenyl)acrylic acid | 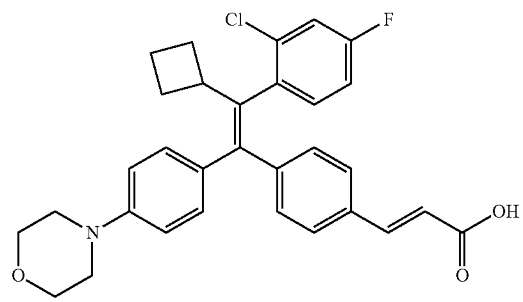 [SMILES: O=C(O)/C=C/c1ccc(/C(=C(\c2ccc(F)cc2Cl)C2CCC2)c2ccc(N3CCOCC3)cc2)cc1] |
| 37 | (E)-3-(4-((E)-1-(4-(1H-Pyrazol-4-yl)phenyl)-2-(2-chloro-4-fluorophenyl)-2-cyclobutylvinyl)phenyl)acrylic acid | 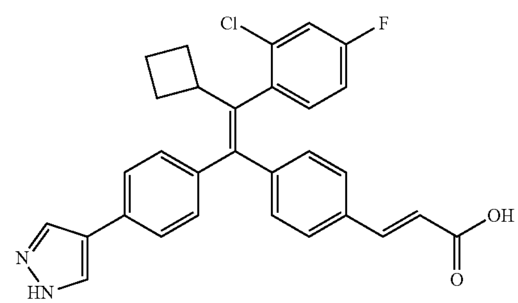 |
| 38 | (E)-3-(4-((E)-1-(4-(1H-Pyrazol-4-yl)phenyl)-2-cyclobutyl-2-(4-methylthiophen-3-yl)vinyl)phenyl)acrylic acid | 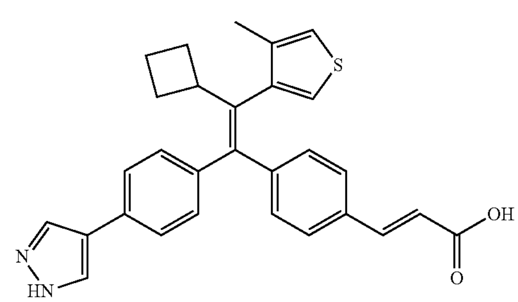 [SMILES: Cc1cscc1/C(=C(\c1ccc(/C=C/C(=O)O)cc1)c1ccc(-c2cn[nH]c2)cc1)C1CCC1] |

TABLE 1-continued

| Example no. | Name | Structure |
|---|---|---|
| 39 | (E)-3-(4-((E)-2-Cyclobutyl-2-(6-methoxy-4-methylpyridin-3-yl)-1-(4-morpholinophenyl)vinyl)phenyl)acrylic acid | 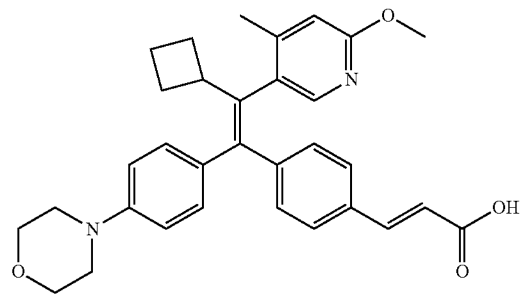 [SMILES: COc1cc(C)c(/C(=C(\c2ccc(/C=C/C(=O)O)cc2)c2ccc(N3CCOCC3)cc2)C2CCC2)cn1] |
| 40 | (E)-3-(4-((E)-1-(4-(1H-Pyrazol-4-yl)phenyl)-2-cyclobutyl-2-(3-methylpyridin-2-yl)vinyl)phenyl)acrylic acid | 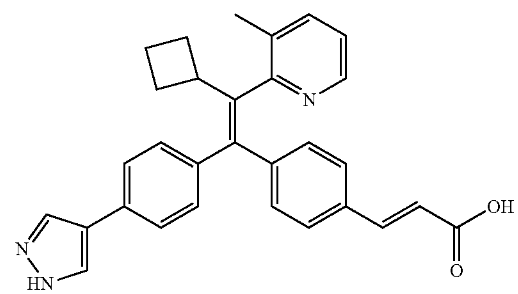 [SMILES: Cc1cccnc1/C(=C(\c1ccc(/C=C/C(=O)O)cc1)c1ccc(-c2cn[nH]c2)cc1)C1CCC1] |
| 41 | (E)-3-(4-((E)-1-(4-(1H-Pyrazol-4-yl)phenyl)-2-cyclobutyl-2-(3-fluoropyridin-2-yl)vinyl)phenyl)acrylic acid | 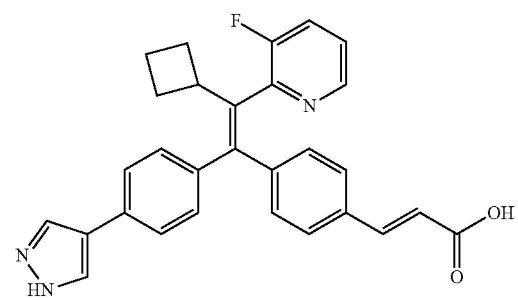 [SMILES: O=C(O)/C=C/c1ccc(/C(=C(\c2ncccc2F)C2CCC2)c2ccc(-c3cn[nH]c3)cc2)cc1] |
| 42 | (E)-3-(4-((E)-1-(4-(1H-Pyrazol-4-yl)phenyl)-2-(3-chloropyridin-2-yl)-2-cyclobutylvinyl)phenyl)acrylic acid | 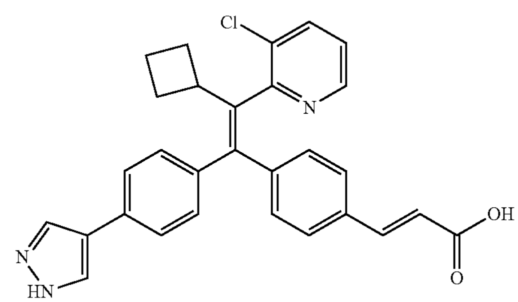 |
| 43 | (E)-3-(4-((E)-2-(3-Chloropyridin-2-yl)-2-cyclobutyl-1-(4-morpholinophenyl)vinyl)phenyl)acrylic acid | 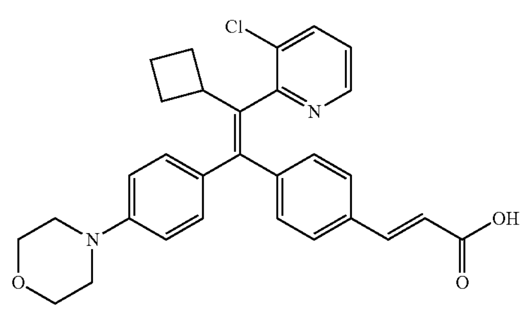 [SMILES: O=C(O)/C=C/c1ccc(/C(=C(\c2ncccc2Cl)C2CCC2)c2ccc(N3CCOCC3)cc2)cc1] |

TABLE 1-continued

| Example no. | Name | Structure |
|---|---|---|
| 44 | (E)-3-(4-((E)-1-(4-(1H-Pyrazol-4-yl)phenyl)-2-(4-chloro-2-cyanophenyl)-2-cyclobutylvinyl)phenyl)acrylic acid | 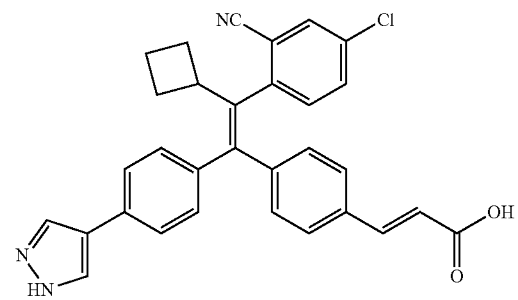 |
| 45 | (E)-3-(4-((E)-2-(2-Chloro-4-cyanophenyl)-2-cyclobutyl-1-(4-morpholinophenyl)vinyl)phenyl)acrylic acid | 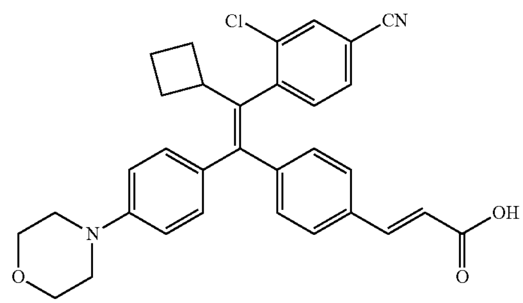 |
| 46 | (E)-3-(4-((E)-2-(4-Chloro-2-cyanophenyl)-2-cyclobutyl-1-(4-morpholinophenyl)vinyl)phenyl)acrylic acid | 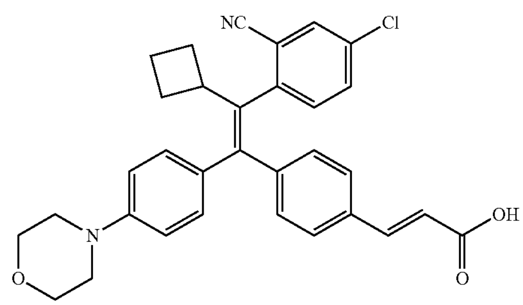 |
| 47 | (E)-3-(4-((E)-2-Cyclobutyl-2-(4-methoxy-2-methylphenyl)-1-(4-morpholinophenyl)vinyl)phenyl)acrylic acid | 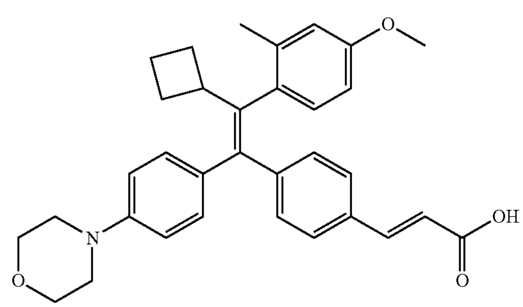 [SMILES: COc1ccc(/C(=C(\c2ccc(/C=C/C(=O)O)cc2)c2ccc(N3CCOCC3)cc2)C2CCC2)c(C)c1] |
| 48 | (E)-3-(4-((E)-2-(2-Chloro-4-(trifluoromethyl)phenyl)-2-cyclobutyl-1-(4-morpholinophenyl)vinyl)phenyl)acrylic acid | 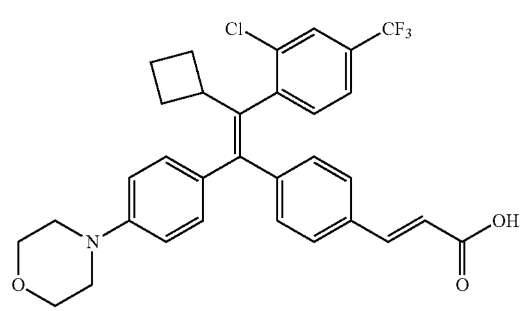 |

TABLE 1-continued

| Example no. | Name | Structure |
|---|---|---|
| 49 | (E)-3-(4-((E)-1-(4-(2H-Tetrazol-5-yl)phenyl)-2-(2-chloro-4-fluorophenyl)-2-cyclobutylvinyl)phenyl)acrylic acid | 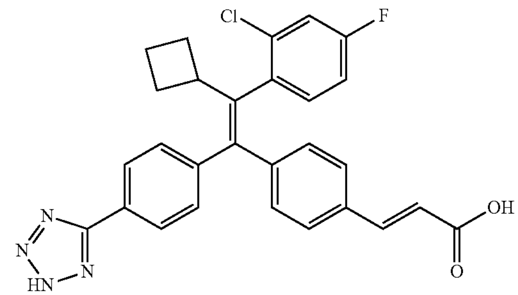 |
| 50 | (E)-3-(4-((E)-1-(4-(2H-Tetrazol-5-yl)phenyl)-2-(2-chloro-4-methoxyphenyl)-2-cyclobutylvinyl)phenyl)acrylic acid | 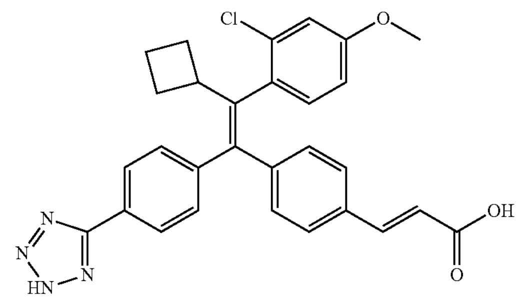 |
| 51 | (E)-3-(4-((E)-1-(4-(1H-Pyrazol-4-yl)phenyl)-2-(2-chloro-4-methoxyphenyl)-2-cyclobutylvinyl)phenyl)acrylic acid | 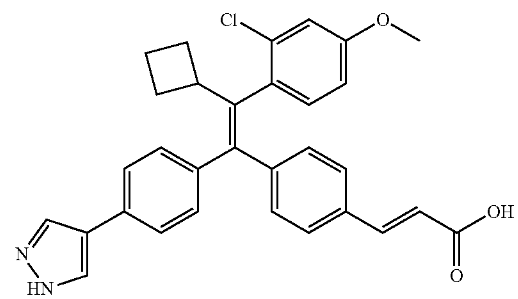 |
| 52 | (E)-3-(4-((E)-1-(4-(1H-Pyrazol-4-yl)phenyl)-2-(2-chloro-4-(trifluoromethoxy)phenyl)-2-cyclobutylvinyl)phenyl)acrylic acid | 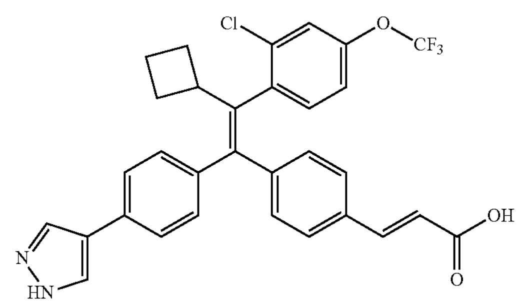 |
| 53 | (E)-3-(4-((E)-2-(2-Chloro-4-methoxyphenyl)-2-cyclobutyl-1-(4-(thiazol-5-yl)phenyl)vinyl)phenyl)acrylic acid | 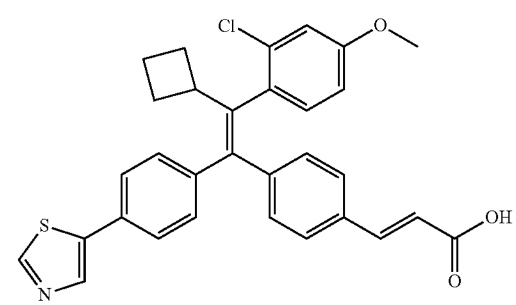 [SMILES: COc1ccc(/C(=C(\c2ccc(/C=C/C(=O)O)cc2)c2ccc(-c3cncs3)cc2)C2CCC2)c(Cl)c1] |

TABLE 1-continued

| Example no. | Name | Structure |
|---|---|---|
| 54 | (E)-3-(4-((E)-2-Cyclobutyl-2-(4-methoxy-2-methylphenyl)-1-(4-(thiazol-5-yl)phenyl)vinyl)phenyl)acrylic acid | 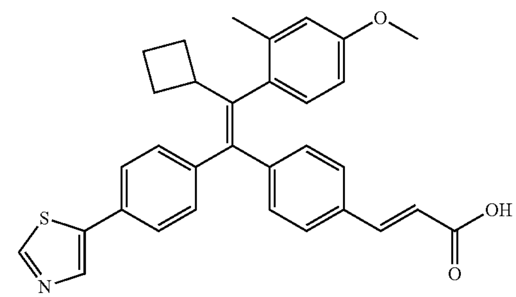 [SMILES: COc1ccc(/C(=C(\c2ccc(/C=C/C(=O)O)cc2)c2ccc(-c3cncs3)cc2)C2CCC2)c(C)c1] |
| 55 | (E)-3-(4-((E)-1-(4-(1H-Pyrazol-4-yl)phenyl)-2-(2-chloro-4-(trifluoromethyl)phenyl)-2-cyclobutylvinyl)phenyl)acrylic acid | 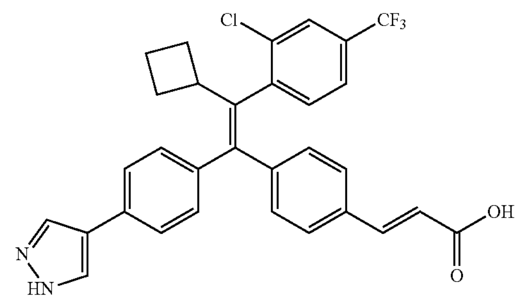 |
| 56 | (E)-3-(4-((E)-2-(2-Chloro-4-fluorophenyl)-2-cyclobutyl-1-(4-(pyridin-4-yl)phenyl)vinyl)phenyl)acrylic acid | 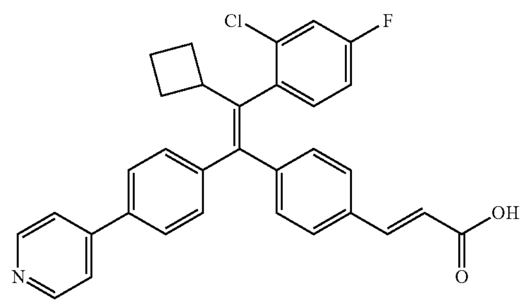 [SMILES: O=C(O)/C=C/c1ccc(/C(=C(\c2ccc(F)cc2Cl)C2CCC2)c2ccc(-c3ccncc3)cc2)cc1] |
| 57 | (E)-3-(4-((E)-2-(3-Chloro-5-(trifluoromethyl)pyridin-2-yl)-2-cyclobutyl-1-(4-morpholinophenyl)vinyl)phenyl)acrylic acid | 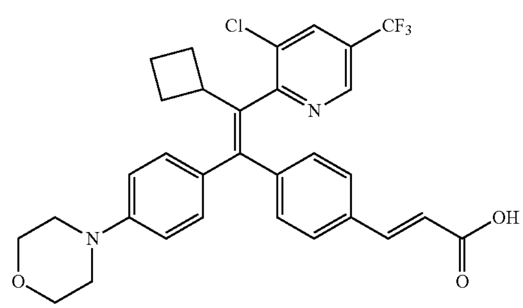 [SMILES: O=C(O)/C=C/c1ccc(/C(=C(\c2ncc(C(F)(F)F)cc2Cl)C2CCC2)c2ccc(N3CCOCC3)cc2)cc1] |
| 58 | (E)-3-(4-((E)-1-(4-(1H-Pyrazol-4-yl)phenyl)-2-(3-chloro-5-(trifluoromethyl)pyridin-2-yl)-2-cyclobutylvinyl)phenyl)acrylic acid | 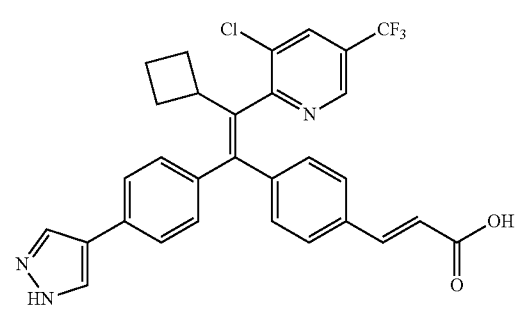 |

TABLE 1-continued

| Example no. | Name | Structure |
|---|---|---|
| 59 | (E)-3-(4-((E)-2-(3-Chloro-5-(trifluoromethyl)pyridin-2-yl)-2-cyclobutyl-1-(4-(thiazol-5-yl)phenyl)vinyl)phenyl)acrylic acid | 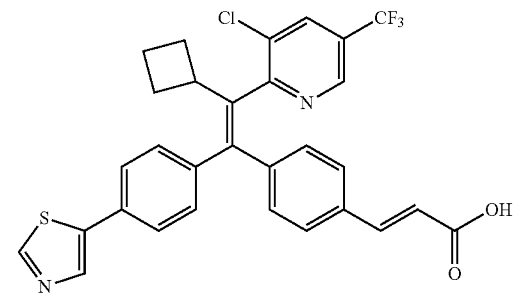 |
| 60 | (E)-3-(4-((E)-2-(2-Chloro-4-fluorophenyl)-1-(2-cyano-4-morpholinophenyl)-2-cyclobutylvinyl)phenyl)acrylic acid | 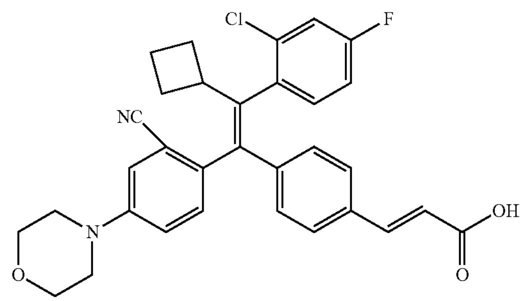 [SMILES: N#Cc1cc(N2CCOCC2)ccc1/C(=C(/c1ccc(F)cc1Cl)C1CCC1)c1ccc(/C=C/C(=O)O)cc1] |
| 61 | (E)-3-(4-((E)-1-(4-(1H-Pyrazol-4-yl)phenyl)-2-cyclobutyl-2-(6-methoxy-4-methylpyridin-3-yl)vinyl)phenyl)acrylic acid | 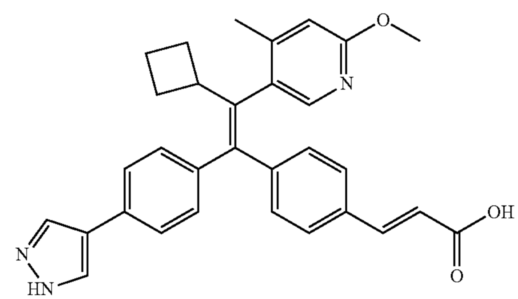 |
| 62 | (E)-3-(4-((E)-2-(4-Chloro-2-cyanophenyl)-2-cyclobutyl-1-(4-(thiazol-5-yl)phenyl)vinyl)phenyl)acrylic acid | 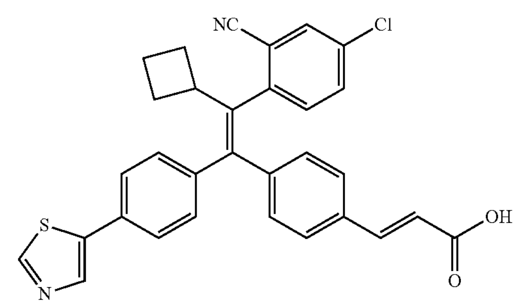 |
| 63 | (Z)-4-(4-(2-cyclobutyl-2-phenyl-1-(4-(2-(pyrrolidin-1-yl)ethoxy)phenyl)vinyl)phenyl)-1H-pyrazole | 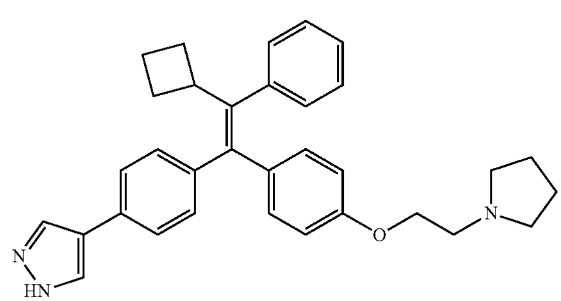 [SMILES: c1ccc(/C(=C(\c2ccc(OCCN3CCCC3)cc2)c2ccc(-c3cn[nH]c3)cc2)C2CCC2)cc1] |

TABLE 1-continued

| Example no. | Name | Structure |
|---|---|---|
| 64 | (E)-3-(4-((E)-2-Cyclobutyl-1-(4-(4-methylpiperidin-1-yl)phenyl)-2-phenylvinyl)phenyl)acrylic acid | 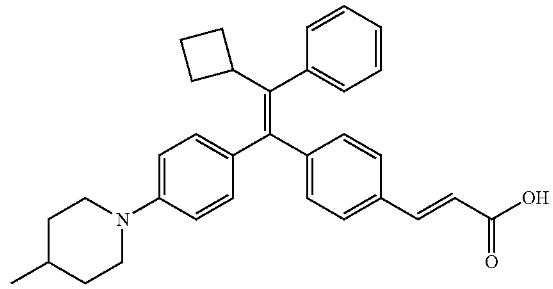 [SMILES: CC1CCN(c2ccc(/C(=C(/c3ccccc3)C3CCC3)c3ccc(/C=C/C(=O)O)cc3)cc2)CC1] |
| 65 | (E)-3-(4-((E)-2-Cyclobutyl-2-phenyl-1-(4-(piperazin-1-yl)phenyl)vinyl)phenyl)acrylic acid | 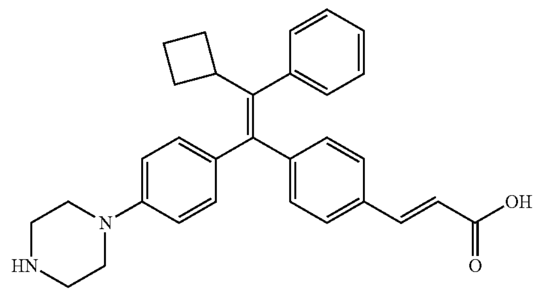 [SMILES: O=C(O)/C=C/c1ccc(/C(=C(\c2ccccc2)C2CCC2)c2ccc(N3CCNCC3)cc2)cc1] |
| 66 | (E)-3-(4-((E)-2-Cyclobutyl-2-phenyl-1-(4-(pyridin-4-yl)phenyl)vinyl)phenyl)acrylic acid | 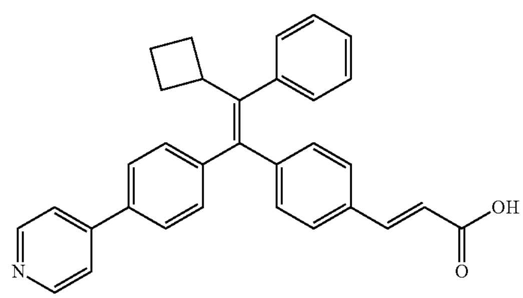 [SMILES: O=C(O)/C=C/c1ccc(/C(=C(\c2ccccc2)C2CCC2)c2ccc(-c3ccncc3)cc2)cc1] |
| 67 | (E)-3-(4-((E)-2-Cyclobutyl-1-(4-(1-(2-hydroxyethyl)-1H-pyrazol-4-yl)phenyl)-2-phenylvinyl)phenyl)acrylic acid | 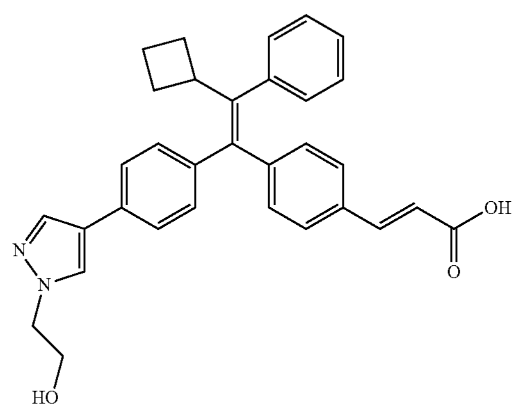 [SMILES: O=C(O)/C=C/c1ccc(/C(=C(\c2ccccc2)C2CCC2)c2ccc(-c3cnn(CCO)c3)cc2)cc1] |

TABLE 1-continued

| Example no. | Name | Structure |
|---|---|---|
| 68 | (E)-3-(4-((E)-2-Cyclobutyl-1-(4-(1-(2-hydroxyethyl)-1H-pyrazol-4-yl)phenyl)-2-(4-methylthiophen-3-yl)vinyl)phenyl)acrylic acid | 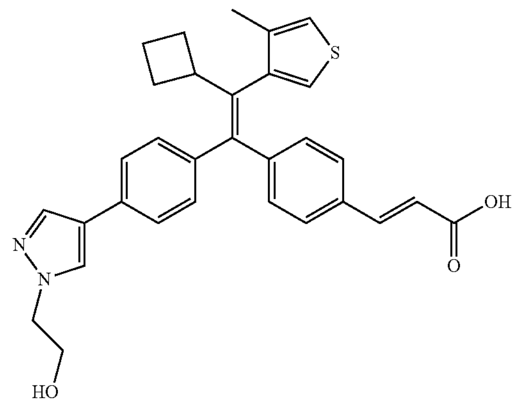 [SMILES: Cc1cscc1/C(=C(\c1ccc(/C=C/C(=O)O)cc1)c1ccc(-c2cnn(CCO)c2)cc1)C1CCC1] |
| 69 | (E)-3-(4-((E)-2-(2-Chloro-4-fluorophenyl)-2-cyclobutyl-1-(4-(1-(2-hydroxyethyl)-1H-pyrazol-4-yl)phenyl)vinyl)phenyl)acrylic acid | 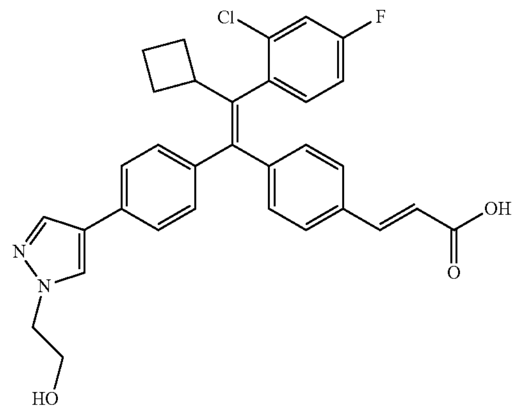 [SMILES: O=C(O)/C=C/c1ccc(/C(=C(\c2ccc(F)cc2Cl)C2CCC2)c2ccc(-c3cnn(CCO)c3)cc2)cc1] |
| 70 | (E)-3-(4-((E)-2-Cyclobutyl-1-(4-(1-(2-(dimethylamino)ethyl)-1H-pyrazol-4-yl)phenyl)-2-phenylvinyl)phenyl)acrylic acid | 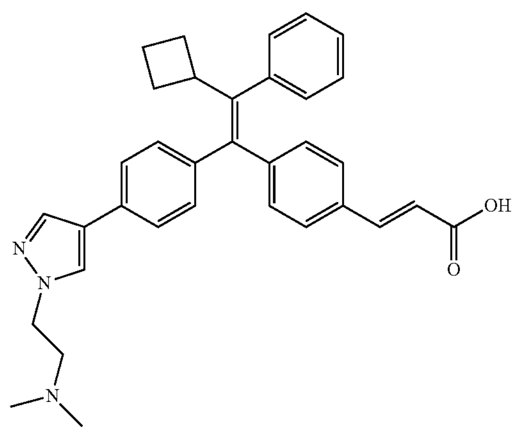 [SMILES: CN(C)CCn1cc(-c2ccc(/C(=C(/c3ccccc3)C3CCC3)c3ccc(/C=C/C(=O)O)cc3)cc2)cn1] |
| 71 | 5-((E)-4-((E)-1-(4-(1H-Pyrazol-4-yl)phenyl)-2-(2-chloro-4-fluorophenyl)-2-cyclobutylvinyl)styryl)-2H-tetrazole | 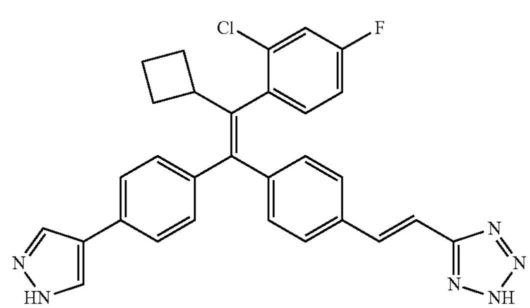 [SMILES: Fc1ccc(/C(=C(\c2ccc(/C=C/c3nn[nH]n3)cc2)c2ccc(-c3cn[nH]c3)cc2)C2CCC2)c(Cl)c1] |

In some embodiments, provided is a pharmaceutically acceptable salt of a compound described in Table 1.

In some embodiments, there are provided methods of treating an estrogen receptor dependent or estrogen receptor mediated disease or condition in mammal comprising administering to the mammal a therapeutically effective amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof. In certain embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects. In some embodiments, the estrogen receptor dependent or estrogen receptor mediated disease or condition is selected from bone cancer, breast cancer, colorectal cancer, lung cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, and infertility. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating cancer in a mammal comprising administering to the mammal a therapeutically effective amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof. In certain embodiments, the cancer is breast cancer, ovarian cancer, endometrial cancer, prostate cancer, or uterine cancer. In certain embodiments, the cancer is breast cancer. In certain embodiments, the cancer is a hormone dependent cancer. In certain embodiments, the cancer is an estrogen receptor dependent cancer. In certain embodiments, the cancer is an estrogen-sensitive cancer. In certain embodiments, the cancer is resistant to anti-hormonal treatment. In certain embodiments, the cancer is an estrogen-sensitive cancer or an estrogen receptor dependent cancer that is resistant to anti-hormonal treatment. In some embodiments, the anti-hormonal treatment includes treatment with at least one agent selected from tamoxifen, fulvestrant, steroidal aromatase inhibitors, and non-steroidal aromatase inhibitors. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating hormone receptor positive metastatic breast cancer in a postmenopausal woman with disease progression following anti-estrogen therapy comprising administering to the woman an estrogen receptor degrading compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, there are provided methods of treating a hormonal dependent benign or malignant disease of the breast or reproductive tract in a mammal comprising administering to the mammal an effective amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof. In certain embodiments, the benign or malignant disease is breast cancer. In some embodiments, the methods further comprise administering to the mammal radiation therapy. In certain embodiments, the compound of the methods is administered prior to or following surgery. In certain embodiments, the methods comprise administering to the mammal at least one additional anti-cancer agent.

In some embodiments, these methods further comprise administering to the mammal at least one additional therapeutic agent selected from abiraterone; abarelix; adriamycin; aactinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin Il (including recombinant interleukin II, or rlL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab; tositumomab and I$^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Synthesis of Compounds

Compounds described herein are synthesized using standard synthetic techniques or using methods known in the art in combination with methods described herein. In additions, solvents, temperatures and other reaction conditions presented herein may vary.

The starting material used for the synthesis of the compounds described herein are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds is optionally modified by the use of appropriate reagents and conditions for the introduction of the various moieties found in the formulae as provided herein.

In some embodiments, exemplary compounds described herein are prepared as outlined in the following schemes.

Scheme 1.

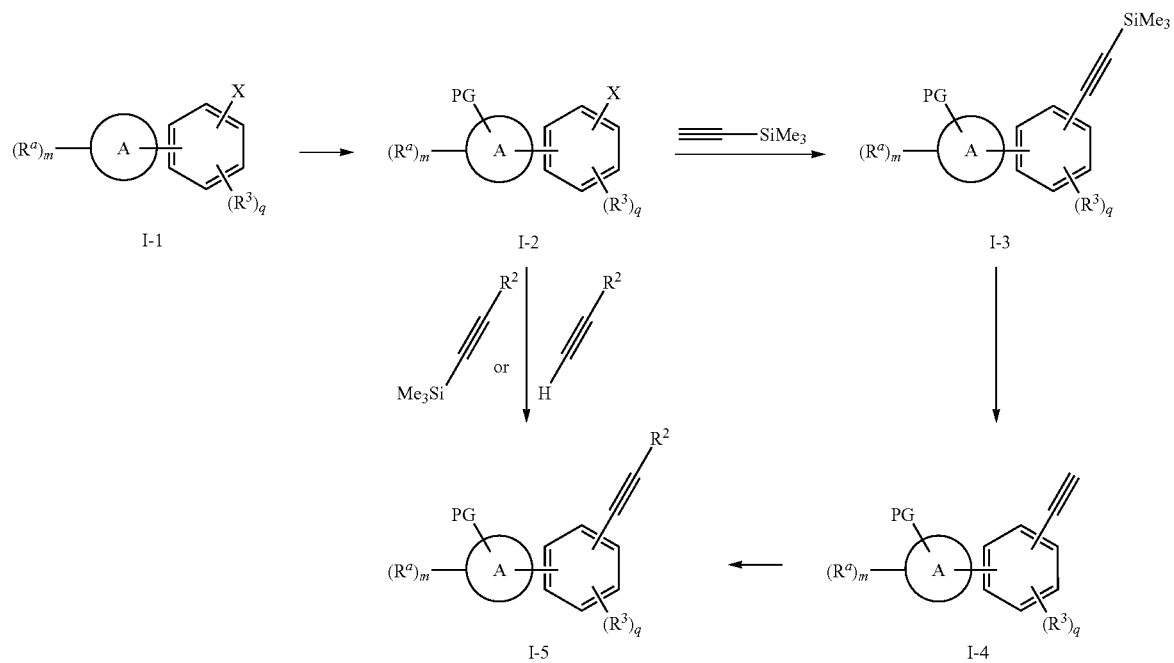

In some embodiments, compounds of structure I-1 are either obtained from commercial sources or synthesized using methods known in the art in combination with methods described herein.

In some embodiments, protection of the acidic proton bearing nitrogen of compounds of structure I-1, where X is a halogen such as bromine or iodine, with a protecting group provides compounds of structure I-2. In some embodiments, the protecting group (PG) is tetrahydropyran (THP). In some embodiments, the conditions for nitrogen protection require dihydropyran (DHP), an organic acid and a suitable solvent. In some embodiments, the organic acid is para-tolunesulfonic acid (p-TsOH) or pyridinium p-toluenesulfonate (PPTS), and the suitable solvent is dicloromethane. In some embodiments, the reaction is performed at room temperature. Other conditions to protect the nitrogen of the starting material are known and include protecting groups such as, but not limited to, methoxymethyl ether (MOM), tert-butyloxycarbonyl (BOC), acetyl (Ac), or triphenylmethyl (trityl). A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, compounds of structure I-2, where X is a halogen such as bromine, iodine or triflate are coupled with an alkynyl-trimethylsilane or a terminal alkyne under Sonogashira reaction conditions to provide compounds of structure I-5.

In some embodiments, the Sonogashira coupling includes the use of a base, a palladium catalyst, and a copper halide salt in a suitable solvent at elevated temperatures. In some embodiments, suitable bases for this reaction include, but are not limited to, cesium carbonate, potassium carbonate, triethylamine, diethylamine, pyrrolidine, cesium fluoride, or tetrabutylammonium fluoride (TBAF). In some embodiments, suitable palladium catalysts for this reaction include, but are not limited to, $Pd(OAc)_2$ with dppf, 1,3-bis(2,4,6-trimethylphenyl)imidazolium chloride, or $PPh_3$; $Pd(PPh_3)_4$; or $PdCl_2(PPh_3)_2$. In some embodiments, suitable copper halide salts for this reaction include, but are not limited to, copper iodide. In some embodiments, suitable solvents for this reaction include, but are not limited to, dimethylacetamide, tetrahydrofuran, triethylamine, or pyrrolidine. In some embodiments, suitable elevated temperatures for this reaction include, but are not limited to, about 50-120° C. In some embodiments, the coupling of an alkynyl-trimethylsilane with the compounds of structure I-2 includes the use of $Pd(OAc)_2$, dppf, CuI, $Cs_2CO_3$, and dimethylacetamide with heating to about 80-90° C. In some embodiments, the coupling of a terminal-alkyne with the compounds of structure I-2 includes the use of $Pd(PPh_3)_2Cl_2$, CuI, and triethylamine with the reaction performed at elevated temperatures (e.g. about 80-120° C.). In some other embodiments, when X is iodine, the coupling of an alkynyl-trimethylsilane with the compounds of structure I-2 includes the use of TBAF, CuI, $Pd(PPh_3)_4$, and tetrahydrofuran, with optional heating to about 50° C. In yet other embodiments, when X is bromine, the coupling of an alkynyl-trimethylsilane with the compounds of structure I-2 includes the use of TBAF, CuI, $Pd(PPh_3)_4$, tetrahydrofuran, and a cosolvent (triethylamine or pyrrolidine) with heating to about 80-120° C.

In some other embodiments, compounds of structure I-2, where X is a halogen or other suitable leaving group, are reacted with a protected acetylene (e.g., trimethylsilylacetylene) under Sonogashira reaction conditions to provide the compounds of structure I-3. In some embodiments, the Sonogashira coupling reaction conditions include the use of a palladium catalyst and a copper halide salt. In some embodiments, the Sonogashira reaction conditions includes the use of $Pd(Ph_3P)_2Cl_2$, CuI, and triethylamine. In one embodiment, the reaction is performed at about 80° C. Other suitable reaction conditions are described in Rafael Chinchilla and Carmen Nájera (2007). Chem. Rev. 107 (3): 874-922.

The silyl protecting group of the compounds of structure I-3 is removed under suitable reaction conditions to provide the compounds of structure I-4. In some embodiments, the silyl protecting group is removed with potassium carbonate ($K_2CO_3$) in methanol. In other embodiments, the silyl protecting group is removed with tetrabutylammoniumfluoride (TBAF) in tetrahydrofuran.

In some embodiments, the compounds of Structure I-4 are reacted with $R^2$—X under basic conditions to prepare the compounds of structure I-5. In these instances, $R^2$ is $C_1$-$C_6$alkyl or $C_1$-$C_6$fluoroalkyl or $C_1$-$C_4$alkoxy or $C_1$-$C_4$fluoroalkoxy or $C_3$-$C_6$cycloalkyl, or the like, and X is a suitable leaving group.

In some embodiments, compounds disclosed herein are prepared as outlined in Scheme 2.

Scheme 2.

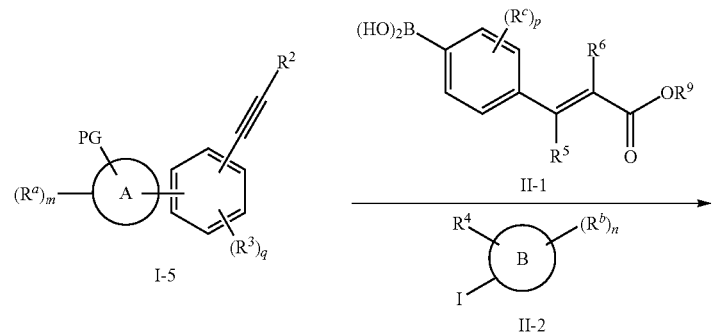

-continued

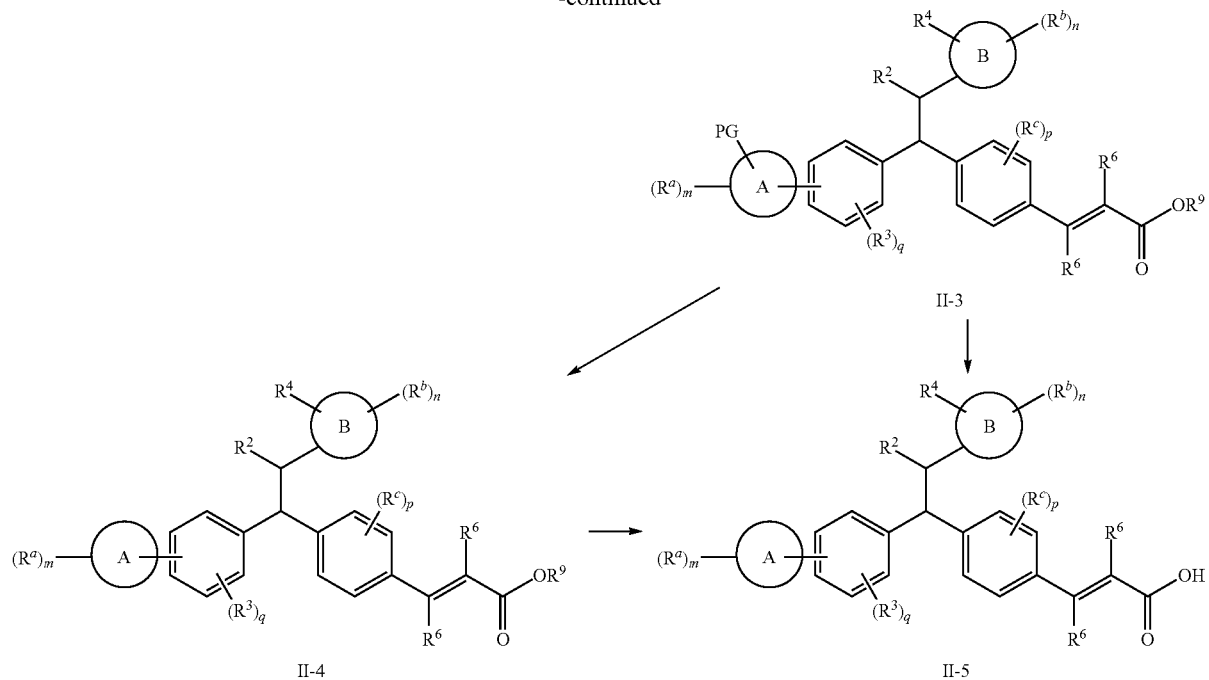

II-3

II-4

II-5

In some embodiments, compounds of Structure I-5, aryl iodides of Structure II-2 and aryl boronic acids of Structure II-1 are then coupled together under suitable reaction conditions to afford compounds of Structure II-3. In some embodiments, the suitable reaction conditions include the use of organometallic reagent(s). In some embodiments, the suitable reaction conditions include the use of a palladium catalyst. In some embodiments, the suitable reaction conditions include the use of $Pd(PhCN)_2Cl_2$, $K_2CO_3$ in dimethylformamide/water. Other suitable reaction conditions include those described in Chengxiang Zhou and Richard C. Larock, Journal of Organic Chemistry, 2005, 70, 3765-3777; Chengxiang Zhou, Daniel E. Emrich, and Richard C. Larock Organic Letters 2003, 1579-1582; Tsutomu Konno, Ken-ichi Taku, Takashi Ishihara, Journal of Fluorine Chemistry 127 (2006) 966-972.

The protecting group of compounds of Structure II-3 is then removed under suitable reaction conditions to provide compounds of Structure II-4. In some embodiments, the suitable reaction conditions include the use of an acid. In some embodiments, the suitable reaction conditions include the use of hydrochloric acid and ethanol with the reaction performed at about 70° C. In some embodiments, the suitable reaction conditions include the use of hydrochloric acid in dioxane at about 50-80° C. In some embodiments, the suitable reaction conditions include the use of trifluoroacetic acid in dichloromethane at room temperature. In some embodiments, when $R^9$ of compounds of structure II-3 is tert-butyl, treatment of compounds of structure II-3 under some of the foregoing acidic conditions (i.e. hydrochloric acid in dioxane or trifluoroacetic acid in dichloromethane) provides compounds of structure II-5.

Hydrolysis of the ester group of compounds of structure II-4 provides carboxylic acid compounds of structure II-5. In some embodiments, the hydrolysis reaction includes the use of lithium hydroxide in a mixture of tetrahydrofuran and ethanol. Other hydrolysis reaction conditions are known.

In some embodiments, compounds disclosed herein are prepared as outlined in Scheme 3.

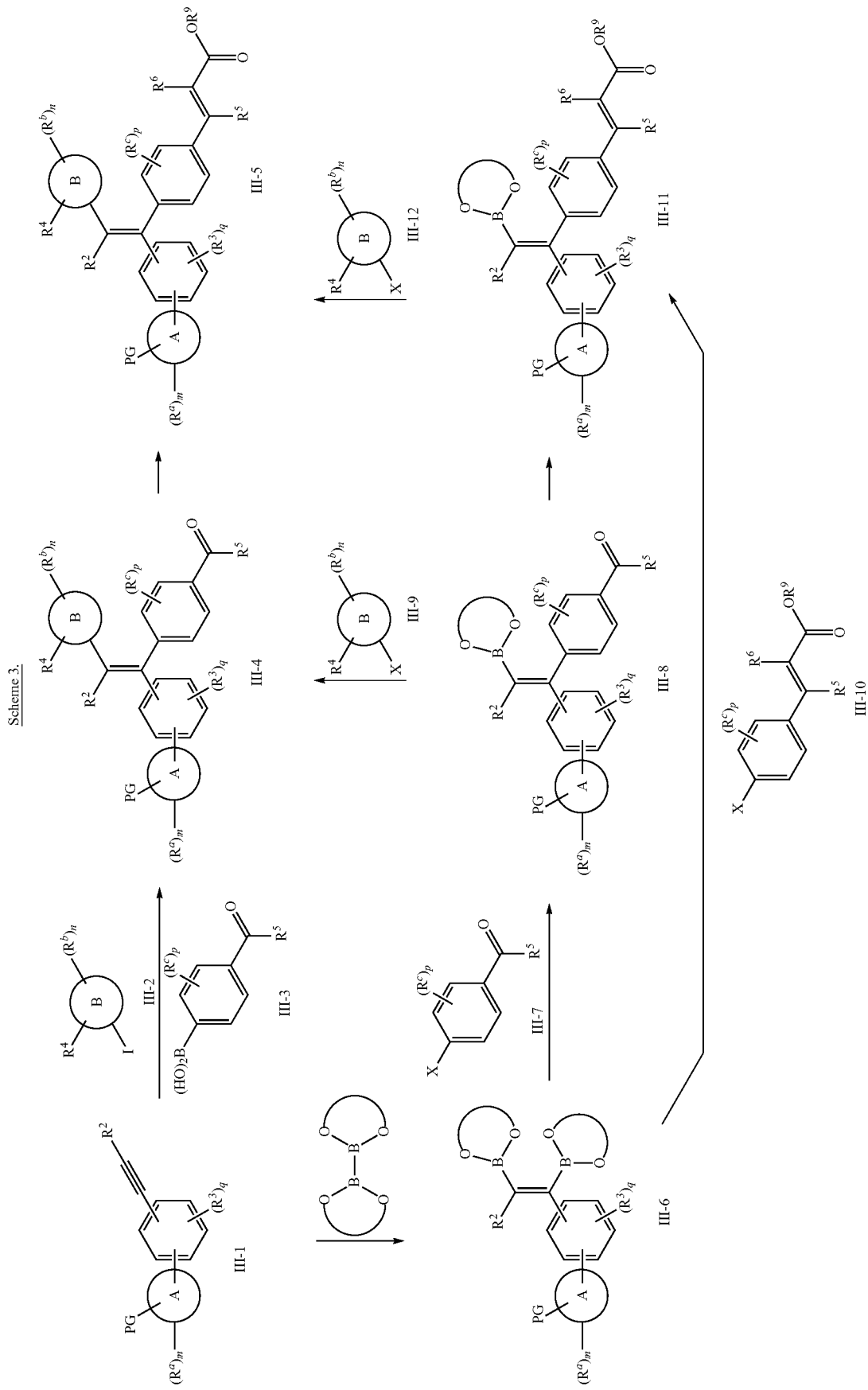

In some embodiments, compounds of structure III-1 are reacted with aryl halides of structure III-2 where X is iodide and boronic acids of structure III-3 under suitable reaction conditions to provide compounds of structure III-4. In some embodiments, the suitable reaction conditions include the use of organometallic reagent(s). In some embodiments, the suitable organometallic reagent is a palladium catalyst. The aldehyde of compounds of structure III-4 is then transformed to an alkene under suitable reaction conditions to provide compounds of structure III-5. Suitable reaction conditions include a Horner-Wadsworth-Emmons olefination reaction or a Wittig olefination reaction conditions.

Alternatively, compounds of structure III-1 are reacted with a borylating agent in the presence of a suitable catalyst and a suitable solvent to provide compounds of structure III-6. In some embodiments, the suitable catalyst is an organometallic catalyst. In some embodiments, the suitable catalyst is a platinum catalyst. In some embodiments, the suitable catalyst is $(\eta^2$—$C_2H_4)Pt(PPh_3)_2$ or $Pt(PPh_3)_4$. Other platinum catalysts are known. In some embodiments,

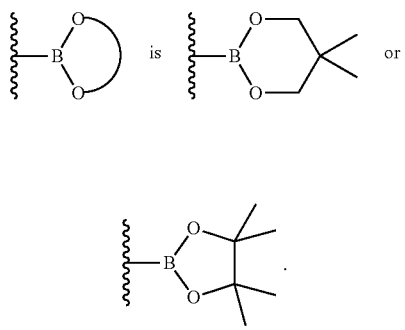

In some embodiments, the borylating agent is bis(pinacolato)diboron, or bis(neopentylglycolato)diboron. Suitable solvents include, but are not limited to, dioxane, dimethoxyethane, 2-methyltetrahydrofuran, toluene, and dimethylacetamide. In some embodiments, the reaction is performed under an inert atmosphere. In some embodiments, the reaction is performed under nitrogen. In some embodiments, the reaction is heated, such as for example, to about 80-120° C.

A Suzuki cross-coupling is then performed with compounds of structure III-6 and aryl halides of structure III-7 to provide compounds of structure III-8. In some embodiments, the Suzuki cross-coupling includes the use a suitable catalyst, a suitable base, and a suitable solvent with optional heating. In some embodiments, the suitable catalysts is a palladium catalyst. Suitable palladium catalysts include but are not limited to, $PdCl_2(PPh_3)_2$, and $PdCl_2(dppf)$. In some embodiments, the suitable base is an inorganic base or an organic base. Suitable bases include, but are not limited to, cesium carbonate, sodium carbonate, potassium carbonate, potassium hydroxide, and sodium hydroxide. Suitable solvents include, but are not limited to, dioxane, dimethoxyethane, 2-methyltetrahydrofuran, toluene, dimethylacetamide, dimethylformamide, and dimethylsulfoxide. In some embodiments, the reaction is performed under an inert atmosphere, such as for example, under nitrogen. In some embodiments, the reaction is performed at room temperature. Alternatively the reaction is performed at about 40-50° C. Other Suzuki reaction conditions are known.

A subsequent Suzuki cross-coupling is then performed between compounds of structure III-8 and aryl/heteroaryl halides of structure III-9 to provide compounds of structure III-4. In some embodiments, this subsequent Suzuki cross-coupling includes the use a suitable catalyst, a suitable base, and a suitable solvent with heating. Suitable reagents for this subsequent Suzuki cross-coupling reaction include, but are not limited to, those described for the Suzuki cross-coupling between compounds of structure III-6 and aryl halides of structure III-7. In some embodiments, this subsequent Suzuki cross-coupling is performed at elevated temperatures, such as, for example, about 80-120° C. Other Suzuki reaction conditions are known.

Alternatively, compounds of structure III-8 are transformed to an alkene under suitable reaction conditions to provide compounds of structure III-11. Suitable reaction conditions include a Horner-Wadsworth-Emmons olefination reaction or a Wittig olefination reaction conditions. In yet an another alternative procedure, a Suzuki cross-coupling is performed with compounds of structure III-6 and aryl halides of structure III-10 to provide compounds of structure III-11. In some embodiments, aryl halides of structure III-10 are replaced with analogous pyridine, pyrimidine or pyrazine compounds. Suitable reaction conditions for this Suzuki reaction include, but are not limited to, those conditions described for coupling of compounds of structure III-6 and III-7 to provide compounds of structure III-8. A subsequent Suzuki cross-coupling is then performed between compounds of structure III-11 and aryl halides of structure III-12 to provide compounds of structure III-5. Suitable reaction conditions for this subsequent Suzuki reaction include, but are not limited to, those conditions described for coupling of compounds of structure III-8 and III-9 to provide compounds of structure III-4. The removal of the protecting group of compounds of structure III-5 and hydrolysis of the ester group include, but are not limited to, those conditioned described for compounds of structure II-3 in Scheme 2.

Scheme 4

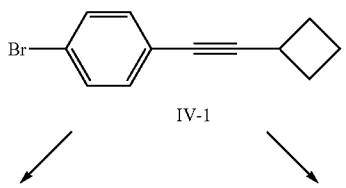

IV-1

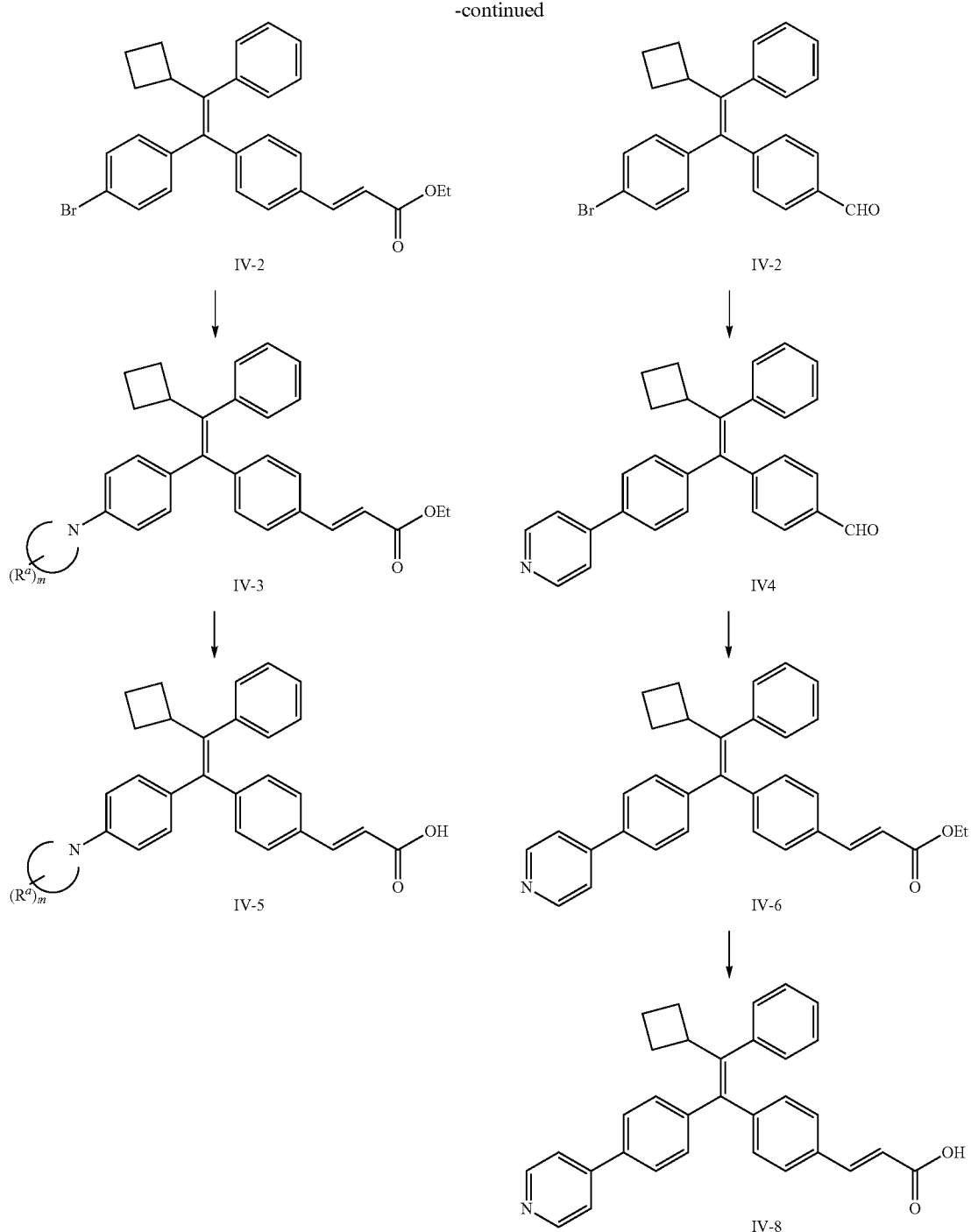

In some embodiments, alkynes of structure IV-1 are reacted with iodobenzene, (E)-(4-(3-ethoxy-3-oxoprop-1-en-1-yl)phenyl)boronic acid, potassium carbonate, $Pd(PhCN)_2Cl_2$, in a mixture of DMF:Water (2:1), at about 45° C. for about 3-18 hours. In some embodiments, when the heterocycles of ring A of the compounds of Formula (I) are N-linked, then a palladium catalyzed Buchwald-Hartwig reaction is utilized to couple NH-heterocycles with the compounds of structure IV-2 to provide compounds of structure IV-3. In some embodiments, compounds of structure IV-2 are reacted with NH-heterocycles, $Pd_2dba_3$, XPHOS, potassium phosphate, 1,4-dioxane, at about 110° C. for about 3-18 hours. Other palladium catalysed Buchwald-Hartwig reaction conditions are known. The ester of compounds IV-3 is then hydrolyzed as described in Scheme 2 to provide compounds of structure IV-4.

In some embodiments, compounds of structure IV-1 are treated with iodobenzene, (4-formylphenyl)boronic acid, potassium carbonate, $Pd(PhCN)_2Cl_2$, DMF:Water (2:1), at about 45° C. for about 3-18 hours to provide compounds of structure IV-5. In some embodiments, when the heterocycles of ring A of the compounds of Formula (I) are C-linked, then a Suzuki cross-coupling reaction is used to couple heterocycles with the compounds of structure IV-5 to provide compounds of structure IV-6. In some embodiments, compounds of structure IV-5 are reacted with pyridin-4-ylboronic acid, Pd(PPh$_3$)$_4$, potassium carbonate, 1,4-dioxane:water (9:1), at about 100° C. for about 1-18 hours to provide compounds of structure IV-6. As described in Scheme 3, a subsequent olefination reaction is carried out followed by hydrolysis of the ester to provide compounds of structure IV-8.

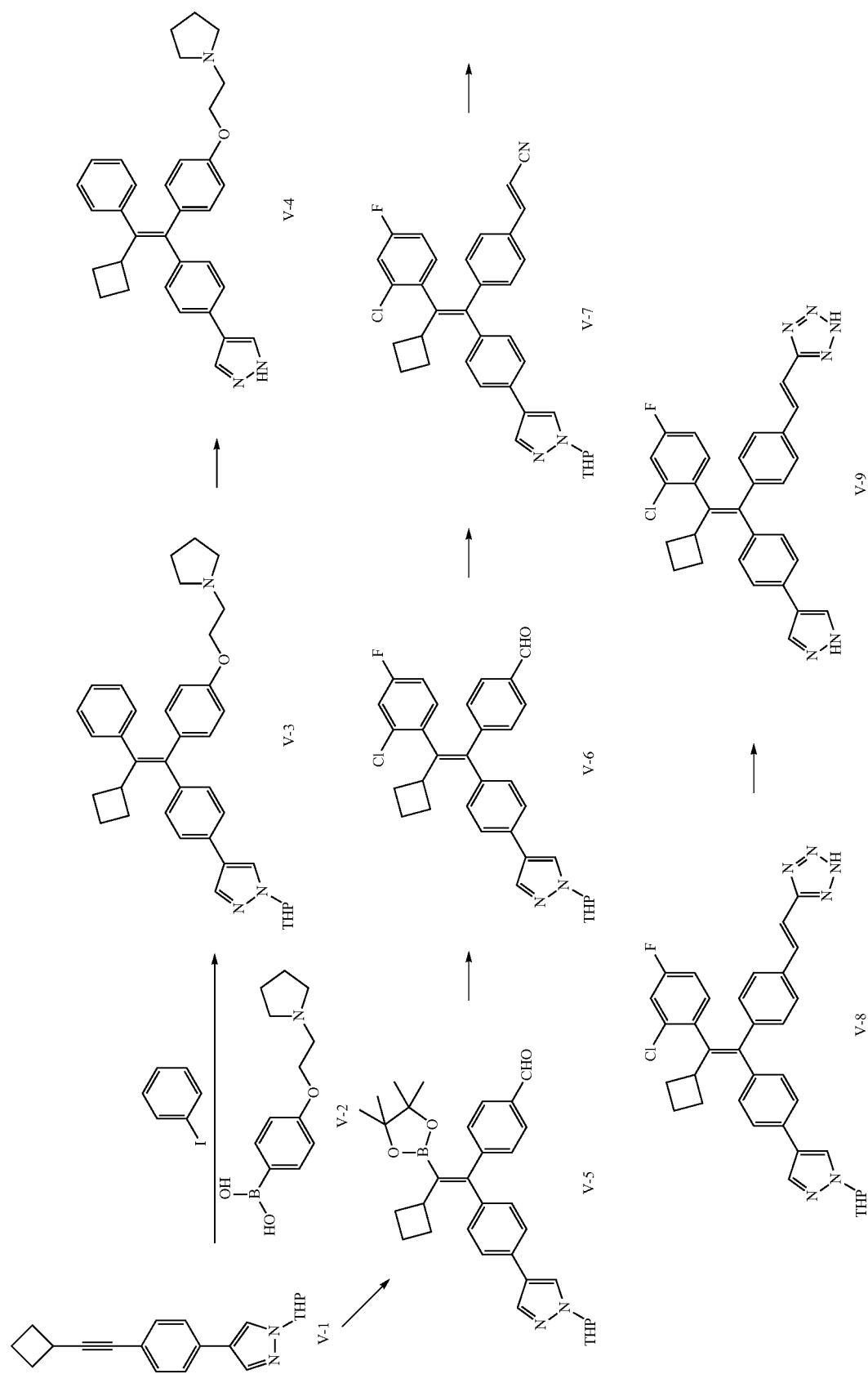

In some embodiments, compound of structure V-1 is reacted with iodobenzene and boronic acid compound V-2 under palladium catalyzed reaction conditions to provide compound V-3. In some embodiments, the palladium reaction conditions include the use of potassium carbonate, Pd(PhCN)$_2$Cl$_2$, DMF:Water (2:1), at about 45° C. for about 3-18 hours. The tetrahydropyran protecting group is then removed to provide compound V-4. In some embodiments, the tetrahydropyran protecting group is removed using hydrochloric acid in ethanol at about 70° C. for about 1-3 hours.

In some embodiments, compound V-1 undergoes a diborylation and a subsequent Suzuki cross coupling reaction as described in Scheme 3 to provide compound V-5. A second Suzuki cross coupling reaction then provides compound V-6. An olefination reaction of compound V-6 provides compound V-7. In some embodiments, the olefination reaction includes the use of DBU, (E)-diethyl (2-cyanovinyl) phosphonate, lithium chloride, acetonitrile, at room temperature for about 1-18 hours. Acrylonitrile compound V-7 is treated with TMSN$_3$, dibutylstannanone, and toluene at about 90° C. for about 3-18 hours to provide tetrazole compound V-8. Deprotection of the tetrahydropyran group with hydrochloric acid in ethanol at about 70° C. for about 1-3 hours provides compound V-9.

In one aspect, compounds described herein are synthesized as outlined in the Examples.

Throughout the specification, groups and substituents thereof are chosen by one skilled in the field to provide stable moieties and compounds.

Further Forms of Compounds

In one aspect, when compounds described herein (e.g. a compound of Formula (I), (II), (III), (IV), (V), (VI), (VII), (VIII), (IX), (X), (XI), (XII), (XIII), or (XIV), or a compound in Table 1) possess one or more stereocenters then each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In certain embodiments, the compounds presented herein are present as atropisomers. Atropisomers refer to stereoisomers resulting from hindered rotation about single bonds where the steric strain barrier to rotation allows for the isolation of conformers. Atropisomers display axial chirality. Separation of atropisomers is possible. In some embodiments, separation of atropisomers is possible by chiral resolution methods such as selective crystallization. Atropisomers are optionally characterized by NMR or other suitable characterization means.

For example, atropisomers of the compound with the structure

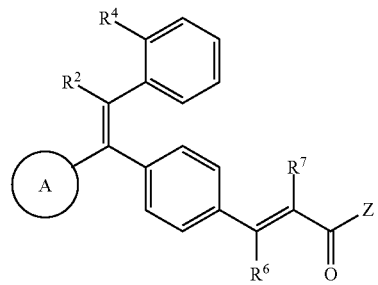

include:

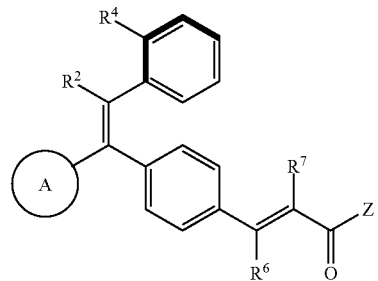

R$^4$ is above the plane of the alkene and

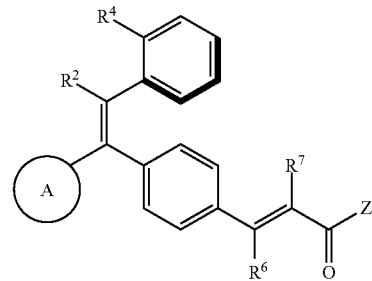

R$^4$ is below the plane of the alkene.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein (e.g. a compound of Formula (I), (II), (III), (IV), (V), (VI), (VII), (VIII), (IX), (X), (XI) (XII), (XIII), or (XIV), or a compound in Table 1) as set forth herein are included within the scope of the claims. In some cases, some of the herein-described compounds is a prodrug for another derivative or active compound.

In some embodiments, sites on the aromatic ring portion of compounds described herein (e.g. a compound of Formula (I), (II), (III), (IV), (V), (VI), (VII), (VIII), (IX), (X), (XI), (XII), (XIII), or (XIV), or a compound in Table 1) are susceptible to various metabolic reactions. Incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound described herein (e.g. a compound of Formula (I), (II), (III), (IV), (V), (VI), (VII), (VIII), (IX), (X), (XI), (XII), (XIII), or (XIV), or a compound in Table 1) with acids. Pharmaceutically acceptable salts are also obtained by reacting a compound described herein (e.g. a compound of Formula (I), (II), (III), (IV), (V), (VI), (VII), (VIII), (IX), (X), (XI), (XII), (XIII), or (XIV), or a compound in Table 1) with a base to form a salt.

Compounds described herein are optionally formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, the compounds provided herein are prepared as lysine salts, sodium salts or other suitable amino acid salts. In some embodiments, the compounds provided herein are prepared as a sodium salt. In some embodiments, the compounds provided herein are prepared as an N-methylglucamine salt. In some embodiments, the compounds provided herein are prepared as a hydrochloride salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts, as well as active metabolites of the compounds described herein (e.g. a compound of Formula (I), (II), (III), (IV), (V), (VI), (VII), (VIII), (IX), (X), (XI), (XII), (XIII), or (XIV), or a compound in Table 1) having the same type of activity.

CERTAIN TERMINOLOGY

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group is branched or straight chain. In some embodiments, the "alkyl" group has 1 to 6 carbon atoms (whenever it appears herein, a numerical range such as "1 to 6" refers to each integer in the given range; e.g., "1 to 6 carbon atoms" means that the alkyl group includes moieties that consist of 1 carbon atom, 2 carbon atoms, 3 carbon atoms, etc., up to and including 6 carbon atoms, although the present definition also covers the occurrence of the term "alkyl" where no numerical range is designated). In one aspect the alkyl is selected from the group consisting of methyl, ethyl, propyl, iso-propyl, n-butyl, iso-butyl, sec-butyl, and t-butyl.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R) =CR$_2$, wherein R refers to the remaining portions of the alkenyl group, which may be the same or different. Non-limiting examples of an alkenyl group include —CH=CH$_2$, —C(CH$_3$)=CH$_2$, —CH=CHCH$_3$ and —C(CH$_3$)=CHCH$_3$. Depending on the structure, an alkenyl group can be a monoradical or a diradical (i.e., an alkenylene group).

The term "alkynyl" refers to a type of alkyl group in which at least one carbon-carbon triple bond is present. In one embodiment, an alkenyl group has the formula —C≡C—R, wherein R refers to the remaining portions of the alkynyl group. Non-limiting examples of an alkynyl group include —C≡CH, —C≡CCH$_3$ and —C≡CCH$_2$CH$_3$. Depending on the structure, an alkynyl group can be a monoradical or a diradical (i.e., an alkynylene group).

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0.

The term "aromatic" refers to a planar ring having a delocalized π-electron system containing 4n+2π electrons, where n is an integer. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. Aryl groups are optionally substituted. In one aspect, an aryl is a phenyl or a naphthalenyl. In one aspect, an aryl is a phenyl. In one aspect, an aryl is a C$_6$-C$_{10}$aryl. Depending on the structure, an aryl group is optionally a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls include moieties that are saturated, or partially unsaturated. Cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups are optionally substituted or unsubstituted. In one aspect, a cycloalkyl is a C$_3$-C$_6$cycloalkyl.

The term "halo" or, alternatively, "halogen" or "halide" means fluoro, chloro, bromo or iodo.

The term "fluoroalkyl" refers to an alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include:

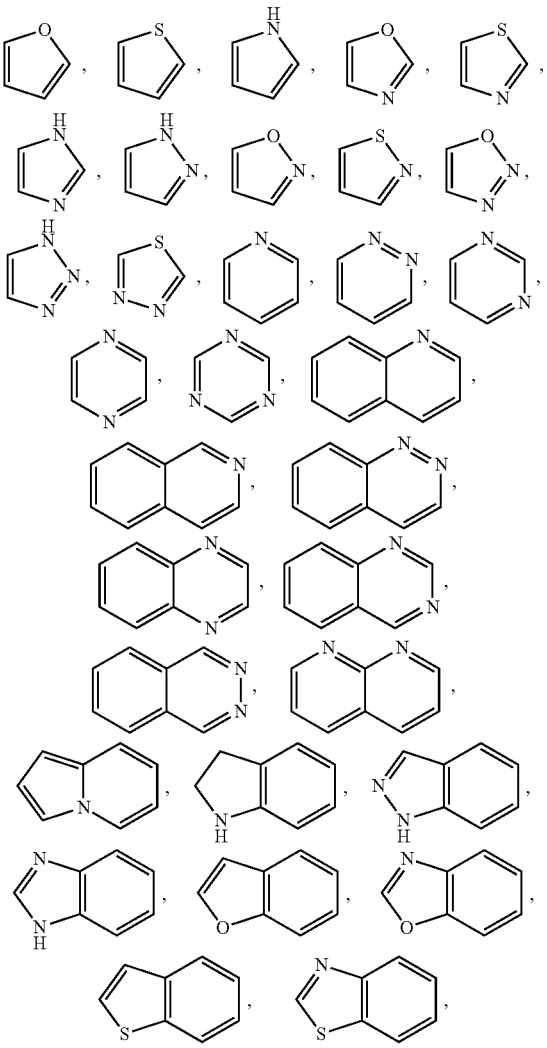

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl. Depending on the structure, a heteroaryl group is optionally a monoradical or a diradical (i.e., a heteroarylene group).

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, a heterocycloalkyl is fused with a phenyl or monocyclic heteroaryl. In some embodiments, a heterocycloalkyl is fused with a phenyl or monocyclic heteroaryl and the point of attachment to the rest of the molecule is through a carbon atom of the fused phenyl or fused monocyclic heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

"Aza" when added to the name of a heterocyclic ring, denotes that the ring includes 1 or 2 additional N atoms in the heterocyclic ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "carboxylic acid bioisostere" refers to a functional group or moiety that exhibits similar physical, biological and/or chemical properties as a carboxylic acid moiety. Examples of carboxylic acid bioisosteres include, but are not limited to,

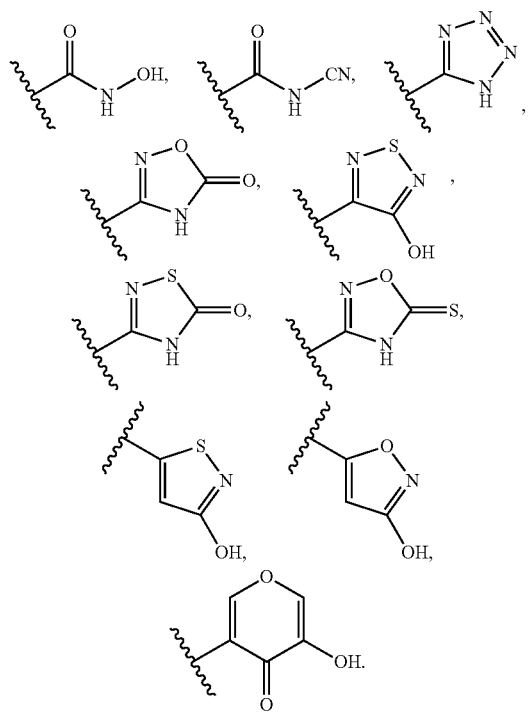

and the like.

The term "optionally substituted" or "substituted" means that the referenced group is optionally substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. In some embodiments, optional substituents are independently selected from halogen, —CN, —NH$_2$, —NH(CH$_3$), —N(CH$_3$)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, —OCH$_2$CH$_3$, —OCF$_3$, —S(=O)$_2$CH$_3$, and —CH$_2$OH. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

"Selective estrogen receptor modulator" or "SERM" as used herein, refers to a molecule that differentially modulates the activity of estrogen receptors in different tissues. For example, in some embodiments, a SERM displays ER antagonist activity in some tissues and ER agonist activity in other tissues. In some embodiments, a SERM displays ER antagonist activity in some tissues and minimal or no ER agonist activity in other tissues. In some embodiments, a SERM displays ER antagonist activity in breast tissues, ovarian tissues, endometrial tissues, and/or cervical tissues but minimal or no ER agonist activity in uterine tissues.

The term "antagonist" as used herein, refers to a small-molecule agent that binds to a nuclear hormone receptor and subsequently decreases the agonist induced transcriptional activity of the nuclear hormone receptor.

The term "agonist" as used herein, refers to a small-molecule agent that binds to a nuclear hormone receptor and subsequently increases nuclear hormone receptor transcriptional activity in the absence of a known agonist.

The term "inverse agonist" as used herein, refers to a small-molecule agent that binds to a nuclear hormone receptor and subsequently decreases the basal level of nuclear hormone receptor transcriptional activity that is present in the absence of a known agonist.

The term "degrader" as used herein, refers to a small molecule agent that binds to a nuclear hormone receptor and subsequently lowers the steady state protein levels of said receptor. In some embodiments, a degrader as described herein lowers steady state estrogen receptor levels by at least 10%, at least 20%, at least 30%, at least 40%, at least 50%, at least 60%, at least 65%, at least 70%, at least 75%, at least 80%, at least 85%, at least 90% or at least 95%.

The term "selective estrogen receptor degrader" or "SERD" as used herein, refers to a small molecule agent that preferentially binds to estrogen receptors versus other receptors and subsequently lowers the steady state estrogen receptor levels.

The term "ER-dependent", as used herein, refers to diseases or conditions that would not occur, or would not occur to the same extent, in the absence of estrogen receptors.

The term "ER-mediated", as used herein, refers to diseases or conditions that would not occur in the absence of estrogen receptors but can occur in the presence of estrogen receptors.

The term "ER-sensitive", as used herein, refers to diseases or conditions that would not occur, or would not occur to the same extent, in the absence of estrogens.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and a co-agent, are both administered to a patient simultaneously in the form of a single entity or dosage. The term "non-fixed combination" means that the active ingredients, e.g. a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, there are provided a pharmaceutical composition comprising a therapeutically effective amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof.

Provided herein are pharmaceutical compositions that include a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and at least one pharmaceutically acceptable inactive ingredient. In some embodiments, the compounds described herein are administered as pharmaceutical compositions in which a compound described herein, or a pharmaceutically acceptable salt thereof, is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to a mammal.

A therapeutically effective amount depends, inter alia, on the severity of the disease, the age and relative health of the subject, the potency of the compound used and other factors. The compounds are optionally used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

The pharmaceutical compositions described herein, which include a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, are formulated into any suitable dosage form, including but not limited to, aqueous oral dispersions, liquids, gels, syrups, elixirs, slurries, suspensions, solid oral dosage forms, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

In some embodiments, the pharmaceutical composition is formulated for intravenous injection, subcutaneous injection, oral administration, or topical administration. In some embodiments, the pharmaceutical composition is a tablet, a pill, a capsule, a liquid, a suspension, a gel, a dispersion, a solution, an emulsion, an ointment, or a lotion.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In some embodiments, the push-fit capsules do not include any other ingredient besides the capsule shell and the active ingredient. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulation is in the form of a capsule.

In some embodiments, solid dosage forms, e.g., tablets, effervescent tablets, and capsules, are prepared by mixing particles of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

In some embodiments, tablets will include a film surrounding the final compressed tablet. In some embodiments, the film coating provides a delayed release of the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, from the formulation. In other embodiments, the film coating aids in patient compliance (e.g., Opadry® coatings or sugar coating). Film coatings including Opadry® typically range from about 1% to about 3% of the tablet weight.

A capsule is prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In still other embodiments, effervescent powders are also prepared. Effervescent salts have been used to disperse medicines in water for oral administration.

In some embodiments, the pharmaceutical solid oral dosage forms are formulated to provide a controlled release of the active compound. Controlled release refers to the release of the active compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the active compound upon ingestion by a mammal. The first group of particles is either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or in the art.

In some embodiments, pharmaceutical formulations are provided that include particles of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and at least one dispersing agent or suspending agent for oral administration to a subject. In some embodiments, the formulations are a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further include a crystalline inhibitor.

Buccal formulations that include a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, are administered using a variety of formulations known in the art. For example, such formulations include, but are not limited to, U.S. Pat. Nos. 4,229,447, 4,596,795, 4,755,386, and 5,739,136. In addition, the buccal dosage forms described herein optionally further include a bioerodible (hydrolysable) polymeric carrier that also serves to adhere the dosage form to the buccal mucosa. For buccal or sublingual administration, the compositions optionally take the form of tablets, lozenges, or gels formulated in a conventional manner.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is prepared part of a transdermal dosage form. In one embodiment, the transdermal formulations described herein include at least three components: (1) a formulation of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof; (2) a penetration enhancer; and (3) an aqueous adjuvant. In some embodiments the transdermal formulations include additional components such as, but not limited to, gelling agents, creams and ointment bases, and the like. In some embodiments, the transdermal formulation further includes a woven or nonwoven backing material to enhance absorption and prevent the removal of the transdermal formulation from the skin. In other embodiments, the transdermal formulations described herein maintain a saturated or supersaturated state to promote diffusion into the skin.

In one aspect, formulations suitable for transdermal administration of compounds described herein employ transdermal delivery devices and transdermal delivery patches and include lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein is accomplished by means of iontophoretic patches and the like. In one aspect, transdermal patches provide controlled delivery of the active compound. In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), vegetable oils and organic esters, such as ethyl oleate. In some embodiments, formulations suitable for subcutaneous injection contain additives such as preserving, wetting, emulsifying, and dispensing agents. Prolonged absorption of the injectable pharmaceutical form is optionally brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer.

For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections involve either bolus injection and/or continuous infusion. Formulations for injection are optionally presented in unit dosage form, e.g., in ampoules or in multi-dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds are employed, such as, for example, liposomes and emulsions. In certain embodiments, compositions provided herein also optionally include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein are administered topically and are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and preservatives.

Methods of Dosing and Treatment Regimens

In one embodiment, the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in the preparation of medicaments for the treatment of diseases or conditions in a mammal that would benefit from a reduction of estrogen receptor activity. Methods for treating any of the diseases or conditions described herein in a mammal in need of such treatment, involves administration of pharmaceutical compositions that include at least one compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Treatments

In certain instances, it is appropriate to administer at least one compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is co-administered with a second therapeutic agent, wherein the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is initiated prior to, during, or after treatment with a second agent described herein, and continues until any time during treatment with the second agent or after termination of treatment with the second agent. It also includes treatments in which a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agents for Use in Combination Therapy

In some embodiments, methods for treatment of estrogen receptor-dependent or estrogen receptor-mediated conditions or diseases, such as proliferative disorders, including cancer, comprises administration to a mammal a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in combination with at least one additional therapeutic agent.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with one or more additional therapeutically active agents selected from: corticosteroids, anti-emetic agents, analgesics, anti-cancer agents, anti-inflammatories, kinase inhibitors, antibodies, HSP90 inhibitors, histone deacetylase (HDAC) inhibitors, modulators of the immune system, PD-1 inhibitors, poly ADP-ribose polymerase (PARP) inhibitors, and aromatase inhibitors.

In certain instances, it is appropriate to administer at least one compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in combination with one or more other therapeutic agents. In certain embodiments, the one or more other therapeutic agents is an anti-cancer agent(s).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

Monoclonal antibodies include, but are not limited to, trastuzumab (Herceptin).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with at least one additional therapeutic agent selected from: abiraterone; abarelix; adriamycin; actinomycin; acivicin; aclarubicin; acodazole hydrochloride; acronine; adozelesin; aldesleukin; alemtuzumab; allopurinol; alitretinoin; altretamine; ambomycin; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin Il (including recombinant interleukin II, or rlL2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I 131 Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Further examples of anti-cancer agents for use in combination with a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole. In some embodiments, the aromatase inhibitor is anastrozole, letrozole or exemestane.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with a CDK 4/6 inhibitor. In some embodiments, the CDK 4/6 inhibitor is LEE011 or LY283519.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235, BYL719, GDC0032, BKM120, BGT226, GDC0068, GDC-0980, GDC0941, INK128 (MLN0128), INK1117, MK-2206, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101, PWT33597, CU-906, or CUDC-907.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with a histone deacetylase inhibitor (HDAC). In some embodiments, the HDAC inhibitor is entinostat or mocetinostat.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with a HER-2 inhibitor. In some embodiments, the HER-2 inhibitor is trastuzumab, pertuzumab or TDM-1.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with an epidermal growth factor receptor (EGFR) inhibitor. In some embodiments, the EGFR inhibitor is lapatinib, gefitinib, erlotinib, cetuximab, canertinib, panitumumab, nimotuzumab, OSI-632, vandetanib, afatinib, MP-412, AEE-788, neratinib, XL-647, dacomitinib, AZD-8931, CUDC-101, AP-26113 or CO-1686.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with an anti-angiogenesis agent. In some embodiments, the anti-angiogenesis agent is a VEGFR inhibitor. In some embodiments, the anti-angiogenesis agent is a multi-kinase targeting agent. In some embodiments, the anti-angiogenesis agent is bevacizumab, ABR-215050 (tasquinimod), CHIR-258 (dovitinib), EXEL-7647, OSI-930, BIBF-1120, BAY-73-4506, BMS-582664 (brivanib), RO-4929097, JNJ-26483327, AZD-2171 (cediranib), sorafenib, aflibercept, enzastaurin, AG-013736 (axitinib), GSK-786034 (pazopanib), AP-23573, or sunitinib In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with an anti-PD-1 agent. In some embodiments, the anti-PD-1 agent is MK-3475, Nivolumab, MPDL3280A, or MEDI4736.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with an AKT inhibitor. In some embodiments, the AKT inhibitor is GDC0068, MK-2206, AT7867, GSK2110183, GSK2141795, or GSK690693.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered in combination with doxorubicin, cyclophosphamide, capecitabine, vinorelbine, paclitaxel, doxetaxel, or cisplatin.

Yet other anticancer agents for use in combination with a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used to treat cancer in combination with: a second antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with anti-emetic agents to treat nausea or emesis, which result from the use of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, *cannabis*, marinol, dronabinol), and others (such as, but not limited to, trimethobenzamide; ginger, emetrol, propofol).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is coadministered with an analgesic.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to $\alpha$, $\beta$, and $\gamma$ radiation and ultraviolet light.

In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used in the treatment of breast cancer in combination with at least one additional treatment option for the breast cancer. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with other agents used to treat breast cancer, including but not limited to aromatase inhibitors, anthracylines, platins, nitrogen mustard, alkylating agents, taxanes, nucleoside analogs, a phosphoinositide 3-kinase (PI3K)/mTOR pathway inhibitor, CDK 4/6 inhibitors, HER-2 inhibitors, EGFR inhibitors, PD-1 inhibitors, poly ADP-ribose polymerase (PARP) inhibitors, histone deacetylase (HDAC) inhibitors, and HSP90 inhibitors. Illustrative agents used to treat breast cancer, include, but are not limited to, fulvestrant, tamoxifen, anastrozole, letrozole, exemestane, GDC0032, goserelin, leuprolide, raloxifene, toremifene, megestrol acetate, bazedoxifene, cisplatin, carboplatin, capecitabine, cyclophosphamide, docetaxel, doxorubicin, epirubicin, eribulin, filgrastim, fluorouracil, gemcitabine, ixabepilone, LEE011, LY2835219, mitoxantrone, methotrexate, paclitaxel, pamidronate, vinorelbine, pegfilgrastim, pertuzumab, trastuzumab, lapatinib, everolimus, bevacizumab, temsirolimus and combinations thereof, as well as others described herein. Additional non-limiting exemplary agents for the treatment of breast cancer are provided elsewhere herein. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with breast cancer surgery. In some embodiments, breast cancer surgery comprises lumpectomy, mastectomy, sentinel node biopsy, or axillary node dissection. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with radiation therapy. In some embodiments, radiation comprises external beam radiation or brachytherapy. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with hormone therapy (i.e. hormone blocking therapy). In some embodiments, hormone therapy comprises the use of a selective estrogen receptor modulator (e.g. tamoxifen), aromatase inhibitor, or fulvestrant. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with surgery to remove the ovaries or medications to stop the ovaries from making estrogen. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with trastuzumab, lapatinib, or bevacizumab. In some embodiments, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is used either alone or in combination with bone-building drugs to prevent breast cancer recurrence (e.g. zoledronic acid (Reclast, Zometa)).

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by antagonism of androgen receptors.

For example, the container(s) include a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

These examples are provided for illustrative purposes only and not to limit the scope of the claims provided herein.

Intermediate 1

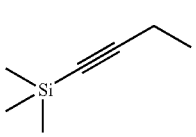

But-1-yn-1-yltrimethylsilane

A 3 L three-necked round bottom flask was charged with (trimethylsilyl)acetylene (116 g, 1.19 mol) and dry THF (400 mL). The solution was cooled to −78° C. To this solution, butyllithium in hexane (2.5 M, 500 mL, 1.25 mol) was added dropwise over 2 hours. The resulting mixture was warmed to 0° C. for 10 minutes and then re-cooled to −78° C. HMPA (234 g, 1.31 mol) was added, and the mixture was stirred at −78° C. for 30 minutes. To this solution, iodoethane (200 g, 1.28 mol) was added. The reaction mixture was allowed to warm to room temperature and stirred overnight. Upon completion, the reaction mixture was washed with water (4×600 mL) and then brine (2×500 mL). The organic layer was dried over sodium sulfate and filtered. Hexane and THF were distilled off at 75~110° C. But-1-yn-1-yltrimethylsilane was distilled between 125 to 135° C. affording 91 g of a colorless liquid (61%). $^1$H NMR (400 MHz, DMSO-d$_6$) δ 2.20 (q, 2H), 1.05 (t, 3H), 0.11 (s, 9H).

Intermediate 2

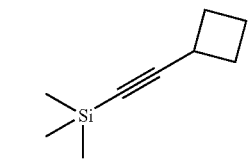

(Cyclobutylethynyl)trimethylsilane

Step 1: (6-chlorohex-1-yn-1-yl)trimethylsilane

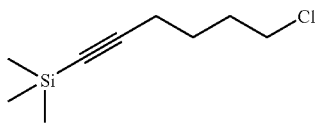

To a solution of 6-chlorohex-1-yne (100 mL, 94.6 g, 0.82 mol) in anhydrous Et$_2$O (500 mL) at −78° C., n-butyllithium (2.5 M in hexane, 360 mL, 0.90 mol) was added over 40 minutes. The resulting mixture was stirred for 30 minutes at −78° C. Chlorotrimethylsilane (125 mL, 1.0 mol) was then added. The mixture was allowed to warm to room temperature and stirred for 16 h. The reaction mixture was carefully quenched with saturated aqueous NH$_4$Cl (300 mL) at room temperature and extracted with Et$_2$O (2×200 mL). The combined organic layers were washed with brine (200 mL), dried over sodium sulfate, filtered, and concentrated in vacuo to afford the title compound (144 g, yield 93%). $^1$H NMR (DMSO-d$_6$, 400 MHz): δ 3.65 (t, 2H), 2.25 (t, 2H), 1.82-1.75 (m, 2H), 1.58-1.51 (m, 2H), 0.12 (s, 9H).

Step 2: (Cyclobutylethynyl)trimethylsilane

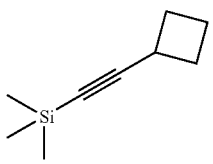

To a solution of diisopropylamine (153 g, 1.52 mol) in anhydrous THF (1.0 L) at 0° C., n-butyllithium (2.5 M in hexane, 608 mL, 1.52 mol) was added dropwise. The mixture was stirred for 20 minutes at 0° C. and then cooled to −78° C. To this mixture, a solution of (6-chlorohex-1-yn-1-yl)trimethylsilane (144 g, 0.76 mol) in anhydrous THF (200 mL) was added dropwise. The resulting mixture was allowed to warm to room temperature and stirred for 16 h. The reaction mixture was carefully quenched at room temperature with saturated aqueous NH$_4$Cl (500 mL), and then extracted with pentane (2×200 mL). The combined organic layers were washed with brine (500 mL), dried over sodium sulfate and filtered. The solvent was evaporated on a rotary evaporator. The residue was distilled at 160-162° C./760 Torr to afford the title compound as a colorless liquid (81 g, yield 70%). $^1$H NMR (CDCl$_3$, 400 MHz): δ 3.05-3.01 (m, 1H), 2.26-2.20 (m, 2H), 2.17-2.10 (m, 2H), 1.93-1.84 (m, 2H), 0.11 (s, 9H).

Intermediate 3

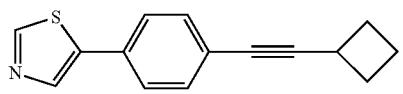

5-(4-(Cyclobutylethynyl)phenyl)thiazole

Step 1: 5-(4-Methoxyphenyl)thiazole

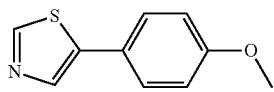

A mixture of (4-methoxyphenyl)boronic acid (7 g, 45.7 mmol), 5-bromothiazole (5 g, 30.5 mmol), potassium carbonate (8.4 g, 61 mmol), and PdCl$_2$(PPh$_3$)$_2$ (2.1 g, 3 mmol) in DME/water (5:1, 60 mL) was heated to 80° C. overnight. After cooling, ethyl acetate and brine were added to the reaction mixture and the two layers were separated. The organic layer was washed with more brine, dried over sodium sulfate, and filtered. The organic layer was evaporated to dryness. The residue was purified by flash chromatography on silica gel to afford 5.1 g of 5-(4-methoxyphenyl)thiazole as a yellow solid. $^1$H NMR (400 MHz, DMSO-d$_6$): δ 9.00 (s, 1H), 8.18 (s, 1H), 7.60 (d, 2H), 7.00 (d, 2H), 3.79 (s, 3H).

Step 2: 4-(Thiazol-5-yl)phenol

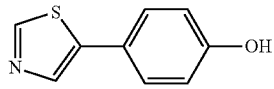

5-(4-Methoxyphenyl)thiazole (5.1 g, 26.9 mmol) was taken in dichloromethane (50 mL) and cooled to 0° C. Boron tribromide (7.8 mL, 80.7 mmol) was added dropwise and the resulting mixture was stirred at 0° C. the room temperature for 3 h. The reaction mixture was cooled back to 0° C. and methanol (50 mL) was slowly added. The solvents were removed and the residue was partitioned between ethyl acetate and 1M sodium hydroxide. The organic layer was extracted with 1M sodium hydroxide (3x). The aqueous phase was acidified with 2M hydrochloric acid, extracted with ethyl acetate, dried over sodium sulfate and filtered. and the organic layer was evaporated to dryness to afford 3.88 g of 4-(thiazol-5-yl)phenol as an orange solid.

Step 3: 4-(Thiazol-5-yl)phenyl trifluoromethanesulfonate

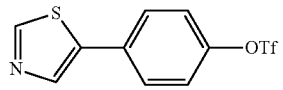

A suspension of 4-(thiazol-5-yl)phenol (3.88 g, 21.9 mmol) and pyridine (2.5 mL, 30.7 mmol) in dichloromethane was cooled to 0° C. Triflic anhydride (1M in dichloromethane, 30 mL, 30.7 mmol) was added dropwise and the mixture was stirred at room temperature for 3 h. Water was added and the two layers were separated. The organic layer was washed with more water, dried over sodium sulfate, and filtered. The organic layer was evaporated to dryness. The residue was purified by flash chromatography on silica gel to afford 4.3 g of 4-(thiazol-5-yl)phenyl trifluoromethanesulfonate as a dark orange oil. $^1$H NMR (400 MHz, DMSO-d$_6$): δ 9.15 (s, 1H), 8.40 (s, 1H), 7.88 (d, 2H), 7.60 (d, 2H).

Step 4: 5-(4-(Cyclobutylethynyl)phenyl)thiazole

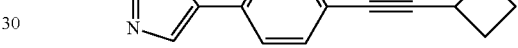

A mixture of 4-(thiazol-5-yl)phenyl trifluoromethanesulfonate (4.3 g, 14.1 mmol), (cyclobutylethynyl)trimethylsilane (Intermediate 2, 3.22 g, 21.2 mmol), Pd(OAc)$_2$ (158 mg, 0.7 mmol), dppf (392 mg, 0.7 mmol), copper iodide (134 mg, 0.7 mmol), and cesium carbonate (7 g, 21.2 mmol) in dimethylacetamide (30 mL) was heated to 90° C. for 2 h. After cooling, ethyl acetate and brine were added to the reaction mixture and the two layers were separated. The organic layer was washed with more brine, dried over sodium sulfate, and filtered. The organic layer was evaporated to dryness. The residue was purified by flash chromatography on silica gel to afford 2.3 g of 5-(4-(cyclobutylethynyl)phenyl)thiazole as a yellow solid. $^1$H NMR (400 MHz, DMSO-d$_6$): δ 9.10 (s, 1H), 8.35 (s, 1H), 7.66 (d, 2H), 7.43 (d, 2H), 3.31 (m, 1H), 2.33-2.27 (m, 2H), 2.16-2.11 (m, 2H), 1.96-1.85 (m, 2H).

The following intermediates were synthesized as described for Intermediate 3 using the appropriate aryl halide and boronic acid in Step 1. But-1-yn-1-yltrimethylsilane (Intermediate 1) was used in Step 4 (instead of (cyclobutylethynyl)trimethylsilane).

| Intermediate | Name | Structure |
|---|---|---|
| 4 | 5-(4-(But-1-yn-1-yl)phenyl)thiazole | 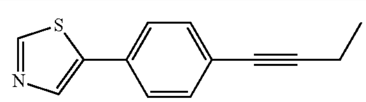 |
| 5 | 2-(4-(But-1-yn-1-yl)phenyl)thiazole | 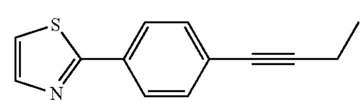 |

| Intermediate | Name | Structure |
|---|---|---|
| 6 | 4-(4-(But-1-yn-1-yl)phenyl)thiazole | 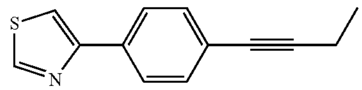 |
| 7 | 4-(4-(But-1-yn-1-yl)phenyl)-isothiazole | 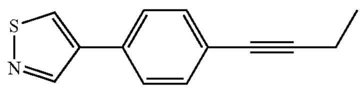 |
| 8 | 5-(4-(But-1-yn-1-yl)-3-fluorophenyl)thiazole | 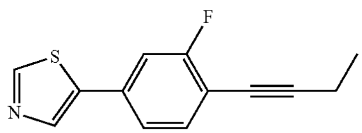 [SMILES: CCC#Cc1ccc(-c2cncs2)cc1F] |
| 9 | 5-(4-(But-1-yn-1-yl)-2-fluorophenyl)thiazole | 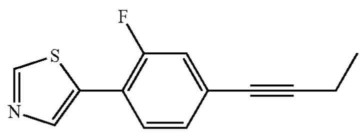 [SMILES: CCC#Cc1ccc(-c2cncs2)c(F)c1] |
| 10 | 5-(6-(cyclobutylethynyl)pyridin-3-yl)thiazole | 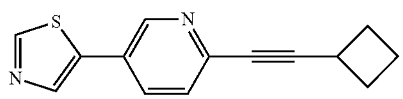 [SMILES: C(#CC1CCC1)c1ccc(-c2cncs2)cn1] |
| 11[a] | 4-(4-(But-1-yn-1-yl)phenyl)-1-methyl-1H-pyrazole | 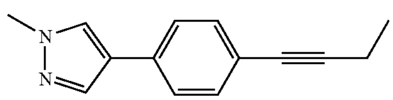 |
| 12 | 2-(3-(But-1-yn-1-yl)phenyl)thiazole | 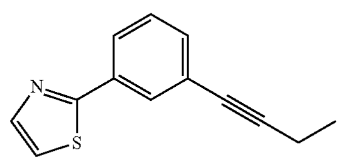 |
| 13 | 4-(3-(But-1-yn-1-yl)phenyl)thiazole | 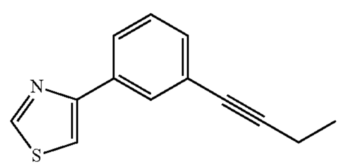 |

1-iodo-4-methoxybenzene and 1-methyl-4-(4,4,5,5-tetramethyl-1,3,2-dioxaborolan-2-yl)-1H-pyrazole were used in Step 1.

Intermediate 14

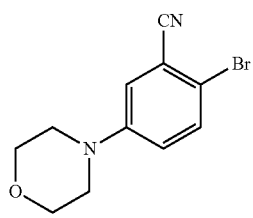

2-Bromo-5-morpholinobenzonitrile

5-Amino-2-bromobenzonitrile (1.0 g, 5.15 mmol) and diisopropylethylamine (3.5 mL, 20.09 mmol) were added to a solution of bis(2-bromoethyl)ether (2.4 g, 10.19 mmol) in dimethylacetamide (10 mL). The reaction was heated at 120° C. for ~18 h and allowed to cool to room temperature. The reaction was diluted with ethyl acetate (40 mL) and washed with water (60 mL). The aqueous layer was re-extracted with ethyl acetate (40 mL). The combined organic layers were dried (magnesium sulfate), filtered, concentrated, and purified by column chromatography on silica gel (0%-25% EtOAc in hexanes) to give 1.2 g of 2-bromo-5-morpholinobenzonitrile as a pale yellow solid. $^1$H NMR (400 MHz, DMSO-$d_6$): δ 7.62 (d, 1H), 7.45 (d, 1H), 7.20 (dd, 1H), 3.72 (t, 4H), 3.18 (t, 4H). LCMS: 267 (M+H)$^+$.

Intermediate 15

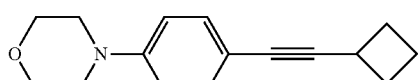

4-(4-(Cyclobutylethynyl)phenyl)morpholine

The title compound was synthesized as described for Intermediate 3, Step 4 using 4-(4-bromophenyl)morpholine (commercially available) instead of 4-(thiazol-5-yl)phenyl trifluoromethanesulfonate as the starting material. ¹H NMR (400 MHz, DMSO-d$_6$): δ 7.21 (d, 2H), 6.87 (d, 2H), 3.71 (m, 4H), 3.22 (m, 1H), 3.10 (m, 4H), 2.30-2.23 (m, 2H), 2.11-2.04 (m, 2H), 1.95-1.82 (m, 2H).

The following intermediates were synthesized by a Sonagashira coupling as described for Intermediate 15 using the appropriate commercially available aryl bromide. Intermediate 24 was prepared from intermediate 14 and intermediate 2.

Step 1: 4-(4-Bromophenyl)-1-(tetrahydro-2H-pyran-2-yl)-1H-pyrazole

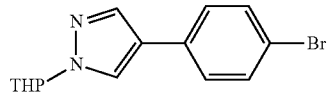

A mixture of 4-(4-bromophenyl)-1H-pyrazole (3 g, 13.5 mmol), 3,4-dihydro-2H-pyran (6.1 mL, 67.7 mmol), pyridinium p-toluenesulfonate (1 g, 4 mmol) in dichloromethane (27 mL) was stirred at room temperature for 5.5 h. Water was added and the two layers were separated. The organic layer was washed with more water, dried over sodium sulfate, and evaporated to dryness. The residue was purified by flash chromatography on silica gel to afford 3.7 g of 4-(4-bromophenyl)-1-(tetrahydro-2H-pyran-2-yl)-1H-pyrazole as a white solid. ¹H NMR (400 MHz, DMSO-d$_6$): δ 8.39 (s, 1H), 7.96 (s, 1H), 7.58 (d, 2H), 7.52 (d, 2H), 5.39 (dd, 1H), 3.92 (m, 1H), 3.66-3.60 (m, 1H), 2.12-2.05 (m, 1H), 1.96-1.90 (m, 2H), 1.69-1.65 (m, 1H), 1.56-1.51 (m, 2H).

| Intermediate | Name | Structure |
|---|---|---|
| 16 | 4-(4-(But-1-yn-1-yl)phenyl)morpholine | 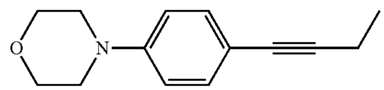 [SMILES: CCC#Cc1ccc(N2CCOCC2)cc1] |
| 17 | 1-(4-(But-1-yn-1-yl)phenyl)-1H-imidazole | 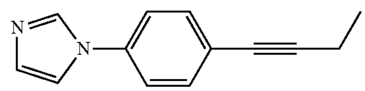 |
| 18 | 5-(4-(But-1-yn-1-yl)phenyl)oxazole | 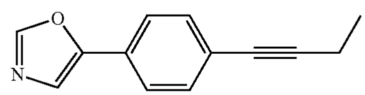 |
| 19 | 1-(4-(But-1-yn-1-yl)phenyl)-4-methylpiperazine | 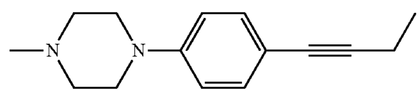 [SMILES: CCC#Cc1ccc(N2CCN(C)CC2)cc1] |
| 20 | 1-(4-(But-1-yn-1-yl)phenyl)piperidine | 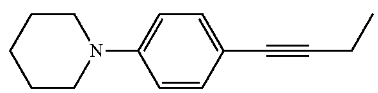 [SMILES: CCC#Cc1ccc(N2CCCCC2)cc1] |
| 21 | 3-(4-(But-1-yn-1-yl)phenyl)isoxazole | 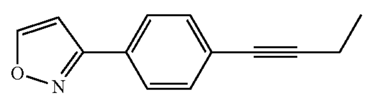 |
| 22 | 3-(4-(But-1-yn-1-yl)phenyl)pyridine | 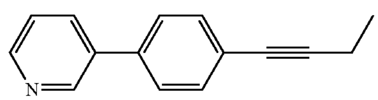 [SMILES: CCC#Cc1ccc(-c2cccnc2)cc1] |
| 23 | 4-(4-(Cyclobutylethynyl)phenyl)pyridine | 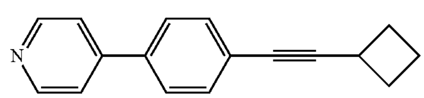 |
| 24 | 2-(Cyclobutylethynyl)-5-morpholinobenzonitrile | 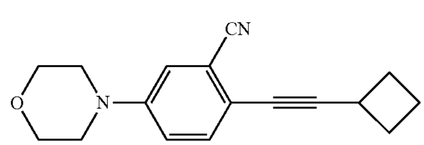 [SMILES: N#Cc1cc(N2CCOCC2)ccc1C#CC1CCC1] |

Intermediate 25

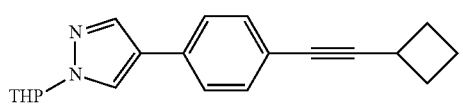

4-(4-(Cyclobutylethynyl)phenyl)-1-(tetrahydro-2H-pyran-2-yl)-1H-pyrazole

Step 2: 4-(4-(Cyclobutylethynyl)phenyl)-1-(tetrahydro-2H-pyran-2-yl)-1H-pyrazole

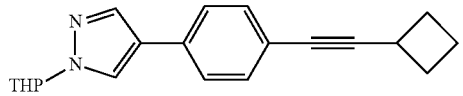

The title compound was synthesized as described in Intermediate 3, Step 4 using 4-(4-bromophenyl)-1-(tetrahydro-2H-pyran-2-yl)-1H-pyrazole instead of 4-(thiazol-5-yl)phenyl trifluoromethanesulfonate as the starting material. $^1$H NMR (400 MHz, DMSO-$d_6$): δ 8.38 (s, 1H), 7.96 (s, 1H), 7.59 (d, 2H), 7.34 (d, 2H), 5.39 (dd, 1H), 3.92 (m, 1H), 3.67-3.63 (m, 1H), 3.25 (m, 1H), 2.31-2.26 (m, 2H), 2.15-2.07 (m, 3H), 1.97-1.86 (m, 4H), 1.81-1.62 (m, 1H), 1.56-1.53 (m, 2H).

The following intermediates were synthesized as described for Intermediate 25 using the appropriate commercially available aryl bromide in Step 1 and Intermediate 1 or 2 in Step 2.

Intermediate 31

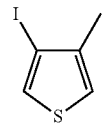

3-Iodo-4-methylthiphene

A mixture of 3-bromo-4-methylthiophene (25 g, 141 mmol), NaI (46.6 g, 310 mmol), copper iodide, (2.68 g, 14 mmol), and N,N'-dimethylethane-1,2-diamine (3 mL, 28 mmol) in n-BuOH (200 mL) was heated to 130° C. for 40 h. The reaction was monitored by NMR. The mixture was cooled and poured into NH$_4$OH, then extracted with hexanes (3×). The organic phases were combined, dried, and evaporated in order to remove all of the hexanes and half of the n-BuOH. The residue (still containing half of the n-BuOH) was purified by column chromatography (100% hexanes) to afford a solution of the desired in n-BuOH (amount of n-BuOH significantly reduced). This solution was chromatographed again through silica to afford 25 g of 3-iodo-4-

| Intermediate | Name | Structure |
|---|---|---|
| 26 | 4-(4-(But-1-yn-1-yl)phenyl)-1-(tetrahydro-2H-pyran-2-yl)-1H-pyrazole | 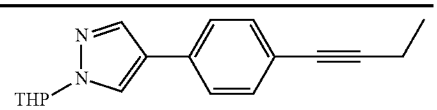 |
| 27 | 5-(4-(But-1-yn-1-yl)phenyl)-1-(tetrahydro-2H-pyran-2-yl)-1H-pyrazole | 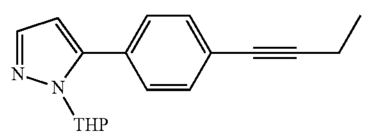 |
| 28 | 5-(3-(But-1-yn-1-yl)phenyl)-1-(tetrahydro-2H-pyran-2-yl)-1H-pyrazole | 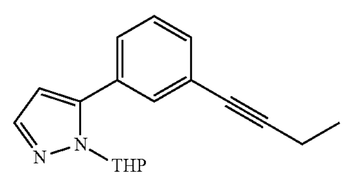 |
| 29 | 4-(3-(Cyclobutylethynyl)phenyl)-1-(tetrahydro-2H-pyran-2-yl)-1H-pyrazole | 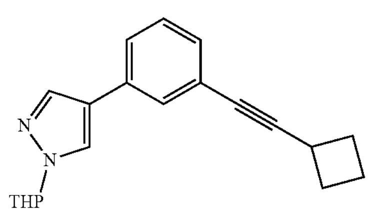 |
| 30 | 5-(4-(Cyclobutylethynyl)phenyl)-1-(tetrahydro-2H-pyran-2-yl)-1H-tetrazole | | methylthiophene as a colorless oil. $^1$H NMR (400 MHz, DMSO-d$_6$): δ 7.72 (s, 1H), 7.27 (s, 1H), 2.15 (s, 3H).

Note: The elution was concentrated by rota-evaporation and the water bath was kept below 35° C. to prevent loss of the desired compound.

Intermediate 32

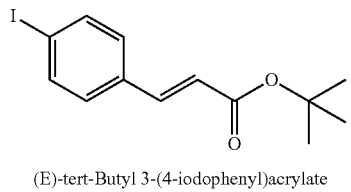

(E)-tert-Butyl 3-(4-iodophenyl)acrylate

A round-bottom flask equipped with a magnetic stir bar, an addition funnel, a rubber septum, and N$_2$ inlet was charged with 4-iodobenzaldehyde (10.0 g, 43.1 mmol), tert-butyl diethylphosphonoacetate (12.1 mL, 51.7 mmol), lithium chloride (3.7 g, 86.2 mmol) and anhydrous acetonitrile (86 mL). To this mixture, DBU (7.1 mL, 47.4 mmol) in anhydrous acetonitrile (14 mL) was slowly added dropwise via addition funnel and stirred at room temperature for 1.5 h. Upon completion, the reaction was concentrated and redissolved in dichloromethane and water. The layers were separated and the organic layer was washed with brine, dried over sodium sulfate and filtered. The crude material was concentrated and purified on a silica gel column eluted with 0-5% ethyl acetate in hexanes affording the title compound as pale yellow foam (13.2 g, 93%). $^1$H NMR (400 MHz, DMSO-d$_6$): δ 7.76 (d, 2H), 7.50-7.46 (m, 3H), 6.54 (d, 1H), 1.47 (s, 9H).

Intermediate 33

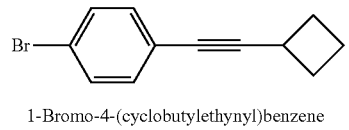

1-Bromo-4-(cyclobutylethynyl)benzene

Tetra-n-butylammonium fluoride (1M in THF, 15 mL, 15 mmol) was added to a mixture of 1-bromo-4-iodobenzene (3.93 mmol, 13.9 mmol), (cyclobutylethynyl)trimethylsilane (2.11 g, 13.9 mmol), Pd(PPh$_3$)$_4$ (1.6 g, 1.3 mmol), and copper iodide (527 mg, 2.7 mmol) in tetrahydrofuran (12 mL) and the mixture was stirred at room temperature for 2.25 h. The reaction mixture was diluted with water and extracted with ethyl acetate. The combined organics were washed with brine, dried over sodium sulfate, filtered, and concentrated to give the crude product. The residue was purified by flash chromatography on silica gel to afford 1.87 g of 1-bromo-4-(cyclobutylethynyl)benzene as a yellow solid. $^1$H NMR (400 MHz, DMSO-d$_6$): δ 7.53 (d, 2H), 7.31 (d, 2H), 3.27 (m, 1H), 2.33-2.25 (m, 2H), 2.17-2.07 (m, 2H), 1.97-1.83 (m, 2H).

Example 1

Procedure A (E)-3-(4-((E)-1-(4-(1H-Pyrazol-4-yl)phenyl)-2-cyclobutyl-2-phenylvinyl)phenyl)acrylic acid

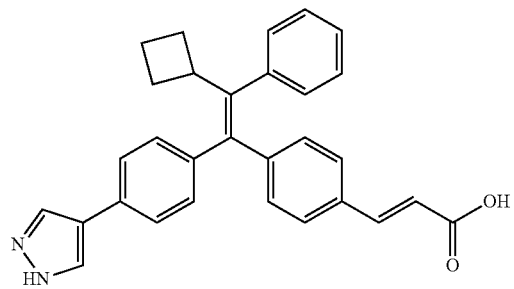 [SMILES: O=C(O)/C=C/c1ccc(/C(=C(\c2ccccc2)C2CCC2)c2ccc(-c3cn[nH]c3)cc2)cc1]

Step 1: (E)-Ethyl 3-(4-((E)-2-cyclobutyl-2-phenyl-1-(4-(1-(tetrahydro-2H-pyran-2-yl)-1H-pyrazol-4-yl)phenyl)vinyl)phenyl)acrylate

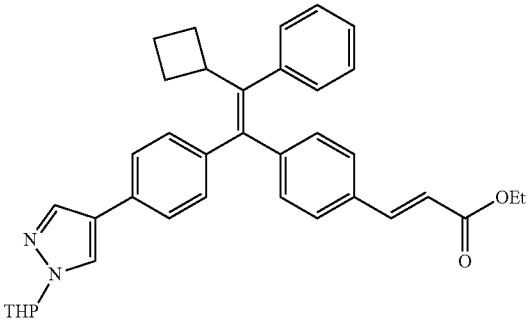

A mixture of 4-(4-(cyclobutylethynyl)phenyl)-1-(tetrahydro-2H-pyran-2-yl)-1H-pyrazole (Intermediate 25, 220 mg, 0.72 mmol), iodobenzene (0.24 mL, 2.15 mmol), (E)-(4-(3-ethoxy-3-oxoprop-1-en-1-yl)phenyl)boronic acid (473 mg, 2.15 mmol), potassium carbonate (297 mg, 2.15 mmol), and N,N-dimethylformamide/water (2:1, 36 mL) was degassed with 3 vacuum/N$_2$ cycles and then heated at 45° C. until it was a homogenous solution. Pd(PhCN)$_2$Cl$_2$ (3 mg, 0.0072 mmol) was added and the resulting mixture was stirred at 45° C. for 3 h (or until done by LCMS). Upon completion, the reaction mixture was cooled to room temperature, quenched with water, and extracted with ethyl acetate. The combined organics were washed with water, washed with brine, dried over sodium sulfate, filtered, and concentrated to give the crude product. The residue was purified by flash chromatography on silica gel to afford 280 mg of a mixture of the title compound (major) and the undesired regioisomer ((E)-ethyl 3-(4-((E)-1-cyclobutyl-2-phenyl-2-(4-(1-(tetrahydro-2H-pyran-2-yl)-1H-pyrazol-4-yl)phenyl)vinyl)phenyl)acrylate-minor). LCMS: 475 (M+H-THP)$^+$.

Step 2: (E)-Ethyl 3-(4-((E)-1-(4-(1H-pyrazol-4-yl)phenyl)-2-cyclobutyl-2-phenylvinyl)phenyl)acrylate

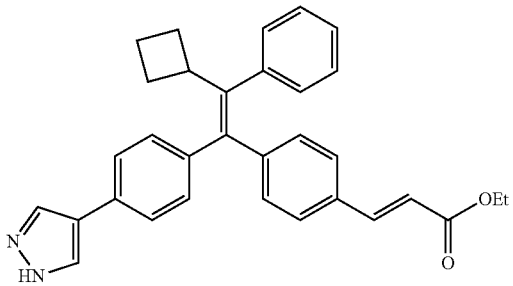 [SMILES: CCOC(=O)/C=C/c1ccc(/C(=C(\c2ccccc2)C2CCC2)c2ccc(-c3cn[nH]c3)cc2)cc1]

To a solution of (E)-ethyl 3-(4-((E)-2-cyclobutyl-2-phenyl-1-(4-(1-(tetrahydro-2H-pyran-2-yl)-1H-pyrazol-4-yl)phenyl)vinyl)phenyl)acrylate (280 mg, 0.5 mmol) in ethyl alcohol (5 mL) was added HCl (1.5 mL, 2M in diethyl ether) at room temperature. The resulting mixture was then heated at 70° C. for 1.5 h. Upon completion, the mixture was cooled to room temperature and concentrated to give the crude product. This crude material was used without further purification. LCMS: 475 (M+H)+.

Step 3: (E)-3-(4-((E)-1-(4-(1H-Pyrazol-4-yl)phenyl)-2-cyclobutyl-2-phenylvinyl)phenyl)acrylic acid

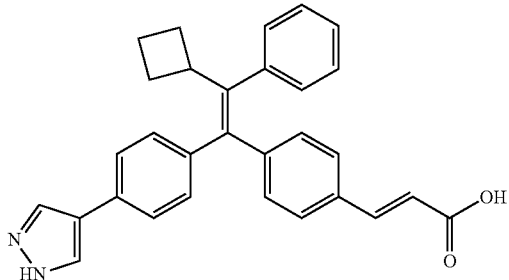 [SMILES: O=C(O)/C=C/c1ccc(/C(=C(\c2ccccc2)C2CCC2)c2ccc(-c3cn[nH]c3)cc2)cc1]

To a solution of (E)-ethyl 3-(4-((E)-1-(4-(1H-pyrazol-4-yl)phenyl)-2-cyclobutyl-2-phenylvinyl)phenyl)acrylate (crude from previous step) in THF-EtOH (1:1, 5 mL) was added LiOH (2M, 2.5 mL) at room temperature. The resulting mixture was stirred overnight. The reaction was monitored by LCMS. Upon completion, 2M aqueous HCl was added until pH was 3 and the mixture was diluted with water and extracted with dichloromethane. The combined organic layers were dried over sodium sulfate, filtered, and concentrated to give the crude product. This crude material was purified by reverse phase chromatography to afford 143 mg of the title compound as a white solid. $^1$H NMR (400 MHz, DMSO-$d_6$): δ OH and NH protons not observed, 8.06 (s, 2H), 7.61 (d, 2H), 7.38 (d, 1H), 7.32-7.08 (m, 9H), 6.91 (d, 2H), 6.33 (d, 1H), 3.44 (m, 1H), 1.85-1.79 (m, 4H), 1.70-1.51 (m, 1H), 1.38-1.23 (m, 1H); LCMS: 447 (M+H)+.

Example 2

Procedure B (E)-3-(4-((E)-2-(2-Chloro-4-fluorophenyl)-1-(4-(thiazol-5-yl)phenyl)but-1-en-1-yl)phenyl)acrylic acid

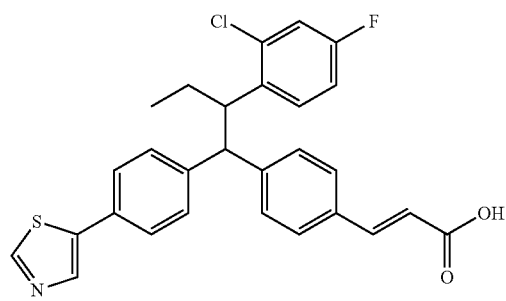 [SMILES: CCC(c1ccc(F)cc1Cl)C(c1ccc(/C=C/C(=O)O)cc1)c1ccc(-c2cncs2)cc1]

Step 1: (Z)-4-(2-(4,4,5,5-Tetramethyl-1,3,2-dioxaborolan-2-yl)-1-(4-(thiazol-5-yl)phenyl)but-1-en-1-yl)benzaldehyde

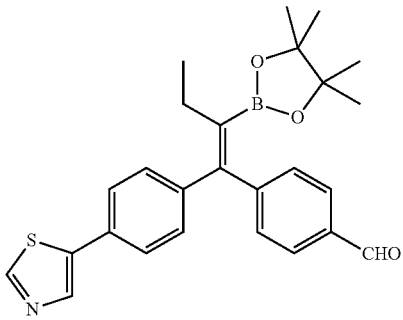 [SMILES: CC/C(B1OC(C)(C)C(C)(C)O1)=C(/c1ccc(C=O)cc1)c1ccc(-c2cncs2)cc1]

A mixture of 5-(4-(but-1-yn-1-yl)phenyl)thiazole (Intermediate 4, 240 mg, 1.13 mmol) and 4,4,4',4',5,5,5',5'-octamethyl-2,2'-bi(1,3,2-dioxaborolane) (286 mg, 1.13 mmol) in 2-methyltetrahydrofuran (5 mL) was degassed with 3 vacuum/$N_2$ cycles. Pt(PPh$_3$)$_4$ (14 mg, 0.011 mmol) was then added and the reaction mixture was heated to 90° C. for 2 h (or until done by LCMS). The reaction mixture was cooled to room temperature. Iodobenzaldehyde (261 mg, 1.13 mmol), cesium carbonate (734 mg, 2.26 mmol), water (0.15 mL), 2-methyltetrahydrofuran (5 mL), and Pd(PPh$_3$)$_2$Cl$_2$ (79 mg, 0.11 mmol) were added and the resulting mixture was stirred at room temperature overnight (or heated to 40° C. for 2 h). The reaction mixture was diluted with water and extracted with ethyl acetate. The combined organics were washed with brine, dried over sodium sulfate, filtered, and concentrated to give the crude product. The residue was purified by flash chromatography on silica gel to afford 329 mg of a mixture of the title compound (major) and the undesired regioisomer (minor). $^1$H NMR (400 MHz, DMSO-$d_6$) of major: δ 9.98 (s, 1H), 9.09 (s, 1H), 8.33 (s, 1H), 7.82 (d, 2H), 7.70 (d, 2H), 7.31 (d, 2H), 7.18 (d, 2H), 2.14 (q, 2H), 1.09 (s, 12H), 1.03 (t, 3H).

Step 2: (E)-4-(2-(2-Chloro-4-fluorophenyl)-1-(4-(thiazol-5-yl)phenyl)but-1-en-1-yl)benzaldehyde

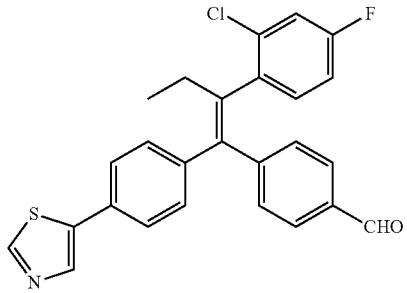 [SMILES: CC/C(=C(/c1ccc(C=O)cc1)c1ccc(-c2cncs2)cc1)c1ccc(F)cc1Cl]

A mixture of (Z)-4-(2-(4,4,5,5-tetramethyl-1,3,2-dioxaborolan-2-yl)-1-(4-(thiazol-5-yl)phenyl)but-1-en-1-yl)benzaldehyde (99 mg, 0.22 mmol), 2-chloro-4-fluoro-1-iodobenzene (114 mg, 0.44 mmol), Pd(PPh$_3$)$_2$Cl$_2$ (15 mg, 0.022 mmol), and KOH (6M, 0.2 mL, 1.32 mmol) in 1,4-dioxane (2.2 mL) was heated to 90° C. overnight. After cooling, ethyl acetate and brine were added to the reaction mixture and the two layers were separated. The organic layer was washed with more brine, dried over sodium sulfate, filtered and evaporated to dryness. The residue was purified by flash chromatography on silica gel to afford 68 mg of a mixture of the title compound (major) and the undesired regioisomer (minor). $^1$H NMR (400 MHz, DMSO-d$_6$) of major: δ 9.84 (s, 1H), 9.11 (s, 1H), 8.35 (s, 1H), 7.75 (d, 2H), 7.64 (d, 2H), 7.40-7.33 (m, 4H), 7.17 (m, 3H), 2.45 (q, 2H), 0.93 (t, 3H).

Step 3: (E)-Ethyl 3-(4-((E)-2-(2-chloro-4-fluorophenyl)-1-(4-(thiazol-5-yl)phenyl)but-1-en-1-yl)phenyl)acrylate

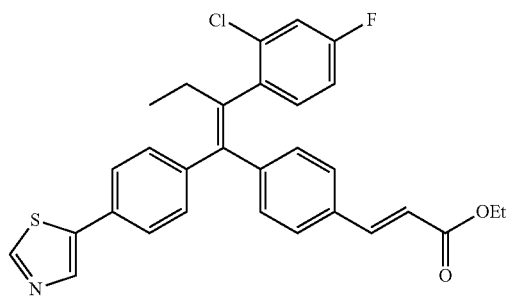 [SMILES: CCOC(=O)/C=C/c1ccc(/C(=C(/CC)c2ccc(F)cc2Cl)c2ccc(-c3cncs3)cc2)cc1]

1,8-Diazabicycloundec-7-ene (DBU, 33 uL, 0.22 mmol) was added to a solution of (E)-4-(2-(2-chloro-4-fluorophenyl)-1-(4-(thiazol-5-yl)phenyl)but-1-en-1-yl)benzaldehyde (68 mg, 0.16 mmol), ethyl 2-(diethoxyphosphoryl)acetate (47 uL, 0.24 mmol), and lithium chloride (13 mg, 0.32 mmol) in acetonitrile (3 mL) and the reaction mixture was stirred at room temperature overnight. The reaction mixture was then absorbed on silica gel and purified by flash chromatography on silica gel to afford 67 mg of a mixture of the title compound (major) and the undesired regioisomer (minor). The major isomer was used for the next step without further purification.

Step 4: (E)-3-(4-((E)-2-(2-Chloro-4-fluorophenyl)-1-(4-(thiazol-5-yl)phenyl)but-1-en-1-yl)phenyl)acrylic acid

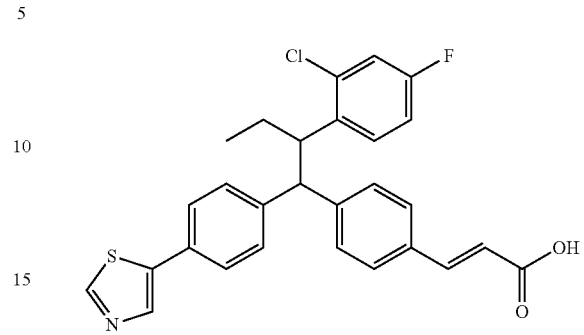

The title compound was synthesized as described in Example 1, Step 3 using (E)-ethyl 3-(4-((E)-2-(2-chloro-4-fluorophenyl)-1-(4-(thiazol-5-yl)phenyl)but-1-en-1-yl)phenyl)acrylate as the starting material. $^1$H NMR (400 MHz, DMSO-d$_6$): δ CO$_2$H proton not observed, 9.10 (s, 1H), 8.35 (s, 1H), 7.74 (d, 2H), 7.44-7.33 (m, 7H), 7.14 (m, 1H), 6.95 (d, 2H), 6.38 (d, 1H), 2.39 (q, 2H), 0.91 (t, 3H). LCMS: 490 (M+H)$^+$.

Example 3

Procedure C (E)-3-(4-((E)-1-(4-(1H-Pyrazol-4-yl)phenyl)-2-(2-chloro-4-cyanophenyl)-2-cyclobutylvinyl)phenyl)acrylic acid

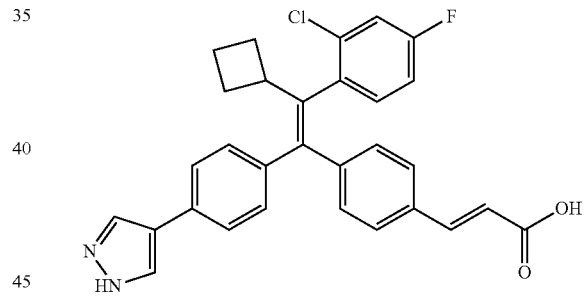

Step 1: (E)-4-(2-Cyclobutyl-2-(5,5-dimethyl-1,3,2-dioxaborinan-2-yl)-1-(4-(1-(tetrahydro-2H-pyran-2-yl)-1H-pyrazol-4-yl)phenyl)vinyl)benzaldehyde

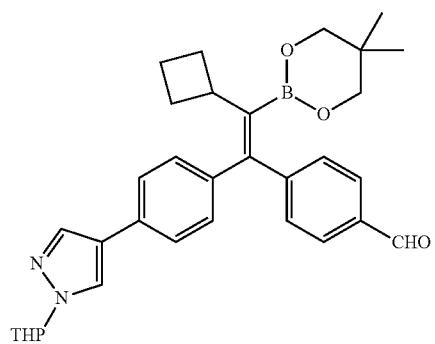

A mixture of 4-(4-(cyclobutylethynyl)phenyl)-1-(tetrahydro-2H-pyran-2-yl)-1H-pyrazole (Intermediate 25, 2.32 g, 7.58 mmol) and 5,5,5',5'-tetramethyl-2,2'-bi(1,3,2-dioxaborinane) (1.88 g, 8.34 mmol) in 1,4-dioxane (15 mL) was degassed with 3 vacuum/N₂ cycles. Ethylenebis(triphenylphosphine)platinum (170 mg, 0.23 mmol) was then added and the reaction mixture was heated to 90° C. for 1 h (or until the completion judged by LCMS). The reaction mixture was cooled to room temperature. Iodobenzaldehyde (1.75 g, 7.58 mmol), cesium carbonate (4.9 g, 15.16 mmol), water (0.45 mL), 1,4-dioxane (15 mL), and Pd(PPh₃)₂Cl₂ (532 mg, 0.75 mmol) were added and the resulting mixture was stirred at room temperature overnight. The reaction mixture was diluted with water and extracted with ethyl acetate. The combined organics were washed with brine, dried over sodium sulfate, filtered, and concentrated to give the crude product. The residue was purified by flash chromatography on silica gel to afford 3 g of a mixture of the title compound (major), undesired regioisomer (minor), and bis-aldehyde (minor). ¹H NMR (400 MHz, DMSO-d₆) of major regioisomer: δ 9.95 (s, 1H), 8.30 (s, 1H), 7.91 (s, 1H), 7.81 (d, 2H), 7.59 (d, 2H), 7.32 (d, 2H), 7.01 (d, 2H), 5.40 (d, 1H), 3.94 (m, 1H), 3.64 (m, 1H), 3.49 (s, 4H), 3.19 (m, 1H), 2.15-1.52 (m, 12H), 0.81 (s, 6H).

Step 2: (Z)-3-Chloro-4-(1-cyclobutyl-2-(4-formylphenyl)-2-(4-(1-(tetrahydro-2H-pyran-2-yl)-1H-pyrazol-4-yl)phenyl)vinyl)benzonitrile

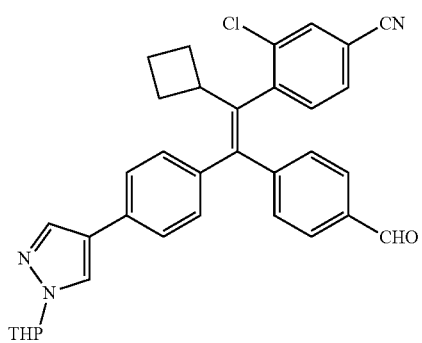

The title compound was synthesized as described in Example 2, Step 2 using (E)-4-(2-cyclobutyl-2-(5,5-dimethyl-1,3,2-dioxaborinan-2-yl)-1-(4-(1-(tetrahydro-2H-pyran-2-yl)-1H-pyrazol-4-yl)phenyl)vinyl)benzaldehyde and 4-bromo-3-chlorobenzonitrile as the starting materials. ¹H NMR (400 MHz, DMSO-d₆): δ 9.81 (s, 1H), 8.35 (s, 1H), 7.96 (d, 2H), 7.75 (d, 1H), 7.67-7.62 (m, 4H), 7.56 (d, 1H), 7.26-7.20 (m, 4H), 5.41 (d, 1H), 3.93 (m, 1H), 3.64 (m, 1H), 3.51 (m, 1H), 2.10 (m, 1H), 1.98-1.84 (m, 4H), 1.69-1.52 (m, 6H), 1.41 (m, 1H); LCMS: 464 (M+H-THP)⁺.

Step 3: (E)-3-(4-((E)-1-(4-(1H-Pyrazol-4-yl)phenyl)-2-(2-chloro-4-cyanophenyl)-2-cyclobutylvinyl)phenyl)acrylic acid

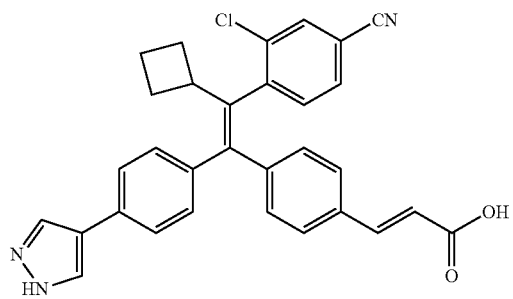

The title compound was synthesized as described in Example 2, Step 3 using (Z)-3-chloro-4-(1-cyclobutyl-2-(4-formylphenyl)-2-(4-(1-(tetrahydro-2H-pyran-2-yl)-1H-pyrazol-4-yl)phenyl)vinyl)benzonitrile as the starting material. Followed by THP-deprotection as in Example 1, Step 2 using (E)-ethyl 3-(4-((E)-2-(2-chloro-4-cyanophenyl)-2-cyclobutyl-1-(4-(1-(tetrahydro-2H-pyran-2-yl)-1H-pyrazol-4-yl)phenyl)vinyl)phenyl)acrylate as the starting material. Followed by ester hydrolysis as in Example 1, Step 3 using (E)-ethyl 3-(4-((E)-1-(4-(1H-pyrazol-4-yl)phenyl)-2-(2-chloro-4-cyanophenyl)-2-cyclobutylvinyl)phenyl)acrylate as the starting material. ¹H NMR (400 MHz, DMSO-d₆): δ NH and CO₂H protons not observed, 8.06 (s, 2H), 7.97 (s, 1H), 7.75 (d, 1H), 7.63 (d, 2H), 7.53 (d, 1H), 7.41-7.34 (m, 3H), 7.21 (d, 2H), 7.00 (d, 2H), 6.36 (d, 1H), 3.47 (m, 1H), 1.87-1.78 (m, 3H), 1.68-1.56 (m, 2H), 1.43-1.35 (m, 1H); LCMS: 506 (M+H)⁺.

Example 4

Procedure D (E)-3-(4-((E)-2-(2-Chloro-4-methoxyphenyl)-2-cyclobutyl-1-(4-morpholinophenyl)vinyl)phenyl)acrylic acid

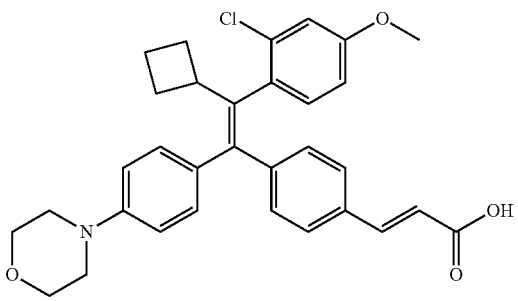 [SMILES: COc1ccc(/C(=C(\c2ccc(/C=C/C(=O)O)cc2)c2ccc(N3CCOCC3)cc2)C2CCC2)c(Cl)c1]

Step 1: (E)-tert-Butyl 3-(4-((Z)-2-cyclobutyl-2-(5,5-dimethyl-1,3,2-dioxaborinan-2-yl)-1-(4-morpholinophenyl)vinyl)phenyl)acrylate

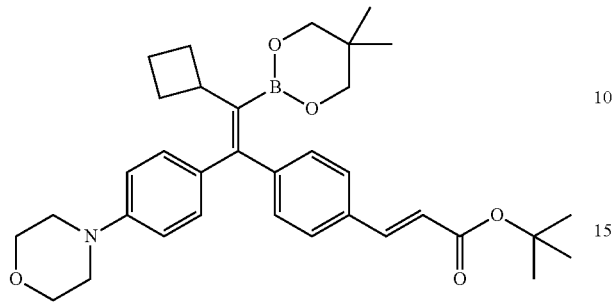

A mixture of 4-(4-(cyclobutylethynyl)phenyl)morpholine (Intermediate 15, 1.84 g, 7.63 mmol) and 5,5,5',5'-tetramethyl-2,2'-bi(1,3,2-dioxaborinane) (1.89 g, 8.39 mmol) in 1,4-dioxane (15 mL) was degassed with 3 vacuum/$N_2$ cycles. Ethylenebis(triphenylphosphine)platinum (228 mg, 0.30 mmol) was then added and the reaction mixture was heated to 90° C. overnight (or until done by LCMS). The reaction mixture was cooled to room temperature. (E)-tert-butyl 3-(4-iodophenyl)acrylate (Intermediate 32, 2.27 g, 6.87 mmol), cesium carbonate (4.9 g, 15.26 mmol), water (0.45 mL), 1,4-dioxane (25 mL), and Pd(PPh$_3$)$_2$Cl$_2$ (535 mg, 0.76 mmol) were added and the resulting mixture was stirred at room temperature for 5 h (or until the completion judged by LCMS). The reaction mixture was diluted with water and extracted with ethyl acetate. The combined organics were washed with brine, dried over sodium sulfate, filtered, and concentrated to give the crude product. The residue was purified by flash chromatography on silica gel to afford 1 g of pure desired regioisomer. $^1$H NMR (400 MHz, DMSO-d$_6$): δ 7.55 (d, 2H), 7.48 (d, 1H), 7.08 (d, 2H), 6.90 (d, 2H), 6.85 (d, 2H), 6.42 (d, 1H), 3.72 (m, 4H), 3.31 (s, 4H), 3.2 (m, 1H), 3.12 (m, 4H), 2.11 (m, 2H), 1.89 (m, 2H), 1.68 (m, 2H), 1.48 (s, 9H), 0.84 (s, 6H).

Step 2: (E)-tert-Butyl 3-(4-((E)-2-(2-chloro-4-methoxyphenyl)-2-cyclobutyl-1-(4-morpholinophenyl)vinyl)phenyl)acrylate

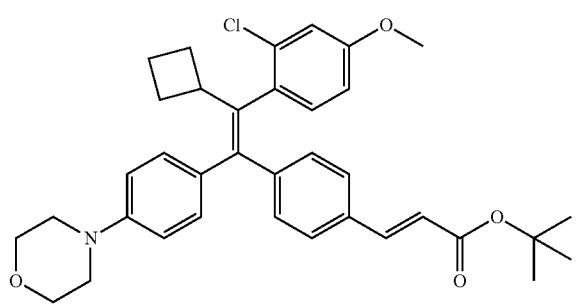 [SMILES: COc1ccc(/C(=C(\c2ccc(/C=C/C(=O)OC(C)(C)C)cc2)c2ccc(N3CCOCC3)cc2)C2CCC2)c(Cl)c1]

A mixture of (E)-tert-butyl 3-(4-((Z)-2-cyclobutyl-2-(5,5-dimethyl-1,3,2-dioxaborinan-2-yl)-1-(4-morpholinophenyl)vinyl)phenyl)acrylate (754 mg, 1.64 mmol), 1-bromo-2-chloro-4-methoxybenzene (545 mg, 2.46 mmol), Pd(PPh$_3$)$_2$Cl$_2$ (115 mg, 0.16 mmol), and KOH (6M, 1.6 mL, 9.9 mmol) in 1,4-dioxane (10 mL) was heated to 90° C. for 1 h. After cooling, ethyl acetate and brine were added to the reaction mixture and the two layers were separated. The organic layer was washed with more brine, dried over sodium sulfate, filtered and evaporated to dryness. The residue was purified by flash chromatography on silica gel to afford 520 mg of the title compound as a yellow foam. $^1$H NMR (400 MHz, DMSO-d$_6$): δ 7.37-7.33 (m, 3H), 7.11 (d, 1H), 7.04 (d, 2H), 6.95-6.90 (m, 5H), 6.82 (m, 1H), 6.34 (d, 1H), 3.74 (m, 4H), 3.71 (s, 3H), 3.42 (m, 1H), 3.13 (m, 4H), 1.87 (m, 3H), 1.67 (m, 2H), 1.46 (m, 1H), 1.43 (s, 9H); LCMS: 586 (M+H)$^+$.

Step 3: (E)-3-(4-((E)-2-(2-Chloro-4-methoxyphenyl)-2-cyclobutyl-1-(4-morpholinophenyl)vinyl)phenyl)acrylic acid

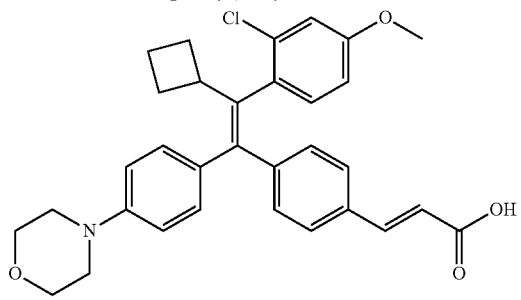

(E)-tert-Butyl 3-(4-((E)-2-(2-chloro-4-methoxyphenyl)-2-cyclobutyl-1-(4-morpholinophenyl)vinyl)phenyl)acrylate (520 mg, 0.88 mmol) in HCl (4M in 1,4-dioxane, 5 mL) was stirred at room temperature for 4 h. The reaction mixture was diluted with water and extracted with dichloromethane. The combined organics were washed with brine, dried over sodium sulfate, filtered, and concentrated to give the crude product. The residue was purified by reverse phase chromatography to afford 370 mg of the TFA salt of the title compound as a yellow foam. The foam was re-dissolved in HCl (4M in 1,4-dioxane, 1 mL) and stirred at room temperature for 15 min. The solvent was then removed and the residue was dried to afford the HCl salt of the title compound as a pink foam. $^1$H NMR (400 MHz, DMSO-d$_6$): δ Acidic (CO$_2$H and NH) protons not observed, 7.38 (d, 1H), 7.35 (d, 2H), 7.13-7.05 (m, 5H), 6.94 (d, 2H), 6.92 (d, 1H), 6.82 (dd, 1H), 6.35 (d, 1H), 3.79 (m, 4H), 3.71 (s, 3H), 3.43 (m, 1H), 3.20 (m, 4H), 1.84 (m, 3H), 1.65 (m, 2H), 1.36 (m, 1H); LCMS: 530 (M+H)$^+$.

Example 5

Procedure E (E)-3-(4-((E)-2-(2-Chloro-4-cyanophenyl)-2-cyclobutyl-1-(4-(thiazol-5-yl)phenyl)vinyl)phenyl)acrylic acid

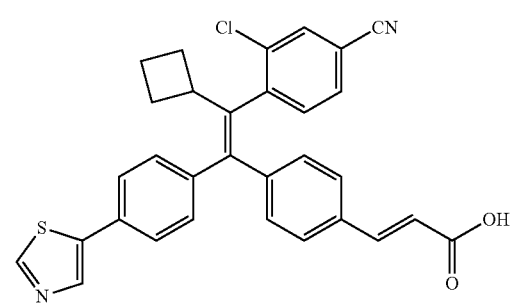 [SMILES: N#Cc1ccc(/C(=C(\c2ccc(/C=C/C(=O)O)cc2)c2ccc(-c3cncs3)cc2)C2CCC2)c(Cl)c1]

Step 1: (E)-3-Chloro-4-(1-cyclobutyl-2-(4-formyl-phenyl)-2-(4-(thiazol-5-yl)phenyl)vinyl)benzonitrile

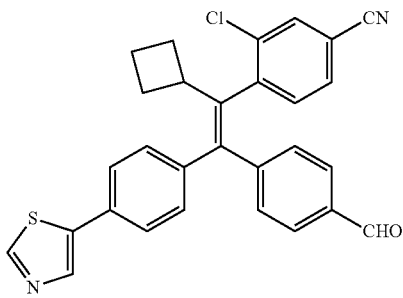 [SMILES: N#Cc1ccc(/C(=C(\c2ccc(C=O)cc2)c2ccc(-c3cncs3)cc2)C2CCC2)c(Cl)c1]

The title compound was synthesized as described in Example 3, Step 1 using 5-(4-(cyclobutylethynyl)phenyl)thiazole as the starting material. Followed by arylation as in Example 2, Step 2 using (Z)-4-(2-cyclobutyl-2-(5,5-dimethyl-1,3,2-dioxaborinan-2-yl)-1-(4-(thiazol-5-yl)phenyl)vinyl)benzaldehyde and 4-bromo-3-chlorobenzonitrile as the starting materials. LCMS: 481 (M+H)$^+$.

Step 2: (E)-tert-Butyl 3-(4-((E)-2-(2-chloro-4-cyanophenyl)-2-cyclobutyl-1-(4-(thiazol-5-yl)phenyl)vinyl)phenyl)acrylate

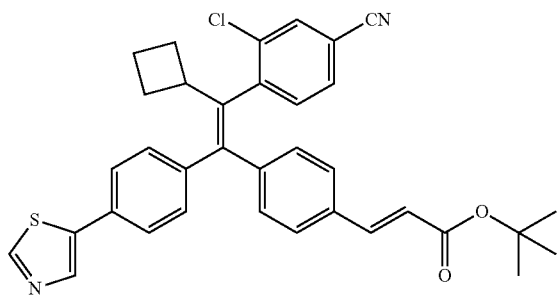 [SMILES: CC(C)(C)OC(=O)/C=C/c1ccc(/C(=C(\c2ccc(C#N)cc2Cl)C2CCC2)c2ccc(-c3cncs3)cc2)cc1]

1,8-Diazabicycloundec-7-ene (DBU, 50 uL, 0.33 mmol) was added to a solution of (E)-3-chloro-4-(1-cyclobutyl-2-(4-formylphenyl)-2-(4-(thiazol-5-yl)phenyl)vinyl)benzonitrile (116 mg, 0.24 mmol), tert-butyl 2-(diethoxyphosphoryl)acetate (85 uL, 0.36 mmol), and lithium chloride (20 mg, 0.48 mmol) in acetonitrile (3 mL) and the reaction mixture was stirred at room temperature for 3 h. The reaction mixture was diluted with water and extracted with ethyl acetate. The combined organics were washed with brine, dried over sodium sulfate, filtered, and concentrated to give the crude product that was used without further purification. LCMS: 579 (M+H)$^+$.

Step 3: (E)-3-(4-((E)-2-(2-Chloro-4-cyanophenyl)-2-cyclobutyl-1-(4-(thiazol-5-yl)phenyl)vinyl)phenyl)acrylic acid

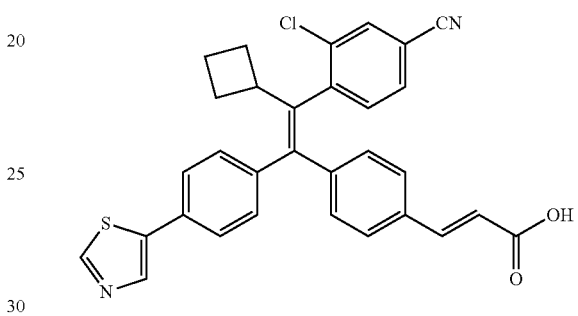

The title compound was synthesized as described in Example 4, Step 3 using (E)-tert-butyl 3-(4-((E)-2-(2-chloro-4-cyanophenyl)-2-cyclobutyl-1-(4-(thiazol-5-yl)phenyl)vinyl)phenyl)acrylate as the starting material. $^1$H NMR (400 MHz, DMSO-d$_6$): δ CO$_2$H proton not observed, 9.10 (s, 1H), 8.36 (s, 1H), 8.00 (s, 1H), 7.80-7.73 (m, 3H), 7.55 (d, 1H), 7.42-7.31 (m, 5H), 7.01 (d, 2H), 6.38 (d, 1H), 3.46 (m, 1H), 1.86 (m, 3H), 1.72 (m, 2H), 1.41 (m, 1H). LCMS: 523 (M+H)$^+$.

The following examples were synthesized following procedures A-E using the appropriate alkyne starting material in Step 1.

| Ex. | Proc | SM | Name | Structure | LC-MS |
|---|---|---|---|---|---|
| 6 | A | 27 | (E)-3-(4-((E)-1-(4-(1H-Pyrazol-5-yl)phenyl)-2-phenylbut-1-en-1-yl)phenyl)acrylic acid | 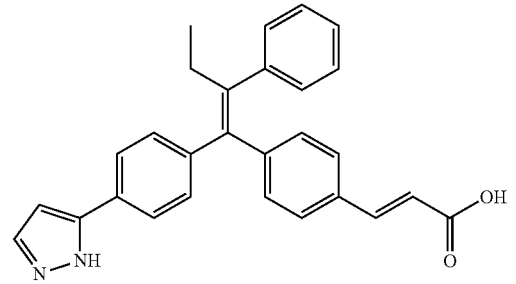 [SMILES: CC/C(=C(/c1ccc(/C=C/C(=O)O)cc1)c1ccc(-c2ccn[nH]2)cc1)c1ccccc1] | 421 |

-continued

| Ex. | Proc | SM | Name | Structure | LC-MS |
|---|---|---|---|---|---|
| 7 | A | 28 | (E)-3-(4-((E)-1-(3-(1H-Pyrazol-5-yl)phenyl)-2-phenylbut-1-en-1-yl)phenyl)acrylic acid | 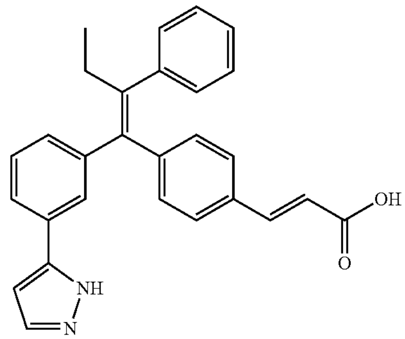 [SMILES: CC/C(=C(/c1ccc(/C=C/C(=O)O)cc1)c1cccc(-c2ccn[nH]2)c1)c1ccccc1] | 421 |
| 8[a] | A | 5 | (E)-3-(4-((E)-2-Phenyl-1-(4-(thiazol-2-yl)phenyl)but-1-en-1-yl)phenyl)acrylic acid | 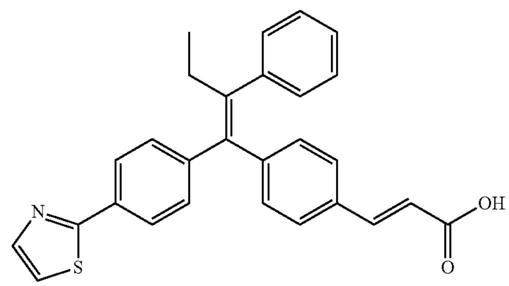 [SMILES: CC/C(=C(/c1ccc(/C=C/C(=O)O)cc1)c1ccc(-c2nccs2)cc1)c1ccccc1] | 438 |
| 9[a] | A | 4 | (E)-3-(4-((E)-2-Phenyl-1-(4-(thiazol-5-yl)phenyl)but-1-en-1-yl)phenyl)acrylic acid | 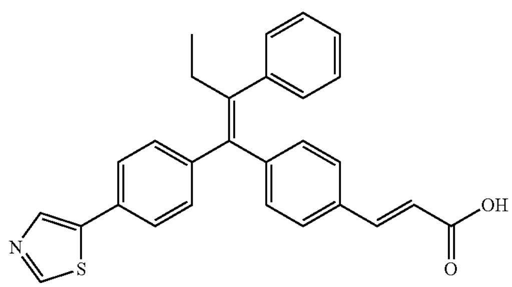 [SMILES: CC/C(=C(/c1ccc(/C=C/C(=O)O)cc1)c1ccc(-c2cncs2)cc1)c1ccccc1] | 438 |
| 10[a] | A | 6 | (E)-3-(4-((E)-2-Phenyl-1-(4-(thiazol-4-yl)phenyl)but-1-en-1-yl)phenyl)acrylic acid | 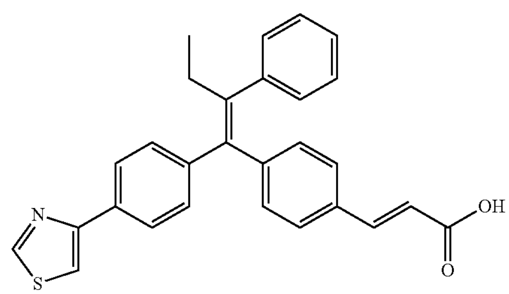 [SMILES: CC/C(=C(/c1ccc(/C=C/C(=O)O)cc1)c1ccc(-c2cscn2)cc1)c1ccccc1] | 438 |
| 11[a] | A | 12 | (E)-3-(4-((E)-2-Phenyl-1-(3-(thiazol-2-yl)phenyl)but-1-en-1-yl)phenyl)acrylic acid | 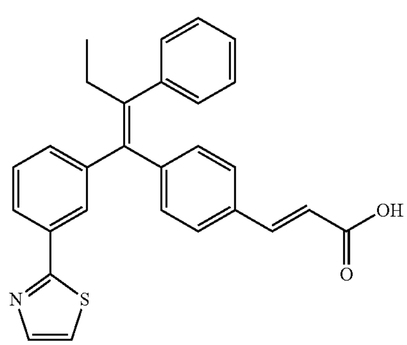 [SMILES: CC/C(=C(/c1ccc(/C=C/C(=O)O)cc1)c1cccc(-c2nccs2)c1)c1ccccc1] | 438 |

-continued

| Ex. | Proc | SM | Name | Structure | LC-MS |
|---|---|---|---|---|---|
| 12[a] | A | 13 | (E)-3-(4-((E)-2-Phenyl-1-(3-(thiazol-4-yl)phenyl)but-1-en-1-yl)phenyl)acrylic acid | 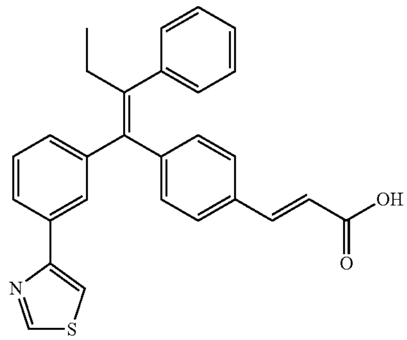 [SMILES: CC/C(=C(/c1ccc(/C=C/C(=O)O)cc1)c1cccc(-c2cscn2)c1)c1ccccc1] | 438 |
| 13[a] | A | 3 | (E)-3-(4-((E)-2-Cyclobutyl-2-phenyl-1-(4-(thiazol-5-yl)phenyl)vinyl)phenyl)-acrylic acid | 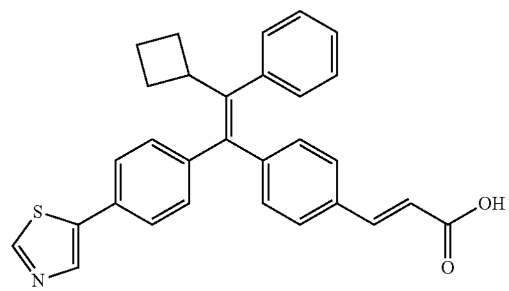 [SMILES: O=C(O)/C=C/c1ccc(/C(=C(\c2ccccc2)C2CCC2)c2ccc(-c3cncs3)cc2)cc1] | 464 |
| 14[a] | A | 22 | (E)-3-(4-((E)-2-Phenyl-1-(4-(pyridin-3-yl)phenyl)but-1-en-1-yl)phenyl)acrylic acid | 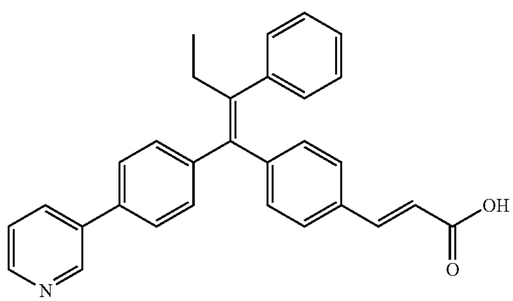 [SMILES: CC/C(=C(/c1ccc(/C=C/C(=O)O)cc1)c1ccc(-c2cccnc2)cc1)c1ccccc1] | 432 |
| 15[a] | A | 7 | (E)-3-(4-((E)-1-(4-(Isothiazol-4-yl)phenyl)-2-phenylbut-1-en-1-yl)phenyl)acrylic acid | 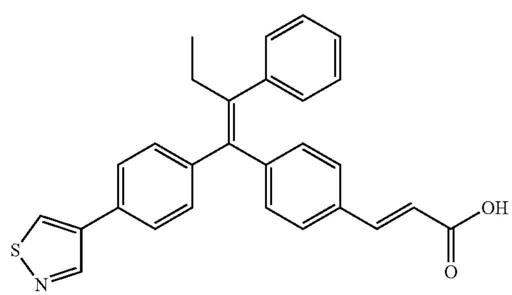 [SMILES: CC/C(=C(/c1ccc(/C=C/C(=O)O)cc1)c1ccc(-c2cnsc2)cc1)c1ccccc1] | 438 |
| 16[a] | A | 16 | (E)-3-(4-((E)-1-(4-Morpholinophenyl)-2-phenylbut-1-en-1-yl)phenyl)acrylic acid | 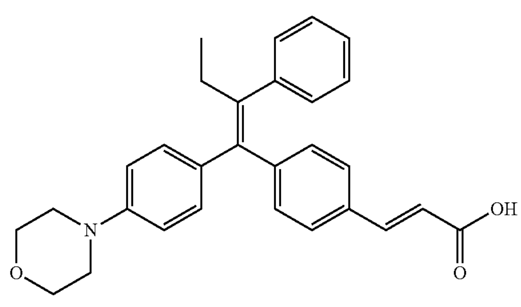 [SMILES: CC/C(=C(/c1ccc(/C=C/C(=O)O)cc1)c1ccc(N2CCOCC2)cc1)c1ccccc1] | 440 |

-continued

| Ex. | Proc | SM | Name | Structure | LC-MS |
|---|---|---|---|---|---|
| 17[a] | A | 17 | (E)-3-(4-((E)-1-(4-(1H-Imidazol-1-yl)phenyl)-2-phenylbut-1-en-1-yl)phenyl)acrylic acid | 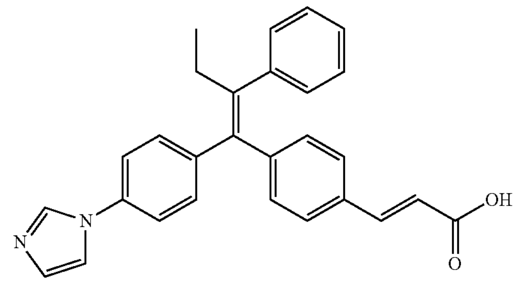 [SMILES: CC/C(=C(/c1ccc(/C=C/C(=O)O)cc1)c1ccc(-n2ccnc2)cc1)c1ccccc1] | 421 |
| 18[a] | A | 18 | (E)-3-(4-((E)-1-(4-(Oxazol-5-yl)phenyl)-2-phenylbut-1-en-1-yl)phenyl)acrylic acid | 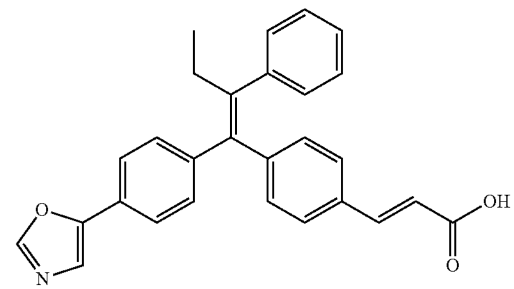 [SMILES: CC/C(=C(/c1ccc(/C=C/C(=O)O)cc1)c1ccc(-c2cnco2)cc1)c1ccccc1] | 422 |
| 19[a] | A | 11 | (E)-3-(4-((E)-1-(4-(1-Methyl-1H-pyrazol-4-yl)phenyl)-2-phenylbut-1-en-1-yl)phenyl)acrylic acid | 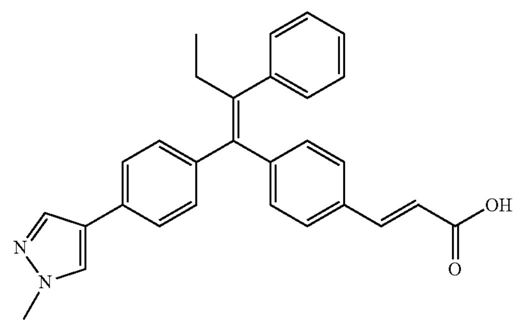 [SMILES: CC/C(=C(/c1ccc(/C=C/C(=O)O)cc1)c1ccc(-c2cnn(C)c2)cc1)c1ccccc1] | 435 |
| 20[a] | A | 8 | (E)-3-(4-((E)-1-(2-Fluoro-4-(thiazol-5-yl)phenyl)-2-phenylbut-1-en-1-yl)phenyl)acrylic acid | 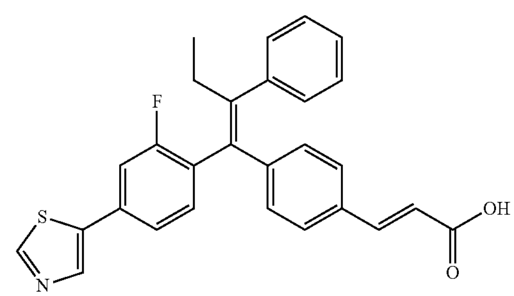 [SMILES: CC/C(=C(/c1ccc(/C=C/C(=O)O)cc1)c1ccc(-c2cncs2)cc1F)c1ccccc1] | 456 |
| 21[a] | A | 9 | (E)-3-(4-((E)-1-(3-Fluoro-4-(thiazol-5-yl)phenyl)-2-phenylbut-1-en-1-yl)phenyl)acrylic acid | 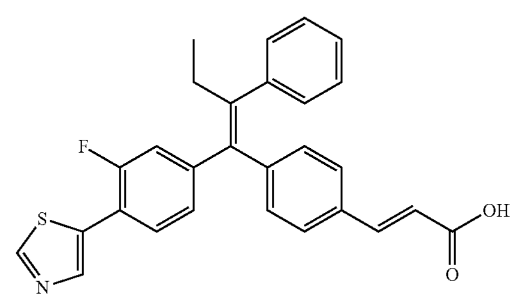 [SMILES: CC/C(=C(/c1ccc(/C=C/C(=O)O)cc1)c1ccc(-c2cncs2)c(F)c1)c1ccccc1] | 456 |

-continued

| Ex. | Proc | SM | Name | Structure | LC-MS |
|---|---|---|---|---|---|
| 22 | A | 25 | (E)-3-(4-((E)-1-(4-(1H-Pyrazol-4-yl)phenyl)-2-phenylbut-1-en-1-yl)phenyl)acrylic acid | 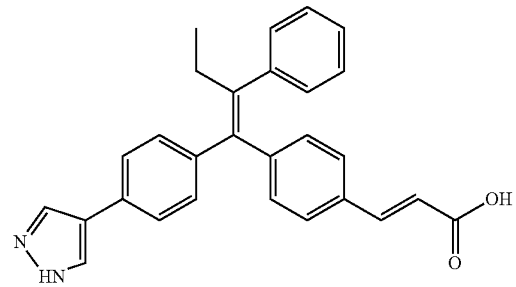 [SMILES: CC/C(=C(/c1ccc(/C=C/C(=O)O)cc1)c1ccc(-c2cn[nH]c2)cc1)c1ccccc1] | 421 |
| 23[a] | A | 19 | (E)-3-(4-((E)-1-(4-(4-Methylpiperazin-1-yl)phenyl)-2-phenylbut-1-en-1-yl)phenyl)acrylic acid | 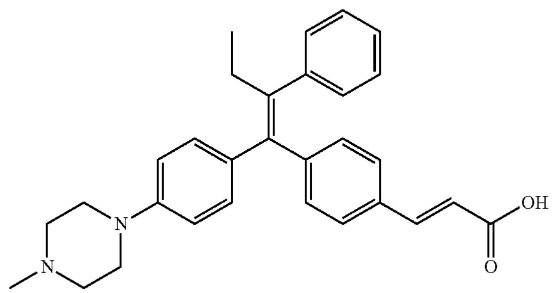 [SMILES: CC/C(=C(/c1ccc(/C=C/C(=O)O)cc1)c1ccc(N2CCN(C)CC2)cc1)c1ccccc1] | 453 |
| 24[a] | A | 20 | (E)-3-(4-((E)-2-Phenyl-1-(4-(piperidin-1-yl)phenyl)but-1-en-1-yl)phenyl)acrylic acid | 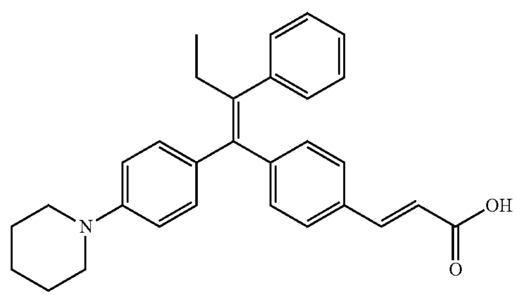 [SMILES: CC/C(=C(/c1ccc(/C=C/C(=O)O)cc1)c1ccc(N2CCCCC2)cc1)c1ccccc1] | 438 |
| 25[a] | A | 10 | (E)-3-(4-((E)-2-Cyclobutyl-2-phenyl-1-(5-(thiazol-5-yl)pyridin-2-yl)vinyl)phenyl)acrylic acid | 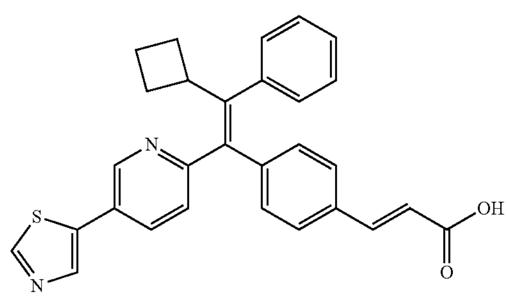 | 465 |
| 26 | A | 29 | (E)-3-(4-((E)-1-(3-(1H-Pyrazol-4-yl)phenyl)-2-cyclobutyl-2-phenylvinyl)phenyl)-acrylic acid | 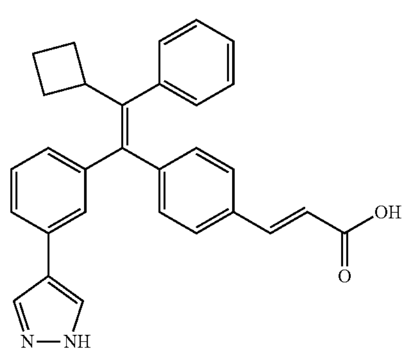 [SMILES: O=C(O)/C=C/c1ccc(/C(=C(\c2ccccc2)C2CCC2)c2cccc(-c3cn[nH]c3)c2)cc1] | 447 |

| Ex. | Proc | SM | Name | Structure | LC-MS |
|---|---|---|---|---|---|
| 27[a] | A | 21 | (E)-3-(4-((E)-2-Cyclobutyl-1-(4-(isoxazol-3-yl)phenyl)-2-phenylvinyl)phenyl)-acrylic acid | 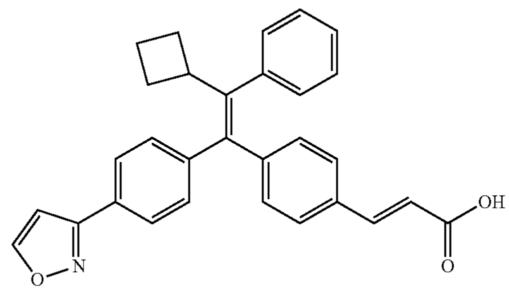 [SMILES: O=C(O)/C=C/c1ccc(/C(=C(\c2ccccc2)C2CCC2)c2ccc(-c3ccon3)cc2)cc1] | 448 |
| 28 | B | 4 | (E)-3-(4-((E)-2-(3-Chloropyridin-4-yl)-1-(4-(thiazol-5-yl)phenyl)but-1-en-1-yl)phenyl)acrylic acid | 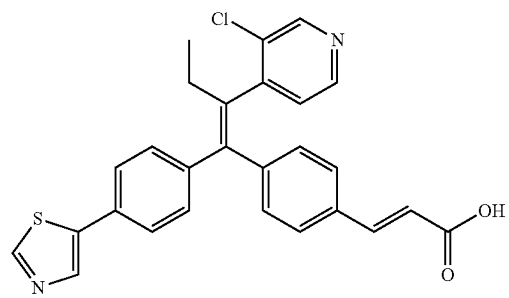 [SMILES: CC/C(=C(/c1ccc(/C=C/C(=O)O)cc1)c1ccc(-c2cncs2)cc1)c1ccncc1Cl] | 473 |
| 29 | B | 4 | (E)-3-(4-((E)-2-(2-Chlorophenyl)-1-(4-(thiazol-5-yl)phenyl)but-1-en-1-yl)phenyl)acrylic acid | 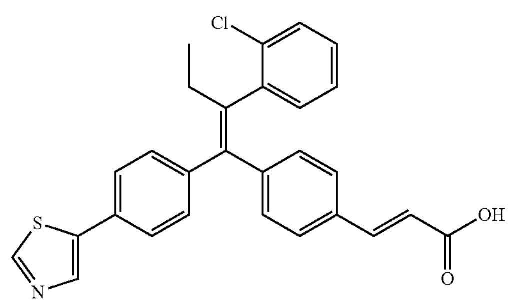 [SMILES: CC/C(=C(/c1ccc(/C=C/C(=O)O)cc1)c1ccc(-c2cncs2)cc1)c1ccccc1Cl] | 472 |
| 30 | B | 4 | (E)-3-(4-((E)-2-(3-Methoxyphenyl)-1-(4-(thiazol-5-yl)phenyl)but-1-en-1-yl)phenyl)acrylic acid | 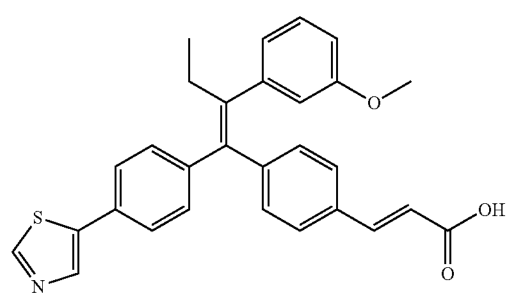 [SMILES: CC/C(=C(/c1ccc(/C=C/C(=O)O)cc1)c1ccc(-c2cncs2)cc1)c1cccc(OC)c1] | 468 |
| 31 | B | 4 | (E)-3-(4-((E)-2-(Benzofuran-5-yl)-1-(4-(thiazol-5-yl)phenyl)but-1-en-1-yl)phenyl)acrylic acid | 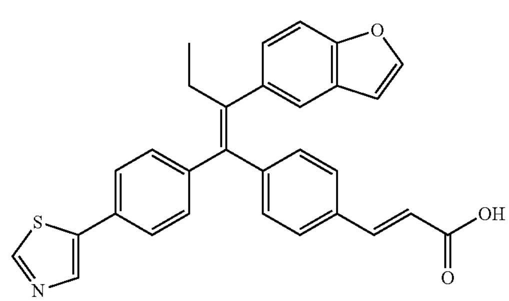 [SMILES: CC/C(=C(/c1ccc(/C=C/C(=O)O)cc1)c1ccc(-c2cncs2)cc1)c1ccc2occc2c1] | 478 |

-continued

| Ex. | Proc | SM | Name | Structure | LC-MS |
|---|---|---|---|---|---|
| 32 | B | 4 | (E)-3-(4-((E)-2-(4-Methylthiophen-3-yl)-1-(4-(thiazol-5-yl)phenyl)but-1-en-1-yl)phenyl)acrylic acid | 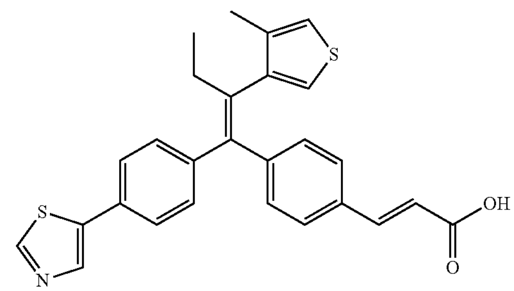 [SMILES: CC/C(=C(/c1ccc(/C=C/C(=O)O)cc1)c1ccc(-c2cncs2)cc1)c1cscc1C] | 458 |
| 33 | B | 3 | (E)-3-(4-((E)-2-(2-Chloro-4-fluorophenyl)-2-cyclobutyl-1-(4-(thiazol-5-yl)phenyl)vinyl)phenyl)-acrylic acid | 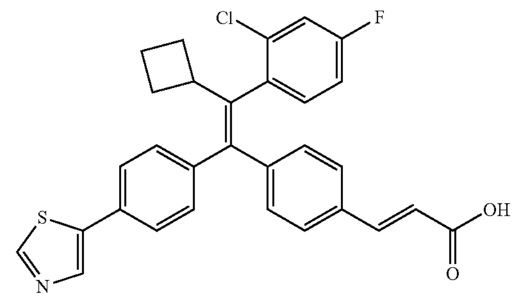 [SMILES: O=C(O)/C=C/c1ccc(/C(=C(\c2ccc(F)cc2Cl)C2CCC2)c2ccc(-c3cncs3)cc2)cc1] | 516 |
| 34 | B | 3 | (E)-3-(4-((E)-2-(3-Chloropyridin-4-yl)-2-cyclobutyl-1-(4-(thiazol-5-yl)phenyl)vinyl)phenyl)-acrylic acid | 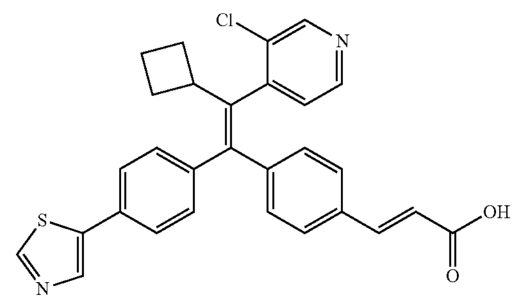 [SMILES: O=C(O)/C=C/c1ccc(/C(=C(\c2ccncc2Cl)C2CCC2)c2ccc(-c3cncs3)cc2)cc1] | 499 |
| 35 | B | 3 | (E)-3-(4-((E)-2-Cyclobutyl-2-(4-methylthiophen-3-yl)-1-(4-(thiazol-5-yl)phenyl)vinyl)phenyl)-acrylic acid | 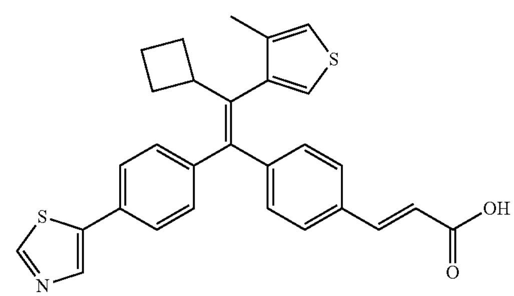 [SMILES: Cc1cscc1/C(=C(\c1ccc(/C=C/C(=O)O)cc1)c1ccc(-c2cncs2)cc1)C1CCC1] | 484 |
| 36[a] | C | 15 | (E)-3-(4-((E)-2-(2-Chloro-4-fluorophenyl)-2-cyclobutyl-1-(4-morpholinophenyl)vinyl)-phenyl)acrylic acid | 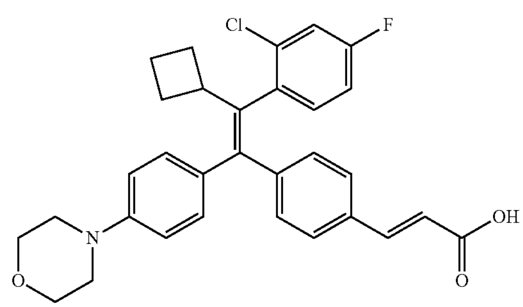 [SMILES: O=C(O)/C=C/c1ccc(/C(=C(\c2ccc(F)cc2Cl)C2CCC2)c2ccc(N3CCOCC3)cc2)cc1] | 518 |

| Ex. | Proc | SM | Name | Structure | LC-MS |
|---|---|---|---|---|---|
| 37 | C | 25 | (E)-3-(4-((E)-1-(4-(1H-Pyrazol-4-yl)phenyl)-2-(2-chloro-4-fluorophenyl)-2-cyclobutylvinyl)phenyl)-acrylic acid | 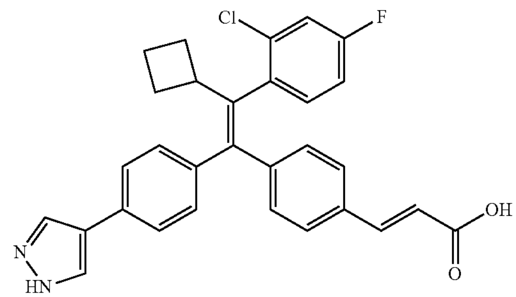 | 499 |
| 38 | C | 25 | (E)-3-(4-((E)-1-(4-(1H-Pyrazol-4-yl)phenyl)-2-cyclobutyl-2-(4-methylthiophen-3-yl)vinyl)phenyl)acrylic acid | 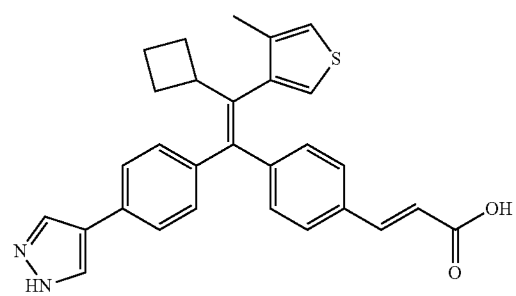 [SMILES: Cc1cscc1/C(=C(\c1ccc(/C=C/C(=O)O)cc1)c1ccc(-c2cn[nH]c2)cc1)C1CCC1] | 467 |
| 39[a] | C | 15 | (E)-3-(4-((E)-2-Cyclobutyl-2-(6-methoxy-4-methylpyridin-3-yl)-1-(4-morpholinophenyl)-vinyl)phenyl)acrylic acid | 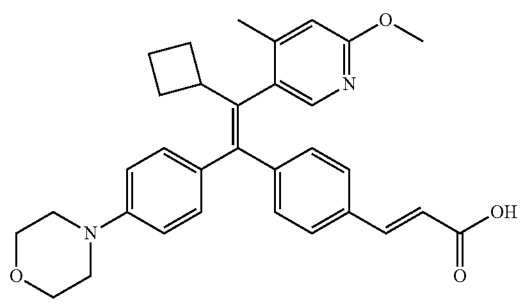 [SMILES: COc1cc(C)c(/C(=C(\c2ccc(/C=C/C(=O)O)cc2)c2ccc(N3CCOCC3)cc2)C2CCC2)cn1] | 511 |
| 40 | C | 25 | (E)-3-(4-((E)-1-(4-(1H-Pyrazol-4-yl)phenyl)-2-cyclobutyl-2-(3-methylpyridin-2-yl)vinyl)phenyl)acrylic acid | 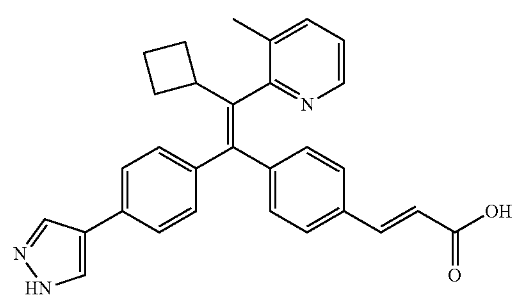 [SMILES: Cc1cccnc1/C(=C(\c1ccc(/C=C/C(=O)O)cc1)c1ccc(-c2cn[nH]c2)cc1)C1CCC1] | 462 |
| 41 | C | 25 | (E)-3-(4-((E)-1-(4-(1H-Pyrazol-4-yl)phenyl)-2-cyclobutyl-2-(3-fluoropyridin-2-yl)vinyl)phenyl)acrylic acid | 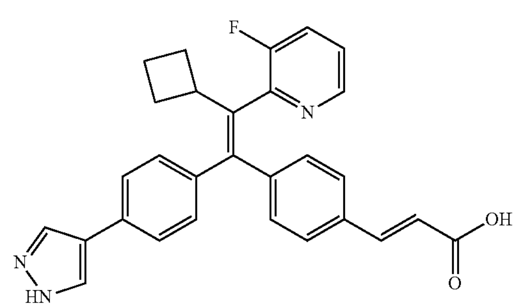 [SMILES: O=C(O)/C=C/c1ccc(/C(=C(\c2ncccc2F)C2CCC2)c2ccc(-c3cn[nH]c3)cc2)cc1] | 466 |

| Ex. | Proc | SM | Name | Structure | LC-MS |
|---|---|---|---|---|---|
| 42 | C | 25 | (E)-3-(4-((E)-1-(4-(1H-Pyrazol-4-yl)phenyl)-2-(3-chloropyridin-2-yl)-2-cyclobutylvinyl)phenyl)-acrylic acid | 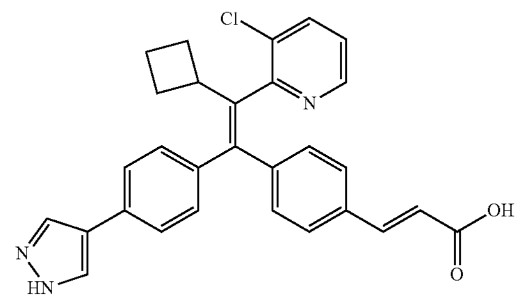 | 482 |
| 43[a] | C | 15 | (E)-3-(4-((E)-2-(3-Chloropyridin-2-yl)-2-cyclobutyl-1-(4-morpholinophenyl)vinyl)-phenyl)acrylic acid | 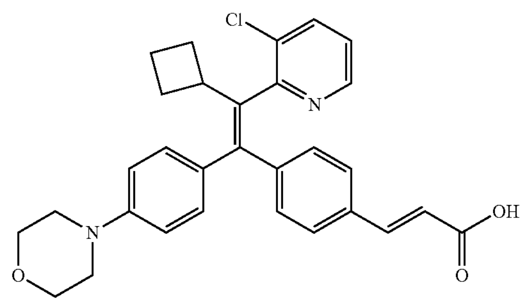 [SMILES: O=C(O)/C=C/c1ccc(/C(=C(\c2ncccc2Cl)C2CCC2)c2ccc(N3CCOCC3)cc2)cc1] | 501 |
| 44 | C | 25 | (E)-3-(4-((E)-1-(4-(1H-Pyrazol-4-yl)phenyl)-2-(4-chloro-2-cyanophenyl)-2-cyclobutylvinyl)phenyl)-acrylic acid | 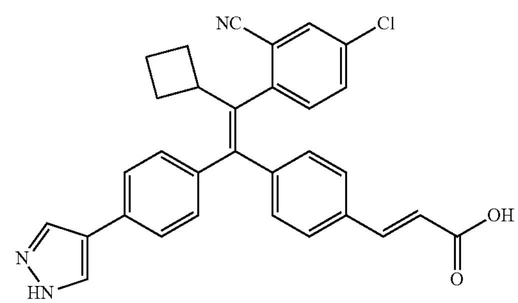 | 506 |
| 45[a] | C | 15 | (E)-3-(4-((E)-2-(2-Chloro-4-cyanophenyl)-2-cyclobutyl-1-(4-morpholinophenyl)vinyl)-phenyl)acrylic acid | 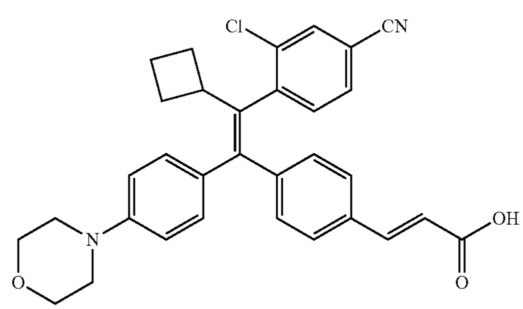 [SMILES: N#Cc1ccc(/C(=C(\c2ccc(/C=C/C(=O)O)cc2)c2ccc(N3CCOCC3)cc2)C2CCC2)c(Cl)c1] | 525 |
| 46[a] | C | 15 | (E)-3-(4-((E)-2-(4-Chloro-2-cyanophenyl)-2-cyclobutyl-1-(4-morpholinophenyl)vinyl)-phenyl)acrylic acid | 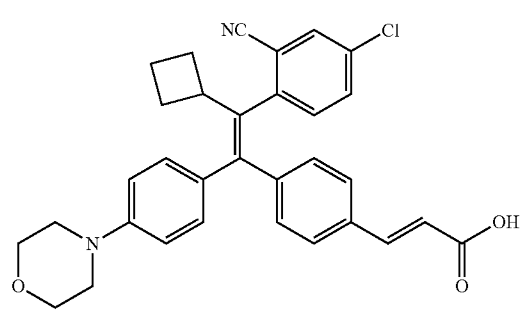 [SMILES: N#Cc1cc(Cl)ccc1/C(=C(\c1ccc(/C=C/C(=O)O)cc1)c1ccc(N2CCOCC2)cc1)C1CCC1] | 525 |

| Ex. | Proc | SM | Name | Structure | LC-MS |
|---|---|---|---|---|---|
| 47[a] | C | 15 | (E)-3-(4-((E)-2-Cyclobutyl-2-(4-methoxy-2-methylphenyl)-1-(4-morpholinophenyl)vinyl)-phenyl)acrylic acid | 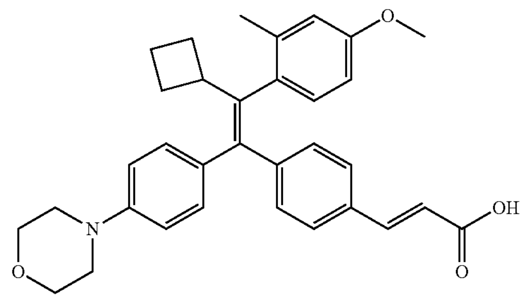 | 510 |
| 48[a] | C | 15 | (E)-3-(4-((E)-2-(2-Chloro-4-(trifluoromethyl)phenyl)-2-cyclobutyl-1-(4-morpholinophenyl)vinyl)-phenyl)acrylic acid | 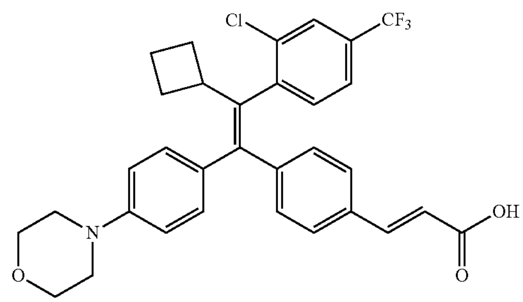 [SMILES: O=C(O)/C=C/c1ccc(/C(=C(\c2ccc(C(F)(F)F)cc2Cl)C2CCC2)c2ccc(N3CCOCC3)cc2)cc1] | 568 |
| 49 | D | 30 | (E)-3-(4-((E)-1-(4-(2H-Tetrazol-5-yl)phenyl)-2-(2-chloro-4-fluorophenyl)-2-cyclobutylvinyl)phenyl)-acrylic acid | 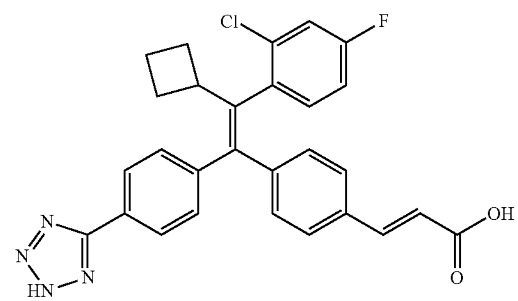 | 501 |
| 50 | D | 30 | (E)-3-(4-((E)-1-(4-(2H-Tetrazol-5-yl)phenyl)-2-(2-chloro-4-methoxyphenyl)-2-cyclobutylvinyl)phenyl)-acrylic acid | 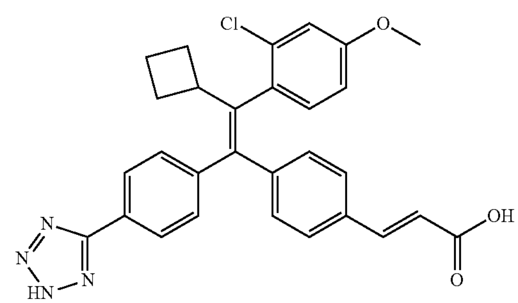 | 513 |
| 51[b] | D | 25 | (E)-3-(4-((E)-1-(4-(1H-Pyrazol-4-yl)phenyl)-2-(2-chloro-4-methoxyphenyl)-2-cyclobutylvinyl)phenyl)-acrylic acid | 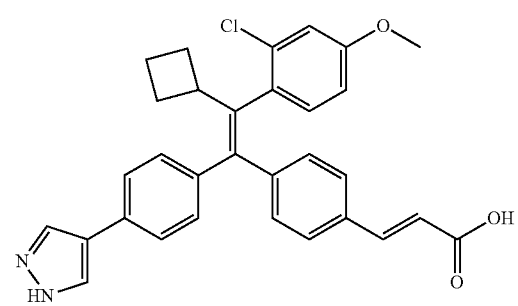 [SMILES: COc1ccc(/C(=C(\c2ccc(/C=C/C(=O)O)cc2)c2ccc(-c3cn[nH]c3)cc2)C2CCC2)c(Cl)c1] | 511 |

-continued

| Ex. | Proc | SM | Name | Structure | LC-MS |
|---|---|---|---|---|---|
| 52[b] | D | 25 | (E)-3-(4-((E)-1-(4-(1H-Pyrazol-4-yl)phenyl)-2-(2-chloro-4-(trifluoromethoxy)phenyl)-2-cyclobutylvinyl)phenyl)-acrylic acid | 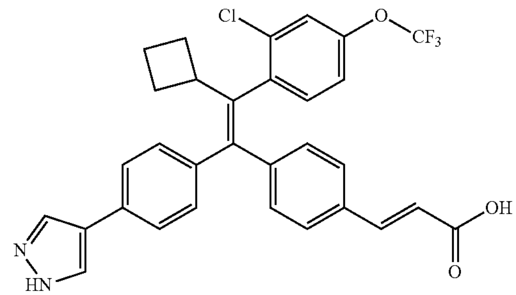 [SMILES: O=C(O)/C=C/c1ccc(/C(=C(\c2ccc(OC(F)(F)F)cc2Cl)C2CCC2)c2ccc(-c3cn[nH]c3)cc2)cc1] | 565 |
| 53 | D | 3 | (E)-3-(4-((E)-2-(2-Chloro-4-methoxyphenyl)-2-cyclobutyl-1-(4-(thiazol-5-yl)phenyl)vinyl)phenyl)-acrylic acid | 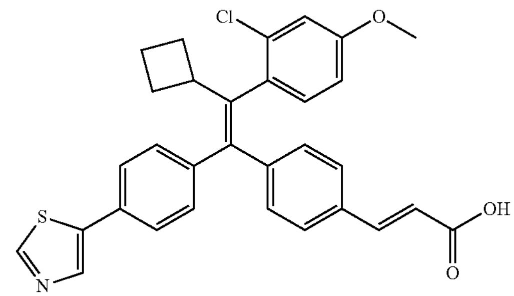 [SMILES: COc1ccc(/C(=C(\c2ccc(/C=C/C(=O)O)cc2)c2ccc(-c3cncs3)cc2)C2CCC2)c(C)c1] | 528 |
| 54 | D | 3 | (E)-3-(4-((E)-2-Cyclobutyl-2-(4-methoxy-2-methylphenyl)-1-(4-(thiazol-5-yl)phenyl)vinyl)phenyl)-acrylic acid | 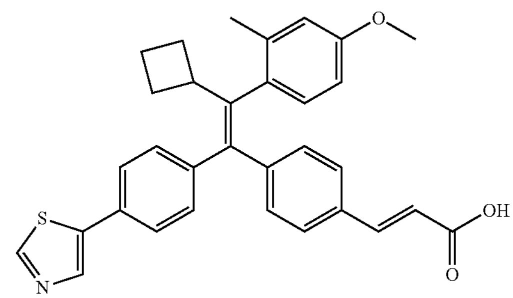 | 508 |
| 55[b] | D | 25 | (E)-3-(4-((E)-1-(4-(1H-Pyrazol-4-yl)phenyl)-2-(2-chloro-4-(trifluoromethyl)phenyl)-2-cyclobutylvinyl)phenyl)-acrylic acid | 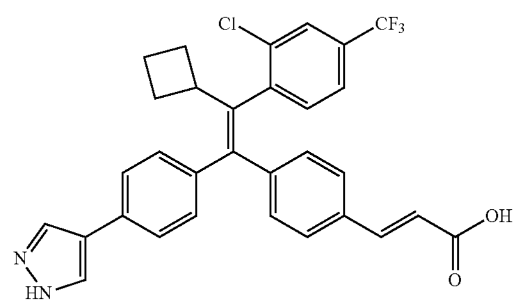 [SMILES: O=C(O)/C=C/c1ccc(/C(=C(\c2ccc(C(F)(F)F)cc2Cl)C2CCC2)c2ccc(-c3cn[nH]c3)cc2)cc1] | 549 |
| 56 | D | 23 | (E)-3-(4-((E)-2-(2-Chloro-4-fluorophenyl)-2-cyclobutyl-1-(4-(pyridin-4-yl)phenyl)vinyl)phenyl)-acrylic acid | 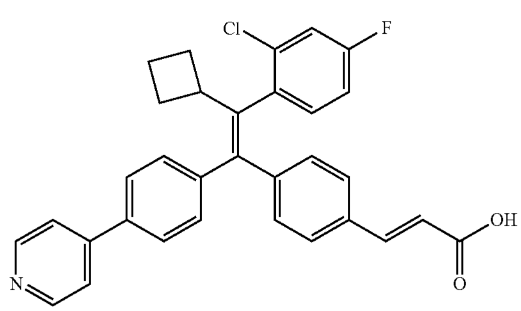 [SMILES: O=C(O)/C=C/c1ccc(/C(=C(\c2ccc(F)cc2Cl)C2CCC2)c2ccc(-c3ccncc3)cc2)cc1] | 510 |

| Ex. | Proc | SM | Name | Structure | LC-MS |
|---|---|---|---|---|---|
| 57 | D | 15 | (E)-3-(4-((E)-2-(3-Chloro-5-(trifluoromethyl)pyridin-2-yl)-2-cyclobutyl-1-(4-morpholinophenyl)vinyl)-phenyl)acrylic acid | 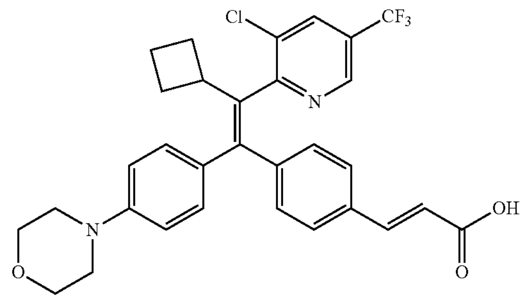 [SMILES: O=C(O)/C=C/c1ccc(/C(=C(\c2ncc(C(F)(F)F)cc2Cl)C2CCC2)c2ccc(N3CCOCC3)cc2)cc1] | 569 |
| 58[b] | D | 25 | (E)-3-(4-((E)-1-(4-(1H-Pyrazol-4-yl)phenyl)-2-(3-chloro-5-(trifluoromethyl)pyridin-2-yl)-2-cyclobutylvinyl)phenyl)-acrylic acid | 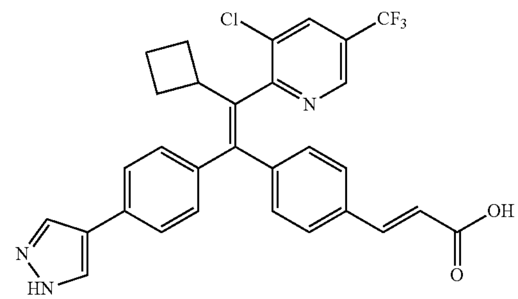 | 550 |
| 59 | D | 15 | (E)-3-(4-((E)-2-(3-Chloro-5-(trifluoromethyl)pyridin-2-yl)-2-cyclobutyl-1-(4-(thiazol-5-yl)phenyl)vinyl)phenyl)-acrylic acid | 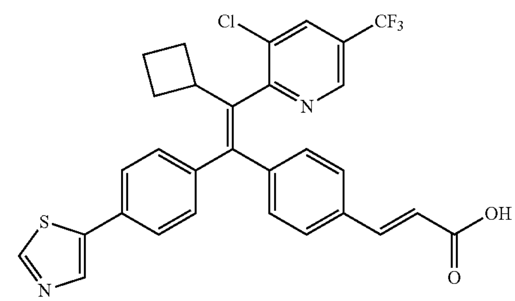 | 567 |
| 60 | D | 14 | (E)-3-(4-((E)-2-(2-Chloro-4-fluorophenyl)-1-(2-cyano-4-morpholinophenyl)-2-cyclobutylvinyl)phenyl)-acrylic acid | 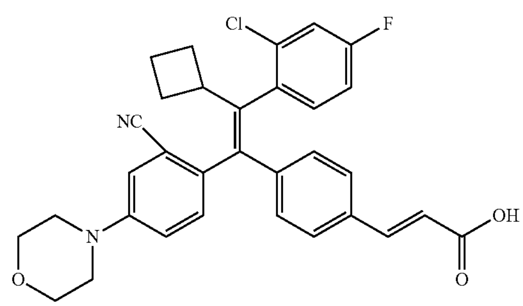 [SMILES: N#Cc1cc(N2CCOCC2)ccc1/C(=C(/c1ccc(F)cc1Cl)C1CCC1)c1ccc(/C=C/C(=O)O)cc1] | 543 |
| 61[b] | E | 25 | (E)-3-(4-((E)-1-(4-(1H-Pyrazol-4-yl)phenyl)-2-cyclobutyl-2-(6-methoxy-4-methylpyridin-3-yl)vinyl)phenyl)-acrylic acid | 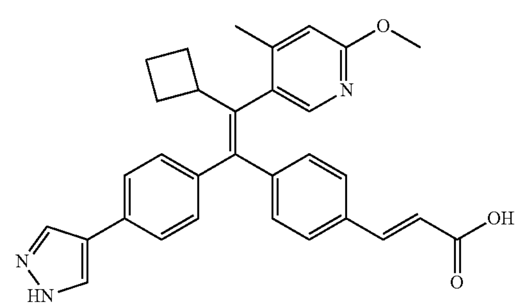 | 492 |

| Ex. | Proc | SM | Name | Structure | LC-MS |
|---|---|---|---|---|---|
| 62 | E | 15 | (E)-3-(4-((E)-2-(4-Chloro-2-cyanophenyl)-2-cyclobutyl-1-(4-(thiazol-5-yl)phenyl)vinyl)phenyl)acrylic acid | 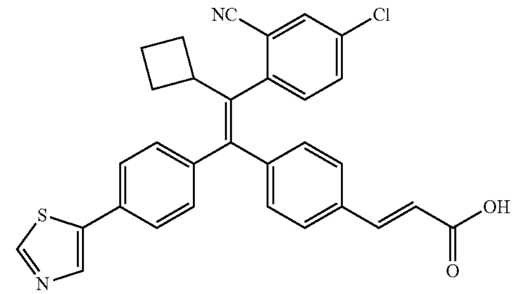 | 523 |
| 63 | A | 25 | (Z)-4-(4-(2-cyclobutyl-2-phenyl-1-(4-(2-(pyrrolidin-1-yl)ethoxy)phenyl)vinyl)phenyl)-1H-pyrazole | 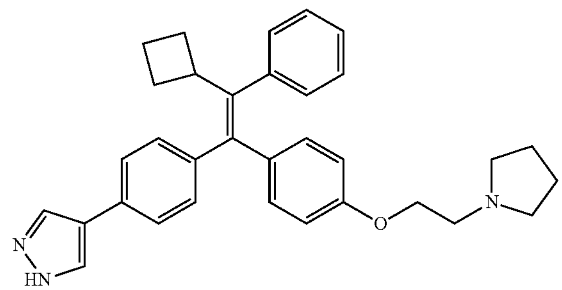 [SMILES: c1ccc(/C(=C(\c2ccc(OCCN3CCCC3)cc2)c2ccc(-c3cn[nH]c3)cc2)C2CCC2)cc1] | 490 |

[a]No THP protecting group used in synthesis. Thus THP-deprotection step not performed.
[b]THP protecting group was also removed in the tert-butyl ester hydrolysis step.

Example 64

(E)-3-(4-((E)-2-Cyclobutyl-1-(4-(4-methylpiperidin-1-yl)phenyl)-2-phenylvinyl)phenyl)acrylic acid

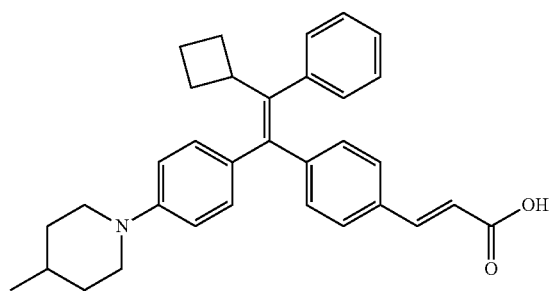 [SMILES: CC1CCN(c2ccc(/C(=C(/c3ccccc3)C3CCC3)c3ccc(/C=C/C(=O)O)cc3)cc2)CC1]

Step 1: (E)-Ethyl 3-(4-((E)-1-(4-bromophenyl)-2-cyclobutyl-2-phenylvinyl)phenyl)acrylate

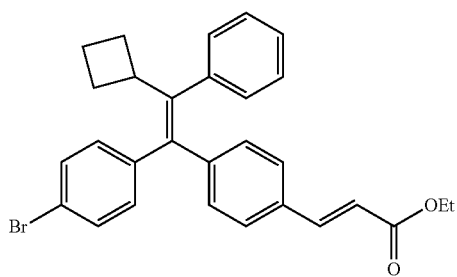 [SMILES: CCOC(=O)/C=C/c1ccc(/C(=C(\c2ccccc2)C2CCC2)c2ccc(Br)cc2)cc1]

The title compound was synthesized as described in Example 1, Step 1 using 1-bromo-4-(cyclobutylethynyl)benzene (Intermediate 33) as the starting material.

Step 2: (E)-Ethyl 3-(4-((E)-2-cyclobutyl-1-(4-(4-methylpiperidin-1-yl)phenyl)-2-phenylvinyl)phenyl)acrylate

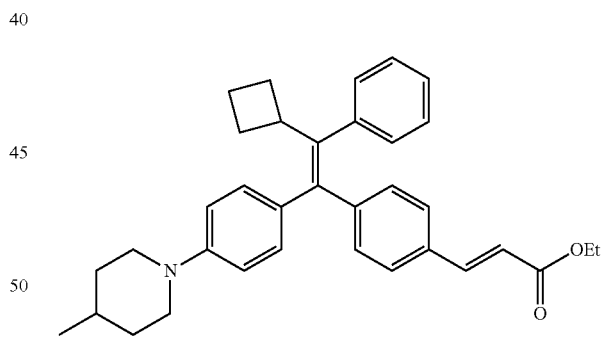

A mixture of (E)-ethyl 3-(4-((E)-1-(4-bromophenyl)-2-cyclobutyl-2-phenylvinyl)phenyl)acrylate (107 mg, 0.22 mmol), 4-methylpiperidine (0.1 mL, 0.89 mmol), $Pd_2dba_3$ (16 mg, 0.016 mmol), XPHOS (16 mg, 0.032 mmol), and potassium phosphate (375 mg, 1.76 mmol) in 1,4-dioxane (6 mL) was heated to 110° C. for 3 h. After cooling to room temperature, the reaction mixture was diluted with water and extracted with ethyl acetate. The combined organics were washed with brine, dried over sodium sulfate, filtered, and concentrated to give the crude product. The residue was purified by flash chromatography on silica gel to afford 87 mg of the title compound as a yellow foam. LCMS: 506 $(M+H)^+$.

Step 3: (E)-3-(4-((E)-2-Cyclobutyl-1-(4-(4-methyl-piperidin-1-yl)phenyl)-2-phenylvinyl)phenyl)acrylic acid

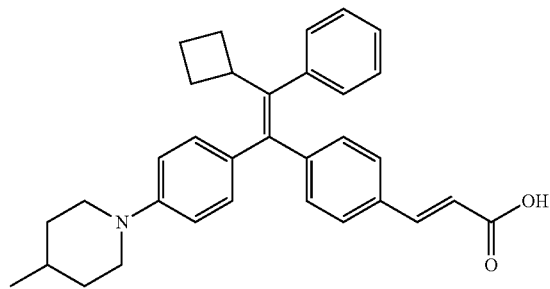 [SMILES: CC1CCN(c2ccc(/C(=C(/c3ccccc3)C3CCC3)c3ccc(/C=C/C(=O)O)cc3)cc2)CC1]

The title compound was synthesized as described in Example 1, Step 3 using (E)-ethyl 3-(4-((E)-2-cyclobutyl-1-(4-(4-methylpiperidin-1-yl)phenyl)-2-phenylvinyl)phenyl)acrylate as the starting material. LCMS: 478 (M+H)$^+$.

Example 65

(E)-3-(4-((E)-2-Cyclobutyl-2-phenyl-1-(4-(piper-azin-1-yl)phenyl)vinyl)phenyl)acrylic acid

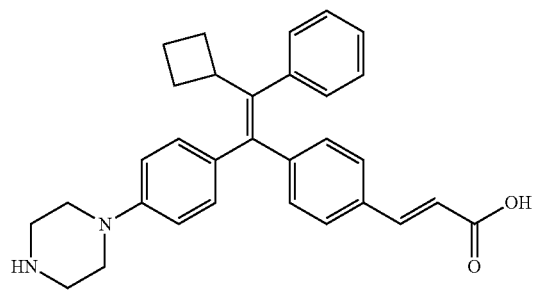 [SMILES: O=C(O)/C=C/c1ccc(/C(=C(\c2ccccc2)C2CCC2)c2ccc(N3CCNCC3)cc2)cc1]

The title compound was synthesized as described in Example 64, Step 2 using (E)-ethyl 3-(4-((E)-1-(4-bromophenyl)-2-cyclobutyl-2-phenylvinyl)phenyl)acrylate and tert-butyl piperazine-1-carboxylate as the starting materials. The BOC group was then deprotected in the same manner as described for the THP deprotection in Example 1, Step 2 using tert-butyl 4-(4-((E)-2-cyclobutyl-1-(4-((E)-3-ethoxy-3-oxoprop-1-en-1-yl)phenyl)-2-phenylvinyl)phenyl)piperazine-1-carboxylate as the starting material. The ethyl ester was then hydrolyzed as in Example 1, Step 3 using (E)-ethyl 3-(4-((E)-2-cyclobutyl-2-phenyl-1-(4-(piperazin-1-yl)phenyl)vinyl)phenyl)acrylate as the starting material. LCMS: 465 (M+H)$^+$.

Example 66

(E)-3-(4-((E)-2-Cyclobutyl-2-phenyl-1-(4-(pyridin-4-yl)phenyl)vinyl)phenyl)acrylic acid

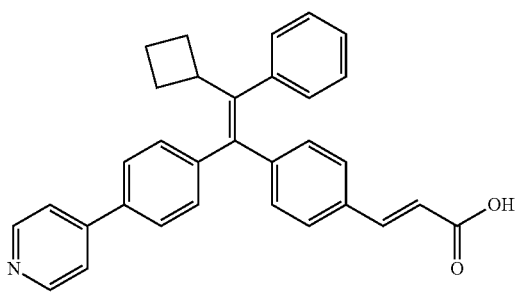 [SMILES: O=C(O)/C=C/c1ccc(/C(=C(\c2ccccc2)C2CCC2)c2ccc(-c3ccncc3)cc2)cc1]

Step 1: (E)-4-(1-(4-Bromophenyl)-2-cyclobutyl-2-phenylvinyl)benzaldehyde

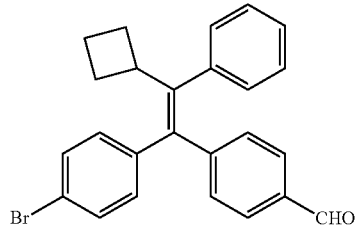 [SMILES: O=Cc1ccc(/C(=C(\c2ccccc2)C2CCC2)c2ccc(Br)cc2)cc1]

The title compound was synthesized as described in Example 1, Step 1 using 1-bromo-4-(cyclobutylethynyl)benzene instead of 4-(4-(cyclobutylethynyl)phenyl)-1-(tetrahydro-2H-pyran-2-yl)-1H-pyrazole (Intermediate 25) and (4-formylphenyl)boronic acid instead of (E)-(4-(3-ethoxy-3-oxoprop-1-en-1-yl)phenyl)boronic acid as the starting materials.

Step 2: (Z)-4-(2-Cyclobutyl-2-phenyl-1-(4-(pyridin-4-yl)phenyl)vinyl)benzaldehyde

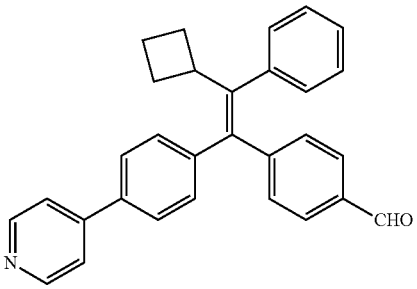 [SMILES: O=Cc1ccc(/C(=C(\c2ccccc2)C2CCC2)c2ccc(-c3ccncc3)cc2)cc1]

A mixture of (E)-4-(1-(4-bromophenyl)-2-cyclobutyl-2-phenylvinyl)benzaldehyde (171 mg, 0.41 mmol), pyridin-4-ylboronic acid (100 mg, 0.82 mmol), Pd(PPh$_3$)$_4$ (95 mg, 0.082 mmol), and potassium carbonate (170 mg, 1.23 mmol) in 1,4-dioxane-water (9:1, 4 mL) was heated to 100° C. overnight. After cooling to room temperature, the reaction mixture was diluted with water and extracted with ethyl acetate. The combined organics were washed with brine, dried over sodium sulfate, filtered, and concentrated to give the crude product. The residue was purified by flash chromatography on silica gel to afford 113 mg of the title compound as a yellow foam. $^1$H NMR (400 MHz, DMSO-$d_6$): δ 9.78 (s, 1H), 8.63 (d, 2H), 7.85 (d, 2H), 7.73 (d, 2H), 7.55 (d, 2H), 7.39 (d, 2H), 7.23 (m, 2H), 7.15 (m, 5H), 3.46 (m, 1H), 1.83 (m, 4H), 1.65 (m, 1H), 1.39 (m, 1H); LCMS: 416 (M+H)$^+$.

Step 3: (E)-3-(4-((E)-2-Cyclobutyl-2-phenyl-1-(4-(pyridin-4-yl)phenyl)vinyl)phenyl)acrylic acid

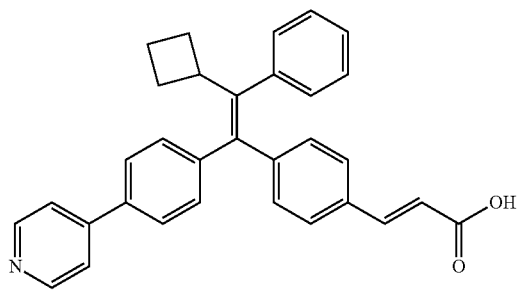

The title compound was synthesized as describe in Example 2, Step 3 using (Z)-4-(2-cyclobutyl-2-phenyl-1-(4-(pyridin-4-yl)phenyl)vinyl)benzaldehyde as the starting material, followed by ester hydrolysis as in Example 1, Step 3 using (E)-ethyl 3-(4-((E)-2-cyclobutyl-2-phenyl-1-(4-(pyridin-4-yl)phenyl)vinyl)phenyl)acrylate as the starting material. $^1$H NMR (400 MHz, DMSO-$d_6$): δ CO$_2$H proton not observed, 8.81 (d, 2H), 8.11 (d, 2H), 7.97 (d, 2H), 7.44 (d, 2H), 7.38 (d, 1H), 7.30 (d, 2H), 7.24 (m, 2H), 7.18-7.11 (m, 3H), 6.95 (d, 2H), 6.34 (d, 1H), 3.43 (m, 1H), 1.83 (m, 4H), 1.61 (m, 1H), 1.40 (m, 1H); LCMS: 458 (M+H)$^+$.

Example 67

(E)-3-(4-((E)-2-Cyclobutyl-1-(4-(1-(2-hydroxyethyl)-1H-pyrazol-4-yl)phenyl)-2-phenylvinyl)phenyl)acrylic acid

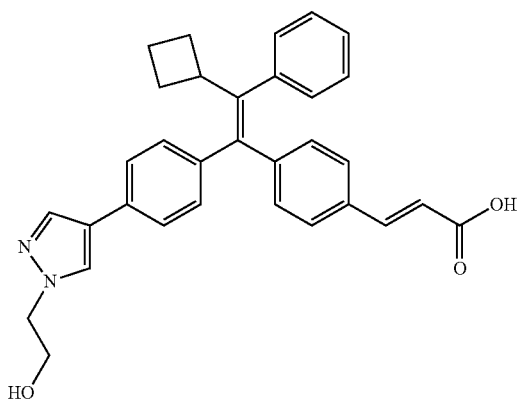 [SMILES: O=C(O)/C=C/c1ccc(/C(=C(\c2ccccc2)C2CCC2)c2ccc(-c3cnn(CCO)c3)cc2)cc1]

Step 1: (E)-Ethyl 3-(4-((E)-2-cyclobutyl-1-(4-(1-(2-hydroxyethyl)-1H-pyrazol-4-yl)phenyl)-2-phenylvinyl)phenyl)acrylate

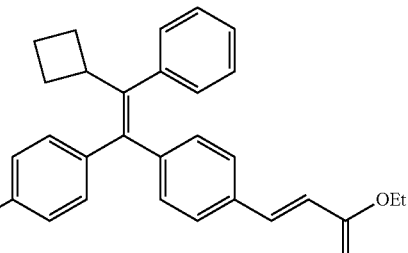

A mixture of (E)-ethyl 3-(4-((E)-1-(4-(1H-pyrazol-4-yl)phenyl)-2-cyclobutyl-2-phenylvinyl)phenyl)acrylate (Example 1, Step 2, 246 mg, 0.52 mmol), ethylene carbonate (229 mg, 2.6 mmol), and cesium carbonate (339 mg, 1.04 mmol) in N,N-dimethylformamide (2 mL) was heated to 100° C. for 2 h. After cooling to room temperature, the reaction mixture was diluted with water and extracted with ethyl acetate. The combined organics were washed with brine, dried over sodium sulfate, filtered, and concentrated to give the crude product. The residue was purified by flash chromatography on silica gel to afford 113 mg of the title compound as a yellow foam. LCMS: 519 (M+H)$^+$.

Step 2: (E)-3-(4-((E)-2-Cyclobutyl-1-(4-(1-(2-hydroxyethyl)-1H-pyrazol-4-yl)phenyl)-2-phenylvinyl)phenyl)acrylic acid The title compound was synthesized as described in Example 1, Step 3 using (E)-ethyl 3-(4-((E)-2-cyclobutyl-1-(4-(1-(2-hydroxyethyl)-1H-pyrazol-4-yl)phenyl)-2-phenylvinyl)phenyl)acrylate as the starting material. $^1$H NMR (400 MHz, DMSO-$d_6$): δ CO$_2$H and OH protons not observed, 8.14 (s, 1H), 7.88 (s, 1H), 7.57 (d, 2H), 7.38 (d, 1H), 7.31 (d, 2H), 7.24-7.08 (m, 7H), 6.91 (d, 2H), 6.33 (d, 1H), 4.16 (t, 2H), 3.77 (t, 2H), 3.45 (m, 1H), 1.81 (m, 4H), 1.61 (m, 1H), 1.35 (m, 1H); LCMS: 491 (M+H)$^+$.

The following compounds were synthesized following the procedure described in Example 67 using the ethyl ester of example 38 as a starting material for example 68 and the ethyl ester of example 37 for example 69.

| Example | Name | Structure | LC-MS |
|---|---|---|---|
| 68 | (E)-3-(4-((E)-2-Cyclobutyl-1-(4-(1-(2-hydroxyethyl)-1H-pyrazol-4-yl)phenyl)-2-(4-methylthiophen-3-yl)vinyl)phenyl)acrylic acid | 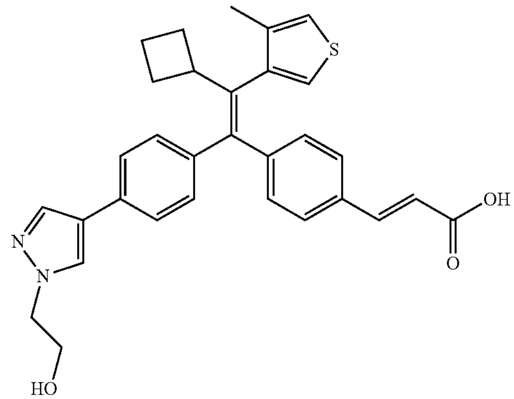 [SMILES: Cc1cscc1/C(=C(\c1ccc(/C=C/C(=O)O)cc1)c1ccc(-c2cnn(CCO)c2)cc1)C1CCC1] | 511 |
| 69 | (E)-3-(4-((E)-2-(2-Chloro-4-fluorophenyl)-2-cyclobutyl-1-(4-(1-(2-hydroxyethyl)-1H-pyrazol-4-yl)phenyl)vinyl)phenyl)-acrylic acid | 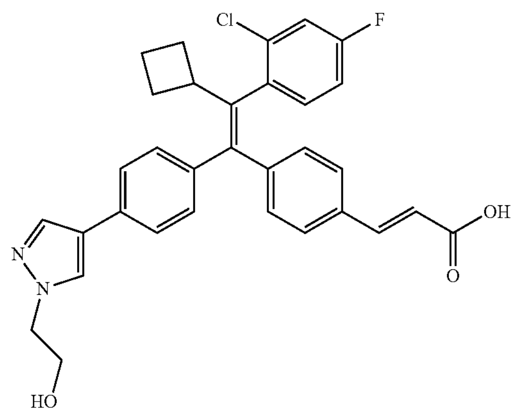 [SMILES: O=C(O)/C=C/c1ccc(/C(=C(\c2ccc(F)cc2Cl)C2CCC2)c2ccc(-c3cnn(CCO)c3)cc2)cc1] | 543 |

Example 70

(E)-3-(4-((E)-2-Cyclobutyl-1-(4-(1-(2-(dimethylamino)ethyl)-1H-pyrazol-4-yl)phenyl)-2-phenylvinyl)phenyl)acrylic acid Step 1: (E)-Ethyl 3-(4-((E)-2-cyclobutyl-1-(4-(1-(2-(dimethylamino)ethyl)-1H-pyrazol-4-yl)phenyl)-2-phenylvinyl)phenyl)acrylate

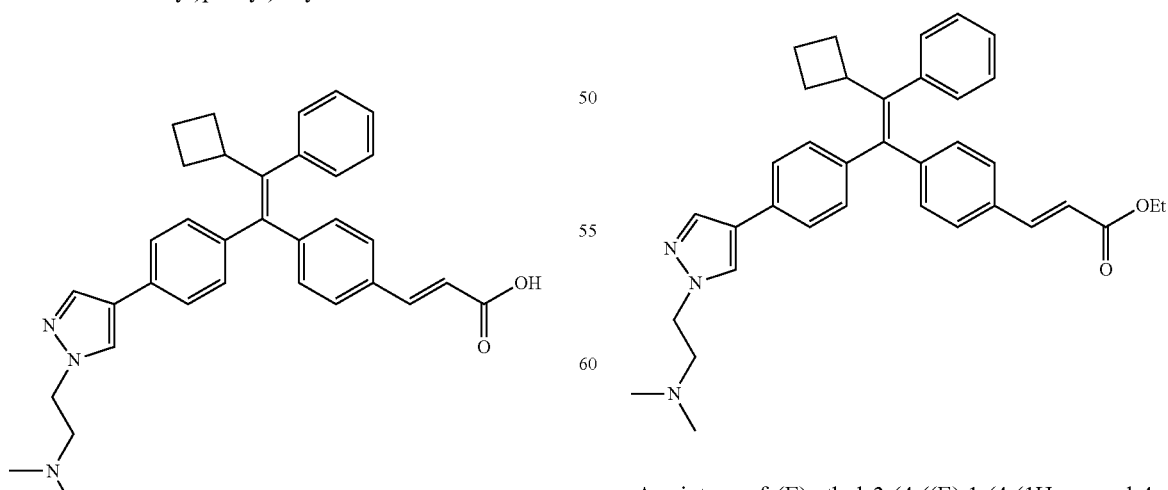

A mixture of (E)-ethyl 3-(4-((E)-1-(4-(1H-pyrazol-4-yl)phenyl)-2-cyclobutyl-2-phenylvinyl)phenyl)acrylate (Example 1, Step 2, 197 mg, 0.41 mmol), 2-chloro-N,N-dimethylethanamine hydrochloride (90 mg, 0.62 mmol), and cesium carbonate (401 mg, 1.23 mmol) in N,N-dimethylformamide (2 mL) was stirred at room temperature for 4 h. The reaction mixture was diluted with water and extracted with ethyl acetate. The combined organics were washed with brine, dried over sodium sulfate, filtered, and concentrated to give the crude product. The residue was purified by flash chromatography on silica gel to afford 62 mg of the title compound as a white foam. LCMS: 546 (M+H)$^+$.

Step 2: (E)-3-(4-((E)-2-Cyclobutyl-1-(4-(1-(2-(dimethylamino)ethyl)-1H-pyrazol-4-yl)phenyl)-2-phenylvinyl)phenyl)acrylic acid

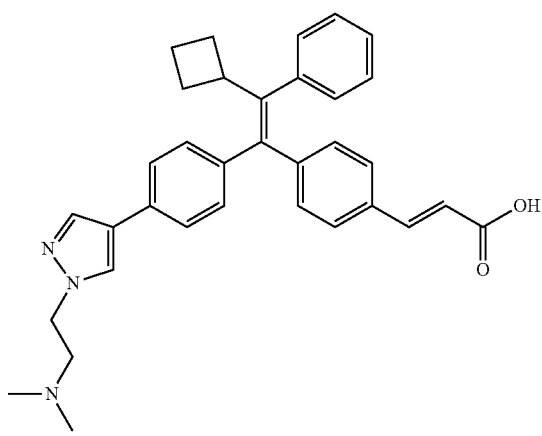 [SMILES: CN(C)CCn1cc(-c2ccc(/C(=C(/c3ccccc3)C3CCC3)c3ccc(/C=C/C(=O)O)cc3)cc2)cn1]

The title compound was synthesized as described in Example 1, Step 3 using (E)-ethyl 3-(4-((E)-2-cyclobutyl-1-(4-(1-(2-(dimethylamino)ethyl)-1H-pyrazol-4-yl)phenyl)-2-phenylvinyl)phenyl)acrylate as the starting material. $^1$H NMR (400 MHz, DMSO-d$_6$): δ CO$_2$H proton not observed, 8.28 (s, 1H), 8.03 (s, 1H), 7.60 (s, 2H), 7.38 (d, 1H), 7.33-7.00 (m, 9H), 6.91 (d, 2H), 6.34 (d, 1H), 4.56 (t, 2H), 3.61 (m, 2H), 3.43 (m, 1H), 2.82 (s, 6H), 1.82 (m, 4H), 1.60 (m, 1H), 1.37 (m, 1H); LCMS: 518 (M+H)$^+$.

Example 71

5-((E)-4-((E)-1-(4-(1H-Pyrazol-4-yl)phenyl)-2-(2-chloro-4-fluorophenyl)-2-cyclobutylvinyl)styryl)-2H-tetrazole

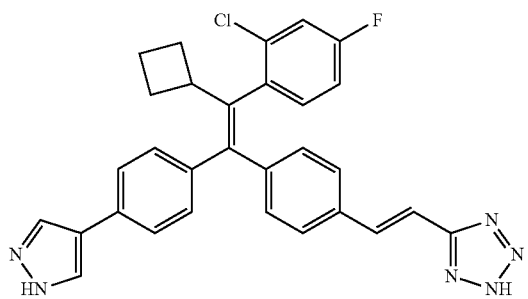 [SMILES: Fc1ccc(/C(=C(\c2ccc(/C=C/c3nn[nH]n3)cc2)c2ccc(-c3cn[nH]c3)cc2)C2CCC2)c(Cl)c1]

Step 1: (E)-3-(4-((E)-2-(2-Chloro-4-fluorophenyl)-2-cyclobutyl-1-(4-(1-(tetrahydro-2H-pyran-2-yl)-1H-pyrazol-4-yl)phenyl)vinyl)phenyl)acrylonitrile

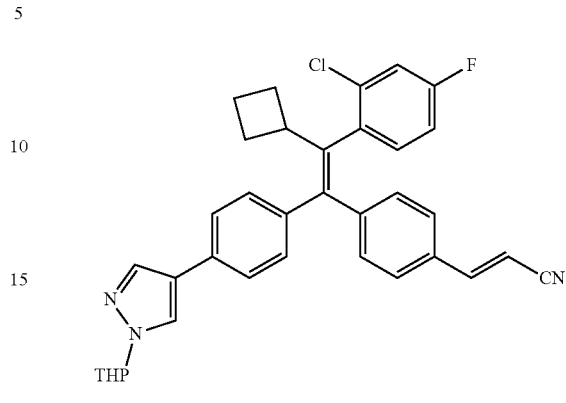

The title compound was synthesized as described in Example 2 using 4-(4-(cyclobutylethynyl)phenyl)-1-(tetrahydro-2H-pyran-2-yl)-1H-pyrazole (Intermediate 25) in Step 1. (E)-diethyl (2-cyanovinyl)phosphonate was used in Step 3 instead of ethyl 2-(diethoxyphosphoryl)acetate. LCMS: 480 (M+H-THP)$^+$.

Step 2: 5-((E)-4-((E)-2-(2-Chloro-4-fluorophenyl)-2-cyclobutyl-1-(4-(1-(tetrahydro-2H-pyran-2-yl)-1H-pyrazol-4-yl)phenyl)vinyl)styryl)-2H-tetrazole

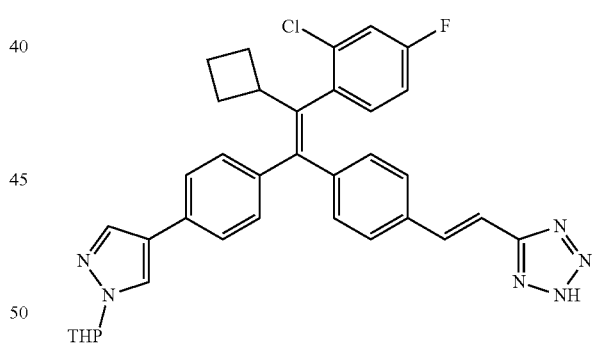

A mixture of (E)-3-(4-((E)-2-(2-chloro-4-fluorophenyl)-2-cyclobutyl-1-(4-(1-(tetrahydro-2H-pyran-2-yl)-1H-pyrazol-4-yl)phenyl)vinyl)phenyl)acrylonitrile (150 mg, 0.26 mmol), TMSN3 (0.35 mL, 2.6 mmol), and dibutylstannanone (6 mg, 0.026 mmol) in toluene (2.6 mL) was heated to 110° C. overnight. The reaction mixture was cooled to room temperature and the solvent was removed. The residue was absorbed on silica gel and purified by flash chromatography on silica gel to afford 38 mg of the title compound. LCMS: 523 (M+H-THP)$^+$.

Step 3: 5-((E)-4-((E)-1-(4-(1H-Pyrazol-4-yl)phenyl)-2-(2-chloro-4-fluorophenyl)-2-cyclobutylvinyl)styryl)-2H-tetrazole

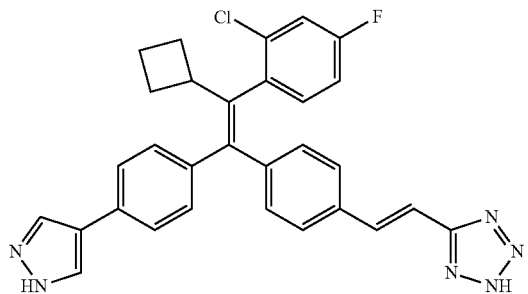 [SMILES: Fc1ccc(/C(=C(\c2ccc(/C=C/c3nn[nH]n3)cc2)c2ccc(-c3cn[nH]c3)cc2)C2CCC2)c(Cl)c1]

The title compound was synthesized as described in Example 1, Step 2 using 5-((E)-4-((E)-2-(2-chloro-4-fluorophenyl)-2-cyclobutyl-1-(4-(1-(tetrahydro-2H-pyran-2-yl)-1H-pyrazol-4-yl)phenyl)vinyl)styryl)-2H-tetrazole as the starting material. $^1$H NMR (400 MHz, DMSO-d$_6$): δ NH protons not observed, 8.07 (s, 2H), 7.64 (d, 2H), 7.47 (d, 1H), 7.41 (d, 2H), 7.37-7.32 (m, 2H), 7.22-7.14 (m, 4H), 7.01 (d, 2H), 3.47 (m, 1H), 1.89 (m, 3H), 1.67 (m, 2H), 1.40 (m, 1H). LCMS: 523 (M+H)$^+$.

Example 72

3×ERE MCF-7 Reporter Assay

MCF7 cells were maintained in RPMI 1640 supplemented with 10% FCS. Transcriptional assays were performed by seeding 100 μL of cells at a density of 250,000 cells/mL into 96-well cell culture plates in RPMI 1640 supplemented with 10% charcoal stripped serum. Cells were allowed to attach overnight, then transiently transfected using Lipofectin (Life Technologies) according to the manufacturer's protocol. Triplicate transfections were performed using 300 ng 3×ERE-TK-Luc (reporter vector), 50 ng CMVpRL (normalization vector), and 130 ng pCMX (filler DNA). Transfected cells were incubated overnight then treated with ligand. For ER agonist assays, the compounds were serially diluted and 50 μL of compound plus RPMI 1640 supplemented with charcoal stripped serum was added to the cells. For ER antagonist assays, the compounds were serially diluted, and 50 μL of compound with RPMI plus 17β-estradiol supplemented with charcoal stripped serum were added to the cells. The final 17β-estradiol concentration used in the antagonist assays was 0.1 nM. Following 24 hour incubation the medium was removed and the cells were lysed in 40 μL of lysis buffer (25 mM Tris Phosphate, 2 mM CDTA, 10% Glycerol, 0.5% Triton X-100, 2 mM DTT). Firefly luciferase activity was measured immediately following the addition of 40 μL luciferase buffer (20 mM tricine, 0.1 mM EDTA, 1.07 mM (MgCo$_3$)$_4$ Mg(OH)$_2$.5H$_2$O, 2.67 mM MgSO$_4$, 33.3 mM DTT, 270 μM Coenzyme A, 470 μM luciferin, 530 μM ATP). *Renilla* luciferase was measured following the addition of 40 μL colelenterazine buffer (1.1 M NaCl, 2.2 mM Na$_2$EDTA, 0.22 M KxPO$_4$ (pH 5.1), 0.44 mg/mL BSA, 1.3 mM NaN$_3$, 1.43 μM coelenterazine, final pH adjusted to 5.0).

Example 73

Breast Cancer Cell Viability Assays

MCF-7 cells were adjusted to a concentration of 20,000 cells per mL in RPMI containing 10% FBS and 20 mM HEPES. 16 microliters of the cell suspension (320 cells) was added to each well of a 384 well plate, and the cells were incubated overnight to allow the cells to adhere. The following day an eleven point, serial semilog dilution of each compound was added to the cells in 16 μL at a final concentration ranging from 0.3-0.000003 μM. After 5 days' compound exposure, 16 μL of CellTiter-GLo (Promega, Madison Wis.) was added to the cells, and the relative luminescence units (RLUs) of each well were determined. CellTiter-Glo added to 32 μL of medium without cells was used to obtain a background value. The Percent viability of each sample was determined as follows: (RLU sample-RLU background/RLU untreated cells-RLU background)×100=% viability.

Viability effects in additional ER+ breast cancer cell lines, including BT474, CAMA1, MDA-MB-361, ZR-75-1, T47D, can be profiled in assays similar to Example 73.

Example 74

Breast Cancer Cell ER-α in Cell Western Assay (SP1)

MCF-7 cells were adjusted to a concentration of 200,000 cells per mL in RPMI containing 10% charcoal-stripped FBS and 20 mM HEPES. 16 microliters of the cell suspension (3200 cells) was added to each well of a poly-D-lysine 384 well plate, and the cells were incubated overnight to allow the cells to adhere. The following day an eleven point, serial semilog dilution of each compound was added to the cells in 16 μL at a final concentration ranging from 0.3-0.000003 μM. At 4 or 24 hr post compound addition, the cells were fixed (10% formalin in PBS) for 20 minutes. Cells were permeablized in PBS 0.1% Triton and blocked with LICOR blocking buffer (50 μl/well, 90'). The wells were then incubated overnight at 4° C. with SP1 rabbit monoclonal Ab (Thermo Scientific) diluted 1:1000 in LICOR blocking buffer/0.1% Tween-20. Wells which were treated with blocking buffer with Tween but no antibody were used as a background control. Wells were washed with 0.1% Tween-20/PBS and then incubated in goat anti-rabbit IRDye™ 800 CW (LICOR Inc.; 1:10000) and DRAQ5 DNA dye (1:2000 for 2 mM stock) diluted in LICOR blocking buffer containing 0.1% Tween-20 and 0.01% SDS for 60 minutes. Cells were washed (50 μl/well, 5' each) in 0.1% Tween-20/PBS. Plates were scanned on a LICOR Odyssey infrared imaging system. Integrated intensities in the 800 nm channel and 700 nm channel were measured to determine levels of ER and DNA respectively. Percent ER levels were determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ breast cancer cell lines, including BT474, CAMA1, MDA-MB-361, ZR-75-1, T47D, can be profiled in assays similar to Example 74.

Illustrative biological data for representative compounds disclosed herein is presented in the following table:

TABLE 17

| | MCF7 Viability Assay | | ER-α In Cell Western Assay (SP1) | |
|---|---|---|---|---|
| Example | $IC_{50}$ | Max Response | $IC_{50}$ | Max Response |
| 1 | A | ++ | A | ++ |
| 2 | A | ++ | A | ++ |
| 3 | A | ++ | A | ++ |
| 4 | A | ++ | A | ++ |
| 5 | A | ++ | A | ++ |
| 6 | B | ++ | A | ++ |
| 7 | B | + | B | ++ |
| 8 | B | ++ | A | ++ |
| 9 | A | ++ | A | ++ |
| 10 | B | ++ | A | ++ |
| 11 | B | + | B | + |
| 12 | B | + | B | + |
| 13 | A | ++ | A | ++ |
| 14 | B | ++ | A | ++ |
| 15 | B | ++ | A | ++ |
| 16 | A | ++ | A | ++ |
| 17 | B | ++ | B | ++ |
| 18 | A | ++ | A | ++ |
| 19 | A | ++ | A | ++ |
| 20 | A | ++ | A | ++ |
| 21 | A | ++ | A | ++ |
| 22 | A | ++ | A | ++ |
| 23 | B | ++ | A | ++ |
| 24 | B | ++ | B | ++ |
| 25 | B | ++ | B | ++ |
| 26 | B | + | B | ++ |
| 27 | A | ++ | A | ++ |
| 28 | A | ++ | A | ++ |
| 29 | A | ++ | A | ++ |
| 30 | A | ++ | A | ++ |
| 31 | A | ++ | A | ++ |
| 32 | A | ++ | A | ++ |
| 33 | A | ++ | A | ++ |
| 34 | A | ++ | A | ++ |
| 35 | A | ++ | A | ++ |
| 36 | A | ++ | A | ++ |
| 37 | A | ++ | A | ++ |
| 38 | A | ++ | A | ++ |
| 39 | A | ++ | A | ++ |
| 40 | B | ++ | A | ++ |
| 41 | B | ++ | A | ++ |
| 42 | A | ++ | A | ++ |
| 43 | A | ++ | A | ++ |
| 44 | A | ++ | A | ++ |
| 45 | A | ++ | A | ++ |
| 46 | A | ++ | A | ++ |
| 47 | A | ++ | A | ++ |
| 48 | A | ++ | A | ++ |
| 49 | B | + | B | + |
| 50 | B | ++ | B | ++ |
| 51 | A | ++ | A | ++ |
| 52 | A | ++ | A | ++ |
| 53 | A | ++ | A | ++ |
| 54 | A | ++ | A | ++ |
| 55 | A | ++ | A | ++ |
| 56 | A | ++ | A | ++ |
| 57 | A | ++ | A | ++ |
| 58 | A | ++ | A | ++ |
| 59 | A | ++ | A | ++ |
| 60 | A | ++ | A | ++ |
| 61 | A | ++ | A | ++ |
| 62 | A | ++ | A | ++ |
| 63 | A | ++ | A | ++ |
| 64 | B | ++ | B | ++ |
| 65 | A | ++ | A | ++ |
| 66 | A | ++ | A | ++ |
| 67 | A | ++ | A | ++ |
| 68 | A | ++ | A | ++ |
| 69 | A | ++ | A | ++ |
| 70 | A | ++ | A | ++ |
| 71 | A | ++ | A | ++ |

A = single $IC_{50}$ ≤ 100 nM;
B = single $IC_{50}$ > 100 nM;
+ = a single % value < 40%;
++ = a single % value ≥ 40%

Example 75

Ishikawa Uterine Cell Alkaline Phosphatase Assay

Subconfuent Ishikawa cells in a T225 are incubated 24 hours in an estrogen free basal medium (EFBM) consisting of DMEM:Ham's F-12 50:50 phenol red free basal medium containing 5% Charcoal Dextran treated FBS and 20 mM HEPES. Cells are plated the following day in EFBM in clear 384 well plates at a concentration of 2.5×105 cells per mL, 16 μL per well (4000 cells per well). A 12 point semilog dilution of each compound is carried out in DMSO and subsequently diluted in EFBM. An equal volume of compound in EFBM is added immediately after plating cells, and the cells are incubated for 3 days. The cells are fixed with 5% formalin, and rinsed with PBS. Alkaline Phosphatase substrate 4-Nitrophenyl phosphate disodium salt hexahydrate is added (1 mg/mL final concentration) to a solution containing 2 mM $MgCl_2$, 1 M diethanolamine, and adjusted to pH 9.0. The substrate solution is added to the cell cultures (16 μL per well), and OD405 is measured in a multiwall plate spectrophotometer when the optical density at 405 nm wavelength of cells treated with 17β-estradiol in the concentration range of 1-30 nM reaches 1.0-1.2 absorbance units. Cells treated with DMSO alone serve as a background control. Percent activity in background subtracted samples is measured as follows: % activity=OD405 sample/OD405 max of 17β-estradiol treated cells×100.

Example 76

Ovarian Cancer Cell Viability Assays

BG-1 cells are diluted in RPMI containing 10% FBS and 20 mM HEPES. 16 microliters of the cell suspension is added to each well of a 384 well plate, and the cells are incubated overnight. The following day an eleven point, serial semilog dilution of each compound is added to the cells in 16 μL at a final concentration ranging from 0.3-0.000003 μM. After 5 to 7 days' compound exposure, 16 μL of CellTiter-GLo (Promega, Madison Wis.) is added to the cells, and the relative luminescence units (RLUs) of each well is determined. CellTiter-Glo added to 32 μL of medium without cells is used to obtain a background value. The Percent viability of each sample is determined as follows: (RLU sample-RLU background/RLU untreated cells-RLU background)×100=% viability.

Viability effects in additional ER+ ovarian cancer cell lines, including OVKATE, OVSAHO, A1847, SKOV3, SW626, A2780, can be profiled in assays similar to Example 76.

Example 77

Ovarian Cancer Cell ER-α in Cell Western Assay

BG-1 cells are diluted in RPMI containing 10% charcoal-stripped FBS and 20 mM HEPES. 16 microliters of the cell suspension is added to each well of a poly-D-lysine 384 well plate, and the cells are incubated overnight. The following day an eleven point, serial semilog dilution of each compound is added to the cells in 16 µL at a final concentration ranging from 0.3-0.000003 µM. At 4 or 24 hr post compound addition, the cells are fixed (10% formalin in PBS) for 20 minutes. Following fixation the cells are permeablized in PBS 0.1% Triton and blocked with LICOR blocking buffer (50 µl/well, 90'). The wells are then incubated overnight at 4° C. with SP1 rabbit monoclonal Ab (Thermo Scientific) diluted 1:1000 in LICOR blocking buffer/0.1% Tween-20. Wells treated with blocking buffer with Tween but no antibody are used as a background control. All wells are washed with 0.1% Tween-20/PBS and then incubated in goat anti-mouse IRDye™ 800 CW (LICOR Inc.; 1:10000) and DRAQ5 DNA dye (1:2000 for 2 mM stock) diluted in LICOR blocking buffer containing 0.1% Tween-20 and 0.01% SDS for 60 minutes. Cells are then washed (50 µl/well, 5' each) in 0.1% Tween-20/PBS. Plates are scanned on a LICOR Odyssey infrared imaging system. Integrated intensities in the 800 nm channel and 700 nm channel are measured to determine levels of ER and DNA respectively. Percent ER levels are determined as follows:

(Integrated intensity 800 nm sample/integrated intensity 700 nm sample)/(Integrated intensity 800 nm untreated cells/integrated intensity 700 nm untreated cells)×100=% ER levels.

Effects on steady state levels of ER-α in additional ER+ ovarian cancer cell lines, including OVKATE, OVSAHO, A1847, SKOV3, SW626, A2780, can be profiled in assays similar to Example 77.

Other cancer cell lines contemplated for testing compounds described herein include: ER-positive endometrial cell lines (Ishikawa, ECC1, HEC-1, EnCa-101) and ER-positive cervical cell lines (Caski, HeLa, SiHa).

Example 78

Breast Cancer Model; Xenograft Assay (MCF-7)

Time release pellets containing 0.72 mg 17-β Estradiol were subcutaneously implanted into nu/nu mice. MCF-7 cells were grown in RPMI containing 10% FBS at 5% $CO_2$, 37° C. Cells were spun down and re-suspended in 50% RPMI (serum free) and 50% Matrigel at $1\times10^7$ cells/mL. MCF-7 cells were subcutaneously injected (100 µL/animal) on the right flank 2-3 days post pellet implantation. Tumor volume (length×width$^2$/2) was monitored bi-weekly. When tumors reached an average volume of ~200 mm$^3$ animals were randomized and treatment was started. Animals were treated with Vehicle or Compound daily for 4 weeks. Tumor volume and body weight were monitored bi-weekly throughout the study. At the conclusion of the treatment period, plasma and tumor samples were taken for pharmacokinetic and pharmacodynamic analyses, respectively.

Example 79

Breast Cancer Model; Xenograft Assay (MCF-7 Derivative)

Female nu/nu mice (with supplemental 17-β Estradiol pellets; 0.72 mg; 60 day slow release) bearing MCF-7 tumors (mean tumor volume 200 mm$^3$) were treated with Tamoxifen (citrate) by oral gavage. Tumor volume (length×width$^2$/2) and body weight were monitored twice weekly. Following a significant anti-tumor response in which tumor volume remained static, evident tumor growth was first observed at approximately 100 days of treatment. At 120 days of treatment, tamoxifen dose was increased. Rapidly growing tumors were deemed tamoxifen resistant and selected for in vivo passage into new host animals. Tumor Fragments (~100 mm$^3$/animal) from the tamoxifen resistant tumors were subcutaneously implanted into the right flank of female nu/nu mice (with 17-β Estradiol pellets (0.72 mg; 60 day slow release)). Passaged tumors were maintained under constant Tamoxifen selection, and Tumor volume (length×width$^2$/2) was monitored weekly. When tumor volume reached ~150-250 mm$^3$, animals were randomized into treatment groups (mean tumor volume 200 mm$^3$) and tamoxifen treatment was terminated (except for a tamoxifen control arm). Animals were treated with Vehicle or Compound daily for 4 weeks. Tumor volume and body weight were monitored twice weekly for the duration of the study. At the conclusion of the treatment period; plasma and tumor samples were taken for pharmacokinetic and pharmacodynamic analyses, respectively.

Example 80

Ovarian Cancer Model; Xenograft Assay (BG-1)

Time release pellets (0.72 mg 17-β Estradiol/60 days) are subcutaneously implanted into female nu/nu mice. BG-1 cells are grown in DMEM Ham's F-12 50/50 containing 10% FBS, 10 mM Sodium Pyruvate, 10 mM Non-Essential Amino Acids at 5% $CO_2$, 37° C. Prior to injection, cells are trypsinized and suspended in 50% DMEM Ham's F-12 (serum free) and 50% Matrigel at $5\times10^7$ cells/mL. BG-1 cells are subcutaneously injected (100 µL/animal) on the right flank 2-3 days post pellet implantation. Tumor volume (length×width$^2$/2) is monitored bi-weekly. When tumors reach an average volume of ~250 mm$^3$ animals are randomized and treatment started. Animals are treated with Vehicle or Compound daily. Tumor volume and body weight are monitored bi-weekly throughout the study. At the conclusion of the treatment period; plasma and tumor samples are taken for pharmacokinetic and pharmacodynamic analyses, respectively.

Example 81

Immature Uterine Wet Weight-Antagonist Mode

Female immature CD-IGS rats (21 days old upon arrival) were treated for three days. Animals were dosed daily for three days. Vehicle or test compound was administered orally by gavage followed 15 minutes later by an oral dose of 0.1 mg/kg Ethynyl Estradiol. On the fourth day 24 hours after dose, plasma was collected for pharmacokinetic analysis. Immediately following plasma collection, the animals were euthanized and the uterus was removed and weighed.

Example 82

Immature Uterine Wet Weight-Agonist Mode

Female immature CD-IGS rats (21 days old upon arrival) were treated for three days. Animals were dosed daily for three days. Vehicle or test compound was administered orally by gavage. On the fourth day 24 hours after dose, plasma was collected for pharmacokinetic analysis. Immediately following plasma collection, the animals were euthanized and the uterus was removed and weighed.

Example 83

Breast Cancer Clinical Trial

A non-limiting example of a breast cancer clinical trial in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as first- or second-line treatment of estrogen receptor (ER) positive metastatic breast cancer, collect information on any side effects the compound may cause, and evaluate the pharmacokinetic properties of the compound.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day.

Outcome Measures:

Primary Outcome Measures: tumor response and/or disease control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working Participation in this study will last until disease progression or unacceptable toxicity.

Eligibility:

Female subjects that are 18 years and older.

Inclusion Criteria:

Histologically or cytologically confirmed diagnosis of invasive breast cancer, stage IV disease; at least one measurable target lesion as defined by RECIST that has not been previously treated with local therapy; post-menopausal status; ER positive breast cancer; HER2-negative breast cancer; up to one prior hormonal therapy for advanced or metastatic disease; ECOG performance status 0-1; life expectancy >12 weeks; adequate liver and bone marrow function: AST <2.5×ULN; Bilirubin <1.5×ULN; ANC >1,500/ul; platelet count >100,000/ul; normal PT and PTT; at least 2 weeks since prior radiation and recovered from treatment-related toxicity.

Exclusion Criteria:

HER2-positive breast cancer; prior chemotherapy regimen for metastatic disease; history of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 84

Endometrial Carcinoma Clinical Trial

A non-limiting example of a endometrial carcinoma clinical trial in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in the treatment of advanced or metastatic endometrial carcinoma, collect information on any side effects the compound may cause, and evaluate the pharmacokinetic properties of the compound.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day.

Outcome Measures:

Primary Outcome Measures: tumor response and/or disease control Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day. Prior to each dosing cycle, a physical exam, blood work and assessment of any side effects will be performed. Every 12 weeks the patient's cancer will be re-evaluated with either a CT scan or MRI to determine whether the treatment is working Participation in this study will last until disease progression or unacceptable toxicity.

Eligibility:

Female subjects that are 18 years and older.

Inclusion Criteria:

Histologically or cytologically confirmed diagnosis of advanced or metastatic endometrial carcinoma; at least one measurable target lesion as defined by RECIST that has not been previously treated with local therapy; hormone receptor positive endometrial carcinoma; ECOG performance status 0-1; life expectancy >12 weeks; adequate liver and bone marrow function: AST <2.5×ULN; Bilirubin <1.5× ULN; ANC >1,500/ul; platelet count >100,000/ul; normal PT and PTT; at least 2 weeks since prior radiation and recovered from prior surgery or treatment-related toxicity.

Exclusion Criteria:

History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 85

Ovarian Cancer Clinical Trial

A non-limiting example of an ovarian cancer clinical trial in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, in the treatment of advanced ovarian cancer, collect information on any side effects the compound may cause, and evaluate the pharmacokinetic properties of the compound.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day.

Outcome Measures:

Primary Outcome Measures: tumor response and/or disease control.

Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day. Prior to each dosing cycle, a physical exam, blood work (including tumor markers, e.g., CA-125) and assessment of any side effects will be performed. Every 12 weeks the patient's cancer will be re-evaluated with either a CT scan or MRI to determine whether the treatment is working Participation in this study will last until disease progression or unacceptable toxicity.

Eligibility:

Female subjects that are 18 years and older.

Inclusion Criteria:

Histologically or cytologically confirmed diagnosis of advanced ovarian cancer; at least one measurable target lesion as defined by RECIST that has not been previously treated with local therapy; ER positive ovarian cancer; ECOG performance status 0-1; life expectancy >12 weeks; adequate liver and bone marrow function: AST <2.5×ULN; Bilirubin <1.5×ULN; ANC >1,500/ul; platelet count >100,000/ul; normal PT and PTT; at least 2 weeks since prior radiation and recovered from prior surgery or treatment-related toxicity.

Exclusion Criteria:

History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infection; active bleeding, or history of bleeding requiring transfusion; active cardiac disease; serious medical or psychiatric illness.

Example 86

ER-Positive NSCLC Clinical Trial

A non-limiting example of an ER-positive non-small cell lung cancer (NSCLC) clinical trial in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as single agent or in combination in the treatment of advanced or metastatic estrogen receptor (ER) positive non-small cell lung cancer (NSCLC), collect information on any side effects the compound may cause as single agent or in combination, and evaluate the pharmacokinetic properties of the compound as single agent or in combination.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day as single agent or in combination.

Outcome Measures:

Primary Outcome Measures: tumor response and/or disease control. Secondary Outcome Measures: (a) side-effects; (b) pharmacokinetic properties; (c) proportion of patients that have complete or partial response or stable disease at defined time points; (d) time to progression and overall survival; and (e) biomarkers predictive of clinical response.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day as single agent or in combination. Prior to each dosing cycle, a physical exam, blood work and assessment of any side effects will be performed. Every 12 weeks the patient's cancer will be re-evaluated with either a CT scan or MRI to determine whether the treatment is working. Participation in this study will last until disease progression or unacceptable toxicity.

Eligibility:

Male and female subjects that are 18 years and older.

Inclusion Criteria:

Histologically or cytologically confirmed diagnosis of advanced or metastatic ER-positive NSCLC; at least one measurable target lesion as defined by RECIST that has not been previously treated with local therapy; ECOG performance status 0-1; life expectancy >12 weeks; adequate liver and bone marrow function: AST <2.5×ULN; Bilirubin <1.5× ULN; ANC >1,500/ul; platelet count >100,000/ul; normal PT and PTT; at least 2 weeks since prior radiation and recovered from prior surgery or treatment-related toxicity.

Exclusion Criteria:

History of, or presence of brain metastases; concurrent investigational drug treatment; prior bone marrow or stem cell transplant; history of other malignancy within the last 5 years, not including curatively-treated carcinoma in situ of the cervix or non-melanoma skin cancer; uncontrolled infec-

Example 87

Endometriosis Clinical Trial

A non-limiting example of an endometriosis clinical trial in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as single agent or in combination in the treatment of patients with symptomatic/severe endometriosis, collect information on any side effects the compound may cause as single agent or in combination, and evaluate the pharmacokinetic properties of the compound as single agent or in combination.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day as single agent or in combination.

Outcome Measures:

The outcome measures of this study are symptoms improvement and/or pain relief and shrinkage of endometrial tissue.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day as single agent or in combination. Prior to each dosing cycle, a physical exam, blood work and assessment of any side effects will be performed.

Eligibility:

Female subjects that are 18 years and older.

Inclusion Criteria:

Diagnosis of symptomatic endometriosis; pre- or peri-menopausal status; ECOG performance status 0-1; adequate liver and bone marrow function: AST <2.5×ULN; Bilirubin <1.5×ULN; ANC >1,500/ul; platelet count >100,000/ul; normal PT and PTT; at least 2 weeks since prior surgery or treatment-related toxicity.

Exclusion Criteria:

Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; aerious medical or psychiatric illness.

Example 88

Uterine Leiomyoma Clinical Trial

A non-limiting example of an uterine leiomyoma in humans is described below.

Purpose:

The purposes of this study are to assess the efficacy of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, as single agent or in combination in the treatment of patients with symptomatic uterine leiomyoma, collect information on any side effects the compound may cause as single agent or in combination, and evaluate the pharmacokinetic properties of the compound as single agent or in combination.

Intervention:

Patients are administered 1-50 mg/kg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, once per day or twice a day as single agent or in combination.

Outcome Measures:

The outcome measures of this study are symptoms improvement and/or pain relief and shrinkage of leiomyomas.

Detailed Description:

Patients will be given a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, orally once or twice a day as single agent or in combination. Prior to each dosing cycle, a physical exam, blood work and assessment of any side effects will be performed.

Eligibility:

Female subjects that are 18 years and older.

Inclusion Criteria:

Diagnosis of symptomatic uterine leiomyoma; pre- or peri-menopausal status; ECOG performance status 0-1; adequate liver and bone marrow function: AST <2.5×ULN; Bilirubin <1.5×ULN; ANC >1,500/ul; platelet count >100,000/ul; normal PT and PTT; at least 2 weeks since prior surgery or treatment-related toxicity.

Exclusion Criteria:

Pregnancy or lactating; history of other malignancy within the last 5 years, not including curatively-treated carcinoma in situ of the cervix or non-melanoma skin cancer; concurrent investigational drug treatment; uncontrolled infection; active cardiac disease; serious medical or psychiatric illness.

Example 89

Parenteral Pharmaceutical Composition

To prepare a parenteral pharmaceutical composition suitable for administration by injection (subcutaneous, intravenous), 100 mg of a water-soluble salt of a compound described herein (e.g. a compound of Formula (I), (II), (III), (IV), (V), (VI), (VII), (VIII), (IX), (X), (XI), (XII), (XIII), or (XIV), or a compound in Table 1), is dissolved in sterile water and then mixed with 10 mL of 0.9% sterile saline. The mixture is incorporated into a dosage unit form suitable for administration by injection In another embodiment, the following ingredients are mixed to form an injectable formulation: 1.2 g of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and (preceding text from previous page: tion; active bleeding, or history of bleeding requiring transfusion; active cardiac disease; serious medical or psychiatric illness.)

stirred and if necessary, with slight heating if necessary. A sufficient quantity of water is then added.

Example 90

Oral Solution

To prepare a pharmaceutical composition for oral delivery, an aqueous 20% propylene glycol solution is prepared. To this is added a sufficient amount of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, to provide a 20 mg/mL solution.

Example 91

Oral Capsule

To prepare a pharmaceutical composition for oral delivery, 100-500 mg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is mixed with starch. The mixture is incorporated into an oral dosage unit such as a hard gelatin capsule, which is suitable for oral administration.

In another embodiment, 100-500 mg of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is placed into Size 4 capsule, or size 1 capsule (hypromellose or hard gelatin) and the capsule is closed.

Example 92

Oral Tablet

A tablet is prepared by mixing 48% by weigh of a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 93

Topical Gel Composition

To prepare a pharmaceutical topical gel composition, a compound described herein (e.g. a compound of Formula (I), (II), (III), (IV), (V), (VI), (VII), (VIII), (IX), (X), (XI), (XII), (XIII), or (XIV), or a compound in Table 1), or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

The examples and embodiments described herein are for illustrative purposes only and various modifications or changes suggested to persons skilled in the art are to be included within the spirit and purview of this application and scope of the appended claims.

What is claimed is:
1. A compound of Formula (VII), or a pharmaceutically acceptable salt, or N-oxide thereof:

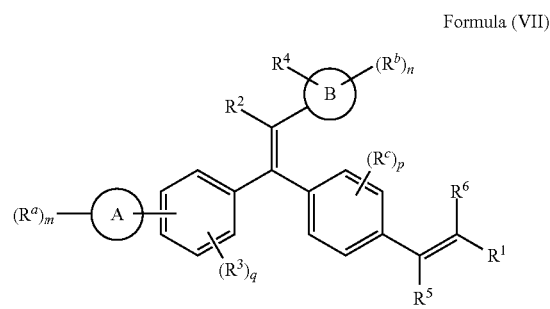

Formula (VII)

wherein,
ring A is 3-7 membered monocyclic $C_2$-$C_6$ heterocycloalkyl, 5-membered monocyclic heteroaryl, or 6-membered monocyclic heteroaryl;
each $R^a$ is independently selected from the group consisting of H, halogen, —$NR^7R^8$, —CN, —OH, —$OR^9$, —$SR^8$, substituted or unsubstituted $C_1$-$C_6$alkyl, substituted or unsubstituted $C_1$-$C_6$fluoroalkyl, and substituted or unsubstituted $C_1$-$C_6$ heteroalkyl;
m is 0, 1, 2, 3, or 4;
ring B is phenyl, indanyl, indenyl, naphthyl, 5-membered monocyclic heteroaryl, 6-membered monocyclic heteroaryl, or 8-, 9- or 10-membered bicyclic heteroaryl;
each $R^b$ is independently selected from the group consisting of H, halogen, —$NR^7R^8$, —CN, —OH, —$OR^9$, —$SR^8$, —S(=O)$R^9$, —S(=O)$_2R^9$, —NHS(=O)$_2R^9$, —S(=O)$_2N(R^8)_2$, —C(=O)$R^9$, —OC(=O)$R^9$, —$CO_2R^8$, —$OCO_2R^9$, —C(=O)N($R^8$)$_2$, —OC(=O)N($R^8$)$_2$, —$NR^7$C(=O)N($R^8$)$_2$, —$NR^7$C(=O)$R^9$, —$NR^7$C(=O)$OR^9$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl and substituted or unsubstituted monocyclic heteroaryl;
n is 0, 1, 2, 3, or 4;
each $R^c$ is independently selected from the group consisting of H, halogen, —CN, —OH, —$OR^9$, $C_1$-$C_6$alkyl, or $C_1$-$C_6$fluoroalkyl;
p is 0, 1, 2, 3 or 4;
$R^5$ is H, $C_1$-$C_4$ alkyl, or halogen;
$R^6$ is H, $C_1$-$C_4$ alkyl, or halogen;
$R^1$ is —C(=O)—Z, a carboxylic acid bioisostere, or a substituted or unsubstituted N-containing $C_2$-$C_8$ heterocycloalkyl;
Z is —OH, —$OR^9$, —$NR^7R^8$, —$NR^7$S(=O)$_2R^9$, —NHOH or —$NR^7OR^9$;
$R^2$ is halogen, —CN, —$NO_2$, —$SR^9$, $C_1$-$C_6$alkyl, $C_1$-$C_6$fluoroalkyl, $C_1$-$C_6$ deuteroalkyl, $C_3$-$C_6$ cycloalkyl, —$C_1$-$C_4$alkylene-W, —$C_1$-$C_4$fluoroalkylene-W, —$C_3$-$C_6$ cycloalkylene-W;
W is hydroxy, halogen, —CN, —$NO_2$, $C_1$-$C_6$alkyl, $C_1$-$C_6$haloalkyl, $C_1$-$C_6$alkoxy, $C_1$-$C_6$ haloalkoxy, and $C_3$-$C_6$ cycloalkyl;

each R³ is independently selected from the group consisting of H, halogen, —CN, C₁-C₆alkyl, C₁-C₆ fluoroalkyl, and C₁-C₆ heteroalkyl;
q is 0, 1, 2, 3 or 4;
R⁴ is H, halogen, —CN, —OH, —OR⁹, —SR⁸, —S(=O) R⁹, —S(=O)₂R⁹, —NHS(=O)₂R⁹, —S(=O)₂N(R⁸)₂, —C(=O)R⁹, —OC(=O)R⁹, —CO₂R⁸, —C(=O)N(R⁸)₂, —OC(=O)N(R⁸)₂, C₁-C₆alkyl, C₂-C₆alkenyl, C₂-C₆alkynyl, C₁-C₆fluoroalkyl, or C₁-C₆heteroalkyl;
each R⁷ is independently H or C₁-C₆alkyl;
each R⁸ is independently selected from H, substituted or unsubstituted C₁-C₆alkyl, substituted or unsubstituted C₂-C₆ alkenyl, substituted or unsubstituted C₂-C₆ alkynyl, substituted or unsubstituted C₁-C₆ fluoroalkyl, substituted or unsubstituted C₁-C₆ heteroalkyl, substituted or unsubstituted C₃-C₁₀ cycloalkyl, substituted or unsubstituted C₂-C₁₀ heterocycloalkyl, substituted or unsubstituted phenyl, substituted or unsubstituted monocyclic heteroaryl, or substituted or unsubstituted benzyl;
each R⁹ is independently selected from substituted or unsubstituted C₁-C₆alkyl, substituted or unsubstituted C₁-C₆heteroalkyl, substituted or unsubstituted C₁-C₆fluoroalkyl, substituted or unsubstituted C₃-C₁₀cycloalkyl, substituted or unsubstituted C₂-C₁₀heterocycloalkyl, substituted or unsubstituted aryl, substituted or unsubstituted heteroaryl and substituted or unsubstituted benzyl.

2. The compound of claim 1, or a pharmaceutically acceptable salt thereof, wherein:
ring A is 3-7 membered monocyclic N-containing C₂-C₆ heterocycloalkyl, N-containing 5-membered monocyclic heteroaryl, or N-containing 6-membered monocyclic heteroaryl; and
ring B is phenyl, indanyl, indenyl, naphthyl, 5-membered monocyclic heteroaryl, 6-membered monocyclic heteroaryl, or 8-, 9- or 10-membered bicyclic heteroaryl.

3. The compound of claim 1, or a pharmaceutically acceptable salt thereof, wherein:
ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl; and
ring B is phenyl, naphthyl, indanyl, indenyl, furanyl, thienyl, oxazolyl, thiazolyl, pyrrolyl, imidazolyl, pyrazolyl, triazolyl, tetrazolyl, pyridinyl, pyridazinyl, pyrimidinyl, pyrazinyl, triazinyl, quinolinyl, isoquinolinyl, cinnolinyl, phthalazinyl, quinazolinyl, quinoxalinyl, naphthyridinyl, pteridinyl, inolizinyl, azainolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, or purinyl.

4. The compound of claim 1, or a pharmaceutically acceptable salt thereof, wherein:

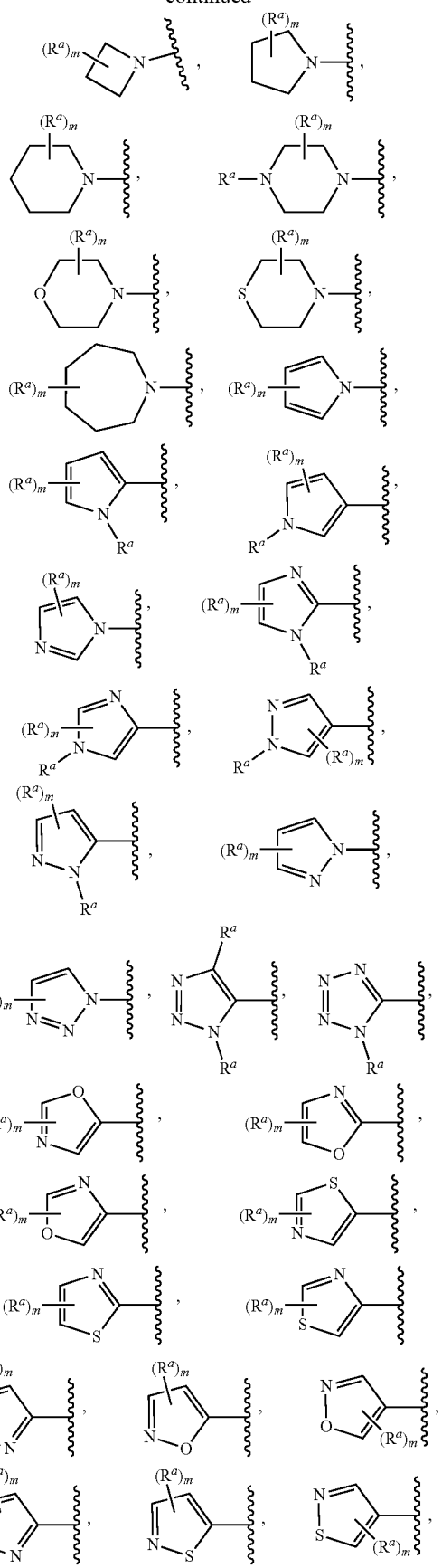

-continued

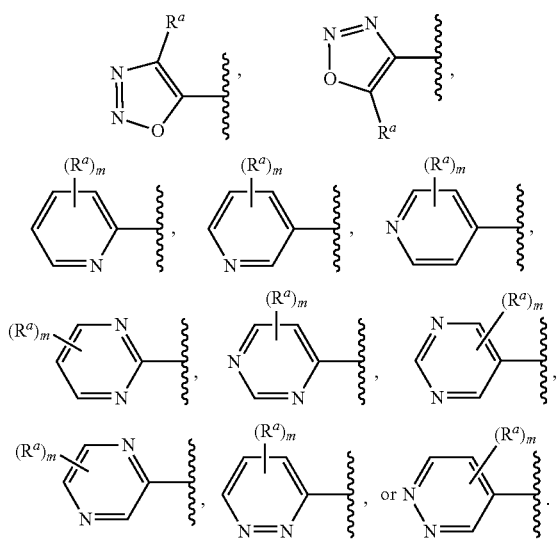

5. The compound of claim 1, or a pharmaceutically acceptable salt thereof, wherein:

$R^1$ is —C(=O)—Z,

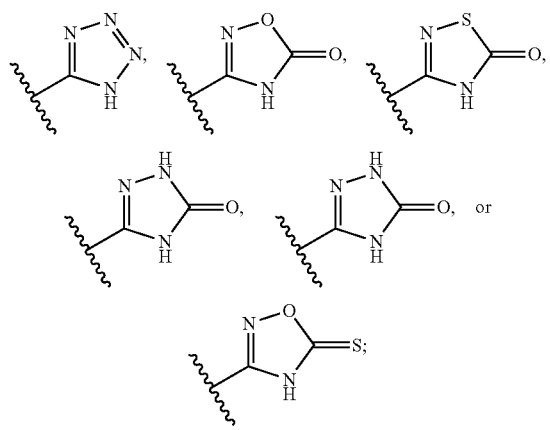

Z is —OH, —$OR^9$, or —$NR^7R^8$.

6. The compound of claim of 1, wherein the compound of Formula (VII) has the following structure of Formula (VIII) or Formula (IX):

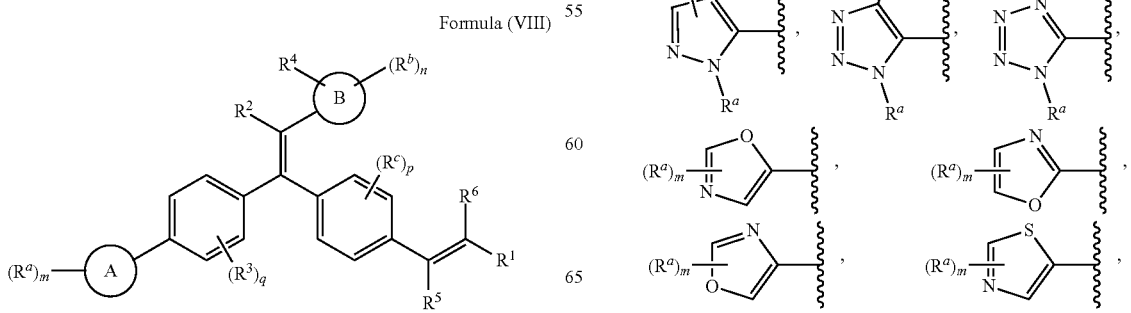

Formula (VIII)

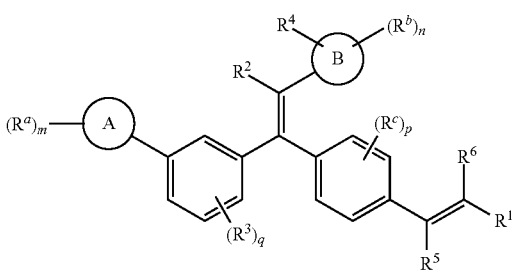

Formula (IX)

or is a pharmaceutically acceptable salt thereof.

7. The compound of claim 6, or a pharmaceutically acceptable salt thereof, wherein:

ring A is aziridinyl, azetindinyl, pyrrolidinyl, piperidinyl, azepanyl, imidazolidinyl, pyrazolidinyl, morpholinyl, thiomorpholinyl, piperazinyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyrimidinyl, pyrazinyl, pyridazinyl, or triazinyl.

8. The compound of claim 6, or a pharmaceutically acceptable salt thereof, wherein:

ring A is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl.

9. The compound of claim 8, or a pharmaceutically acceptable salt thereof, wherein:

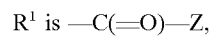 is

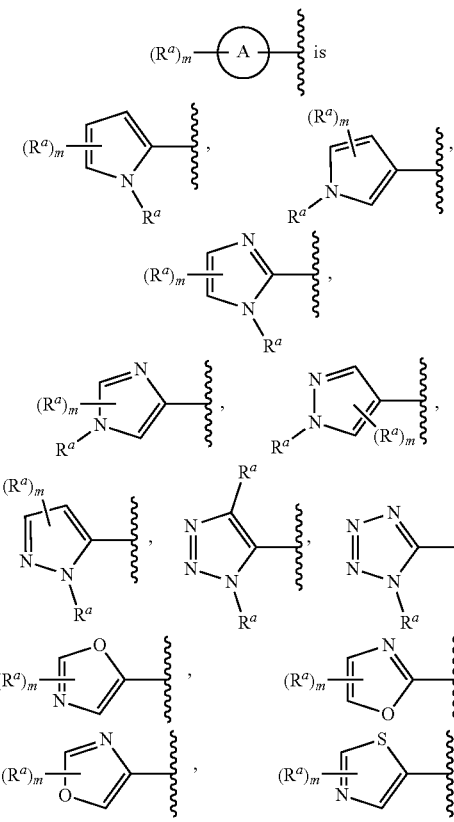

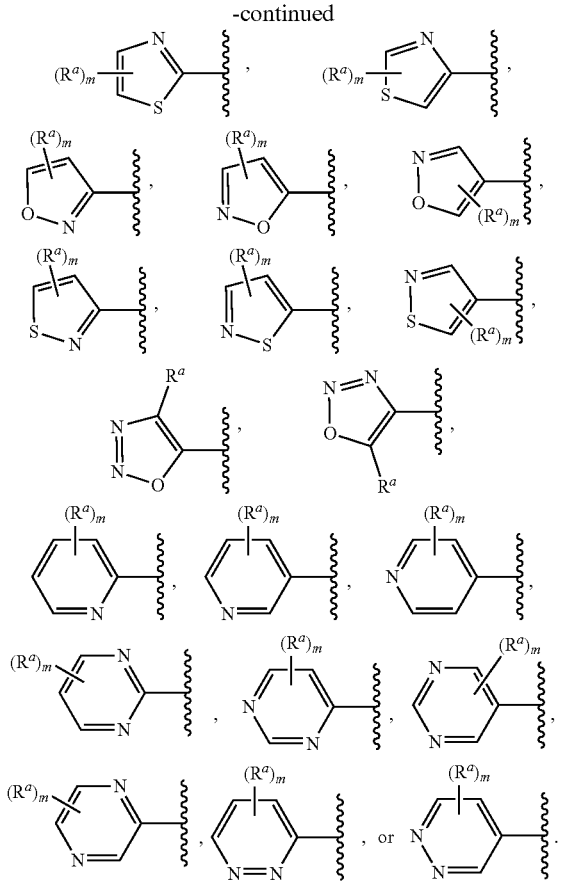

10. The compound of claim 6, or a pharmaceutically acceptable salt thereof, wherein:

ring A is N-linked 3-7 membered monocyclic N-containing $C_2$-$C_6$heterocycloalkyl, or N-linked N-containing 5-membered monocyclic heteroaryl.

11. The compound of claim 10, or a pharmaceutically acceptable salt thereof, wherein:

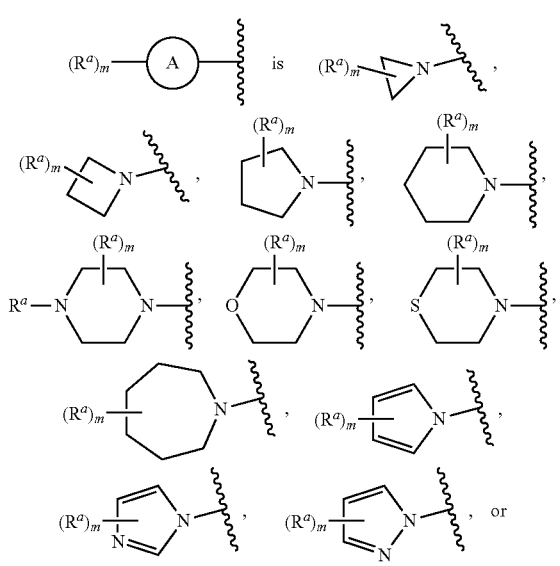

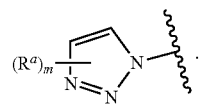

12. The compound of claim 1, or a pharmaceutically acceptable salt thereof, wherein:

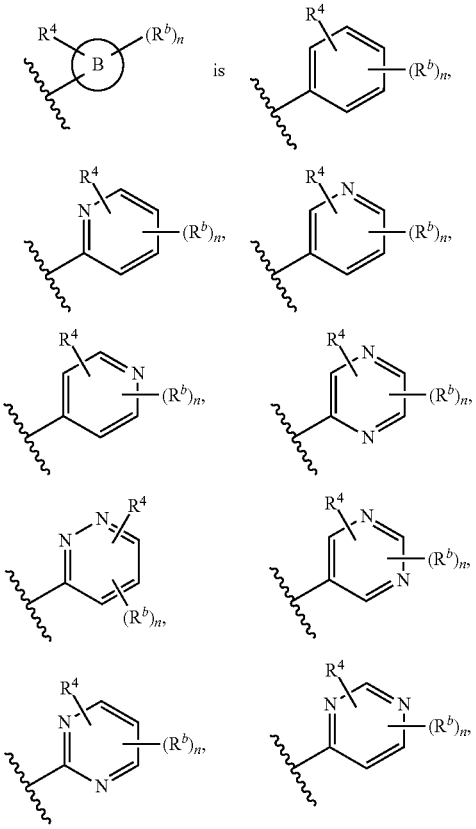

13. The compound of claim 1, or a pharmaceutically acceptable salt thereof, wherein:

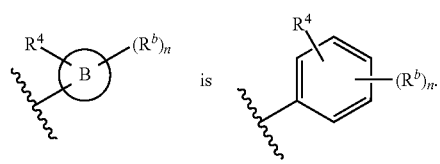

14. The compound of claim 1, or a pharmaceutically acceptable salt thereof, wherein:

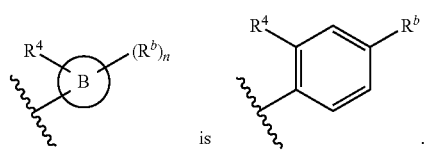

is

15. The compound of claim 1, or a pharmaceutically acceptable salt thereof, wherein:

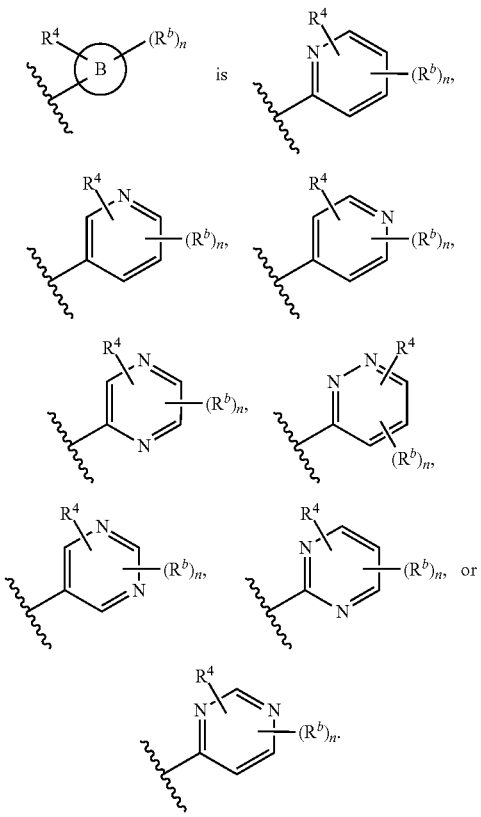

16. The compound claim 1, or a pharmaceutically acceptable salt thereof, wherein:

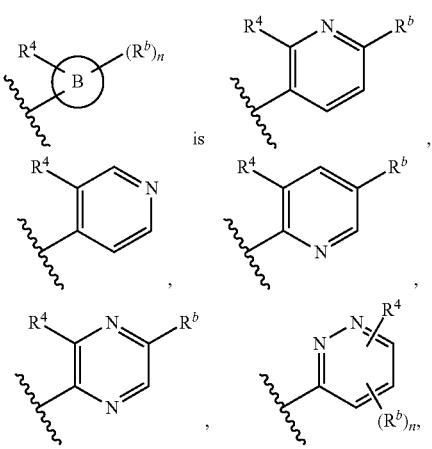

-continued

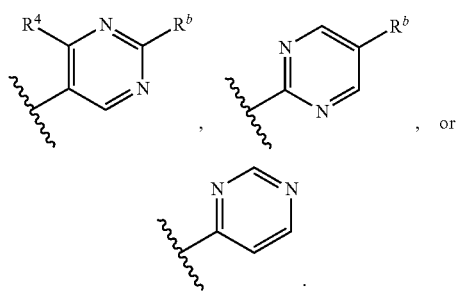

17. The compound of claim 1, or a pharmaceutically acceptable salt thereof, wherein:

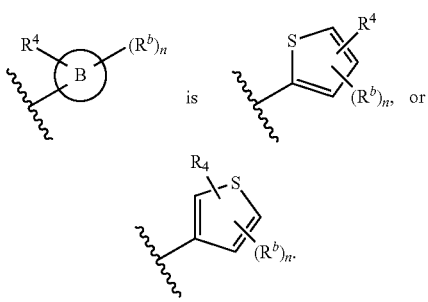

18. The compound of claim 1, or a pharmaceutically acceptable salt thereof, wherein:

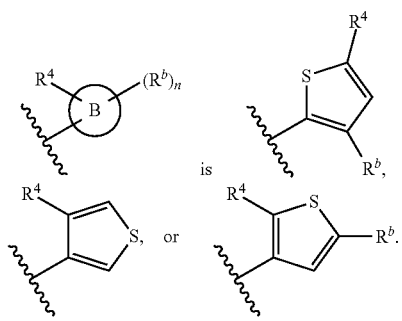

19. The compound of claim 1, or a pharmaceutically acceptable salt thereof, wherein $R^5$ is H;

$R^6$ is H.

20. The compound of claim 1, or a pharmaceutically acceptable salt thereof, wherein:

$R^2$ is $C_1$-$C_6$ alkyl or $C_3$-$C_6$ cycloalkyl.

21. The compound of claim 20, or a pharmaceutically acceptable salt thereof, wherein:

$R^2$ is —$CH_2CH_3$.

22. The compound of claim 20, or a pharmaceutically acceptable salt thereof, wherein:

$R^2$ is cyclobutyl.

23. The compound of claim 1, wherein the compound of Formula (I) has the following structure of Formula (X):

Formula (X)

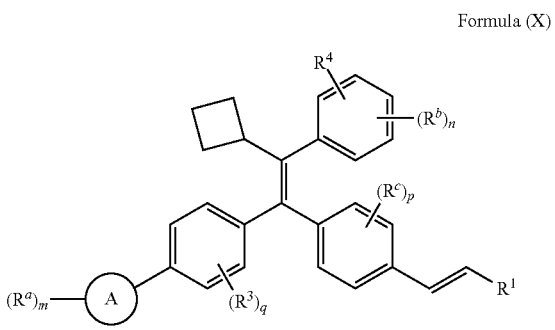

or is a pharmaceutically acceptable salt thereof.

24. The compound of claim 23, wherein the compound of Formula (X) has the following structure of Formula (XI):

Formula (XI)

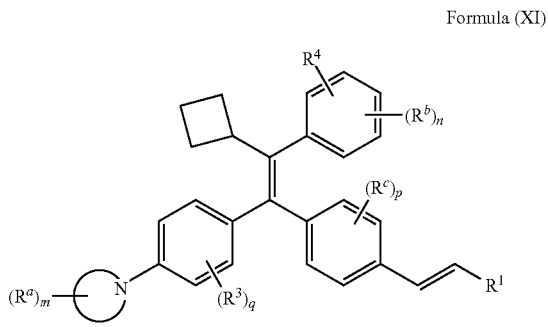

wherein,

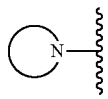

is N-linked 3-7 membered monocyclic N-containing $C_2$-$C_6$heterocycloalkyl or N-linked N-containing 5-membered monocyclic heteroaryl;

or is a pharmaceutically acceptable salt thereof.

25. The compound of claim 23, wherein the compound of Formula (X) has the following structure of Formula (XII):

Formula (XII)

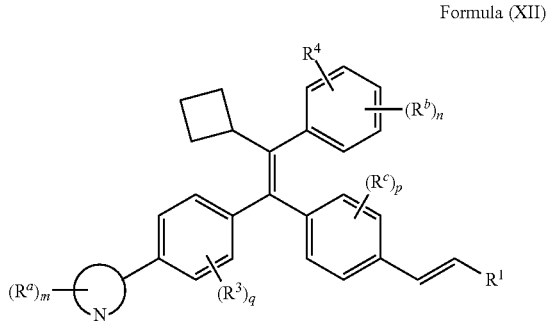

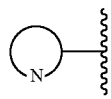

is C-linked 3-7 membered monocyclic N-containing $C_2$-$C_6$heterocycloalkyl, C-linked N-containing 5-membered monocyclic heteroaryl, or C-linked N-containing 6-membered monocyclic heteroaryl;

or is a pharmaceutically acceptable salt thereof.

26. The compound of claim 1, or a pharmaceutically acceptable salt thereof, wherein
$R^b$ is H, F, Cl, —CN, —OH, —OR$^9$, —SR$^8$, —S(=O)R$^9$, —S(=O)$_2$R$^9$, $C_1$-$C_6$alkyl, $C_1$-$C_6$fluoroalkyl, or $C_1$-$C_6$heteroalkyl;
$R^4$ is H, F, Cl, —CN, —OH, —OR$^9$, —SR$^8$, —S(=O)R$^9$, —S(=O)$_2$R$^9$, $C_1$-$C_6$alkyl, $C_1$-$C_6$fluoroalkyl, or $C_1$-$C_6$heteroalkyl.

27. The compound of claim 1, or a pharmaceutically acceptable salt thereof, wherein
$R^b$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH;
$R^4$ is H, F, Cl, —CN, —OH, —OCH$_3$, —OCH$_2$CH$_3$, —OCF$_3$, —S(=O)$_2$CH$_3$, —CH$_3$, —CF$_3$, or —CH$_2$OH.

28. The compound of claim 1, or a pharmaceutically acceptable salt thereof, wherein:
each $R^a$ is independently selected from the group consisting of H, halogen, —CN, —OH, —OR$^9$, $C_1$-$C_6$alkyl, $C_1$-$C_6$fluoroalkyl, and $C_1$-$C_6$heteroalkyl;
m is 0 or 1.

29. The compound of claim 1, or a pharmaceutically acceptable salt thereof, wherein:
m is 0.

30. The compound of claim 1, or a pharmaceutically acceptable salt thereof, wherein:
p is 0.

31. The compound of claim 1, or a pharmaceutically acceptable salt thereof, wherein:
q is 0.

32. The compound of claim 1, or a pharmaceutically acceptable salt thereof, wherein:
$R^1$ is —C(=O)—OH.

33. A compound that is:
(E)-3-(4-((E)-1-(4-(1H-Pyrazol-4-yl)phenyl)-2-cyclobutyl-2-phenylvinyl)phenyl)acrylic acid;
(E)-3-(4-(E)-2-(2-Chloro-4-fluorophenyl)-1-(4-(thiazol-5-yl)phenyl)but-1-en-1-yl)phenyl)acrylic acid;
(E)-3-(4-((E)-1-(4-(1H-Pyrazol-4-yl)phenyl)-2-(2-chloro-4-cyanophenyl)-2-cyclobutylvinyl)phenyl) acrylic acid;
(E)-3-(4-((E)-2-(2-Chloro-4-methoxyphenyl)-2-cyclobutyl-1-(4-morpholinophenyl)vinyl)phenyl)acrylic acid;
(E)-3-(4-((E)-2-(2-Chloro-4-cyanophenyl)-2-cyclobutyl-1-(4-(thiazol-5-yl)phenyl)vinyl)phenyl)acrylic acid;
(E)-3-(4-((E)-1-(4-(1H-Pyrazol-5-yl)phenyl)-2-phenyl-but-1-en-1-yl)phenyl)acrylic acid;
(E)-3-(4-((E)-1-(3-(1H-Pyrazol-5-yl)phenyl)-2-phenyl-but-1-en-1-yl)phenyl)acrylic acid;
(E)-3-(4-((E)-2-Phenyl-1-(4-(thiazol-2-yl)phenyl)but-1-en-1-yl)phenyl)acrylic acid;
(E)-3-(4-((E)-2-Phenyl-1-(4-(thiazol-5-yl)phenyl)but-1-en-1-yl)phenyl)acrylic acid;
(E)-3-(4-((E)-2-Phenyl-1-(4-(thiazol-4-yl)phenyl)but-1-en-1-yl)phenyl)acrylic acid;

(E)-3-(4-((E)-2-Phenyl-1-(3-(thiazol-2-yl)phenyl)but-1-en-1-yl)phenyl)acrylic acid;
(E)-3-(4-((E)-2-Phenyl-1-(3-(thiazol-4-yl)phenyl)but-1-en-1-yl)phenyl)acrylic acid;
(E)-3-(4-((E)-2-Cyclobutyl-2-phenyl-1-(4-(thiazol-5-yl)phenyl)vinyl)phenyl)acrylic acid;
(E)-3-(4-((E)-2-Phenyl-1-(4-(pyridin-3-yl)phenyl)but-1-en-1-yl)phenyl)acrylic acid;
(E)-3-(4-((E)-1-(4-(Isothiazol-4-yl)phenyl)-2-phenylbut-1-en-1-yl)phenyl)acrylic acid;
(E)-3-(4-((E)-1-(4-Morpholinophenyl)-2-phenylbut-1-en-1-yl)phenyl)acrylic acid;
(E)-3-(4-((E)-1-(4-(1H-Imidazol-1-yl)phenyl)-2-phenylbut-1-en-1-yl)phenyl)acrylic acid;
(E)-3-(4-((E)-1-(4-(Oxazol-5-yl)phenyl)-2-phenylbut-1-en-1-yl)phenyl)acrylic acid;
(E)-3-(4-((E)-1-(4-(1-Methyl-1H-pyrazol-4-yl)phenyl)-2-phenylbut-1-en-1-yl)phenyl)acrylic acid;
(E)-3-(4-((E)-1-(2-Fluoro-4-(thiazol-5-yl)phenyl)-2-phenylbut-1-en-1-yl)phenyl)acrylic acid;
(E)-3-(4-((E)-1-(3-Fluoro-4-(thiazol-5-yl)phenyl)-2-phenylbut-1-en-1-yl)phenyl)acrylic acid;
(E)-3-(4-((E)-1-(4-(1H-Pyrazol-4-yl)phenyl)-2-phenylbut-1-en-1-yl)phenyl)acrylic acid;
(E)-3-(4-((E)-1-(4-(4-Methylpiperazin-1-yl)phenyl)-2-phenylbut-1-en-1-yl)phenyl)acrylic acid;
(E)-3-(4-((E)-2-Phenyl-1-(4-(piperidin-1-yl)phenyl)but-1-en-1-yl)phenyl)acrylic acid;
(E)-3-(4-((E)-2-Cyclobutyl-2-phenyl-1-(5-(thiazol-5-yl)pyridin-2-yl)vinyl)phenyl)acrylic acid;
(E)-3-(4-((E)-1-(3-(1H-Pyrazol-4-yl)phenyl)-2-cyclobutyl-2-phenylvinyl)phenyl)acrylic acid;
(E)-3-(4-((E)-2-Cyclobutyl-1-(4-(isoxazol-3-yl)phenyl)-2-phenylvinyl)phenyl)acrylic acid;
(E)-3-(4-((E)-2-(3-Chloropyridin-4-yl)-1-(4-(thiazol-5-yl)phenyl)but-1-en-1-yl)phenyl)acrylic acid;
(E)-3-(4-((E)-2-(2-Chlorophenyl)-1-(4-(thiazol-5-yl)phenyl)but-1-en-1-yl)phenyl)acrylic acid;
(E)-3-(4-((E)-2-(3-Methoxyphenyl)-1-(4-(thiazol-5-yl)phenyl)but-1-en-1-yl)phenyl)acrylic acid;
(E)-3-(4-((E)-2-(Benzofuran-5-yl)-1-(4-(thiazol-5-yl)phenyl)but-1-en-1-yl)phenyl)acrylic acid;
(E)-3-(4-((E)-2-(4-Methylthiophen-3-yl)-1-(4-(thiazol-5-yl)phenyl)but-1-en-1-yl)phenyl)acrylic acid;
(E)-3-(4-((E)-2-(2-Chloro-4-fluorophenyl)-2-cyclobutyl-1-(4-(thiazol-5-yl)phenyl)vinyl)phenyl)acrylic acid;
(E)-3-(4-((E)-2-(3-Chloropyridin-4-yl)-2-cyclobutyl-1-(4-(thiazol-5-yl)phenyl)vinyl)phenyl)acrylic acid;
(E)-3-(4-((E)-2-Cyclobutyl-2-(4-methylthiophen-3-yl)-1-(4-(thiazol-5-yl)phenyl)vinyl)phenyl)acrylic acid;
(E)-3-(4-((E)-2-(2-Chloro-4-fluorophenyl)-2-cyclobutyl-1-(4-morpholinophenyl)vinyl)phenyl)acrylic acid;
(E)-3-(4-((E)-1-(4-(1H-Pyrazol-4-yl)phenyl)-2-(2-chloro-4-fluorophenyl)-2-cyclobutylvinyl)phenyl)acrylic acid;
(E)-3-(4-((E)-1-(4-(1H-Pyrazol-4-yl)phenyl)-2-cyclobutyl-2-(4-methylthiophen-3-yl)vinyl)phenyl)acrylic acid;
(E)-3-(4-((E)-2-Cyclobutyl-2-(6-methoxy-4-methylpyridin-3-yl)-1-(4-morpholinophenyl)vinyl)phenyl)acrylic acid;
(E)-3-(4-((E)-1-(4-(1H-Pyrazol-4-yl)phenyl)-2-cyclobutyl-2-(3-methylpyridin-2-yl)vinyl)phenyl)acrylic acid;
(E)-3-(4-((E)-1-(4-(1H-Pyrazol-4-yl)phenyl)-2-cyclobutyl-2-(3-fluoropyridin-2-yl)vinyl)phenyl)acrylic acid;
(E)-3-(4-((E)-1-(4-(1H-Pyrazol-4-yl)phenyl)-2-(3-chloropyridin-2-yl)-2-cyclobutylvinyl)phenyl)acrylic acid;
(E)-3-(4-((E)-2-(3-Chloropyridin-2-yl)-2-cyclobutyl-1-(4-morpholinophenyl)vinyl)phenyl)acrylic acid;
(E)-3-(4-((E)-1-(4-(1H-Pyrazol-4-yl)phenyl)-2-(4-chloro-2-cyanophenyl)-2-cyclobutylvinyl)phenyl)acrylic acid;
(E)-3-(4-((E)-2-(2-Chloro-4-cyanophenyl)-2-cyclobutyl-1-(4-morpholinophenyl)vinyl)phenyl)acrylic acid;
(E)-3-(4-((E)-2-(4-Chloro-2-cyanophenyl)-2-cyclobutyl-1-(4-morpholinophenyl)vinyl)phenyl)acrylic acid;
(E)-3-(4-((E)-2-Cyclobutyl-2-(4-methoxy-2-methylphenyl)-1-(4-morpholinophenyl)vinyl)phenyl)acrylic acid;
(E)-3-(4-((E)-2-(2-Chloro-4-(trifluoromethyl)phenyl)-2-cyclobutyl-1-(4-morpholinophenyl)vinyl)phenyl)acrylic acid;
(E)-3-(4-((E)-1-(4-(2H-Tetrazol-5-yl)phenyl)-2-(2-chloro-4-fluorophenyl)-2-cyclobutylvinyl)phenyl)acrylic acid;
(E)-3-(4-((E)-1-(4-(2H-Tetrazol-5-yl)phenyl)-2-(2-chloro-4-methoxyphenyl)-2-cyclobutylvinyl)phenyl)acrylic acid;
(E)-3-(4-((E)-1-(4-(1H-Pyrazol-4-yl)phenyl)-2-(2-chloro-4-methoxyphenyl)-2-cyclobutylvinyl)phenyl)acrylic acid;
(E)-3-(4-((E)-1-(4-(1H-Pyrazol-4-yl)phenyl)-2-(2-chloro-4-(trifluoromethoxy)phenyl)-2-cyclobutylvinyl)phenyl)acrylic acid;
(E)-3-(4-((E)-2-(2-Chloro-4-methoxyphenyl)-2-cyclobutyl-1-(4-(thiazol-5-yl)phenyl)vinyl)phenyl)acrylic acid;
(E)-3-(4-((E)-2-Cyclobutyl-2-(4-methoxy-2-methylphenyl)-1-(4-(thiazol-5-yl)phenyl)vinyl)phenyl)acrylic acid;
(E)-3-(4-((E)-1-(4-(1H-Pyrazol-4-yl)phenyl)-2-(2-chloro-4-(trifluoromethyl)phenyl)-2-cyclobutylvinyl)phenyl)acrylic acid;
(E)-3-(4-((E)-2-(2-Chloro-4-fluorophenyl)-2-cyclobutyl-1-(4-(pyridin-4-yl)phenyl)vinyl)phenyl)acrylic acid;
(E)-3-(4-((E)-2-(3-Chloro-5-(trifluoromethyl)pyridin-2-yl)-2-cyclobutyl-1-(4-morpholinophenyl)vinyl)phenyl)acrylic acid;
(E)-3-(4-((E)-1-(4-(1H-Pyrazol-4-yl)phenyl)-2-(3-chloro-5-(trifluoromethyl)pyridin-2-yl)-2-cyclobutylvinyl)phenyl)acrylic acid;
(E)-3-(4-((E)-2-(3-Chloro-5-(trifluoromethyl)pyridin-2-yl)-2-cyclobutyl-1-(4-(thiazol-5-yl)phenyl)vinyl)phenyl)acrylic acid;
(E)-3-(4-((E)-2-(2-Chloro-4-fluorophenyl)-1-(2-cyano-4-morpholinophenyl)-2-cyclobutylvinyl)phenyl)acrylic acid;
(E)-3-(4-((E)-1-(4-(1H-Pyrazol-4-yl)phenyl)-2-cyclobutyl-2-(6-methoxy-4-methylpyridin-3-yl)vinyl)phenyl)acrylic acid;
(E)-3-(4-((E)-2-(4-Chloro-2-cyanophenyl)-2-cyclobutyl-1-(4-(thiazol-5-yl)phenyl)vinyl)phenyl)acrylic acid;
(E)-3-(4-((E)-2-Cyclobutyl-1-(4-(4-methylpiperidin-1-yl)phenyl)-2-phenylvinyl)phenyl)acrylic acid;
(E)-3-(4-((E)-2-Cyclobutyl-2-phenyl-1-(4-(piperazin-1-yl)phenyl)vinyl)phenyl)acrylic acid;
(E)-3-(4-((E)-2-Cyclobutyl-2-phenyl-1-(4-(pyridin-4-yl)phenyl)vinyl)phenyl)acrylic acid;
(E)-3-(4-((E)-2-Cyclobutyl-1-(4-(1-(2-hydroxyethyl)-1H-pyrazol-4-yl)phenyl)-2-phenylvinyl)phenyl)acrylic acid;
(E)-3-(4-((E)-2-Cyclobutyl-1-(4-(1-(2-hydroxyethyl)-1H-pyrazol-4-yl)phenyl)-2-(4-methylthiophen-3-yl)vinyl)phenyl)acrylic acid;

(E)-3-(4-((E)-2-(2-Chloro-4-fluorophenyl)-2-cyclobutyl-1-(4-(1-(2-hydroxyethyl)-1H-pyrazol-4-yl)phenyl)vinyl)phenyl)acrylic acid;

(E)-3-(4-((E)-2-Cyclobutyl-1-(4-(1-(2-(dimethylamino)ethyl)-1H-pyrazol-4-yl)phenyl)-2-phenylvinyl)phenyl)acrylic acid; or 5-((E)-4-((E)-1-(4-(1H-Pyrazol-4-yl)phenyl)-2-(2-chloro-4-fluorophenyl)-2-cyclobutylvinyl)styryl)-2H-tetrazole;

or a pharmaceutically acceptable salt thereof.

34. A pharmaceutical composition comprising a compound as claimed in claim 1, or a pharmaceutically acceptable salt thereof.

35. The pharmaceutical composition of claim 34, wherein the pharmaceutical composition is formulated for intravenous injection, subcutaneous injection, oral administration, or topical administration.

36. The pharmaceutical composition of claim 34, wherein the pharmaceutical composition is a tablet, a pill, a capsule, a liquid, a suspension, a gel, a dispersion, a solution, an emulsion, an ointment, or a lotion.

37. A method of treating cancer in a mammal comprising administering to the mammal a therapeutically effective amount of a compound of claim 1 wherein the cancer is breast cancer, ovarian cancer, endometrial cancer, prostate cancer, lung cancer or uterine cancer.

* * * * *